US011980640B2

(12) United States Patent
Qin et al.

(10) Patent No.: US 11,980,640 B2
(45) Date of Patent: May 14, 2024

(54) BICISTRONIC CHIMERIC ANTIGEN RECEPTORS AND THEIR USES

(71) Applicant: The United States of America, as represented by the Secretary, Department of Health and Human Services, Bethesda, MD (US)

(72) Inventors: Haiying Qin, Potomac, MD (US); Crystal L Mackall, Stanford, CA (US); Terry J. Fry, Bethesda, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 1200 days.

(21) Appl. No.: 16/613,187

(22) PCT Filed: May 15, 2018

(86) PCT No.: PCT/US2018/032809
§ 371 (c)(1),
(2) Date: Nov. 13, 2019

(87) PCT Pub. No.: WO2018/213337
PCT Pub. Date: Nov. 22, 2018

(65) Prior Publication Data
US 2020/0147134 A1    May 14, 2020

Related U.S. Application Data

(60) Provisional application No. 62/506,268, filed on May 15, 2017.

(51) Int. Cl.
| A61K 35/17 | (2015.01) |
| A61P 35/00 | (2006.01) |
| C07K 14/395 | (2006.01) |
| C07K 14/725 | (2006.01) |
| C07K 16/28 | (2006.01) |
| C12N 15/85 | (2006.01) |

(52) U.S. Cl.
CPC .............. *A61K 35/17* (2013.01); *A61P 35/00* (2018.01); *C07K 14/395* (2013.01); *C07K 14/7051* (2013.01); *C07K 16/2803* (2013.01); *C12N 15/85* (2013.01)

(58) Field of Classification Search
None
See application file for complete search history.

(56) References Cited

U.S. PATENT DOCUMENTS

| 8,591,889 | B2 | 11/2013 | Dimitrov et al. |
| 8,906,682 | B2 | 12/2014 | June et al. |
| 9,279,019 | B2 | 3/2016 | Dimitrov et al. |
| 10,072,078 | B2 | 9/2018 | Orentas et al. |
| 2013/0280220 | A1 | 10/2013 | Ahmed et al. |
| 2014/0274909 | A1 | 9/2014 | Orentas et al. |
| 2015/0038684 | A1 | 2/2015 | Jensen |
| 2015/0299317 | A1 | 10/2015 | Orentas et al. |
| 2016/0068601 | A1 | 3/2016 | Brogdon et al. |
| 2016/0096892 | A1* | 4/2016 | Brogdon ................. A61P 35/00 |
| | | | 435/328 |
| 2016/0362472 | A1 | 12/2016 | Bitter et al. |
| 2017/0107286 | A1 | 4/2017 | Kochenderfer |
| 2018/0111992 | A1 | 4/2018 | Fry et al. |
| 2018/0187149 | A1 | 7/2018 | Matsuo et al. |
| 2020/0087396 | A1 | 3/2020 | Schneider et al. |

FOREIGN PATENT DOCUMENTS

| CN | 105647873 A | 6/2016 |
| WO | WO 2013/059593 A1 | 4/2013 |
| WO | WO 2013/123061 A1 | 8/2013 |
| WO | WO 2014/065961 A1 | 5/2014 |
| WO | WO 2015/187528 A1 | 12/2015 |
| WO | WO 2016/102965 A1 | 6/2016 |
| WO | WO 2016/149578 A1 | 9/2016 |
| WO | 2016/0164731 A2 | 10/2016 |
| WO | WO 2016/210293 A1 | 12/2016 |
| WO | WO 2018/213337 A1 | 11/2018 |

OTHER PUBLICATIONS

Lemieux et al., "Simultaneous dual car expression to prevent relapse in pre-B acute lymphoblastic leukemia," *Cytotherapy*, 20(5): S8-S9 (May 2018).
Kim et al., "High Cleavage Efficiency of a 2A Peptide Derived from Porcine Teschovirus-1 in Human Cell Lines, Zebrafish and Mice," *PLoS ONE*, vol. 6 issue 4: e18556, 10 pages (Apr. 2011).
Wilkie et al., "Dual Targeting of ErbB2 and MUC1 in Breast Cancer Using Chimeric Antigen Receptors Engineered to Provide Complementary Signaling," *J Clin Immunol* 32: 1059-1070 (2012).
U.S. Appl. No. 17/276,959, filed Mar. 17, 2021, Pending.
Ruella et al., "Dual CD19 and CD123 Targeting Prevents Antigen-loss Relapses After CD19-directed Immunotherapies," *The Journal of Clinical Investigation* 126(10): 3814-3826 (Oct. 2016).
Xiong et al., 648. "Mitigating Tumor Escape: Tandem Anti-CD20- and CD19 SCFV-Based Chimeric Antigen Receptors (CARs) in Leukemia/Lymphoma," *Molecular Therapy* vol. 24, Supplement 1: p. S257 (May 2016) (1 page).
Bang et al., "HA22 (R490A) Is a Recombinant Immunotoxin with Increased Antitumor Activity without an Increase in Animal Toxicity," *Clinical Cancer Research*, 11: 1545-1550 (2005).

(Continued)

*Primary Examiner* — Michael D Burkhart
(74) *Attorney, Agent, or Firm* — Leydig, Voit & Mayer

(57) ABSTRACT

An embodiment of the invention provides bicistronic chimeric antigen receptor (CAR) amino acid constructs. Nucleic acids, recombinant expression vectors, host cells, populations of cells, and pharmaceutical compositions relating to the CAR constructs are disclosed. Methods of detecting the presence of cancer in a mammal and methods of treating or preventing cancer in a mammal are also disclosed. Methods of making the CAR constructs are disclosed.

20 Claims, 68 Drawing Sheets
Specification includes a Sequence Listing.

(56) References Cited

OTHER PUBLICATIONS

Clay et al., "Efficient Transfer of a Tumor Antigen-Reactive TCR to Human Peripheral Blood Lymphocytes Confers Anti-Tumor Reactivity," *J. Immunol.*, 163: 507-513 (1999).
Grada et al., "TanCAR: A Novel Bispecific Chimeric Antigen Receptor for Cancer Immunotherapy," *Molecular Therapy—Nucleic Acids*, 2(e105): pp. 1-11 (2013).
Haso et al., "Anti-CD22-chimeric antigen receptors targeting B cell precursor acute lymphoblastic leukemia," *Blood*, 121(7): 1165-1174, Feb. 14, 2013, prepublished online Dec. 14, 2012.
Hegde et al., "Combinational Targeting Offsets Antigen Escape and Enhances Effector Functions of Adoptively Transferred T Cells in Glioblastoma," *Molecular Therapy*, 21(11): 2087-2101 (Nov. 2013).
International Preliminary Report on Patentability, PCT patent application PCT/US2018/032809, dated Nov. 19, 2019 (11 pages).
International Search Report, PCT patent application PCT/US2018/032809, dated Oct. 2, 2018 (7 pages).
Kochenderfer et al., "Construction and preclinical evaluation of an anti-CD19 chimeric antigen receptor," *J. Immunother.*, 32(7): 689-702 (2009) Author Manuscript published in PubMed.
Lee et al., "T cells expressing CD19 chimeric antigen receptors for acute lymphoblastic leukaemia in children and young adults: a phase 1 dose-escalation trial," *Lancet*, pp. 1-12, S0140-6736 (14) 61403-3, published online Oct. 13, 2014 (12 pages).
Long et al., "Lessons learned from a highly-active CD22-specific chimeric antigen receptor," *Oncoimmunology*, 2(4): e23621-3 (Apr. 2013) (3 pages).
Maude et al., "Chimeric Antigen Receptor T Cells for Sustained Remissions in Leukemia," *The New England Journal of Medicine*, 371(16): 1507-17 (Oct. 16, 2014).
Nicholson et al., "Construction and characterisation of a functional CD19 specific single chain Fv fragment for immunotherapy of B lineage leukaemia and lymphoma," *Mol Immunol.*, 34(16-17): 1157-1165 (1997).
Qin et al., "Novel CD19/CD22 Bicistronic Chimeric Antigen Receptors Outperform Single or Bivalent Cars in Eradicating CD19+ CD22+, CD19- and CD22- Pre-B Leukemia," American Society of Hematology abstract 810 for oral presentation of Dec. 11, 2017; *Blood*, 130: 180, published Dec. 7, 2017 (1 page).
Qin et al., "Preclinical Development of Bispecific Chimeric Antigen Receptor Targeting Both CD19 and CD22", American Society of Hematology abstract 4427 for poster presentation of Dec. 7, 2015; *Blood*, 126: 4427, published Dec. 3, 2015 (1 page).
Qin et al., "Preclinical Development of Bivalent Chimeric Antigen Receptors Targeting Both CD19 and CD22," *Molecular Therapy: Oncolytics*, 11: 127-137 (Dec. 2018), includes supplementary material (total of 19 pages).
Qin, "Novel CD19/CD22 Multispecific Chimeric Antigen Receptor T cells for Treatment of Pre-B Leukemia," American Society of Hematology oral presentation, Dec. 11, 2017 (20 pages).
Qin, "Preclinical Development of Bispecific Chimeric Antigen Receptor Targeting Both CD19 and CD22," American Society of Hematology poster presentation, Dec. 7, 2015 (1 page).
Szymczak et al., "Correction of multi-gene deficiency in vivo using a single 'self-cleaving' 2A peptide-based retroviral vector," Nat. Biotechnol., 22(5): 589-594 (2004) and corrigendum (1 additional page).
Tedder et al., "Isolation of cDNAs encoding the CD19 antigen of human and mouse B lymphocytes. A new member of the immunoglobulin superfamily," *J. Immunol*, 143(2): 712-717 (Jul. 15, 1989).
Vaickus et al., "Immune markers in hematologic malignancies," *Crit Rev Oncol Hematol*, 11(4): 267-97, Dec. 1991.
Written Opinion of the International Searching Authority (European Patent Office), PCT patent application PCT/US2018/032809, dated Jun. 17, 2016 (7 pages).
Wu, "Diabodies: Molecular Engineering and Therapeutic Applications," *Drug News Perspect* 22(8): 453-458 (Oct. 2009).
Zhao et al., "Primary Human Lymphocytes Transduced with NY-ESO-1 Antigen-Specific TCR Genes Recognize and Kill Diverse Human Tumor Cell Lines," *J. Immunol.* 174: 4415-4423, 2005.
U.S. Appl. No. 15/559,485, filed Sep. 19, 2017, Pending.
U.S. Appl. No. 15/315,533, filed Dec. 1, 2016, Patented.
U.S. Appl. No. 16/360,281, filed Mar. 21, 2019, Pending.
U.S. Appl. No. 14/437,889, filed Apr. 23, 2015, Patented.
U.S. Appl. No. 16/107,271, filed Aug. 21, 2018, Pending.
U.S. Appl. No. 16/869,792, filed May 8, 2020, Pending.
U.S. Appl. No. 14/352,530, filed Apr. 17, 2014, Patented.

* cited by examiner

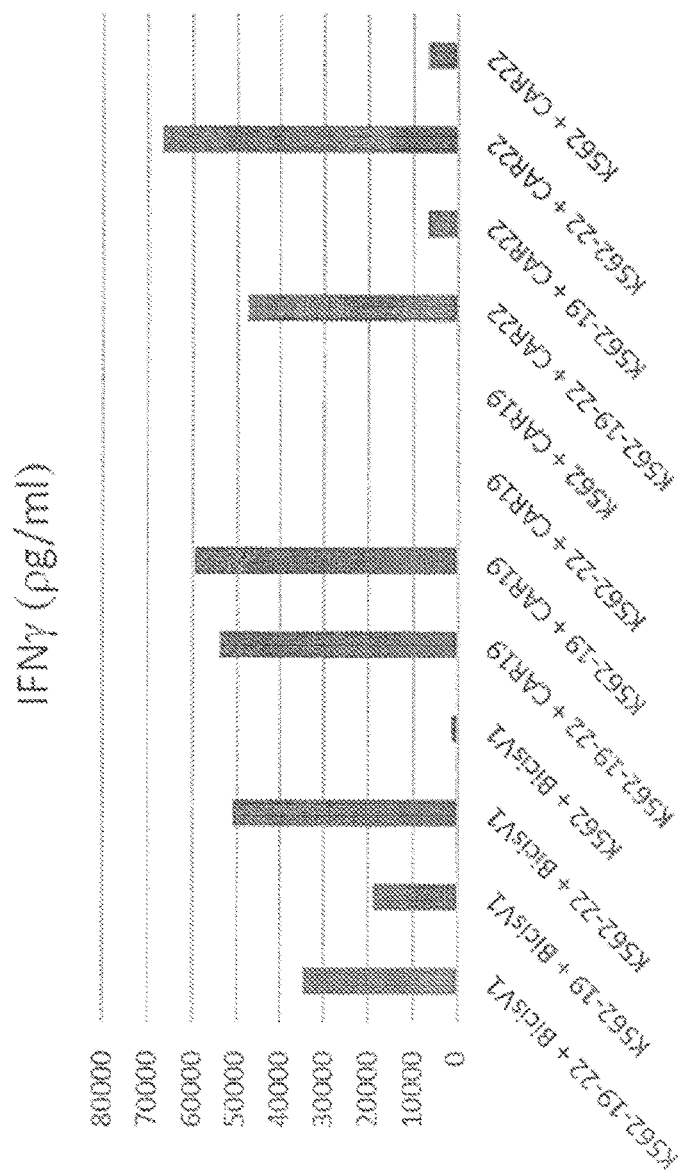

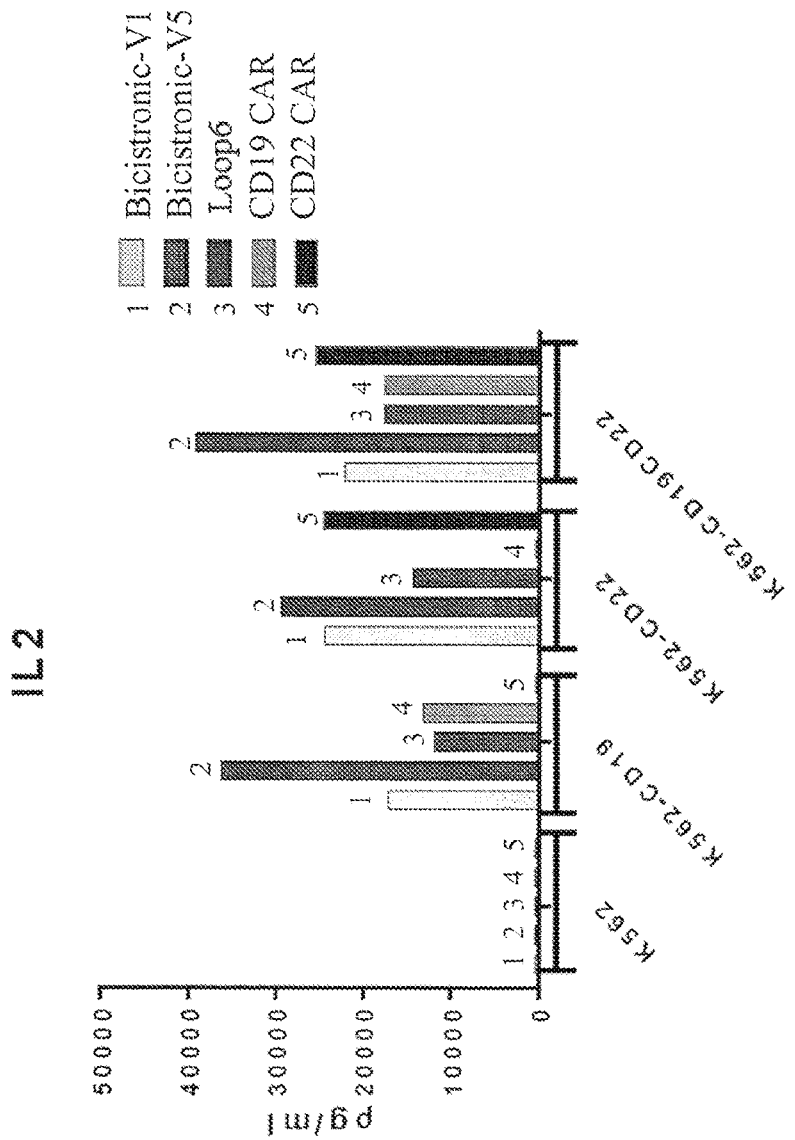

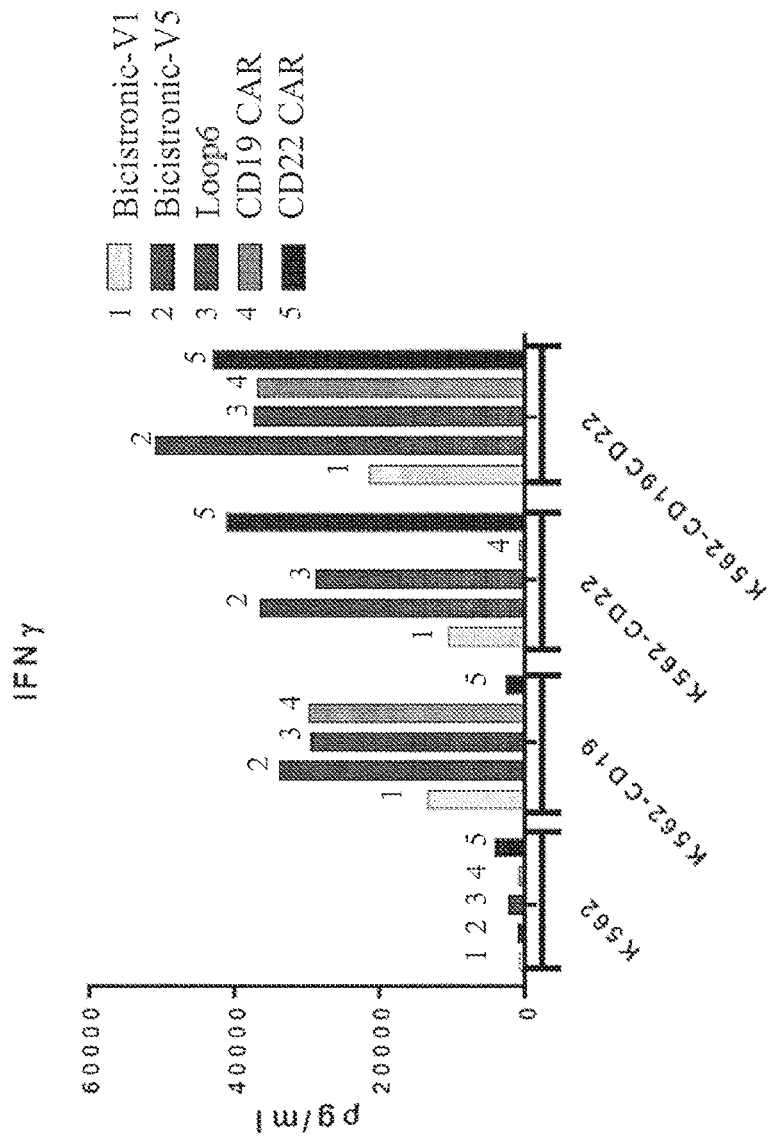

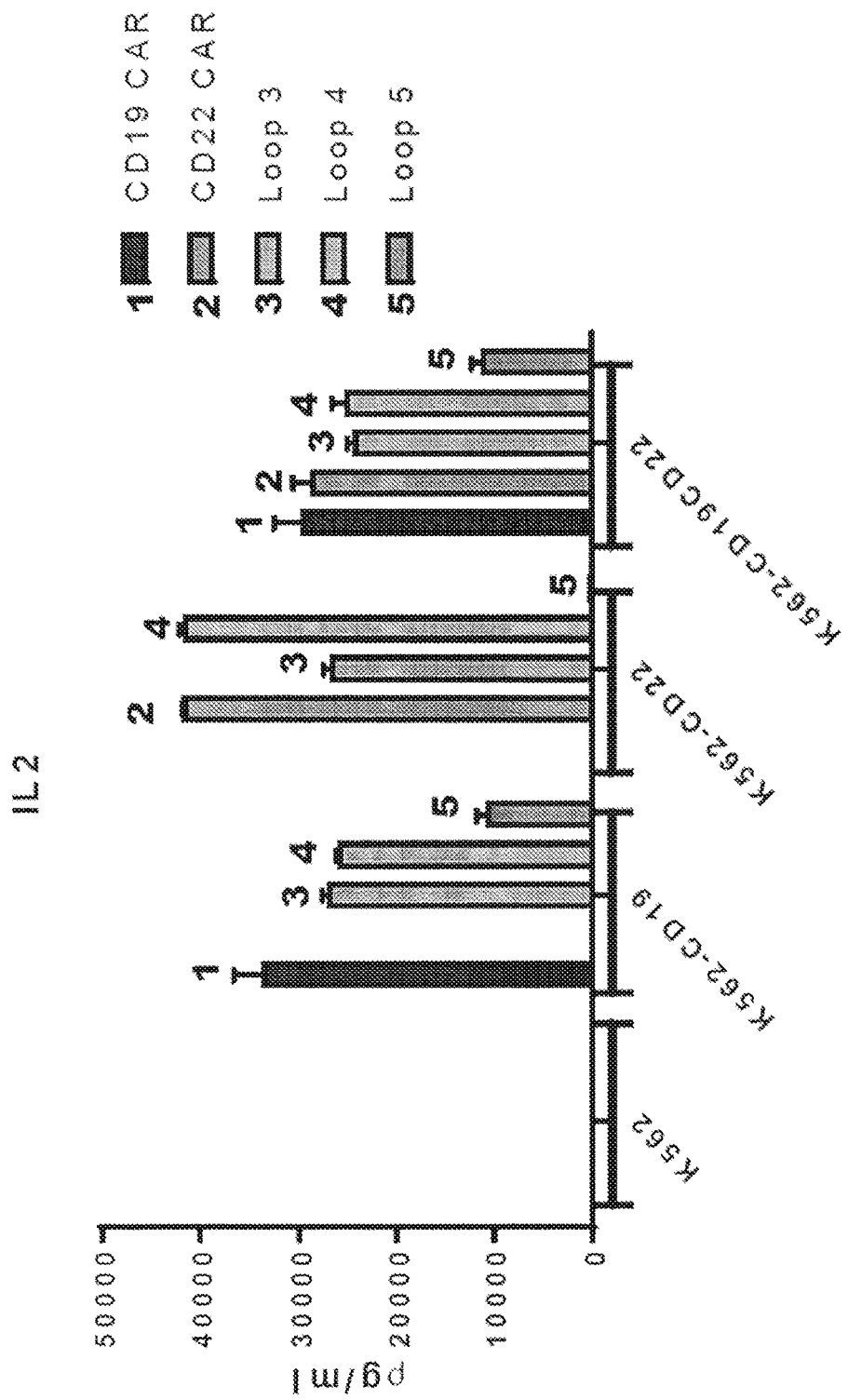

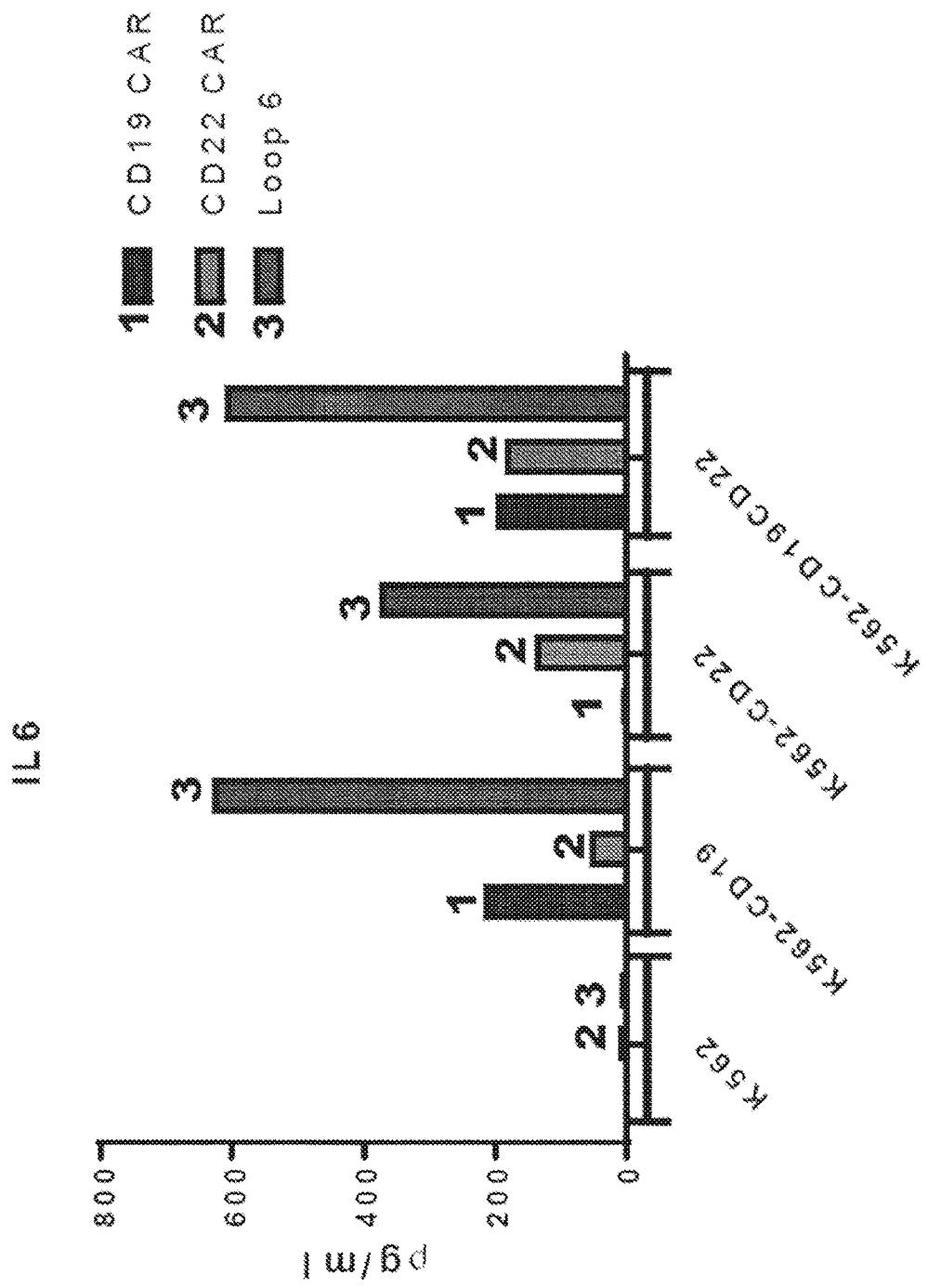

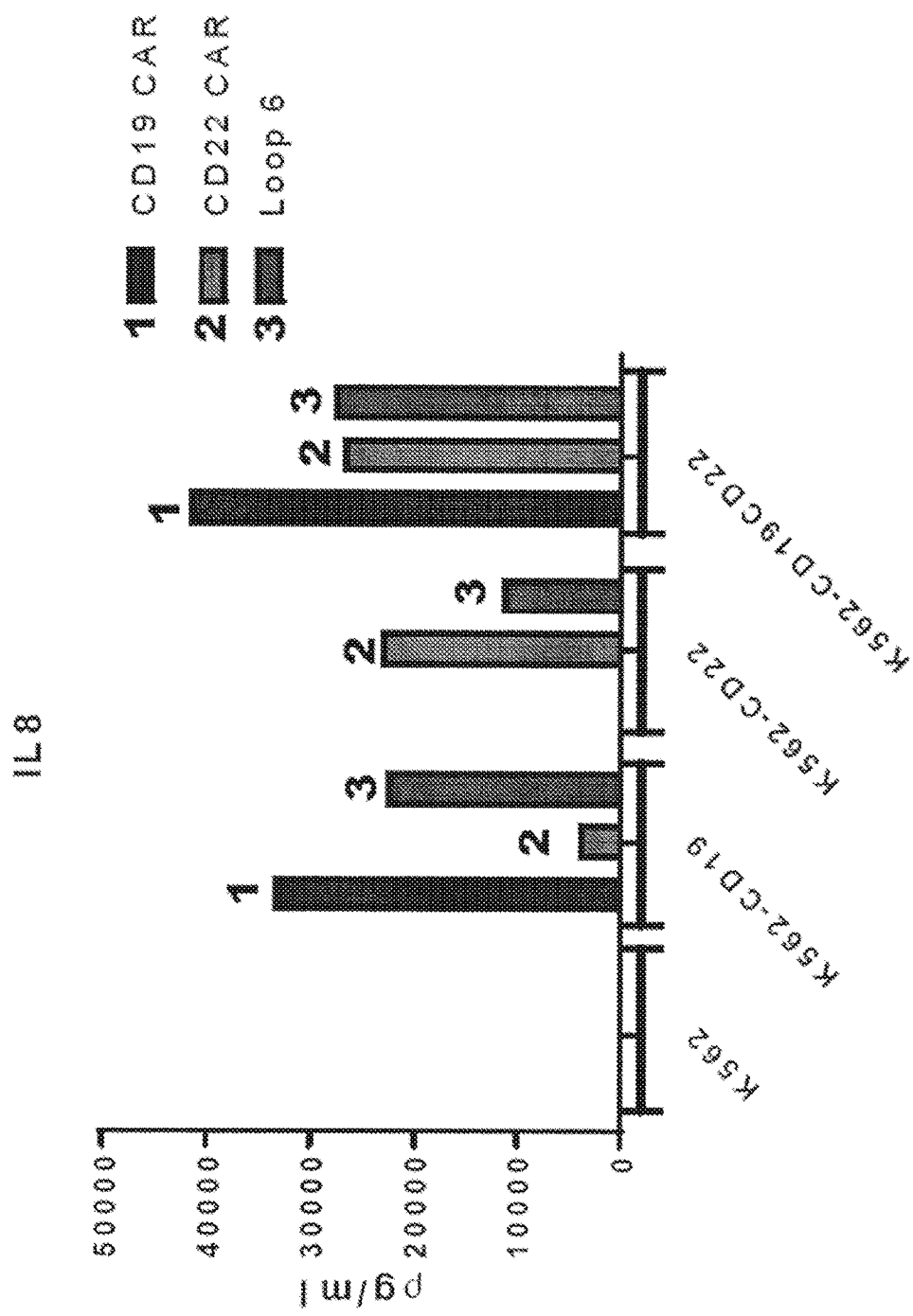

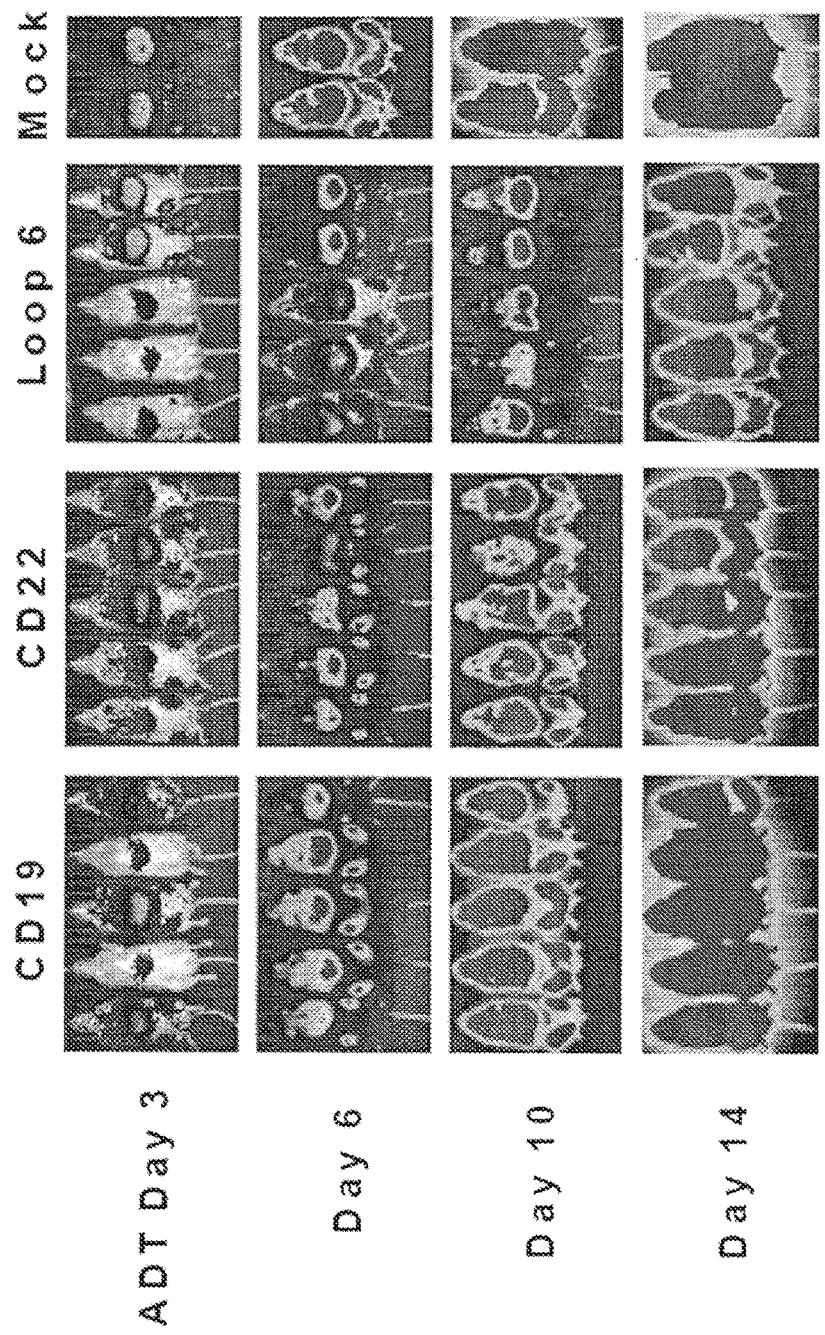

Figure 33B

D0: 1E6 HMB28, CD19 Neg, CD22 CAR Failure;
D7: IV 8E6 CAR

Figure 37A
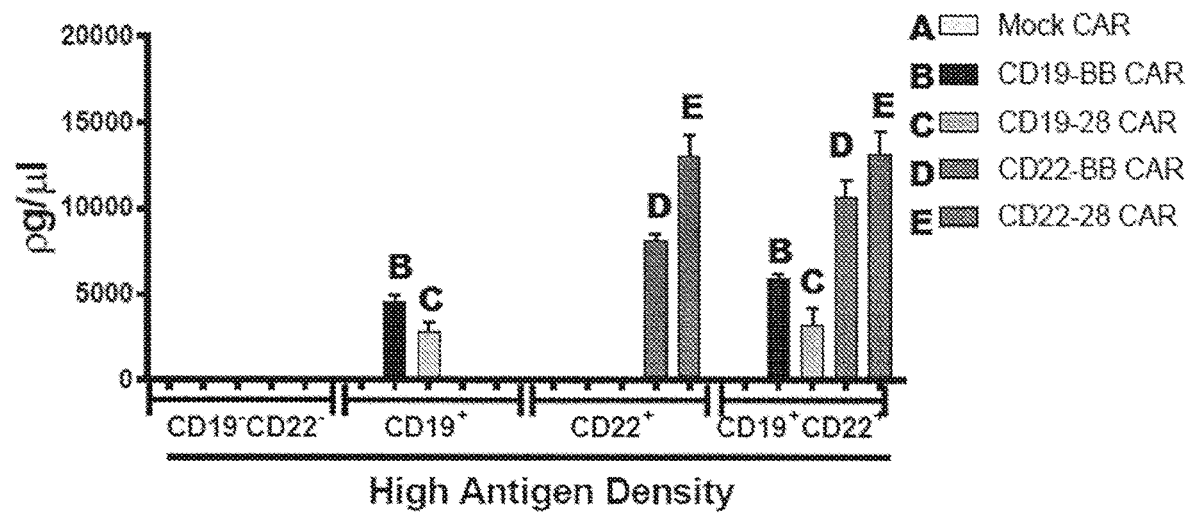
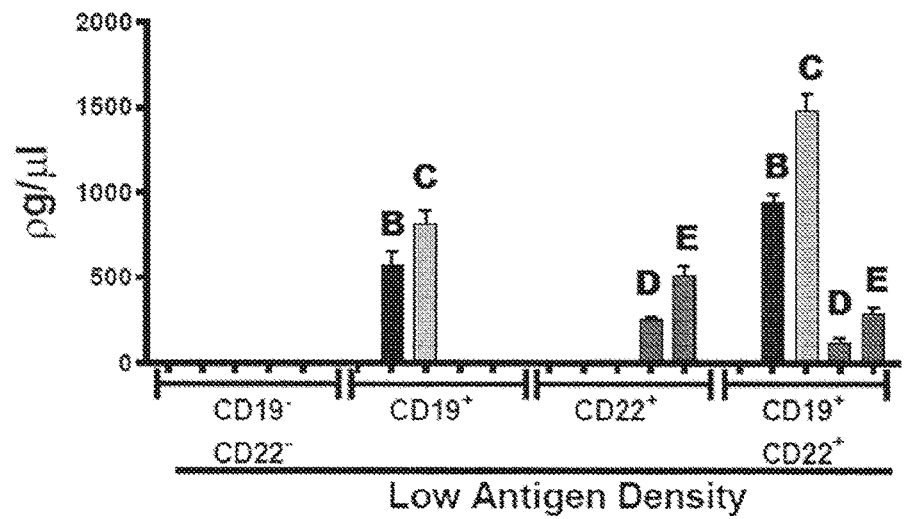

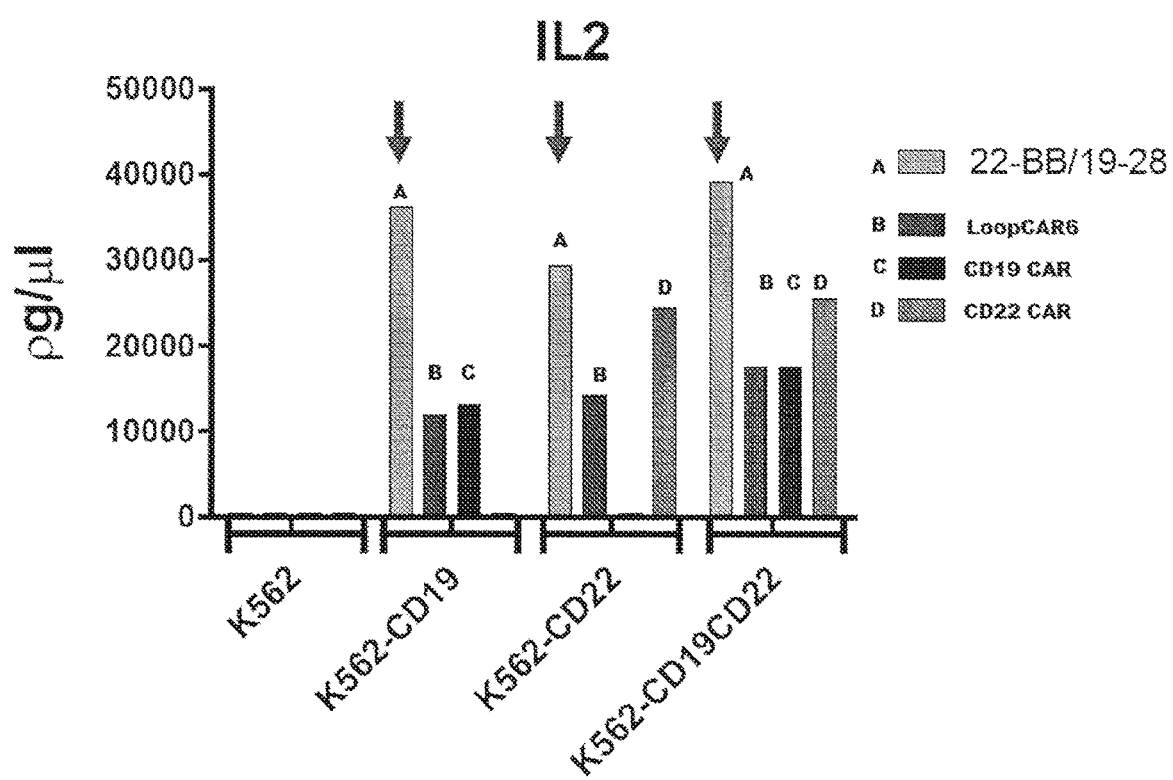

BICISTRONIC CHIMERIC ANTIGEN RECEPTORS AND THEIR USES

CROSS-REFERENCE TO RELATED APPLICATIONS

This patent application is a U.S. national phase of International Patent Application No. PCT/US2018/032809, filed May 15, 2018, which claims the benefit of U.S. Provisional Patent Application No. 62/506,268, filed May 15, 2017, each of which is incorporated by reference herein in its entirety.

STATEMENT REGARDING FEDERALLY SPONSORED RESEARCH AND DEVELOPMENT

This invention was made with Government support under project number Z01 BC011565 by the National Institutes of Health, National Cancer Institute. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: one 182,104 Byte ASCII (Text) file named "746138-2 ST25.txt" dated Sep. 7, 2023.

BACKGROUND OF THE INVENTION

Cancer is a public health concern. Despite advances in treatments such as chemotherapy, the prognosis for many cancers, including hematological malignancies, may be poor. Accordingly, there exists an unmet need for additional treatments for cancer, particularly hematological malignancies.

BRIEF SUMMARY OF THE INVENTION

An embodiment of the invention provides a chimeric antigen receptor (CAR) amino acid construct comprising (a) a cleavable domain; (b) a first CAR comprising a first antigen binding domain, a first transmembrane domain, and a first intracellular T cell signaling domain; and (c) a second CAR comprising a second antigen binding domain, a second transmembrane domain, and a second intracellular T cell signaling domain; wherein the first and second CARs are linked through the cleavable domain, wherein the first antigen binding domain comprises an antigen binding domain of the m971 antibody, wherein when the first CAR is cleaved from the construct, the first antigen binding domain has antigenic specificity for CD22.

Another embodiment of the invention provides a chimeric antigen receptor (CAR) amino acid construct comprising (a) a cleavable domain; (b) a first CAR comprising a first antigen binding domain, a first transmembrane domain, and a first intracellular T cell signaling domain; and (c) a second CAR comprising a second antigen binding domain, a second transmembrane domain, and a second intracellular T cell signaling domain; wherein the first and second CARs are linked through the cleavable domain, wherein the first antigen binding domain comprises an antigen binding domain of the FMC63 antibody, wherein when the first CAR is cleaved from the construct, the first antigen binding domain has antigenic specificity for CD19.

Another embodiment of the invention provides chimeric antigen receptor (CAR) amino acid construct comprising (a) two or more cleavable domains; (b) a first CAR comprising a first antigen binding domain, a first transmembrane domain, and a first intracellular T cell signaling domain; and (c) a second CAR comprising a second antigen binding domain, a second transmembrane domain, and a second intracellular T cell signaling domain; wherein the first and second CARs are linked through the two or more cleavable domains.

Another embodiment of the invention provides a method of making a chimeric antigen receptor (CAR) amino acid construct, the method comprising designing two or more cleavable domains between (a) a first CAR comprising a first antigen binding domain, a first transmembrane domain, and a first intracellular T cell signaling domain; and (b) a second CAR comprising a second antigen binding domain, a second transmembrane domain, and a second intracellular T cell signaling domain; wherein the first and second CARs are linked through the two or more cleavable domains; and cloning into a plasmid a sequence comprising from N-terminus to C-terminus the first CAR, the two or more cleavable domains, and the second CAR.

Another embodiment of the invention provides CAR amino acid constructs comprising the amino acid sequences as described herein.

Further embodiments of the invention provide related nucleic acids, recombinant expression vectors, host cells, populations of cells, and pharmaceutical compositions relating to the CAR amino acid constructs of the invention.

Additional embodiments of the invention provide methods of detecting the presence of cancer in a mammal and methods of treating or preventing cancer in a mammal.

BRIEF DESCRIPTION OF THE DRAWINGS

FIGS. 5A, 5B, 6A, 6B, 7A, 7B, and 8 are bar graphs showing in vitro activity based on cytokine production, in accordance with embodiments of the invention. FIG. 5A shows IL2 levels, and FIG. 5B shows IFNα levels, measured when K562 cells expressing CD19, CD22, both, or none are contacted with T cells transduced with a vector encoding the V1 CAR construct, the single anti-CD19 CAR (CAR19), or the single anti-CD22 CAR (CAR22), in accordance with embodiments of the invention. FIG. 6A shows IL2 levels, and FIG. 6B shows IFNα levels, measured when K562 cells expressing CD19, CD22, both, or none are contacted with T cells transduced with a vector encoding the V1 CAR construct, the V5 CAR construct, the LoopCAR6, the single anti-CD19 CAR, or the single anti-CD22 CAR, in accordance with embodiments of the invention. FIG. 7A shows IL2 levels, and FIG. 7B shows IFNγ levels, measured when CD19 KO and/or CD22 KO NALM6 cells are contacted with T cells transduced with a vector encoding the V1 CAR construct, the V5 CAR construct, the LoopCAR6, the single anti-CD19 CAR, or the single anti-CD22 CAR, in accordance with embodiments of the invention. FIG. 8 shows CAR T cells were co-incubated with NALM6 tumor cells for 18 hours, and the levels of IL2 production in the culture supernatant were measured by ELISA ("-N": NALM6; "—N-19": NALM6-CD19neg; "—N-19-22": NALM6-CD19neg-CD22neg).

FIGS. 25A-25C present bar graphs showing cytokine production of various CARs with K562, K562-CD19, K562-CD22, and K562-CD19CD22 target cell lines, in accordance with embodiments of the invention.

FIGS. 29A-29F are bar graphs showing LoopCAR6 produces a variety of cytokines when co-Incubated with target antigens. FIG. 29A: Interferon gamma; FIG. 29B: IL6; FIG. 29C: TNF alpha; FIG. 29D: IL8; FIG. 29E: IL13; FIG. 29F: IL2.

FIG. 33A presents images. NSG mice were challenged with a mixture of 5E5 NALM6-CD19neg and 5E5 NALM6-CD22neg luciferase-expressing leukemia on day 0. On day 3, mice were treated with 3E6 CAR expressing T cells. Bioluminescent intensity, as shown by increased levels of shading, represents tumor burden.

FIG. 33B presents images. NSG mice were challenged with 1E6 luciferase-expressing leukemia cells as indicated on the figure on day 0. Leukemia in several of these groups were spiked in with 1% of NALM6-CD19neg or NALM6-CD22neg cells. On day 3, mice were treated with 6E6 of CAR expressing T cells. Bioluminescent intensity, as shown by increased levels of shading, represents tumor burden.

FIGS. 37A-37G: For cytokine production, CAR T cells (1E5) were washed 3 times with 1×PBS and co-incubated with an equal number of target cells in 200 ml RPMI media in a 96-well plate in a 37° C. incubator for 15 to 20 hours. For high antigen target cells, K562 expression CD19 or CD22 or both CD19 and CD22 were used, and K562 cells served as the negative control. For low target antigen line, NALM6 and the NALM6-CD19$^{neg}$ and NALM6-CD22$^{neg}$ were used, and the NALM6-CD19$^{neg}$ CD22$^{neg}$ was used as the negative control. All tests were in triplicates. The cytokine levels of the IL2 in the culture supernatant were detected with R&D's ELISA kit. FIG. 37A: Cytokine production of CD19 and CD22 CAR with different con-stimulation domains and at different antigen density level. FIG. 37B: Cytokine production of bicistronic CARs with different con-stimulation domains and at different antigen density level. FIG. 37C: Comparison of the cytokine production of bicistronic CAR with that of the bivalent CAR. FIG. 37D-37F: For incucyte killing assay, an equal amount of CAR T cells were co-incubated with 5E4 of target tumor cells. The plate was scanned for the GFP fluorescent expression to monitor the cells every 30 minutes for 40 hours. The percentage of cell killing at each time point was baseline-corrected. FIG. 37G: Incucyte killing assay with NALM6CD19negCD22neg cell.

FIG. 39A: NSG mice were challenged with 1E6 of luciferase-expressing NALM6 leukemia on day 0. On day 3, mice were IV injected with 5E6 of CAR expressing T cells. Bioluminescent intensity represents tumor burden. FIG. 39B: NSG mice were challenged with 1E5 of luciferase-expressing NALM6, NALM6-CD19neg, and NALM6-CD22neg leukemia cells on day 0. On day 3, mice were IV injected with 3E6 of CAR Expressing T cells.

DETAILED DESCRIPTION OF THE INVENTION

Figure 1:
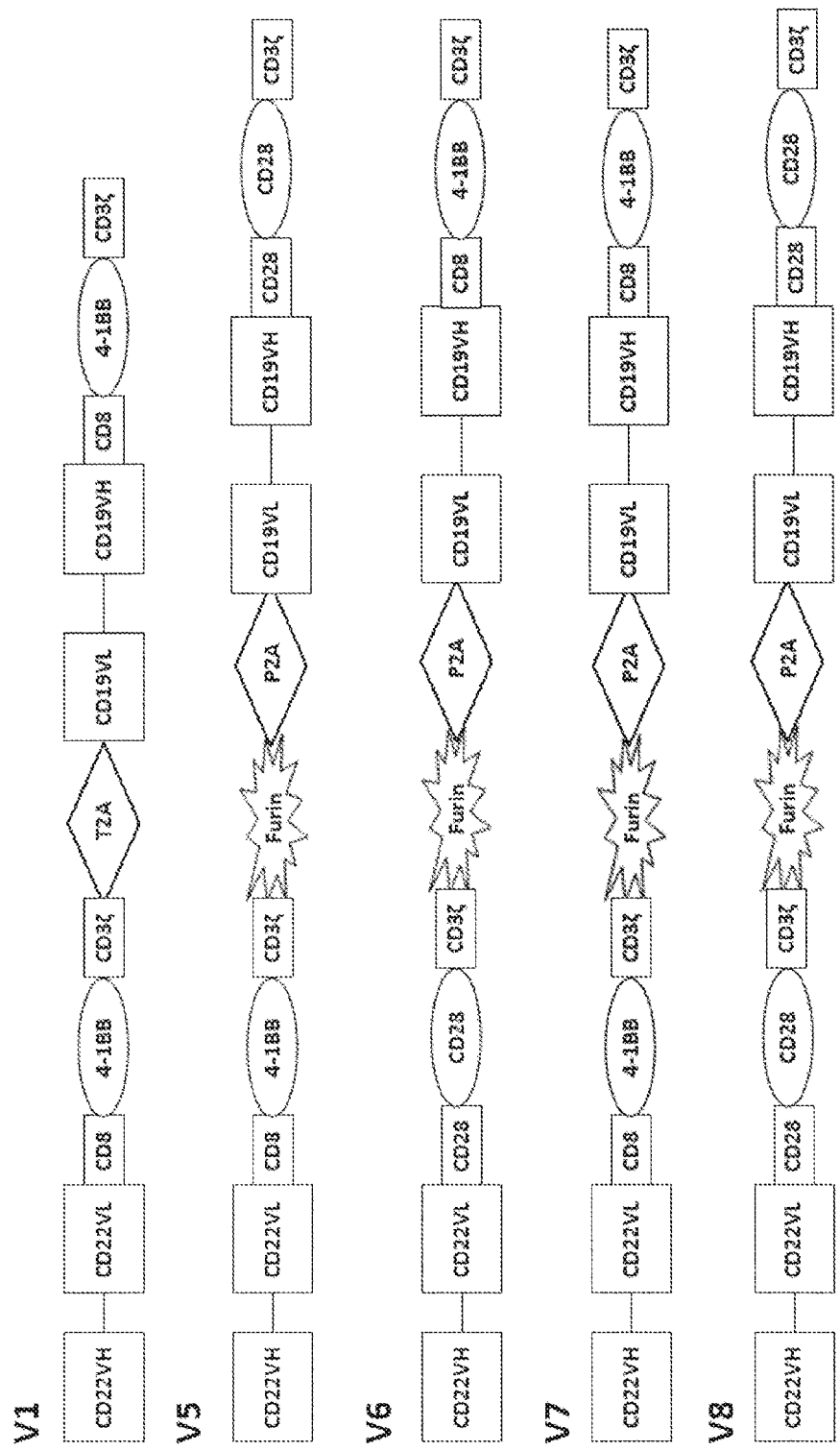
FIG. 1 presents schematic diagrams of exemplary CAR constructs, in accordance with embodiments of the invention.

An embodiment of the invention provides a chimeric antigen receptor (CAR) amino acid construct comprising (a) a cleavable domain; (b) a first CAR comprising a first antigen binding domain, a first transmembrane domain, and a first intracellular T cell signaling domain; and (c) a second CAR comprising a second antigen binding domain, a second transmembrane domain, and a second intracellular T cell signaling domain; wherein the first and second CARs are linked through the cleavable domain, wherein the first antigen binding domain comprises an antigen binding domain of the m971 antibody, wherein when the first CAR is cleaved from the construct, the first antigen binding domain has antigenic specificity for CD22.

A CAR is an artificially constructed hybrid protein or polypeptide containing the antigen binding domain of one or more antibodies (e.g., single chain variable fragment (scFv)) linked to T-cell signaling domains. Characteristics of CARs include their ability to redirect T-cell specificity and reactivity toward a selected target in a non-MHC-restricted manner, exploiting the antigen-binding properties of monoclonal antibodies. The non-MHC-restricted antigen recognition gives T cells expressing CARs the ability to recognize antigen independent of antigen processing, thus bypassing a major mechanism of tumor escape. Moreover, when expressed in T-cells, CARs advantageously do not dimerize with endogenous T cell receptor (TCR) alpha and beta chains. The phrases "antigen(ic) specificity" and "elicit antigen-specific response," as used herein, means that the CAR can specifically bind to and immunologically recognize antigen, such that binding of the CAR to the antigen elicits an immune response.

CD22 is a lineage-restricted B cell antigen belonging to the immunoglobulin (Ig) superfamily. CD22 is expressed in 60-70% of B cell lymphomas and leukemias (e.g., B-chronic lymphocytic leukemia, hairy cell leukemia, acute lymphocytic leukemia (ALL), and Burkitt's lymphoma) and is not present on the cell surface in early stages of B cell development or on stem cells (Vaickus et al., *Crit. Rev. Oncol./Hematol.*, 11:267-297 (1991); Bang et al., *Clin. Cancer Res.*, 11: 1545-50 (2005)). CD19 (also known as B-lymphocyte antigen CD19, B4, and CVID3) is a cell surface molecule expressed only by B lymphocytes and follicular dendritic cells of the hematopoietic system. It is the earliest of the B-lineage-restricted antigens to be expressed and is present on most pre-B-cells and most non-T-cell acute lymphocytic leukemia cells and B-cell type chronic lymphocytic leukemia cells (Tedder and Isaacs, *J. Immun.*, 143: 712-717 (1989)).

In embodiments of the invention, the invention provides multiple CARs (e.g., two, three, four, five, or more) that each bind to a single antigen, wherein each CAR is separated by a cleavable domain. In an embodiment of the invention, cleaving the cleavable domain releases each CAR, e.g., a first and second CAR, from the CAR construct such that each cleaved CAR is separately present on the T cell surface, each has antigenic specificity for its respective target, and each can elicit an antigen-specific response. In an embodiment, such a CAR construct can have two CARs cleaved/released, e.g., a bicistronic CAR. Without wishing to be bound by theory or mechanism, the cleavable domains of these CARs may be cleaved after full translation of the full sequence or after translation of each CAR and cleavable domain, such that a CAR is cleaved/released prior to translation of the next CAR in the sequence. Examples of such CARs herein include V1, V5, V6, V7, and V8.

In embodiments of the invention, the invention provides CARs, where each CAR can bind to two antigens (e.g., CD19 and CD22) simultaneously. These CARs have dual specificity for CD22 and CD19. The phrases "dual specificity," "dual specific," "bispecific," and "bivalent" as used herein with respect to a CAR, mean that the same CAR can specifically bind to and immunologically recognize two different antigens, such that binding of the CAR to at least one of the two antigens elicits an immune response. Examples of such CARs herein include TanCARs 2-4 and LoopCARs 1-5. In another embodiment, dual specific CARs may be linked by cleavable domains.

An embodiment of the invention provides a CAR comprising an anti-CD22 antigen binding domain of the m971 antibody ("m971"). The antigen binding domain of m971 specifically binds to CD22. In this regard, a preferred embodiment of the invention provides CARs comprising an anti-CD22 antigen-binding domain comprising, consisting of, or consisting essentially of, a single chain variable fragment (scFv) of the antigen binding domain of m971. The HA22 immunotoxin and the m971 antibody bind to different CD22 epitopes.

The anti-CD22 antigen binding domain may comprise a light chain variable region and/or a heavy chain variable region. In an embodiment of the invention, the heavy chain variable region comprises a CDR1 region, a CDR2 region, and a CDR3 region. In this regard, the anti-CD22 antigen binding domain may comprise one or more of a heavy chain CDR1 region comprising the amino acid sequence of SEQ ID NO: 4; a heavy chain CDR2 region comprising the amino acid sequence of SEQ ID NO: 6; and a heavy chain CDR3 region comprising the amino acid sequence of SEQ ID NO: 8. Preferably, the heavy chain of the anti-CD22 antigen binding domain comprises the amino acid sequences of all of SEQ ID NOs: 4, 6, and 8.

In an embodiment of the invention, the light chain variable region of the anti-CD22 antigen binding domain may comprise a light chain CDR1 region, a light chain CDR2 region, and a light chain CDR3 region. In this regard, the anti-CD22 antigen binding domain may comprise one or more of a light chain CDR1 region comprising the amino acid sequence of SEQ ID NO: 12; a light chain CDR2 region comprising the amino acid sequence of SEQ ID NO: 14; and a light chain CDR3 region comprising the amino acid sequence of SEQ ID NO: 16. Preferably, the light chain of the anti-CD22 antigen binding domain comprises the amino acid sequences of all of SEQ ID NOs: 12, 14, and 16. In an especially preferred embodiment, the anti-CD22 antigen binding domain comprises the amino acid sequences of all of SEQ ID NO: 4, 6, 8, 12, 14, and 16.

The heavy chain variable region of the anti-CD22 antigen binding domain may comprise, consist of, or consist essentially of the amino acid sequence of SEQ ID NO: 3-9. The light chain variable region of the anti-CD22 antigen binding domain may comprise, consist of, or consist essentially of the amino acid sequence of SEQ ID NO: 11-17. Accordingly, in an embodiment of the invention, the anti-CD22 antigen binding domain comprises a heavy chain variable region comprising the amino acid sequence of SEQ ID NO: 3-9 and/or a light chain variable region comprising the amino acid sequence of SEQ ID NO: 11-17. Preferably, the anti-CD22 antigen binding domain comprises the amino acid sequence of SEQ ID NOs: 3-9 and 11-17.

In embodiments of the invention, when the second CAR is cleaved from the construct, the second antigen binding domain has antigenic specificity for CD19.

In embodiments of the invention, the second antigen binding domain comprises an antigen binding domain of the FMC63 antibody. In embodiments of the invention, the second antigen binding domain comprises a heavy chain variable region comprising the amino acid sequence of FMC63 as described below and a light chain variable region comprising the amino acid sequence of FMC63 as described below. In embodiments of the invention, the second antigen binding domain comprises the amino acid sequence of FMC63 as described below.

Another embodiment of the invention provides a chimeric antigen receptor (CAR) amino acid construct comprising (a) a cleavable domain; (b) a first CAR comprising a first antigen binding domain, a first transmembrane domain, and a first intracellular T cell signaling domain; and (c) a second CAR comprising a second antigen binding domain, a second transmembrane domain, and a second intracellular T cell signaling domain; wherein the first and second CARs are linked through the cleavable domain, wherein the first antigen binding domain comprises an antigen binding domain of the FMC63 antibody, wherein when the first CAR is cleaved from the construct, the first antigen binding domain has antigenic specificity for CD19. In embodiments, when the second CAR is cleaved from the construct, the second antigen binding domain has antigenic specificity for CD22.

An embodiment of the invention provides a CAR comprising an anti-CD19 antigen binding domain of the FMC63 antibody ("FMC63"). The antigen binding domain of FMC63 specifically binds to CD19. In this regard, a preferred embodiment of the invention provides CARs comprising an anti-CD19 antigen-binding domain comprising, consisting of, or consisting essentially of, a single chain variable fragment (scFv) of the antigen binding domain of FMC63.

The anti-CD19 antigen binding domain may comprise a light chain variable region and/or a heavy chain variable region.

In an embodiment of the invention, the light chain variable region of the anti-CD19 antigen binding domain may comprise a light chain CDR1 region, a light chain CDR2 region, and a light chain CDR3 region. In this regard, the anti-CD19 antigen binding domain may comprise one or more of a light chain CDR1 region comprising the amino acid sequence of SEQ ID NO: 24; a light chain CDR2 region comprising the amino acid sequence of SEQ ID NO: 26; and a light chain CDR3 region comprising the amino acid sequence of SEQ ID NO: 28. Preferably, the light chain of the anti-CD19 antigen binding domain comprises the amino acid sequences of all of SEQ ID NOs: 24, 26, and 28.

In an embodiment of the invention, the heavy chain variable region of the anti-CD19 antigen binding domain comprises a CDR1 region, a CDR2 region, and a CDR3 region. In this regard, the anti-CD19 antigen binding domain may comprise one or more of a heavy chain CDR1 region comprising the amino acid sequence of SEQ ID NO: 32; a heavy chain CDR2 region comprising the amino acid sequence of SEQ ID NO: 34; and a heavy chain CDR3 region comprising the amino acid sequence of SEQ ID NO: 36. Preferably, the heavy chain of the anti-CD19 antigen binding domain comprises the amino acid sequences of all of SEQ ID NOs: 32, 34, and 36. In an especially preferred embodiment, the anti-CD19 antigen binding domain comprises the amino acid sequences of all of SEQ ID NO: 24, 26, 28, 32, 34, and 36.

The heavy chain variable region of the anti-CD19 antigen binding domain may comprise, consist of, or consist essentially of the amino acid sequence of SEQ ID NO: 31-37. The light chain variable region of the anti-CD19 antigen binding domain may comprise, consist of, or consist essentially of the amino acid sequence of SEQ ID NO: 23-29. Accordingly, in an embodiment of the invention, the anti-CD19 antigen binding domain comprises a heavy chain variable region comprising the amino acid sequence of SEQ ID NO: 31-37 and/or a light chain variable region comprising the amino acid sequence of SEQ ID NO: 23-29. Preferably, the anti-CD19 antigen binding domain comprises the amino acid sequences of both SEQ ID NOs: 23-29 and 31-37.

The anti-CD22 antigen binding domain and the anti-CD19 antigen binding domain may comprise any antigen binding portion of the anti-CD22 or anti-CD19 antibody, respectively. The antigen binding portion can be any portion that has at least one antigen binding site, such as Fab, F(ab')2, dsFv, scFv, diabodies, and triabodies. Preferably, the antigen binding portion is a single-chain variable region fragment (scFv) antibody fragment. An scFv is a truncated Fab fragment including the variable (V) domain of an antibody heavy chain linked to a V domain of a light antibody chain via a synthetic peptide linker, which can be generated using routine recombinant DNA technology techniques. Similarly, disulfide-stabilized variable region fragments (dsFv) can be prepared by recombinant DNA technology.

In an embodiment of the invention, the light chain variable region and the heavy chain variable region of the anti-CD22 antigen binding domain can be joined to each other by a linker. The linker may comprise any suitable amino acid sequence. In an embodiment of the invention, the linker is a Gly/Ser linker from about 1 to about 100, from about 3 to about 20, from about 5 to about 30, from about 5 to about 18, or from about 3 to about 8 amino acids in length and consists of glycine and/or serine residues in sequence. Accordingly, the Gly/Ser linker may consist of glycine and/or serine residues. Preferably, the Gly/Ser linker comprises the amino acid sequence of GGGGS (SEQ ID NO: 10), and multiple SEQ ID NOs: 10 may be present within the linker. In another embodiment of the invention, the linker comprises the amino acid sequence of SEQ ID NO: 30. Any linker sequence may be used as a spacer between the antigen binding domain and the transmembrane domain.

In an embodiment of the invention, the light chain variable region and the heavy chain variable region of the anti-CD19 antigen binding domain can be joined to each other by a linker. The linker may be any of the linkers described herein with respect to other aspects of the invention. In an embodiment of the invention, the light chain variable region and the heavy chain variable region of the anti-CD19 antigen binding domain are joined to each other by a linker comprising the amino acid sequence of SEQ ID NO: 10 or 30.

In an embodiment, the anti-CD22 antigen binding domain comprises a light chain variable region, a heavy chain variable region, and a linker. In this regard, an embodiment of the anti-CD22 antigen binding domain comprising a light chain variable region, a heavy chain variable region, and the linker comprises, consists of, or consists essentially of, all of SEQ ID NOs: 3-17.

In an embodiment, the anti-CD19 antigen binding domain comprises a light chain variable region, a heavy chain variable region, and a linker. In this regard, an embodiment of the anti-CD19 antigen binding domain comprising a light chain variable region, a heavy chain variable region, and the linker comprises, consists of, or consists essentially of, all of SEQ ID NOs: 23-37.

The first CAR and the second CAR of the inventive CAR constructs are joined to each other through 1, 2, 3, 4 or more cleavable domains. The cleavable domain(s) may comprise one or more of any suitable cleavable domain, including domains recognized by cleavage enzymes or domains that are self-cleaving. Suitable domains include, for example, the 2A domain, such as T2A and/or P2A, and furin cleavage sequences. Table 1 presents exemplary suitable cleavable domains.

TABLE 1

| Peptide | Amino acid sequence* |
|---------|----------------------|
| T2A: | (GSG)EGRGSLLTCGDVEENPGP (SEQ ID NO: 43) |
| P2A: | (GSG)ATNFSLLKQAGDVEENPGP (SEQ ID NO: 44) |
| E2A: | (GSG)QCTNYALLKLAGDVESNPGP (SEQ ID NO: 45) |
| F2A: | (GSG)VKQTLNFDLLKLAGDVESNPGP (SEQ ID NO: 46) |
| Furin: | RKRR (SEQ ID NO: 47) |

*The GSG residues may be added to improve cleavage efficiency.

In an embodiment of the invention, the CAR construct contains more than one cleavable domain, wherein the cleavable domains are all the same. In an embodiment of the invention, the CAR construct contains more than one cleavable domain adjacent within the CAR construct, wherein at least one cleavable domain is different.

In an embodiment, the antigen binding domain comprises a leader sequence. In an embodiment of the invention, the leader sequence may be positioned at the amino terminus of the anti-CD19 CAR within the CAR construct. In another embodiment of the invention, the leader sequence may be positioned at the amino terminus of the anti-CD22 CAR within the CAR construct. The leader sequence may comprise any suitable leader sequence. In an embodiment, the leader sequence comprises, consists of, or consists essentially of the amino acid sequence of SEQ ID NO: 2 or SEQ ID NO: 62. In an embodiment of the invention, while the leader sequence may facilitate expression of the released/cleaved CARs on the surface of the cell, the presence of the leader sequence in an expressed CAR is not necessary in order for the CAR to function. In an embodiment of the invention, upon expression of the CAR on the cell surface, the leader sequence may be cleaved off released CARs. Accordingly, in an embodiment of the invention, the released CARs lack a leader sequence. In an embodiment of the invention, the CARs within the CAR construct lack a leader sequence.

In an embodiment of the invention, the CAR construct comprises a hinge domain. In an embodiment of the invention, the hinge domain is a CD8 hinge domain. In a preferred embodiment, the CD8 hinge domain is human. Preferably, the CD8 hinge domain comprises, consists of, or consists essentially of SEQ ID NO: 18. In an embodiment of the invention, the hinge domain is a CD28 hinge domain. In a preferred embodiment, the CD28 hinge domain is human. Preferably, the CD28 hinge domain comprises, consists of, or consists essentially of SEQ ID NO: 40.

In an embodiment of the invention, the CAR construct comprises a transmembrane (TM) domain. In an embodiment of the invention, the TM domain is a CD8 TM domain. In a preferred embodiment, the CD8 TM domain is human. Preferably, the CD8 TM domain comprises, consists of, or consists essentially of SEQ ID NO: 19. In an embodiment of the invention, the TM domain is a CD28 TM domain. In a preferred embodiment, the CD28 TM domain is human. Preferably, the CD28 TM domain comprises, consists of, or consists essentially of SEQ ID NO: 41.

In an embodiment of the invention, the CAR construct comprises an intracellular T cell signaling domain. In an embodiment of the invention, the intracellular T cell signaling domain comprises a 4-1BB intracellular T cell signaling sequence. 4-1BB, also known as CD137, transmits a potent costimulatory signal to T cells, promoting differentiation and enhancing long-term survival of T lymphocytes. Preferably, the 4-1BB intracellular T cell signaling sequence is human. In a preferred embodiment, the 4-1BB intracellular T cell signaling sequence comprises, consists of, or consists essentially of the amino acid sequence of SEQ ID NO: 20.

In an embodiment of the invention, the intracellular T cell signaling domain comprises a CD3 zeta (t) intracellular T cell signaling sequence. CD3 associates with TCRs to produce a signal and contains immunoreceptor tyrosine-based activation motifs (ITAMs). Preferably, the CD3(intracellular T cell signaling sequence is human. In a preferred embodiment, the CD3(intracellular T cell signaling sequence comprises, consists of, or consists essentially of the amino acid sequence of SEQ ID NO: 21.

In an embodiment of the invention, the intracellular T cell signaling domain comprises a CD28 intracellular T cell signaling sequence. Preferably, the CD28 intracellular T cell signaling sequence is human. In a preferred embodiment, the CD28 intracellular T cell signaling sequence comprises, consists of, or consists essentially of the amino acid sequence of SEQ ID NO: 42.

The first and second CARs may be positioned in the CAR construct in any suitable orientation. In an embodiment of the invention, the CAR construct comprises from the N- to C-terminus: the anti-CD19 CAR, one or more cleavable domains, and then the anti-CD22 CAR. In another embodiment of the invention, the CAR construct comprises from the N- to C-terminus: the anti-CD22 CAR, one or more cleavable domains, and then the anti-CD19 CAR.

FIG. 1 presents schematic diagrams of exemplary CAR constructs, in accordance with embodiments of the invention.

Additional embodiments of the invention provide full-length CAR constructs comprising, consisting of, or consisting essentially of, any one of the amino acid sequences set forth in Tables 2-6.

TABLE 2

V1 CAR Construct

| Sequence | SEQ ID NO: | Segment | Notes |
|---|---|---|---|
| M | 1 | | start methionine |
| LLLVTSLLLCELPHPAFLLIP | 2 | | signal peptide |
| QVQLQQSGPGLVKPSQTLSL TCAIS | 3 | Anti-CD22 scFv | heavy chain |
| GDSVSSNSAA | 4 | Anti-CD22 scFv | heavy chain: CDR1 |
| WNWIRQSPSRGLEWLGR | 5 | Anti-CD22 scFv | heavy chain |
| TYYRSKWYN | 6 | Anti-CD22 scFv | heavy chain: CDR2 |
| DYAVSVKSRITINPDTSKNQF SLQLNSVTPEDTAVYYC | 7 | Anti-CD22 scFv | heavy chain |
| AREVTGDLEDAFDI | 8 | Anti-CD22 scFv | heavy chain: CDR3 |
| WGQGTMVTVSS | 9 | Anti-CD22 scFv | heavy chain |
| GGGGS | 10 | Anti-CD22 scFv | linker |
| DIQMTQSPSSLSASVGDRVTI TCRAS | 11 | Anti-CD22 scFv | light chain |
| QTIWSY | 12 | Anti-CD22 scFv | light chain: CDR1 |
| LNWYQQRPGRAPNLLIY | 13 | Anti-CD22 scFv | light chain |

TABLE 2-continued

V1 CAR Construct

| Sequence | SEQ ID NO: | Segment | Notes |
|---|---|---|---|
| AAS | 14 | Anti-CD22 scFv | light chain: CDR2 |
| SLQSGVPSRFSGRGSGTDFTL TISSLQAEDFATYYC | 15 | Anti-CD22 scFv | light chain |
| QQSYSIPQT | 16 | Anti-CD22 scFv | light chain: CDR3 |
| FGQGTKLEIK | 17 | Anti-CD22 scFv | light chain |
| TSTTTPAPRPPTPAPTIASQPL SLRPEACRPAAGGAVHTRGL DFACD | 18 | CD8 | CD8alpha hinge |
| IYIWAPLAGTCGVLLLSLVIT LYC | 19 | CD8 | CD8alpha transmembrane domain |
| KRGRKKLLYIFKQPFMRPVQ TTQEEDGCSCRFPEEEEGGC EL | 20 | 4-1BB | intracellular domain |
| RVKFSRSADAPAYQQGQNQ LYNELNLGRREEYDVLDKR RGRDPEMGGKPRRKNPQEG LYNELQKDKMAEAYSEIGM KGERRRGKGHDGLYQGLST ATKDTYDALHMQALPPR | 21 | CD3 zeta | intracellular domain |
| GSGEGRGSLLTCGDVEENPG PR | 22 | | T2A cleavable domain |
| M | 1 | | start methionine |
| LLLVTSLLLCELPHPAFLLIP | 2 | | signal peptide |
| DIQMTQTTSSLSASLGDRVTI SCRAS | 23 | Anti-CD19 scFv | light chain |
| QDISKY | 24 | Anti-CD19 scFv | light chain: CDR1 |
| LNWYQQKPDGTVKLLIY | 25 | Anti-CD19 scFv | light chain |
| HTS | 26 | Anti-CD19 scFv | light chain: CDR2 |
| RLHSGVPSRFSGSGSGTDYS LTISNLEQEDIATYFC | 27 | Anti-CD19 scFv | light chain |
| QQGNTLPYT | 28 | Anti-CD19 scFv | light chain: CDR3 |
| FGGGTKLEIT | 29 | Anti-CD19 scFv | light chain |
| GSTSGSGKPGSGEGSTKG | 30 | Anti-CD19 scFv | linker |
| EVKLQESGPGLVAPSQSLSV TCTVS | 31 | Anti-CD19 scFv | heavy chain |
| GVSLPDYG | 32 | Anti-CD19 scFv | heavy chain: CDR1 |
| VSWIRQPPRKGLEWLGV | 33 | Anti-CD19 scFv | heavy chain |
| IWGSETT | 34 | Anti-CD19 scFv | heavy chain: CDR2 |
| YYNSALKSRLTIIKDNSKSQV FLKMNSLQTDDTAIYYC | 35 | Anti-CD19 scFv | heavy chain |
| AKHYYYGGSYAMDY | 36 | Anti-CD19 scFv | heavy chain: CDR3 |
| WGQGTSVTVSS | 37 | Anti-CD19 scFv | heavy chain |
| SGTTTPAPRPPTPAPTIASQPL SLRPEACRPAAGGAVHTRGL DFACD | 18 | CD8 | CD8alpha hinge |
| IYIWAPLAGTCGVLLLSLVIT LYC | 19 | CD8 | CD8alpha transmembrane domain |

TABLE 2-continued

| | | V1 CAR Construct | |
|---|---|---|---|
| Sequence | SEQ ID NO: | Segment | Notes |
| KRGRKKLLYIFKQPFMRPVQ TTQEEDGCSCRFPEEEEGGC EL | 20 | 4-1BB | intracellular domain |
| RVKFSRSADAPAYQQGQNQ LYNELNLGRREEYDVLDKR RGRDPEMGGKPRRKNPQEG LYNELQKDKMAEAYSEIGM KGERRRGKGHDGLYQGLST ATKDTYDALHMQALPPR | 21 | CD3zeta | intracellular domain |

TABLE 3

| | | V5 CAR Construct | |
|---|---|---|---|
| Sequence | SEQ ID NO: | Segment | Notes |
| M | 1 | | start methionine |
| ALPVTALLLPLALLLHAARP | 2 | | signal peptide |
| QVQLQQSGPGLVKPSQTLSL TCAIS | 3 | Anti-CD22 scFv | heavy chain |
| GDSVSSNSAA | 4 | Anti-CD22 scFv | heavy chain: CDR1 |
| WNWIRQSPSRGLEWLGR | 5 | Anti-CD22 scFv | heavy chain |
| TYYRSKWYN | 6 | Anti-CD22 scFv | heavy chain: CDR2 |
| DYAVSVKSRITINPDTSKNQF SLQLNSVTPEDTAVYYC | 7 | Anti-CD22 scFv | heavy chain |
| AREVTGDLEDAFDI | 8 | Anti-CD22 scFv | heavy chain: CDR3 |
| WGQGTMVTVSS | 9 | Anti-CD22 scFv | heavy chain |
| GGGGS | 10 | Anti-CD22 scFv | linker |
| DIQMTQSPSSLSASVGDRVTI TCRAS | 11 | Anti-CD22 scFv | light chain |
| QTIWSY | 12 | Anti-CD22 scFv | light chain: CDR1 |
| LNWYQQRPGKAPNLLIY | 13 | Anti-CD22 scFv | light chain |
| AAS | 14 | Anti-CD22 scFv | light chain: CDR2 |
| SLQSGVPSRFSGRGSGTDFTL TISSLQAEDFATYYC | 15 | Anti-CD22 scFv | light chain |
| QQSYSIPQT | 16 | Anti-CD22 scFv | light chain: CDR3 |
| FGQGTKLEIK | 17 | Anti-CD22 scFv | light chain |
| SGTTTPAPRPPTPAPTIASQPL SLRPEACRPAAGGAVHTRGL DFACD | 18 | CD8 | CD8alpha hinge |
| IYIWAPLAGTCGVLLLSLVIT LYC | 19 | CD8 | CD8alpha transmembrane domain |
| KRGRKKLLYIFKQPFMRPVQ TTQEEDGCSCRFPEEEEGGC EL | 20 | 4-1BB | intracellular domain |

TABLE 3-continued

V5 CAR Construct

| Sequence | SEQ ID NO: | Segment | Notes |
| --- | --- | --- | --- |
| RVKFSRSADAPAYQQGQNQLYNELNLNGRREEYDVLDKRRGRDPEMGGKPRRKNPQEGLYNELQKDKMAEAYSEIGMKGERRRGKGHDGLYQGLSTATKDTYDALHMQALPPR | 21 | CD3zeta | intracellular domain |
| RKRRGSGTPDPW | 38 | | Furin cleavable domain |
| GSGATNFSLLKQAGDVEENPGPLE | 39 | | P2A cleavable domain |
| M | 1 | | start methionine |
| EFGLSWLFLVAILKGVQCSR | 2 | | signal peptide |
| DIQMTQTTSSLSASLGDRVTISCRAS | 23 | Anti-CD19 scFv light chain | |
| QDISKY | 24 | Anti-CD19 scFv light chain: CDR1 | |
| LNWYQQKPDGTVKLLIY | 25 | Anti-CD19 scFv light chain | |
| HTS | 26 | Anti-CD19 scFv light chain: CDR2 | |
| RLHSGVPSRFSGSGSGTDYSLTISNLEQEDIATYFC | 27 | Anti-CD19 scFv light chain | |
| QQGNTLPYT | 28 | Anti-CD19 scFv light chain: CDR3 | |
| FGGGTKLEIT | 29 | Anti-CD19 scFv light chain | |
| GSTSGSGKPGSGEGSTKG | 30 | Anti-CD19 scFv linker | |
| EVKLQESGPGLVAPSQSLSVTCTVS | 31 | Anti-CD19 scFv heavy chain | |
| GVSLPDYG | 32 | Anti-CD19 scFv heavy chain: CDR1 | |
| VSWIRQPPRKGLEWLGV | 33 | Anti-CD19 scFv heavy chain | |
| IWGSETT | 34 | Anti-CD19 scFv heavy chain: CDR2 | |
| YYNSALKSRLTIIKDNSKSQVFLKMNSLQTDDTAIYYC | 35 | Anti-CD19 scFv heavy chain | |
| AKHYYYGGSYAMDY | 36 | Anti-CD19 scFv heavy chain: CDR3 | |
| WGQGTSVTVSS | 37 | Anti-CD19 scFv heavy chain | |
| TSAAAIEVMYPPPYLDNEKSNGTIIHVKGKHLCPSPLFPGPSKP | 40 | CD28 hinge | Extracellular |
| FWVLVVVGGVLACYSLLVTVAFIIFWV | 41 | CD28 | transmembrane domain |
| RSKRSRLLHSDYMNMTPRRPGPTRKHYQPYAPPRDFAAYRS | 42 | CD28 | intracellular domain |
| RVKFSRSADAPAYQQGQNQLYNELNLNGRREEYDVLDKRRGRDPEMGGKPRRKNPQEGLYNELQKDKMAEAYSEIGMKGERRRGKGHDGLYQGLSTATKDTYDALHMQALPPR | 21 | CD3zeta | intracellular domain |

TABLE 4

V6 CAR Construct

| Sequence | SEQ ID NO: | Segment | Notes |
|---|---|---|---|
| M | 1 | | start methionine |
| ALPVTALLLPLALLLHAARP | 2 | | signal peptide |
| QVQLQQSGPGLVKPSQTLSL TCAIS | 3 | Anti-CD22 scFv | heavy chain |
| GDSVSSNSAA | 4 | Anti-CD22 scFv | heavy chain: CDR1 |
| WNWIRQSPSRGLEWLGR | 5 | Anti-CD22 scFv | heavy chain |
| TYYRSKWYN | 6 | Anti-CD22 scFv | heavy chain: CDR2 |
| DYAVSVKSRITINPDTSKNQF SLQLNSVTPEDTAVYYC | 7 | Anti-CD22 scFv | heavy chain |
| AREVTGDLEDAFDI | 8 | Anti-CD22 scFv | heavy chain: CDR3 |
| WGQGTMVTVSS | 9 | Anti-CD22 scFv | heavy chain |
| GGGGS | 10 | Anti-CD22 scFv | linker |
| DIQMTQSPSSLSASVGDRVTI TCRAS | 11 | Anti-CD22 scFv | light chain |
| QTIWSY | 12 | Anti-CD22 scFv | light chain: CDR1 |
| LNWYQQRPGKAPNLLIY | 13 | Anti-CD22 scFv | light chain |
| AAS | 14 | Anti-CD22 scFv | light chain: CDR2 |
| SLQSGVPSRFSGRGSGTDFTL TISSLQAEDFATYYC | 15 | Anti-CD22 scFv | light chain |
| QQSYSIPQT | 16 | Anti-CD22 scFv | light chain: CDR3 |
| FGQGTKLEIK | 17 | Anti-CD22 scFv | light chain |
| SGAAAIEVMYPPPYLDNEKS NGTIIHVKGKHLCPSPLFPGP SKP | 40 | CD28 hinge | Extracellular |
| FWVLVVVGGVLACYSLLVT VAFIIFWV | 41 | CD28 | transmembrane domain |
| RSKRSRLLHSDYMNMTPRRP GPTRKHYQPYAPPRDFAAYR S | 42 | CD28 | intracellular domain |
| RVKFSRSADAPAYQQGQNQ LYNELNLGRREEYDVLDKR RGRDPEMGGKPRRKNPQEG LYNELQKDKMAEAYSEIGM KGERRRGKGHDGLYQGLST ATKDTYDALHMQALPPR | 21 | CD3zeta | intracellular domain |
| RKRRGSGTPDPW | 38 | | Furin cleavable domain |
| GSGATNFSLLKQAGDVEENP GPLE | 39 | | P2A cleavable domain |
| M | 1 | | start methionine |
| EFGLSWLFLVAILKGVQCSR | 2 | | signal peptide |
| DIQMTQTTSSLSASLGDRVTI SCRAS | 23 | Anti-CD19 scFv | light chain |
| QDISKY | 24 | Anti-CD19 scFv | light chain: CDR1 |
| LNWYQQKPDGTVKLLIY | 25 | Anti-CD19 scFv | light chain |
| HTS | 26 | Anti-CD19 scFv | light chain: CDR2 |

TABLE 4-continued

V6 CAR Construct

| Sequence | SEQ ID NO: | Segment | Notes |
|---|---|---|---|
| RLHSGVPSRFSGSGSGTDYS LTISNLEQEDIATYFC | 27 | Anti-CD19 scFv | light chain |
| QQGNTLPYT | 28 | Anti-CD19 scFv | light chain: CDR3 |
| FGGGTKLEIT | 29 | Anti-CD19 scFv | light chain |
| GSTSGSGKPGSGEGSTKG | 30 | Anti-CD19 scFv | linker |
| EVKLQESGPGLVAPSQSLSV TCTVS | 31 | Anti-CD19 scFv | heavy chain |
| GVSLPDYG | 32 | Anti-CD19 scFv | heavy chain: CDR1 |
| VSWIRQPPRKGLEWLGV | 33 | Anti-CD19 scFv | heavy chain |
| IWGSETT | 34 | Anti-CD19 scFv | heavy chain: CDR2 |
| YYNSALKSRLTIIKDNSKSQV FLKMNSLQTDDTAIYYC | 35 | Anti-CD19 scFv | heavy chain |
| AKHYYYGGSYAMDY | 36 | Anti-CD19 scFv | heavy chain: CDR3 |
| WGQGTSVTVSS | 37 | Anti-CD19 scFv | heavy chain |
| TSTTTPAPRPPTPAPTIASQPL SLRPEACRPAAGGAVHTRGL DFACD | 18 | CD8 | CD8 alpha hinge |
| IYIWAPLAGTCGVLLLSLVIT LYC | 19 | CD8 | CD8 alpha transmembrane domain |
| KRGRKKLLYIFKQPFMRPVQ TTQEEDGCSCRFPEEEEGGC EL | 20 | 4-1BB | intracellular domain |
| RVKFSRSADAPAYQQGQNQ LYNELNLGRREEYDVLDKR RGRDPEMGGKPRRKNPQEG LYNELQKDKMAEAYSEIGM KGERRRGKGHDGLYQGLST ATKDTYDALHMQALPPR | 21 | CD3 zeta | intracellular domain |

TABLE 5

V7 CAR Construct

| Sequence | SEQ ID NO: | Segment | Notes |
|---|---|---|---|
| M | 1 | | start methionine |
| ALPVTALLLPLALLLHAARP | 2 | | signal peptide |
| QVQLQQSGPGLVKPSQTLSL TCAIS | 3 | Anti-CD22 scFv | heavy chain |
| GDSVSSNSAA | 4 | Anti-CD22 scFv | heavy chain: CDR1 |
| WNWIRQSPSRGLEWLGR | 5 | Anti-CD22 scFv | heavy chain |
| TYYRSKWYN | 6 | Anti-CD22 scFv | heavy chain: CDR2 |
| DYAVSVKSRITINPDTSKNQF SLQLNSVTPEDTAVYYC | 7 | Anti-CD22 scFv | heavy chain |
| AREVTGDLEDAFDI | 8 | Anti-CD22 scFv | heavy chain: CDR3 |
| WGQGTMVTVSS | 9 | Anti-CD22 scFv | heavy chain |
| GGGGS | 10 | Anti-CD22 scFv | linker |

TABLE 5-continued

V7 CAR Construct

| Sequence | SEQ ID NO: | Segment | Notes |
|---|---|---|---|
| DIQMTQSPSSLSASVGDRVTITCRAS | 11 | | Anti-CD22 scFv light chain |
| QTIWSY | 12 | | Anti-CD22 scFv light chain: CDR1 |
| LNWYQQRPGKAPNLLIY | 13 | | Anti-CD22 scFv light chain |
| AAS | 14 | | Anti-CD22 scFv light chain: CDR2 |
| SLQSGVPSRFSGRGSGTDFTLTISSLQAEDFATYYC | 15 | | Anti-CD22 scFv light chain |
| QQSYSIPQT | 16 | | Anti-CD22 scFv light chain: CDR3 |
| FGQGTKLEIK | 17 | | Anti-CD22 scFv light chain |
| SGTTTPAPRPPTPAPTIASQPLSLRPEACRPAAGGAVHTRGLDFACD | 18 | CD8 | CD8alpha hinge |
| IYIWAPLAGTCGVLLLSLVITLYC | 19 | CD8 | CD8alpha transmembrane domain |
| KRGRKKLLYIFKQPFMRPVQTTQEEDGCSCRFPEEEEGGCEL | 20 | 4-1BB | intracellular domain |
| RVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR | 21 | CD3zeta | intracellular domain |
| RKRRGSGTPDPW | 38 | | Furin cleavable domain |
| GSGATNFSLLKQAGDVEENPGPLE | 39 | | P2A cleavable domain |
| M | 1 | | start methionine |
| EFGLSWLFLVAILKGVQCSR | 2 | | signal peptide |
| DIQMTQTTSSLSASLGDRVTISCRAS | 23 | | Anti-CD19 scFv light chain |
| QDISKY | 24 | | Anti-CD19 scFv light chain: CDR1 |
| LNWYQQKPDGTVKLLIY | 25 | | Anti-CD19 scFv light chain |
| HTS | 26 | | Anti-CD19 scFv light chain: CDR2 |
| RLHSGVPSRFSGSGSGTDYSLTISNLEQEDIATYFC | 27 | | Anti-CD19 scFv light chain |
| QQGNTLPYT | 28 | | Anti-CD19 scFv light chain: CDR3 |
| FGGGTKLEIT | 29 | | Anti-CD19 scFv light chain |
| GSTSGSGKPGSGEGSTKG | 30 | | Anti-CD19 scFv linker |
| EVKLQESGPGLVAPSQSLSVTCTVS | 31 | | Anti-CD19 scFv heavy chain |
| GVSLPDYG | 32 | | Anti-CD19 scFv heavy chain: CDR1 |
| VSWIRQPPRKGLEWLGV | 33 | | Anti-CD19 scFv heavy chain |
| IWGSETT | 34 | | Anti-CD19 scFv heavy chain: CDR2 |
| YYNSALKSRLTIIKDNSKSQVFLKMNSLQTDDTAIYYC | 35 | | Anti-CD19 scFv heavy chain |
| AKHYYYGGSYAMDY | 36 | | Anti-CD19 scFv heavy chain: CDR3 |

TABLE 5-continued

V7 CAR Construct

| Sequence | SEQ ID NO: | Segment | Notes |
| --- | --- | --- | --- |
| WGQGTSVTVSS | 37 | | Anti-CD19 scFv heavy chain |
| TSTTTPAPRPPTPAPTIASQPLSLRPEACRPAAGGAVHTRGLDFACD | 18 | CD8 | CD8alpha hinge |
| IYIWAPLAGTCGVLLLSLVITLYC | 19 | CD8 | CD8alpha transmembrane domain |
| KRGRKKLLYIFKQPFMRPVQTTQEEDGCSCRFPEEEEGGCEL | 20 | 4-1BB | intracellular domain |
| RVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR | 21 | CD3zeta | intracellular domain |

TABLE 6

V8 CAR Construct

| Sequence | SEQ ID NO: | Segment | Notes |
| --- | --- | --- | --- |
| M | 1 | | start methionine |
| ALPVTALLLPLALLLHAARP | 2 | | signal peptide |
| QVQLQQSGPGLVKPSQTLSLTCAIS | 3 | | Anti-CD22 scFv heavy chain |
| GDSVSSNSAA | 4 | | Anti-CD22 scFv heavy chain: CDR1 |
| WNWIRQSPSRGLEWLGR | 5 | | Anti-CD22 scFv heavy chain |
| TYYRSKWYN | 6 | | Anti-CD22 scFv heavy chain: CDR2 |
| DYAVSVKSRITINPDTSKNQFSLQLNSVTPEDTAVYYC | 7 | | Anti-CD22 scFv heavy chain |
| AREVTGDLEDAFDI | 8 | | Anti-CD22 scFv heavy chain: CDR3 |
| WGQGTMVTVSS | 9 | | Anti-CD22 scFv heavy chain |
| GGGGS | 10 | | Anti-CD22 scFv linker |
| DIQMTQSPSSLSASVGDRVTITCRAS | 11 | | Anti-CD22 scFv light chain |
| QTIWSY | 12 | | Anti-CD22 scFv light chain: CDR1 |
| LNWYQQRPGKAPNLLIY | 13 | | Anti-CD22 scFv light chain |
| AAS | 14 | | Anti-CD22 scFv light chain: CDR2 |
| SLQSGVPSRFSGRGSGTDFTLTISSLQAEDFATYYC | 15 | | Anti-CD22 scFv light chain |
| QQSYSIPQT | 16 | | Anti-CD22 scFv light chain: CDR3 |
| FGQGTKLEIK | 17 | | Anti-CD22 scFv light chain |
| SGAAAIEVMYPPPYLDNEKSNGTIIHVKGKHLCPSPLFPGPSKP | 40 | CD28 | CD28 hinge |
| FWVLVVVGGVLACYSLLVTVAFIIFWV | 41 | CD28 | transmembrane domain |

TABLE 6-continued

V8 CAR Construct

| Sequence | SEQ ID NO: | Segment | Notes |
|---|---|---|---|
| RSKRSRLLHSDYMNMTPRRP GPTRKHYQPYAPPRDFAAYR S | 42 | CD28 | intracellular domain |
| RVKFSRSADAPAYQQGQNQ LYNELNLGRREEYDVLDKR RGRDPEMGGKPRRKNPQEG LYNELQKDKMAEAYSEIGM KGERRRGKGHDGLYQGLST ATKDTYDALHMQALPPR | 21 | CD3 zeta | intracellular domain |
| RKRRGSGTPDPW | 38 | | Furin cleavable domain |
| GSGATNFSLLKQAGDVEENP GPLE | 39 | | P2A cleavable domain |
| M | 1 | | start methionine |
| EFGLSWLFLVAILKGVQCSR | 2 | | signal peptide |
| DIQMTQTTSSLSASLGDRVTI SCRAS | 23 | Anti-CD19 scFv | light chain |
| QDISKY | 24 | Anti-CD19 scFv | light chain: CDR1 |
| LNWYQQKPDGTVKLLIY | 25 | Anti-CD19 scFv | light chain |
| HTS | 26 | Anti-CD19 scFv | light chain: CDR2 |
| RLHSGVPSRFSGSGSGTDYS LTISNLEQEDIATYFC | 27 | Anti-CD19 scFv | light chain |
| QQGNTLPYT | 28 | Anti-CD19 scFv | light chain: CDR3 |
| FGGGTKLEIT | 29 | Anti-CD19 scFv | light chain |
| GSTSGSGKPGSGEGSTKG | 30 | Anti-CD19 scFv | linker |
| EVKLQESGPGLVAPSQSLSV TCTVS | 31 | Anti-CD19 scFv | heavy chain |
| GVSLPDYG | 32 | Anti-CD19 scFv | heavy chain: CDR1 |
| VSWIRQPPRKGLEWLGV | 33 | Anti-CD19 scFv | heavy chain |
| IWGSETT | 34 | Anti-CD19 scFv | heavy chain: CDR2 |
| YYNSALKSRLTIIKDNSKSQV FLKMNSLQTDDTAIYYC | 35 | Anti-CD19 scFv | heavy chain |
| AKHYYYGGSYAMDY | 36 | Anti-CD19 scFv | heavy chain: CDR3 |
| WGQGTSVTVSS | 37 | Anti-CD19 scFv | heavy chain |
| TSAAAIEVMYPPPYLDNEKS NGTIIHVKGKHLCPSPLFPGP SKP | 40 | CD28 | CD28 hinge |
| FWVLVVVGGVLACYSLLVT VAFIIFWV | 41 | CD28 | transmembrane domain |
| RSKRSRLLHSDYMNMTPRRP GPTRKHYQPYAPPRDFAAYR S | 42 | CD28 | intracellular domain |
| RVKFSRSADAPAYQQGQNQ LYNELNLGRREEYDVLDKR RGRDPEMGGKPRRKNPQEG LYNELQKDKMAEAYSEIGM KGERRRGKGHDGLYQGLST ATKDTYDALHMQALPPR | 21 | CD3zeta | intracellular domain |

TABLE 7

| Sequence | SEQ ID NO: | Segment | Notes |
|---|---|---|---|
| M | 1 | | start methionine |
| LLLVTSLLLCELPHPAFLLIP | 2 | | signal peptide |
| QVQLQQSGPGLVKPSQTLSLTCAIS | 3 | Anti-CD22 scFv | heavy chain |
| GDSVSSNSAA | 4 | Anti-CD22 scFv | heavy chain: CDR1 |
| WNWIRQSPSRGLEWLGR | 5 | Anti-CD22 scFv | heavy chain |
| TYYRSKWYN | 6 | Anti-CD22 scFv | heavy chain: CDR2 |
| DYAVSVKSRITINPDTSKNQFSLQLNSVTPEDTAVYYC | 7 | Anti-CD22 scFv | heavy chain |
| AREVTGDLEDAFDI | 8 | Anti-CD22 scFv | heavy chain: CDR3 |
| WGQGTMVTVSS | 9 | Anti-CD22 scFv | heavy chain |
| GGGGS | 10 | Anti-CD22 scFv | Linker 1 |
| DIQMTQSPSSLSASVGDRVTITCRAS | 11 | Anti-CD22 scFv | light chain |
| QTIWSY | 12 | Anti-CD22 scFv | light chain: CDR1 |
| LNWYQQRPGKAPNLLIY | 13 | Anti-CD22 scFv | light chain |
| AAS | 14 | Anti-CD22 scFv | light chain: CDR2 |
| SLQSGVPSRFSGRGSGTDFTLTISSLQAEDFATYYC | 15 | Anti-CD22 scFv | light chain |
| QQSYSIPQT | 16 | Anti-CD22 scFv | light chain: CDR3 |
| FGQGTKLEIK | 17 | Anti-CD22 scFv | light chain |
| GGGGSGGGGSGGGGSGGGGSGGGGS | 79 | Linker | Linker 5 |
| DIQMTQTTSSLSASLGDRVTISCRAS | 23 | Anti-CD19 scFv | Light chain |
| QDISKY | 24 | Anti-CD19 scFv | light chain: CDR1 |
| LNWYQQKPDGTVKLLIY | 25 | Anti-CD19 scFv | light chain |
| HTS | 26 | Anti-CD19 scFv | light chain: CDR2 |
| RLHSGVPSRFSGSGSGTDYSLTISNLEQEDIATYFC | 27 | Anti-CD19 scFv | light chain |
| QQGNTLPYT | 28 | Anti-CD19 scFv | light chain: CDR3 |
| FGGGTKLEIT | 29 | Anti-CD19 scFv | light chain |
| GSTSGSGKPGSGEGSTKG | 30 | Anti-CD19 scFv | Linker 6 |
| EVKLQESGPGLVAPSQSLSVTCTVS | 31 | Anti-CD19 scFv | heavy chain |
| GVSLPDYG | 32 | Anti-CD19 scFv | heavy chain: CDR1 |
| VSWIRQPPRKGLEWLGV | 33 | Anti-CD19 scFv | heavy chain |
| IWGSETT | 34 | Anti-CD19 scFv | heavy chain: CDR2 |
| YYNSALKSRLTIIKDNSKSQVFLKMNSLQTDDTAIYYC | 35 | Anti-CD19 scFv | heavy chain |
| AKHYYYGGSYAMDY | 36 | Anti-CD19 scFv | heavy chain: CDR3 |
| WGQGTSVTVSS | 37 | Anti-CD19 scFv | heavy chain |

TABLE 7-continued

TanCAR 1 Construct

| Sequence | SEQ ID NO: | Segment | Notes |
|---|---|---|---|
| SGTTTPAPRPPTPAPTIASQPLSLRPEACRPAAGGAVHTRGLDFACD | 18 | CD8 | CD8alpha hinge |
| IYIWAPLAGTCGVLLLSLVITLYC | 19 | CD8 | CD8alpha transmembrane domain |
| KRGRKKLLYIFKQPFMRPVQTTQEEDGCSCRFPEEEEGGCEL | 20 | 4-1BB | intracellular domain |
| RVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR* | 21 | CD3zeta | intracellular domain |

TABLE 8

TanCAR 2 Construct

| Sequence | SEQ ID NO: | Segment | Notes |
|---|---|---|---|
| M | 1 | | start methionine |
| LLLVTSLLLCELPHPAFLLIP | 2 | | signal peptide |
| DIQMTQTTSSLSASLGDRVTISCRAS | 23 | Anti-CD19 scFv | Light chain |
| QDISKY | 24 | Anti-CD19 scFv | light chain: CDR1 |
| LNWYQQKPDGTVKLLIY | 25 | Anti-CD19 scFv | light chain |
| HTS | 26 | Anti-CD19 scFv | light chain: CDR2 |
| RLHSGVPSRFSGSGSGTDYSLTISNLEQEDIATYFC | 27 | Anti-CD19 scFv | light chain |
| QQGNTLPYT | 28 | Anti-CD19 scFv | light chain: CDR3 |
| FGGGTKLEIT | 29 | Anti-CD19 scFv | light chain |
| GSTSGSGKPGSGEGSTKG | 30 | Anti-CD19 scFv | Linker 6 |
| EVKLQESGPGLVAPSQSLSVTCTVS | 31 | Anti-CD19 scFv | heavy chain |
| GVSLPDYG | 32 | Anti-CD19 scFv | heavy chain: CDR1 |
| VSWIRQPPRKGLEWLGV | 33 | Anti-CD19 scFv | heavy chain |
| IWGSETT | 34 | Anti-CD19 scFv | heavy chain: CDR2 |
| YYNSALKSRLTIIKDNSKSQVFLKMNSLQTDDTAIYYC | 35 | Anti-CD19 scFv | heavy chain |
| AKHYYYGGSYAMDY | 36 | Anti-CD19 scFv | heavy chain: CDR3 |
| WGQGTSVTVSS | 37 | Anti-CD19 scFv | heavy chain |
| GGGGSGGGGSGGGGSGGGGSGGGGS | 79 | Linker | Linker 5 |
| QVQLQQSGPGLVKPSQTLSLTCAIS | 3 | Anti-CD22 scFv | heavy chain |
| GDSVSSNSAA | 4 | Anti-CD22 scFv | heavy chain: CDR1 |
| WNWIRQSPSRGLEWLGR | 5 | Anti-CD22 scFv | heavy chain |

TABLE 8-continued

TanCAR 2 Construct

| Sequence | SEQ ID NO: | Segment | Notes |
|---|---|---|---|
| TYYRSKWYN | 6 | Anti-CD22 scFv heavy chain: CDR2 | |
| DYAVSVKSRITINPDTSKNQFSLQLNSVTPEDTAVYYC | 7 | Anti-CD22 scFv heavy chain | |
| AREVTGDLEDAFDI | 8 | Anti-CD22 scFv heavy chain: CDR3 | |
| WGQGTMVTVSS | 9 | Anti-CD22 scFv heavy chain | |
| GGGGS | 10 | Anti-CD22 scFv Linker 1 | |
| DIQMTQSPSSLSASVGDRVTITCRAS | 11 | Anti-CD22 scFv light chain | |
| QTIWSY | 12 | Anti-CD22 scFv light chain: CDR1 | |
| LNWYQQRPGKAPNLLIY | 13 | Anti-CD22 scFv light chain | |
| AAS | 14 | Anti-CD22 scFv light chain: CDR2 | |
| SLQSGVPSRFSGRGSGTDFTLTISSLQAEDFATYYC | 15 | Anti-CD22 scFv light chain | |
| QQSYSIPQT | 16 | Anti-CD22 scFv light chain: CDR3 | |
| FGQGTKLEIK | 17 | Anti-CD22 scFv light chain | |
| SGTTTPAPRPPTPAPTIASQPLSLRPEACRPAAGGAVHTRGLDFACD | 18 | CD8 | CD8alpha hinge |
| IYIWAPLAGTCGVLLLSLVITLYC | 19 | CD8 | CD8alpha transmembrane domain |
| KRGRKKLLYIFKQPFMRPVQTTQEEDGCSCRFPEEEEGGCEL | 20 | 4-1BB | intracellular domain |
| RVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR* | 21 | CD3 zeta | intracellular domain |

TABLE 9

TanCAR 3 Construct

| Sequence | SEQ ID NO: | Segment | Notes |
|---|---|---|---|
| M | 1 | | start methionine |
| LLLVTSLLLCELPHPAFLLIP | 2 | | signal peptide |
| QVQLQQSGPGLVKPSQTLSLTCAIS | 3 | Anti-CD22 scFv heavy chain | |
| GDSVSSNSAA | 4 | Anti-CD22 scFv heavy chain: CDR1 | |
| WNWIRQSPSRGLEWLGR | 5 | Anti-CD22 scFv heavy chain | |
| TYYRSKWYN | 6 | Anti-CD22 scFv heavy chain: CDR2 | |
| DYAVSVKSRITINPDTSKNQFSLQLNSVTPEDTAVYYC | 7 | Anti-CD22 scFv heavy chain | |
| AREVTGDLEDAFDI | 8 | Anti-CD22 scFv heavy chain: CDR3 | |
| WGQGTMVTVSS | 9 | Anti-CD22 scFv heavy chain | |

TABLE 9-continued

TanCAR 3 Construct

| Sequence | SEQ ID NO: | Segment | Notes |
|---|---|---|---|
| GSTSGSGKPGSGEGSTKG | 30 | Anti-CD22 scFv | Linker 6 |
| DIQMTQSPSSLSASVGDRVTI TCRAS | 11 | Anti-CD22 scFv | light chain |
| QTIWSY | 12 | Anti-CD22 scFv | light chain: CDR1 |
| LNWYQQRPGKAPNLLIY | 13 | Anti-CD22 scFv | light chain |
| AAS | 14 | Anti-CD22 scFv | light chain: CDR2 |
| SLQSGVPSRFSGRGSGTDFTL TISSLQAEDFATYYC | 15 | Anti-CD22 scFv | light chain |
| QQSYSIPQT | 16 | Anti-CD22 scFv | light chain: CDR3 |
| FGQGTKLEIK | 17 | Anti-CD22 scFv | light chain |
| GGGGSGGGGSGGGGSGGGG SGGGGS | 79 | Linker | Linker 5 |
| DIQMTQTTSSLSASLGDRVTI SCRAS | 23 | Anti-CD19 scFv | Light chain |
| QDISKY | 24 | Anti-CD19 scFv | light chain: CDR1 |
| LNWYQQKPDGTVKLLIY | 25 | Anti-CD19 scFv | light chain |
| HTS | 26 | Anti-CD19 scFv | light chain: CDR2 |
| RLHSGVPSRFSGSGSGTDYS LTISNLEQEDIATYFC | 27 | Anti-CD19 scFv | light chain |
| QQGNTLPYT | 28 | Anti-CD19 scFv | light chain: CDR3 |
| FGGGTKLEIT | 29 | Anti-CD19 scFv | light chain |
| GSTSGSGKPGSGEGSTKG | 30 | Anti-CD19 scFv | Linker 6 |
| EVKLQESGPGLVAPSQSLSV TCTVS | 31 | Anti-CD19 scFv | heavy chain |
| GVSLPDYG | 32 | Anti-CD19 scFv | heavy chain: CDR1 |
| VSWIRQPPRKGLEWLGV | 33 | Anti-CD19 scFv | heavy chain |
| IWGSETT | 34 | Anti-CD19 scFv | heavy chain: CDR2 |
| YYNSALKSRLTIIKDNSKSQV FLKMNSLQTDDTAIYYC | 35 | Anti-CD19 scFv | heavy chain |
| AKHYYYGGSYAMDY | 36 | Anti-CD19 scFv | heavy chain: CDR3 |
| WGQGTSVTVSS | 37 | Anti-CD19 scFv | heavy chain |
| SGTTTPAPRPPTPAPTIASQPL SLRPEACRPAAGGAVHTRGL DFACD | 18 | CD8 | CD8alpha hinge |
| IYIWAPLAGTCGVLLLSLVIT LYC | 19 | CD8 | CD8alpha transmembrane domain |
| KRGRKKLLYIFKQPFMRPVQ TTQEEDGCSCRFPEEEEGGC EL | 20 | 4-1BB | intracellular domain |
| RVKFSRSADAPAYQQGQNQ LYNELNLGRREEYDVLDKR RGRDPEMGGKPRRKNPQEG LYNELQKDKMAEAYSEIGM KGERRRGKGHDGLYQGLST ATKDTYDALHMQALPPR* | 21 | CD3zeta | intracellular domain |

TABLE 10

TanCAR 4 Construct

| Sequence | SEQ ID NO: | Segment | Notes |
|---|---|---|---|
| M | 1 | | start methionine |
| ALPVTALLLPLALLLHAARP | 2 | | signal peptide |
| QVQLQQSGPGLVKPSQTLSLTCAIS | 3 | Anti-CD22 scFv | heavy chain |
| GDSVSSNSAA | 4 | Anti-CD22 scFv | heavy chain: CDR1 |
| WNWIRQSPSRGLEWLGR | 5 | Anti-CD22 scFv | heavy chain |
| TYYRSKWYN | 6 | Anti-CD22 scFv | heavy chain: CDR2 |
| DYAVSVKSRITINPDTSKNQFSLQLNSVTPEDTAVYYC | 7 | Anti-CD22 scFv | heavy chain |
| AREVTGDLEDAFDI | 8 | Anti-CD22 scFv | heavy chain: CDR3 |
| WGQGTMVTVSS | 9 | Anti-CD22 scFv | heavy chain |
| GGGGS | 10 | Anti-CD22 scFv | Linker 1 |
| DIQMTQSPSSLSASVGDRVTITCRAS | 11 | Anti-CD22 scFv | light chain |
| QTIWSY | 12 | Anti-CD22 scFv | light chain: CDR1 |
| LNWYQQRPGKAPNLLIY | 13 | Anti-CD22 scFv | light chain |
| AAS | 14 | Anti-CD22 scFv | light chain: CDR2 |
| SLQSGVPSRFSGRGSGTDFTLTISSLQAEDFATYYC | 15 | Anti-CD22 scFv | light chain |
| QQSYSIPQT | 16 | Anti-CD22 scFv | light chain: CDR3 |
| FGQGTKLEIK | 17 | Anti-CD22 scFv | light chain |
| GGGGSGGGGSGGGGSGGGGS | | Linker | Linker 4 |
| DIQMTQTTSSLSASLGDRVTISCRAS | 23 | Anti-CD19 scFv | Light chain |
| QDISKY | 24 | Anti-CD19 scFv | light chain: CDR1 |
| LNWYQQKPDGTVKLLIY | 25 | Anti-CD19 scFv | light chain |
| HTS | 26 | Anti-CD19 scFv | light chain: CDR2 |
| RLHSGVPSRFSGSGSGTDYSLTISNLEQEDIATYFC | 27 | Anti-CD19 scFv | light chain |
| QQGNTLPYT | 28 | Anti-CD19 scFv | light chain: CDR3 |
| FGGGTKLEIT | 29 | Anti-CD19 scFv | light chain |
| GSTSGSGKPGSGEGSTKG | 30 | Anti-CD19 scFv | Linker 6 |
| EVKLQESGPGLVAPSQSLSVTCTVS | 31 | Anti-CD19 scFv | heavy chain |
| GVSLPDYG | 32 | Anti-CD19 scFv | heavy chain: CDR1 |
| VSWIRQPPRKGLEWLGV | 33 | Anti-CD19 scFv | heavy chain |
| IWGSETT | 34 | Anti-CD19 scFv | heavy chain: CDR2 |
| YYNSALKSRLTIIKDNSKSQVFLKMNSLQTDDTAIYYC | 35 | Anti-CD19 scFv | heavy chain |
| AKHYYYGGSYAMDY | 36 | Anti-CD19 scFv | heavy chain: CDR3 |
| WGQGTSVTVSS | 37 | Anti-CD19 scFv | heavy chain |

TABLE 10-continued

TanCAR 4 Construct

| Sequence | SEQ ID NO: | Segment | Notes |
|---|---|---|---|
| SGTTTPAPRPPTPAPTIASQPLSLRPEACRPAAGGAVHTRGLDFACD | 18 | CD8 | CD8alpha hinge |
| IYIWAPLAGTCGVLLLSLVITLYC | 19 | CD8 | CD8alpha transmembrane domain |
| KRGRKKLLYIFKQPFMRPVQTTQEEDGCSCRFPEEEEGGCEL | 20 | 4-1BB | intracellular domain |
| RVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR* | 21 | CD3zeta | intracellular domain |

TABLE 11

Loop CAR 1 Construct

| Sequence | SEQ ID NO: | Segment | Notes |
|---|---|---|---|
| M | 1 | | start methionine |
| LLLVTSLLLCELPHPAFLLIP | 2 | | signal peptide |
| DIQMTQTTSSLSASLGDRVTISCRAS | 23 | Anti-CD19 scFv | Light chain |
| QDISKY | 24 | Anti-CD19 scFv | light chain: CDR1 |
| LNWYQQKPDGTVKLLIY | 25 | Anti-CD19 scFv | light chain |
| HTS | 26 | Anti-CD19 scFv | light chain: CDR2 |
| RLHSGVPSRFSGSGSGTDYSLTISNLEQEDIATYFC | 27 | Anti-CD19 scFv | light chain |
| QQGNTLPYT | 28 | Anti-CD19 scFv | light chain: CDR3 |
| FGGGTKLEIT | 29 | Anti-CD19 scFv | light chain |
| GGGGSGGGGSGGGGS | 80 | Linker | Linker 3 |
| QVQLQQSGPGLVKPSQTLSLTCAIS | 3 | Anti-CD22 scFv | heavy chain |
| GDSVSSNSAA | 4 | Anti-CD22 scFv | heavy chain: CDR1 |
| WNWIRQSPSRGLEWLGR | 5 | Anti-CD22 scFv | heavy chain |
| TYYRSKWYN | 6 | Anti-CD22 scFv | heavy chain: CDR2 |
| DYAVSVKSRITINPDTSKNQFSLQLNSVTPEDTAVYYC | 7 | Anti-CD22 scFv | heavy chain |
| AREVTGDLEDAFDI | 8 | Anti-CD22 scFv | heavy chain: CDR3 |
| WGQGTMVTVSS | 9 | Anti-CD22 scFv | heavy chain |
| GGGGS | 10 | Anti-CD22 scFv | Linker 1 |
| DIQMTQSPSSLSASVGDRVTITCRAS | 11 | Anti-CD22 scFv | light chain |
| QTIWSY | 12 | Anti-CD22 scFv | light chain: CDR1 |
| LNWYQQRPGKAPNLLIY | 13 | Anti-CD22 scFv | light chain |

TABLE 11-continued

Loop CAR 1 Construct

| Sequence | SEQ ID NO: | Segment | Notes |
|---|---|---|---|
| AAS | 14 | Anti-CD22 scFv | light chain: CDR2 |
| SLQSGVPSRFSGRGSGTDFTLTISSLQAEDFATYYC | 15 | Anti-CD22 scFv | light chain |
| QQSYSIPQT | 16 | Anti-CD22 scFv | light chain: CDR3 |
| FGQGTKLEIK | 17 | Anti-CD22 scFv | light chain |
| GGGGSGGGGSGGGGS | 80 | Anti-CD22 scFv | Linker 3 |
| EVKLQESGPGLVAPSQSLSVTCTVS | 31 | Anti-CD19 scFv | heavy chain |
| GVSLPDYG | 32 | Anti-CD19 scFv | heavy chain: CDR1 |
| VSWIRQPPRKGLEWLGV | 33 | Anti-CD19 scFv | heavy chain |
| IWGSETT | 34 | Anti-CD19 scFv | heavy chain: CDR2 |
| YYNSALKSRLTIIKDNSKSQVFLKMNSLQTDDTAIYYC | 35 | Anti-CD19 scFv | heavy chain |
| AKHYYYGGSYAMDY | 36 | Anti-CD19 scFv | heavy chain: CDR3 |
| WGQGTSVTVSS | 37 | Anti-CD19 scFv | heavy chain |
| SGTTTPAPRPPTPAPTIASQPLSLRPEACRPAAGGAVHTRGLDFACD | 18 | CD8 | CD8alpha hinge |
| IYIWAPLAGTCGVLLLSLVITLYC | 19 | CD8 | CD8alpha transmembrane domain |
| KRGRKKLLYIFKQPFMRPVQTTQEEDGCSCRFPEEEEGGCEL | 20 | 4-1BB | intracellular domain |
| RVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR* | 21 | CD3zeta | intracellular domain |

TABLE 12

Loop CAR 2 Construct

| Sequence | SEQ ID NO: | Segment | Notes |
|---|---|---|---|
| M | 1 | | start methionine |
| LLLVTSLLLCELPHPAFLLIP | 2 | | signal peptide |
| DIQMTQTTSSLSASLGDRVTISCRAS | 23 | Anti-CD19 scFv | Light chain |
| QDISKY | 24 | Anti-CD19 scFv | light chain: CDR1 |
| LNWYQQKPDGTVKLLIY | 25 | Anti-CD19 scFv | light chain |
| HTS | 26 | Anti-CD19 scFv | light chain: CDR2 |
| RLHSGVPSRFSGSGSGTDYSLTISNLEQEDIATYFC | 27 | Anti-CD19 scFv | light chain |
| QQGNTLPYT | 28 | Anti-CD19 scFv | light chain: CDR3 |
| FGGGTKLEIT | 29 | Anti-CD19 scFv | light chain |

TABLE 12-continued

Loop CAR 2 Construct

| Sequence | SEQ ID NO: | Segment | Notes |
|---|---|---|---|
| GGCGSGGGGSGGGGS | 81 | Linker | Linker 3A |
| QVQLQQSGPGLVKPSQTLSLTCAIS | 3 | Anti-CD22 scFv | heavy chain |
| GDSVSSNSAA | 4 | Anti-CD22 scFv | heavy chain: CDR1 |
| WNWIRQSPSRGLEWLGR | 5 | Anti-CD22 scFv | heavy chain |
| TYYRSKWYN | 6 | Anti-CD22 scFv | heavy chain: CDR2 |
| DYAVSVKSRITINPDTSKNQFSLQLNSVTPEDTAVYYC | 7 | Anti-CD22 scFv | heavy chain |
| AREVTGDLEDAFDI | 8 | Anti-CD22 scFv | heavy chain: CDR3 |
| WGQGTMVTVSS | 9 | Anti-CD22 scFv | heavy chain |
| GSTSGSGKPGSGEGSTKG | 30 | Anti-CD22 scFv | Linker 6 |
| DIQMTQSPSSLSASVGDRVTITCRAS | 11 | Anti-CD22 scFv | light chain |
| QTIWSY | 12 | Anti-CD22 scFv | light chain: CDR1 |
| LNWYQQRPGKAPNLLIY | 13 | Anti-CD22 scFv | light chain |
| AAS | 14 | Anti-CD22 scFv | light chain: CDR2 |
| SLQSGVPSRFSGRGSGTDFTLTISSLQAEDFATYYC | 15 | Anti-CD22 scFv | light chain |
| QQSYSIPQT | 16 | Anti-CD22 scFv | light chain: CDR3 |
| FGQGTKLEIK | 17 | Anti-CD22 scFv | light chain |
| GGGGSGGGGSGGCGS | 82 | Anti-CD22 scFv | Linker 3B |
| EVKLQESGPGLVAPSQSLSVTCTVS | 31 | Anti-CD19 scFv | heavy chain |
| GVSLPDYG | 32 | Anti-CD19 scFv | heavy chain: CDR1 |
| VSWIRQPPRKGLEWLGV | 33 | Anti-CD19 scFv | heavy chain |
| IWGSETT | 34 | Anti-CD19 scFv | heavy chain: CDR2 |
| YYNSALKSRLTIIKDNSKSQVFLKMNSLQTDDTAIYYC | 35 | Anti-CD19 scFv | heavy chain |
| AKHYYYGGSYAMDY | 36 | Anti-CD19 scFv | heavy chain: CDR3 |
| WGQGTSVTVSS | 37 | Anti-CD19 scFv | heavy chain |
| SGTTTPAPRPPTPAPTIASQPLSLRPEACRPAAGGAVHTRGLDFACD | 18 | CD8 | CD8alpha hinge |
| IYIWAPLAGTCGVLLLSLVITLYC | 19 | CD8 | CD8alpha transmembrane domain |
| KRGRKKLLYIFKQPFMRPVQTTQEEDGCSCRFPEEEEGGCEL | 20 | 4-1BB | intracellular domain |
| RVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR* | 21 | CD3zeta | intracellular domain |

TABLE 13

Loop CAR 3 Construct

| Sequence | SEQ ID NO: | Segment | Notes |
|---|---|---|---|
| M | 1 | | start methionine |
| ALPVTALLLPLALLLHAARP | 2 | | signal peptide |
| DIQMTQTTSSLSASLGDRVTISCRAS | 23 | Anti-CD19 scFv | Light chain |
| QDISKY | 24 | Anti-CD19 scFv | light chain: CDR1 |
| LNWYQQKPDGTVKLLIY | 25 | Anti-CD19 scFv | light chain |
| HTS | 26 | Anti-CD19 scFv | light chain: CDR2 |
| RLHSGVPSRFSGSGSGTDYSLTISNLEQEDIATYFC | 27 | Anti-CD19 scFv | light chain |
| QQGNTLPYT | 28 | Anti-CD19 scFv | light chain: CDR3 |
| FGGGTKLEIT | 29 | Anti-CD19 scFv | light chain |
| GGGGSGGGGS | 83 | Linker | Linker 2 |
| QVQLQQSGPGLVKPSQTLSLTCAIS | 3 | Anti-CD22 scFv | heavy chain |
| GDSVSSNSAA | 4 | Anti-CD22 scFv | heavy chain: CDR1 |
| WNWIRQSPSRGLEWLGR | 5 | Anti-CD22 scFv | heavy chain |
| TYYRSKWYN | 6 | Anti-CD22 scFv | heavy chain: CDR2 |
| DYAVSVKSRITINPDTSKNQFSLQLNSVTPEDTAVYYC | 7 | Anti-CD22 scFv | heavy chain |
| AREVTGDLEDAFDI | 8 | Anti-CD22 scFv | heavy chain: CDR3 |
| WGQGTMVTVSS | 9 | Anti-CD22 scFv | heavy chain |
| GSTSGSGKPGSGEGSTKG | 30 | Anti-CD22 scFv | Linker 6 |
| DIQMTQSPSSLSASVGDRVTITCRAS | 11 | Anti-CD22 scFv | light chain |
| QTIWSY | 12 | Anti-CD22 scFv | light chain: CDR1 |
| LNWYQQRPGKAPNLLIY | 13 | Anti-CD22 scFv | light chain |
| AAS | 14 | Anti-CD22 scFv | light chain: CDR2 |
| SLQSGVPSRFSGRGSGTDFTLTISSLQAEDFATYYC | 15 | Anti-CD22 scFv | light chain |
| QQSYSIPQT | 16 | Anti-CD22 scFv | light chain: CDR3 |
| FGQGTKLEIK | 17 | Anti-CD22 scFv | light chain |
| GGGGSGGGGS | 83 | Linker | Linker 2 |
| EVKLQESGPGLVAPSQSLSVTCTVS | 31 | Anti-CD19 scFv | heavy chain |
| GVSLPDYG | 32 | Anti-CD19 scFv | heavy chain: CDR1 |
| VSWIRQPPRKGLEWLGV | 33 | Anti-CD19 scFv | heavy chain |
| IWGSETT | 34 | Anti-CD19 scFv | heavy chain: CDR2 |
| YYNSALKSRLTIIKDNSKSQVFLKMNSLQTDDTAIYYC | 35 | Anti-CD19 scFv | heavy chain |
| AKHYYYGGSYAMDY | 36 | Anti-CD19 scFv | heavy chain: CDR3 |
| WGQGTSVTVSS | 37 | Anti-CD19 scFv | heavy chain |

TABLE 13-continued

Loop CAR 3 Construct

| Sequence | SEQ ID NO: | Segment | Notes |
|---|---|---|---|
| SGTTTPAPRPPTPAPTIASQPL SLRPEACRPAAGGAVHTRGL DFACD | 18 | CD8 | CD8alpha hinge |
| IYIWAPLAGTCGVLLLSLVIT LYC | 19 | CD8 | CD8alpha transmembrane domain |
| KRGRKKLLYIFKQPFMRPVQ TTQEEDGCSCRFPEEEEGGC EL | 20 | 4-1BB | intracellular domain |
| RVKFSRSADAPAYQQGQNQ LYNELNLGRREEYDVLDKR RGRDPEMGGKPRRKNPQEG LYNELQKDKMAEAYSEIGM KGERRRGKGHDGLYQGLST ATKDTYDALHMQALPPR* | 21 | CD3 zeta | intracellular domain |

TABLE 14

Loop CAR 4 Construct

| Sequence | SEQ ID NO: | Segment | Notes |
|---|---|---|---|
| M | 1 | | start methionine |
| LLLVTSLLLCELPHPAFLLIP | 2 | | signal peptide |
| QVQLQQSGPGLVKPSQTLSL TCAIS | 3 | Anti-CD22 scFv heavy chain | |
| GDSVSSNSAA | 4 | Anti-CD22 scFv heavy chain: CDR1 | |
| WNWIRQSPSRGLEWLGR | 5 | Anti-CD22 scFv heavy chain | |
| TYYRSKWYN | 6 | Anti-CD22 scFv heavy chain: CDR2 | |
| DYAVSVKSRITINPDTSKNQF SLQLNSVTPEDTAVYYC | 7 | Anti-CD22 scFv heavy chain | |
| AREVTGDLEDAFDI | 8 | Anti-CD22 scFv heavy chain: CDR3 | |
| WGQGTMVTVSS | 9 | Anti-CD22 scFv heavy chain | |
| GGGGSGGGGS | 83 | Linker | Linker 2 |
| DIQMTQTTSSLSASLGDRVTI SCRAS | 23 | Anti-CD19 scFv Light chain | |
| QDISKY | 24 | Anti-CD19 scFv light chain: CDR1 | |
| LNWYQQKPDGTVKLLIY | 25 | Anti-CD19 scFv light chain | |
| HTS | 26 | Anti-CD19 scFv light chain: CDR2 | |
| RLHSGVPSRFSGSGSGTDYS LTISNLEQEDIATYFC | 27 | Anti-CD19 scFv light chain | |
| QQGNTLPYT | 28 | Anti-CD19 scFv light chain: CDR3 | |
| FGGGTKLEIT | 29 | Anti-CD19 scFv light chain | |
| GSTSGSGKPGSGEGSTKG | 30 | Anti-CD19 scFv Linker 6 | |
| EVKLQESGPGLVAPSQSLSV TCTVS | 31 | Anti-CD19 scFv heavy chain | |
| GVSLPDYG | 32 | Anti-CD19 scFv heavy chain: CDR1 | |
| VSWIRQPPRKGLEWLGV | 33 | Anti-CD19 scFv heavy chain | |

TABLE 14-continued

Loop CAR 4 Construct

| Sequence | SEQ ID NO: | Segment | Notes |
|---|---|---|---|
| IWGSETT | 34 | Anti-CD19 scFv heavy chain: CDR2 | |
| YYNSALKSRLTIIKDNSKSQVFLKMNSLQTDDTAIYYC | 35 | Anti-CD19 scFv heavy chain | |
| AKHYYYGGSYAMDY | 36 | Anti-CD19 scFv heavy chain: CDR3 | |
| WGQGTSVTVSS | 37 | Anti-CD19 scFv heavy chain | |
| GGGGSGGGGS | 83 | Linker | Linker 2 |
| DIQMTQSPSSLSASVGDRVTITCRAS | 11 | Anti-CD22 scFv light chain | |
| QTIWSY | 12 | Anti-CD22 scFv light chain: CDR1 | |
| LNWYQQRPGKAPNLLIY | 13 | Anti-CD22 scFv light chain | |
| AAS | 14 | Anti-CD22 scFv light chain: CDR2 | |
| SLQSGVPSRFSGRGSGTDFTLTISSLQAEDFATYYC | 15 | Anti-CD22 scFv light chain | |
| QQSYSIPQT | 16 | Anti-CD22 scFv light chain: CDR3 | |
| FGQGTKLEIK | 17 | Anti-CD22 scFv light chain | |
| SGTTTPAPRPPTPAPTIASQPLSLRPEACRPAAGGAVHTRGLDFACD | 18 | CD8 | CD8alpha hinge |
| IYIWAPLAGTCGVLLLSLVITLYC | 19 | CD8 | CD8alpha transmembrane domain |
| KRGRKKLLYIFKQPFMRPVQTTQEEDGCSCRFPEEEEGGCEL | 20 | 4-1BB | intracellular domain |
| RVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR* | 21 | CD3zeta | intracellular domain |

TABLE 15

Loop CAR 5 Construct

| Sequence | SEQ ID NO: | Segment | Notes |
|---|---|---|---|
| M | 1 | | start methionine |
| LLLVTSLLLCELPHPAFLLIP | 2 | | signal peptide |
| DIQMTQTTSSLSASLGDRVTISCRAS | 23 | Anti-CD19 scFv Light chain | |
| QDISKY | 24 | Anti-CD19 scFv light chain: CDR1 | |
| LNWYQQKPDGTVKLLIY | 25 | Anti-CD19 scFv light chain | |
| HTS | 26 | Anti-CD19 scFv light chain: CDR2 | |
| RLHSGVPSRFSGSGSGTDYSLTISNLEQEDIATYFC | 27 | Anti-CD19 scFv light chain | |
| QQGNTLPYT | 28 | Anti-CD19 scFv light chain: CDR3 | |
| FGGGTKLEIT | 29 | Anti-CD19 scFv light chain | |

TABLE 15-continued

Loop CAR 5 Construct

| Sequence | SEQ ID NO: | Segment | Notes |
|---|---|---|---|
| GGGGSGGGGSCGGGS | 84 | Linker | Linker 3C |
| QVQLQQSGPGLVKPSQTLSLTCAIS | 3 | Anti-CD22 scFv | heavy chain |
| GDSVSSNSAA | 4 | Anti-CD22 scFv | heavy chain: CDR1 |
| WNWIRQSPSRGLEWLGR | 5 | Anti-CD22 scFv | heavy chain |
| TYYRSKWYN | 6 | Anti-CD22 scFv | heavy chain: CDR2 |
| DYAVSVKSRITINPDTSKNQFSLQLNSVTPEDTAVYYC | 7 | Anti-CD22 scFv | heavy chain |
| AREVTGDLEDAFDI | 8 | Anti-CD22 scFv | heavy chain: CDR3 |
| WGQGTMVTVSS | 9 | Anti-CD22 scFv | heavy chain |
| GSTSGSGKPGSGEGSTKG | 30 | Anti-CD22 scFv | Linker 6 |
| DIQMTQSPSSLSASVGDRVTITCRAS | 11 | Anti-CD22 scFv | light chain |
| QTIWSY | 12 | Anti-CD22 scFv | light chain: CDR1 |
| LNWYQQRPGKAPNLLIY | 13 | Anti-CD22 scFv | light chain |
| AAS | 14 | Anti-CD22 scFv | light chain: CDR2 |
| SLQSGVPSRFSGRGSGTDFTLTISSLQAEDFATYYC | 15 | Anti-CD22 scFv | light chain |
| QQSYSIPQT | 16 | Anti-CD22 scFv | light chain: CDR3 |
| FGQGTKLEIK | 17 | Anti-CD22 scFv | light chain |
| GGGGCGGGGSGGGGS | 85 | Linker | Linker 3D |
| EVKLQESGPGLVAPSQSLSVTCTVS | 31 | Anti-CD19 scFv | heavy chain |
| GVSLPDYG | 32 | Anti-CD19 scFv | heavy chain: CDR1 |
| VSWIRQPPRKGLEWLGV | 33 | Anti-CD19 scFv | heavy chain |
| IWGSETT | 34 | Anti-CD19 scFv | heavy chain: CDR2 |
| YYNSALKSRLTIIKDNSKSQVFLKMNSLQTDDTAIYYC | 35 | Anti-CD19 scFv | heavy chain |
| AKHYYYGGSYAMDY | 36 | Anti-CD19 scFv | heavy chain: CDR3 |
| WGQGTSVTVSS | 37 | Anti-CD19 scFv | heavy chain |
| SGTTTPAPRPPTPAPTIASQPLSLRPEACRPAAGGAVHTRGLDFACD | 18 | CD8 | CD8alpha hinge |
| IYIWAPLAGTCGVLLLSLVITLYC | 19 | CD8 | CD8alpha transmembrane domain |
| KRGRKKLLYIFKQPFMRPVQTTQEEDGCSCRFPEEEEGGCEL | 20 | 4-1BB | intracellular domain |
| RVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR* | 21 | CD3 zeta | intracellular domain |

TABLE 16

Loop CAR 6 Construct

| Sequence | SEQ ID NO: | Segment | Notes |
|---|---|---|---|
| M | 1 | | start methionine |
| LLLVTSLLLCELPHPAFLLIP | 2 | | signal peptide |
| DIQMTQTTSSLSASLGDRVTISCRAS | 23 | Anti-CD19 scFv | Light chain |
| QDISKY | 24 | Anti-CD19 scFv | light chain: CDR1 |
| LNWYQQKPDGTVKLLIY | 25 | Anti-CD19 scFv | light chain |
| HTS | 26 | Anti-CD19 scFv | light chain: CDR2 |
| RLHSGVPSRFSGSGSGTDYSLTISNLEQEDIATYFC | 27 | Anti-CD19 scFv | light chain |
| QQGNTLPYT | 28 | Anti-CD19 scFv | light chain: CDR3 |
| FGGGTKLEIT | 29 | Anti-CD19 scFv | light chain |
| GGGGS | 10 | Linker | Linker 1 |
| QVQLQQSGPGLVKPSQTLSLTCAIS | 3 | Anti-CD22 scFv | heavy chain |
| GDSVSSNSAA | 4 | Anti-CD22 scFv | heavy chain: CDR1 |
| WNWIRQSPSRGLEWLGR | 5 | Anti-CD22 scFv | heavy chain |
| TYYRSKWYN | 6 | Anti-CD22 scFv | heavy chain: CDR2 |
| DYAVSVKSRITINPDTSKNQFSLQLNSVTPEDTAVYYC | 7 | Anti-CD22 scFv | heavy chain |
| AREVTGDLEDAFDI | 8 | Anti-CD22 scFv | heavy chain: CDR3 |
| WGQGTMVTVSS | 9 | Anti-CD22 scFv | heavy chain |
| GSTSGSGKPGSGEGSTKG | 30 | Anti-CD22 scFv | Linker 6 |
| DIQMTQSPSSLSASVGDRVTITCRAS | 11 | Anti-CD22 scFv | light chain |
| QTIWSY | 12 | Anti-CD22 scFv | light chain: CDR1 |
| LNWYQQRPGKAPNLLIY | 13 | Anti-CD22 scFv | light chain |
| AAS | 14 | Anti-CD22 scFv | light chain: CDR2 |
| SLQSGVPSRFSGRGSGTDFTLTISSLQAEDFATYYC | 15 | Anti-CD22 scFv | light chain |
| QQSYSIPQT | 16 | Anti-CD22 scFv | light chain: CDR3 |
| FGQGTKLEIK | 17 | Anti-CD22 scFv | light chain |
| GGGGS | 10 | Linker | Linker 1 |
| EVKLQESGPGLVAPSQSLSVTCTVS | 31 | Anti-CD19 scFv | heavy chain |
| GVSLPDYG | 32 | Anti-CD19 scFv | heavy chain: CDR1 |
| VSWIRQPPRKGLEWLGV | 33 | Anti-CD19 scFv | heavy chain |
| IWGSETT | 34 | Anti-CD19 scFv | heavy chain: CDR2 |
| YYNSALKSRLTIIKDNSKSQVFLKMNSLQTDDTAIYYC | 35 | Anti-CD19 scFv | heavy chain |
| AKHYYYGGSYAMDY | 36 | Anti-CD19 scFv | heavy chain: CDR3 |
| WGQGTSVTVSS | 37 | Anti-CD19 scFv | heavy chain |

TABLE 16-continued

Loop CAR 6 Construct

| Sequence | SEQ ID NO: | Segment | Notes |
|---|---|---|---|
| SGTTTPAPRPPTPAPTIASQPL SLRPEACRPAAGGAVHTRGL DFACD | 18 | CD8 | CD8alpha hinge |
| IYIWAPLAGTCGVLLLSLVIT LYC | 19 | CD8 | CD8alpha transmembrane domain |
| KRGRKKLLYIFKQPFMRPVQ TTQEEDGCSCRFPEEEEGGC EL | 20 | 4-1BB | intracellular domain |
| RVKFSRSADAPAYQQGQNQ LYNELNLGRREEYDVLDKR RGRDPEMGGKPRRKNPQEG LYNELQKDKMAEAYSEIGM KGERRRGKGHDGLYQGLST ATKDTYDALHMQALPPR* | 21 | CD3 zeta | intracellular domain |

In an embodiment, the CAR construct (herein denoted V1) has the sequence:

(SEQ ID NO: 48)
MLLLVTSLLLCELPHPAFLLIPQVQLQQSGPGLVKPSQTLSLTCAISGDS
VSSNSAAWNWIRQSPSRGLEWLGRTYYRSKWYNDYAVSVKSRITINPDTS
KNQFSLQLNSVTPEDTAVYYCAREVTGDLEDAFDIWGQGTMVTVSSGGGG
SDIQMTQSPSSLSASVGDRVTITCRASQTIWSYLNWYQQRPGKAPNLLIY
AASSLQSGVPSRFSGRGSGTDFTLTISSLQAEDFATYYCQQSYSIPQTFG
QGTKLEIKTSTTTPAPRPPTPAPTIASQPLSLRPEACRPAAGGAVHTRGL
DFACDIYIWAPLAGTCGVLLLSLVITLYCKRGRKKLLYIFKQPFMRPVQT
TQEEDGCSCRFPEEEEGGCELRVKFSRSADAPAYQQGQNQLYNELNLGRR
EEYDVLDKRRGRDPEMGGKPRRKNPQEGLYNELQKDKMAEAYSEIGMKGE
RRRGKGHDGLYQGLSTATKDTYDALHMQALPPRGSGEGRGSLLTCGDVEE
NPGPRMLLLVTSLLLCELPHPAFLLIPDIQMTQTTSSLSASLGDRVTISC
RASQDISKYLNWYQQKPDGTVKLLIYHTSRLHSGVPSRFSGSGSGTDYSL
TISNLEQEDIATYFCQQGNTLPYTFGGGTKLEITGSTSGSGKPGSGEGST
KGEVKLQESGPGLVAPSQSLSVTCTVSGVSLPDYGVSWIRQPPRKGLEWL
GVIWGSETTYYNSALKSRLTIIKDNSKSQVFLKMNSLQTDDTAIYYCAKH
YYYGGSYAMDYWGQGTSVTVSSSGTTTPAPRPPTPAPTIASQPLSLRPEA
CRPAAGGAVHTRGLDFACDIYIWAPLAGTCGVLLLSLVITLYCKRGRKKL
LYIFKQPFMRPVQTTQEEDGCSCRFPEEEEGGCELRVKFSRSADAPAYQQ
GQNQLYNELNLGRREEYDVLDKRRGRDPEMGGKPRRKNPQEGLYNELQKD
KMAEAYSEIGMKGERRRGKGHDGLYQGLSTATKDTYDALHMQALPPR.

In an embodiment, the CAR construct (herein denoted V5) has the sequence:

(SEQ ID NO: 49)
MALPVTALLLPLALLLHAARPQVQLQQSGPGLVKPSQTLSLTCAISGDSV
SSNSAAWNWIRQSPSRGLEWLGRTYYRSKWYNDYAVSVKSRITINPDTSK
NQFSLQLNSVTPEDTAVYYCAREVTGDLEDAFDIWGQGTMVTVSSGGGS
DIQMTQSPSSLSASVGDRVTITCRASQTIWSYLNWYQQRPGKAPNLLIYA
ASSLQSGVPSRFSGRGSGTDFTLTISSLQAEDFATYYCQQSYSIPQTFGQ
GTKLEIKSGTTTPAPRPPTPAPTIASQPLSLRPEACRPAAGGAVHTRGLD
FACDIYIWAPLAGTCGVLLLSLVITLYCKRGRKKLLYIFKQPFMRPVQTT
QEEDGCSCRFPEEEEGGCELRVKFSRSADAPAYQQGQNQLYNELNLGRRE
EYDVLDKRRGRDPEMGGKPRRKNPQEGLYNELQKDKMAEAYSEIGMKGER
RRGKGHDGLYQGLSTATKDTYDALHMQALPPRRKRRGSGTPDPWGSGATN
FSLLKQAGDVEENPGPLEMEFGLSWLFLVAILKGVQCSRDIQMTQTTSSL
SASLGDRVTISCRASQDISKYLNWYQQKPDGTVKLLIYHTSRLHSGVPSR
FSGSGSGTDYSLTISNLEQEDIATYFCQQGNTLPYTFGGGTKLEITGSTS
GSGKPGSGEGSTKGEVKLQESGPGLVAPSQSLSVTCTVSGVSLPDYGVSW
IRQPPRKGLEWLGVIWGSETTYYNSALKSRLTIIKDNSKSQVFLKMNSLQ
TDDTAIYYCAKHYYYGGSYAMDYWGQGTSVTVSSTSAAAIEVMYPPPYLD
NEKSNGTIIHVKGKHLCPSPLFPGPSKPFWVLVVVGGVLACYSLLVTVAF
IIFWVRSKRSRLLHSDYMNMTPRRPGPTRKHYQPYAPPRDFAAYRSVKF
SRSADAPAYQQGQNQLYNELNLGRREEYDVLDKRRGRDPEMGGKPRRKNP
QEGLYNELQKDKMAEAYSEIGMKGERRRGKGHDGLYQGLSTATKDTYDAL
HMQALPPR.

In an embodiment, the CAR construct (herein denoted V6) has the sequence:

(SEQ ID NO: 50)
MALPVTALLLPLALLLHAARPQVQLQQSGPGLVKPSQTLSLTCAISGDSV
SSNSAAWNWIRQSPSRGLEWLGRTYYRSKWYNDYAVSVKSRITINPDTSK
NQFSLQLNSVTPEDTAVYYCAREVTGDLEDAFDIWGQGTMVTVSSGGGGS
DIQMTQSPSSLSASVGDRVTITCRASQTIWSYLNWYQQRPGKAPNLLIYA

ASSLQSGVPSRFSGRGSGTDFTLTISSLQAEDFATYYCQQSYSIPQTFGQ

GTKLEIKSGAAAIEVMYPPPYLDNEKSNGTIIHVKGKHLCPSPLFPGPSK

PFWVLVVVGGVLACYSLLVTVAFIIFWVRSKRSRLLHSDYMNMTPRRPGP

TRKHYQPYAPPRDFAAYRSRVKFSRSADAPAYQQGQNQLYNELNLGRREE

YDVLDKRRGRDPEMGGKPRRKNPQEGLYNELQKDKMAEAYSEIGMKGERR

RGKGHDGLYQGLSTATKDTYDALHMQALPPRRKRRGSGTPDPWGSGATNF

SLLKQAGDVEENPGPLEMEFGLSWLFLVAILKGVQCSRDIQMTQTTSSLS

ASLGDRVTISCRASQDISKYLNWYQQKPDGTVKLLIYHTSRLHSGVPSRF

SGSGSGTDYSLTISNLEQEDIATYFCQQGNTLPYTFGGGTKLEITGSTSG

SGKPGSGEGSTKGEVKLQESGPGLVAPSQSLSVTCTVSGVSLPDYGVSWI

RQPPRKGLEWLGVIWGSETTYYNSALKSRLTIIKDNSKSQVFLKMNSLQT

DDTAIYYCAKHYYYGGSYAMDYWGQGTSVTVSSTSTTTPAPRPPTPAPTI

ASQPLSLRPEACRPAAGGAVHTRGLDFACDIYIWAPLAGTCGVLLLSLVI

TLYCKRGRKKLLYIFKQPFMRPVQTTQEEDGCSCRFPEEEEGGCELRVKF

SRSADAPAYQQGQNQLYNELNLGRREEYDVLDKRRGRDPEMGGKPRRKNP

QEGLYNELQKDKMAEAYSEIGMKGERRRGKGHDGLYQGLSTATKDTYDAL

HMQALPPR.

In an embodiment, the CAR construct (herein denoted V7) has the sequence:

```
                                              (SEQ ID NO: 51)
MALPVTALLLPLALLLHAARPQVQLQQSGPGLVKPSQTLSLTCAISGDSV

SSNSAAWNWIRQSPSRGLEWLGRTYYRSKWYNDYAVSVKSRITINPDTSK

NQFSLQLNSVTPEDTAVYYCAREVTGDLEDAFDIWGQGTMVTVSSGGGGS

DIQMTQSPSSLSASVGDRVTITCRASQTIWSYLNWYQQRPGKAPNLLIYA

ASSLQSGVPSRFSGRGSGTDFTLTISSLQAEDFATYYCQQSYSIPQTFGQ

GTKLEIKSGTTTPAPRPPTPAPTIASQPLSLRPEACRPAAGGAVHTRGLD

FACDIYIWAPLAGTCGVLLLSLVITLYCKRGRKKLLYIFKQPFMRPVQTT

QEEDGCSCRFPEEEEGGCELRVKFSRSADAPAYQQGQNQLYNELNLGRRE

EYDVLDKRRGRDPEMGGKPRRKNPQEGLYNELQKDKMAEAYSEIGMKGER

RRGKGHDGLYQGLSTATKDTYDALHMQALPPRRKRRGSGTPDPWGSGATN

FSLLKQAGDVEENPGPLEMEFGLSWLFLVAILKGVQCSRDIQMTQTTSSL

SASLGDRVTISCRASQDISKYLNWYQQKPDGTVKLLIYHTSRLHSGVPSR

FSGSGSGTDYSLTISNLEQEDIATYFCQQGNTLPYTFGGGTKLEITGSTS

GSGKPGSGEGSTKGEVKLQESGPGLVAPSQSLSVTCTVSGVSLPDYGVSW

IRQPPRKGLEWLGVIWGSETTYYNSALKSRLTIIKDNSKSQVFLKMNSLQ

TDDTAIYYCAKHYYYGGSYAMDYWGQGTSVTVSSTSTTTPAPRPPTPAPT

IASQPLSLRPEACRPAAGGAVHTRGLDFACDIYIWAPLAGTCGVLLLSLV

ITLYCKRGRKKLLYIFKQPFMRPVQTTQEEDGCSCRFPEEEEGGCELRVK

FSRSADAPAYQQGQNQLYNELNLGRREEYDVLDKRRGRDPEMGGKPRRKN
```

PQEGLYNELQKDKMAEAYSEIGMKGERRRGKGHDGLYQGLSTATKDTYDA

LHMQALPPR.

In an embodiment, the CAR construct (herein denoted V8) has the sequence:

```
                                              (SEQ ID NO: 52)
MALPVTALLLPLALLLHAARPQVQLQQSGPGLVKPSQTLSLTCAISGDSV

SSNSAAWNWIRQSPSRGLEWLGRTYYRSKWYNDYAVSVKSRITINPDTSK

NQFSLQLNSVTPEDTAVYYCAREVTGDLEDAFDIWGQGTMVTVSSGGGGS

DIQMTQSPSSLSASVGDRVTITCRASQTIWSYLNWYQQRPGKAPNLLIYA

ASSLQSGVPSRFSGRGSGTDFTLTISSLQAEDFATYYCQQSYSIPQTFGQ

GTKLEIKSGAAAIEVMYPPPYLDNEKSNGTIIHVKGKHLCPSPLFPGPSK

PFWVLVVVGGVLACYSLLVTVAFIIFWVRSKRSRLLHSDYMNMTPRRPGP

TRKHYQPYAPPRDFAAYRSRVKFSRSADAPAYQQGQNQLYNELNLGRREE

YDVLDKRRGRDPEMGGKPRRKNPQEGLYNELQKDKMAEAYSEIGMKGERR

RGKGHDGLYQGLSTATKDTYDALHMQALPPRRKRRGSGTPDPWGSGATNF

SLLKQAGDVEENPGPLEMEFGLSWLFLVAILKGVQCSRDIQMTQTTSSLS

ASLGDRVTISCRASQDISKYLNWYQQKPDGTVKLLIYHTSRLHSGVPSRF

SGSGSGTDYSLTISNLEQEDIATYFCQQGNTLPYTFGGGTKLEITGSTSG

SGKPGSGEGSTKGEVKLQESGPGLVAPSQSLSVTCTVSGVSLPDYGVSWI

RQPPRKGLEWLGVIWGSETTYYNSALKSRLTIIKDNSKSQVFLKMNSLQT

DDTAIYYCAKHYYYGGSYAMDYWGQGTSVTVSSTSAAAIEVMYPPPYLDN

EKSNGTIIHVKGKHLCPSPLFPGPSKPFWVLVVVGGVLACYSLLVTVAFI

IFWVRSKRSRLLHSDYMNMTPRRPGPTRKHYQPYAPPRDFAAYRSRVKFS

RSADAPAYQQGQNQLYNELNLGRREEYDVLDKRRGRDPEMGGKPRRKNPQ

EGLYNELQKDKMAEAYSEIGMKGERRRGKGHDGLYQGLSTATKDTYDALH

MQALPPR.
```

In an embodiment, the CAR construct (herein denoted TanCAR2) has the sequence:

```
                                              (SEQ ID NO: 63)
MLLLVTSLLLCELPHPAFLLIPDIQMTQTTSSLSASLGDRVTISCRASQD

ISKYLNWYQQKPDGTVKLLIYHTSRLHSGVPSRFSGSGSGTDYSLTISNL

EQEDIATYFCQQGNTLPYTFGGGTKLEITGSTSGSGKPGSGEGSTKGEVK

LQESGPGLVAPSQSLSVTCTVSGVSLPDYGVSWIRQPPRKGLEWLGVIWG

SETTYYNSALKSRLTIIKDNSKSQVFLKMNSLQTDDTAIYYCAKHYYYGG

SYAMDYWGQGTSVTVSSGGGGSGGGGSGGGGSGGGGSGGGGSQVQLQQSG

PGLVKPSQTLSLTCAISGDSVSSNSAAWNWIRQSPSRGLEWLGRTYYRSK

WYNDYAVSVKSRITINPDTSKNQFSLQLNSVTPEDTAVYYCAREVTGDLE

DAFDIWGQGTMVTVSSGGGGSDIQMTQSPSSLSASVGDRVTITCRASQTI

WSYLNWYQQRPGKAPNLLIYAASSLQSGVPSRFSGRGSGTDFTLTISSLQ

AEDFATYYCQQSYSIPQTFGQGTKLEIKTTTPAPRPPTPAPTIASQPLSL
```

-continued
RPEACRPAAGGAVHTRGLDFACDIYIWAPLAGTCGVLLLSLVITLYCKRG
RKKLLYIFKQPFMRPVQTTQEEDGCSCRFPEEEEGGCELRVKFSRSADAP
AYKQGQNQLYNELNLGRREEYDVLDKRRGRDPEMGGKPRRKNPQEGLYNE
LQKDKMAEAYSEIGMKGERRRGKGHDGLYQGLSTATKDTYDALHMQALPP
R.

In an embodiment, the CAR construct (herein denoted TanCAR3) has the sequence:

(SEQ ID NO: 64)
MLLLVTSLLLCELPHPAFLLIPQVQLQQSGPGLVKPSQTLSLTCAISGDS
VSSNSAAWNWIRQSPSRGLEWLGRTYYRSKWYNDYAVSVKSRITINPDTS
KNQFSLQLNSVTPEDTAVYYCAREVTGDLEDAFDIWGQGTMVTVSSGSTS
GSGKPGSGEGSTKGDIQMTQSPSSLSASVGDRVTITCRASQTIWSYLNWY
QQRPGKAPNLLIYAASSLQSGVPSRFSGRGSGTDFTLTISSLQAEDFATY
YCQQSYSIPQTFGQGTKLEIKGGGGSGGGGSGGGGSGGGGSGGGGSDIQM
TQTTSSLSASLGDRVTISCRASQDISKYLNWYQQKPDGTVKLLIYHTSRL
HSGVPSRFSGSGSGTDYSLTISNLEQEDIATYFCQQGNTLPYTFGGGTKL
EITGSTSGSGKPGSGEGSTKGEVKLQESGPGLVAPSQSLSVTCTVSGVSL
PDYGVSWIRQPPRKGLEWLGVIWGSETTYYNSALKSRLTIIKDNSKSQVF
LKMNSLQTDDTAIYYCAKHYYYGGSYAMDYWGQGTSVTVSSSGTTTPAPR
PPTPAPTIASQPLSLRPEACRPAAGGAVHTRGLDFACDIYIWAPLAGTCG
VLLLSLVITLYCKRGRKKLLYIFKQPFMRPVQTTQEEDGCSCRFPEEEEG
GCELRVKFSRSADAPAYQQGQNQLYNELNLGRREEYDVLDKRRGRDPEMG
GKPRRKNPQEGLYNELQKDKMAEAYSEIGMKGERRRGKGHDGLYQGLSTA
TKDTYDALHMQALPPR.

In an embodiment, the CAR construct (herein denoted TanCAR4) has the sequence:

(SEQ ID NO: 65)
MALPVTALLLPLALLLHAARPQVQLQQSGPGLVKPSQTLSLTCAISGDSV
SSNSAAWNWIRQSPSRGLEWLGRTYYRSKWYNDYAVSVKSRITINPDTSK
NQFSLQLNSVTPEDTAVYYCAREVTGDLEDAFDIWGQGTMVTVSSGGGGS
DIQMTQSPSSLSASVGDRVTITCRASQTIWSYLNWYQQRPGKAPNLLIYA
ASSLQSGVPSRFSGRGSGTDFTLTISSLQAEDFATYYCQQSYSIPQTFGQ
GTKLEIKGGGGSGGGGSGGGGSGGGGSDIQMTQTTSSLSASLGDRVTISC
RASQDISKYLNWYQQKPDGTVKLLIYHTSRLHSGVPSRFSGSGSGTDYSL
TISNLEQEDIATYFCQQGNTLPYTFGGGTKLEITGSTSGSGKPGSGEGST
KGEVKLQESGPGLVAPSQSLSVTCTVSGVSLPDYGVSWIRQPPRKGLEWL
GVIWGSETTYYNSALKSRLTIIKDNSKSQVFLKMNSLQTDDTAIYYCAKH
YYYGGSYAMDYWGQGTSVTVSSTSSGTTTPAPRPPTPAPTIASQPLSLRP
EACRPAAGGAVHTRGLDFACDIYIWAPLAGTCGVLLLSLVITLYCKRGRK
KLLYIFKQPFMRPVQTTQEEDGCSCRFPEEEEGGCELRVKFSRSADAPAY

QQGQNQLYNELNLGRREEYDVLDKRRGRDPEMGGKPRRKNPQEGLYNELQ
KDKMAEAYSEIGMKGERRRGKGHDGLYQGLSTATKDTYDALHMQALPPR.

In an embodiment, the CAR construct (herein denoted LoopCAR1) has the sequence:

(SEQ ID NO: 66)
ATMLLLVTSLLLCELPHPAFLLIPDIQMTQTTSSLSASLGDRVTISCRAS
QDISKYLNWYQQKPDGTVKLLIYHTSRLHSGVPSRFSGSGSGTDYSLTIS
NLEQEDIATYFCQQGNTLPYTFGGGTKLEITGGGGSGGGGSGGGGSQVQL
QQSGPGLVKPSQTLSLTCAISGDSVSSNSAAWNWIRQSPSRGLEWLGRTY
YRSKWYNDYAVSVKSRITINPDTSKNQFSLQLNSVTPEDTAVYYCAREVT
GDLEDAFDIWGQGTMVTVSSGGGGSDIQMTQSPSSLSASVGDRVTITCRA
SQTIWSYLNWYQQRPGKAPNLLIYAASSLQSGVPSRFSGRGSGTDFTLTI
SSLQAEDFATYYCQQSYSIPQTFGQGTKLEIKGGGGSGGGGSGGGGSEVK
LQESGPGLVAPSQSLSVTCTVSGVSLPDYGVSWIRQPPRKGLEWLGVIWG
SETTYYNSALKSRLTIIKDNSKSQVFLKMNSLQTDDTAIYYCAKHYYYGG
SYAMDYWGQGTSVTVSSSGTTTPAPRPPTPAPTIASQPLSLRPEACRPAA
GGAVHTRGLDFACDIYIWAPLAGTCGVLLLSLVITLYCKRGRKKLLYIFK
QPFMRPVQTTQEEDGCSCRFPEEEEGGCELRVKFSRSADAPAYQQGQNQL
YNELNLGRREEYDVLDKRRGRDPEMGGKPRRKNPQEGLYNELQKDKMAEA
YSEIGMKGERRRGKGHDGLYQGLSTATKDTYDALHMQALPPR.

In an embodiment, the CAR construct (herein denoted LoopCAR2) has the sequence:

(SEQ ID NO: 67)
ATMLLLVTSLLLCELPHPAFLLIPDIQMTQTTSSLSASLGDRVTISCRAS
QDISKYLNWYQQKPDGTVKLLIYHTSRLHSGVPSRFSGSGSGTDYSLTIS
NLEQEDIATYFCQQGNTLPYTFGGGTKLEITGGCGSGGGGSGGGGSQVQL
QQSGPGLVKPSQTLSLTCAISGDSVSSNSAAWNWIRQSPSRGLEWLGRTY
YRSKWYNDYAVSVKSRITINPDTSKNQFSLQLNSVTPEDTAVYYCAREVT
GDLEDAFDIWGQGTMVTVSSGSTSGSGKPGSGEGSTKGDIQMTQSPSSLS
ASVGDRVTITCRASQTIWSYLNWYQQRPGKAPNLLIYAASSLQSGVPSRF
SGRGSGTDFTLTISSLQAEDFATYYCQQSYSIPQTFGQGTKLEIKGGGGS
GGGGSGGCGSEVKLQESGPGLVAPSQSLSVTCTVSGVSLPDYGVSWIRQP
PRKGLEWLGVIWGSETTYYNSALKSRLTIIKDNSKSQVFLKMNSLQTDDT
AIYYCAKHYYYGGSYAMDYWGQGTSVTVSSSGTTTPAPRPPTPAPTIASQ
PLSLRPEACRPAAGGAVHTRGLDFACDIYIWAPLAGTCGVLLLSLVITLY
CKRGRKKLLYIFKQPFMRPVQTTQEEDGCSCRFPEEEEGGCELRVKFSRS
ADAPAYQQGQNQLYNELNLGRREEYDVLDKRRGRDPEMGGKPRRKNPQEG
LYNELQKDKMAEAYSEIGMKGERRRGKGHDGLYQGLSTATKDTYDALHMQ
ALPPR.

In an embodiment, the CAR construct (herein denoted LoopCAR3) has the sequence:

(SEQ ID NO: 68)
MALPVTALLLPLALLLHAARPDIQMTQTTSSLSASLGDRVTISCRASQDI

SKYLNWYQQKPDGTVKLLIYHTSRLHSGVPSRFSGSGSGTDYSLTISNLE

QEDIATYFCQQGNTLPYTFGGGTKLEITGGGGSGGGGSQVQLQQSGPGLV

KPSQTLSLTCAISGDSVSSNSAAWNWIRQSPSRGLEWLGRTYYRSKWYND

YAVSVKSRITINPDTSKNQFSLQLNSVTPEDTAVYYCAREVTGDLEDAFD

IWGQGTMVTVSSGSTSGSGKPGSGEGSTKGDIQMTQSPSSLSASVGDRVT

ITCRASQTIWSYLNWYQQRPGKAPNLLIYAASSLQSGVPSRFSGRGSGTD

FTLTISSLQAEDFATYYCQQSYSIPQTFGQGTKLEIKGGGGSGGGGSEVK

LQESGPGLVAPSQSLSVTCTVSGVSLPDYGVSWIRQPPRKGLEWLGVIWG

SETTYYNSALKSRLTIIKDNSKSQVFLKMNSLQTDDTAIYYCAKHYYYGG

SYAMDYWGQGTSVTVSSTSSGTTTPAPRPPTPAPTIASQPLSLRPEACRP

AAGGAVHTRGLDFACDIYIWAPLAGTCGVLLLSLVITLYCKRGRKKLLYI

FKQPFMRPVQTTQEEDGCSCRFPEEEEGGCELRVKFSRSADAPAYKQGQN

QLYNELNLGRREEYDVLDKRRGRDPEMGGKPRRKNPQEGLYNELQKDKMA

EAYSEIGMKGERRRGKGHDGLYQGLSTATKDTYDALHMQALPPR.

In an embodiment, the CAR construct (herein denoted LoopCAR4) has the sequence:

(SEQ ID NO: 69)
MLLLVTSLLLCELPHPAFLLIPQVQLQQSGPGLVKPSQTLSLTCAISGDS

VSSNSAAWNWIRQSPSRGLEWLGRTYYRSKWYNDYAVSVKSRITINPDTS

KNQFSLQLNSVTPEDTAVYYCAREVTGDLEDAFDIWGQGTMVTVSSGGGG

SGGGGSDIQMTQTTSSLSASLGDRVTISCRASQDISKYLNWYQQKPDGTV

KLLIYHTSRLHSGVPSRFSGSGSGTDYSLTISNLEQEDIATYFCQQGNTL

PYTFGGGTKLEITGSTSGSGKPGSGEGSTKGEVKLQESGPGLVAPSQSLS

VTCTVSGVSLPDYGVSWIRQPPRKGLEWLGVIWGSETTYYNSALKSRLTI

IKDNSKSQVFLKMNSLQTDDTAIYYCAKHYYYGGSYAMDYWGQGTSVTVS

SGGGGSGGGGSDIQMTQSPSSLSASVGDRVTITCRASQTIWSYLNWYQQR

PGKAPNLLIYAASSLQSGVPSRFSGRGSGTDFTLTISSLQAEDFATYYCQ

QSYSIPQTFGQGTKLEIKTSSGTTTPAPRPPTPAPTIASQPLSLRPEACR

PAAGGAVHTRGLDFACDIYIWAPLAGTCGVLLLSLVITLYCKRGRKKLLY

IFKQPFMRPVQTTQEEDGSCRFPEEEEGGCELRVKFSRSADAPAYKQGQN

QLYNELNLGRREEYDVLDKRRGRDPEMGGKPRRKNPQEGLYNELQKDKMA

EAYSEIGMKGERRRGKGHDGLYQGLSTATKDTYDALHMQALPPR.

In an embodiment, the CAR construct (herein denoted LoopCAR5) has the sequence:

(SEQ ID NO: 70)
MLLLVTSLLLCELPHPAFLLIPDIQMTQTTSSLSASLGDRVTISCRASQD

ISKYLNWYQQKPDGTVKLLIYHTSRLHSGVPSRFSGSGSGTDYSLTISNL

EQEDIATYFCQQGNTLPYTFGGGTKLEITGGGGSGGGGSCGGGSQVQLQQ

SGPGLVKPSQTLSLTCAISGDSVSSNSAAWNWIRQSPSRGLEWLGRTYYR

-continued

SKWYNDYAVSVKSRITINPDTSKNQFSLQLNSVTPEDTAVYYCAREVTGD

LEDAFDIWGQGTMVTVSSGGGGSGGGGSDIQMTQSPSSLSASVGDRVTIT

CRASQTIWSYLNWYQQRPGKAPNLLIYAASSLQSGVPSRFSGRGSGTDFT

LTISSLQAEDFATYYCQQSYSIPQTFGQGTKLEIKGGGGCGGGGSGGGGS

EVKLQESGPGLVAPSQSLSVTCTVSGVSLPDYGVSWIRQPPRKGLEWLGV

IWGSETTYYNSALKSRLTIIKDNSKSQVFLKMNSLQTDDTAIYYCAKHYY

YGGSYAMDYWGQGTSVTVSSTSSGTTTPAPRPPTPAPTIASQPLSLRPEA

CRPAAGGAVHTRGLDFACDIYIWAPLAGTCGVLLLSLVITLYCKRGRKKL

LYIFKQPFMRPVQTTQEEDGCSCRFPEEEEGGCELRVKFSRSADAPAYKQ

GQNQLYNELNLGRREEYDVLDKRRGRDPEMGGKPRRKNPQEGLYNELQKD

KMAEAYSEIGMKGERRRGKGHDGLYQGLSTATKDTYDALHMQALPPR.

The inventive CAR constructs may provide many advantages. In an embodiment of the invention, for example, the inventive CAR constructs may, advantageously, reduce or prevent cancer cell escape due to loss of expression of one antigen, e.g., CD19 or CD22, by the cancer cell. For example, it is believed that the inventive CAR constructs may reduce or prevent relapses that have been observed in cancer patients following treatment with a CAR having antigenic specificity for only CD19 or CD22 and whose cancer has lost expression of that antigen. Also, the inventive CAR constructs may also be advantageous for treating patients who have heterogeneous level of expression of CD19 or CD22. The inventive CAR constructs may also increase the patient population that may be successfully treated. For example, a patient that may fail to respond to a CAR therapy that targets only CD19 may respond to a CAR therapy that targets CD22, and a patient that may fail to respond to a CAR therapy that targets only CD22 may respond to a CAR therapy that targets CD19. Additionally, regarding the inventive cleavable CARs, co-transduction of T cells using two vectors, each having a single CAR, provides only a low percentage of cells expressing both CARs and substantial numbers of T cells expressing one or the other CAR only; an advantage of using the inventive cleavable CAR constructs is that there may be equal or substantially equal expression of each CAR in each T cell that successfully integrates the construct. Moreover, by targeting both CD19 and CD22, the inventive cleavable and non-cleavable CAR constructs may, advantageously, provide synergistic responses as compared to therapies which target only a single antigen, and may also provide a more broadly active therapy to patients with heterogeneous expression of one or both of CD19 and CD22 on cancer cells.

Thus, without being bound to a particular theory or mechanism, it is believed that by eliciting an antigen-specific response against two antigens, e.g., CD22 and CD19, the inventive CAR constructs provide for one or more of any of the following: targeting and destroying CD22-expressing cancer cells, targeting and destroying CD19-expressing cancer cells, reducing or eliminating cancer cells, facilitating infiltration of immune cells to tumor site(s), and enhancing/extending anti-cancer responses.

Included in the scope of the invention are functional portions of the inventive CAR constructs described herein. The term "functional portion" when used in reference to a CAR refers to any part or fragment of the CAR constructs of the invention, which part or fragment retains the biological activity of the CAR construct of which it is a part (the parent CAR construct). Functional portions encompass, for example, those parts of a CAR construct that retain the ability to recognize target cells, or detect, treat, or prevent cancer, to a similar extent, the same extent, or to a higher extent, as the parent CAR construct. In reference to the parent CAR construct, the functional portion can comprise, for instance, about 10%, about 25%, about 30%, about 50%, about 68%, about 80%, about 90%, about 95%, or more, of the parent CAR.

The functional portion can comprise additional amino acids at the amino or carboxy terminus of the portion, or at both termini, which additional amino acids are not found in the amino acid sequence of the parent CAR construct. Desirably, the additional amino acids do not interfere with the biological function of the functional portion, e.g., recognize target cells, detect cancer, treat or prevent cancer, etc. More desirably, the additional amino acids enhance the biological activity as compared to the biological activity of the parent CAR construct.

Included in the scope of the invention are functional variants of the inventive CAR constructs described herein. The term "functional variant," as used herein, refers to a CAR construct, polypeptide, or protein having substantial or significant sequence identity or similarity to a parent CAR construct, which functional variant retains the biological activity of the CAR of which it is a variant. Functional variants encompass, for example, those variants of the CAR construct described herein (the parent CAR construct) that retain the ability to recognize target cells to a similar extent, the same extent, or to a higher extent, as the parent CAR construct. In reference to the parent CAR construct, the functional variant can, for instance, be at least about 30%, about 50%, about 75%, about 80%, about 90%, about 91%, about 92%, about 93%, about 94%, about 95%, about 96%, about 97%, about 98%, about 99% or more identical in amino acid sequence to the parent CAR construct.

A functional variant can, for example, comprise the amino acid sequence of the parent CAR with at least one conservative amino acid substitution. Alternatively or additionally, the functional variants can comprise the amino acid sequence of the parent CAR construct with at least one non-conservative amino acid substitution. In this case, it is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to the parent CAR construct.

Amino acid substitutions of the inventive CAR constructs are preferably conservative amino acid substitutions. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic/negatively charged polar amino acid substituted for another acidic/negatively charged polar amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Cys, Val, etc.), a basic/positively charged polar amino acid substituted for another basic/positively charged polar amino acid (e.g. Lys, His, Arg, etc.), an uncharged amino acid with a polar side chain substituted for another uncharged amino acid with a polar side chain (e.g., Asn, Gln, Ser, Thr, Tyr, etc.), an amino acid with a beta-branched side-chain substituted for another amino acid with a beta-branched side-chain (e.g., Ile, Thr, and Val), an amino acid with an aromatic side-chain substituted for another amino acid with an aromatic side chain (e.g., His, Phe, Trp, and Tyr), etc.

The CAR construct can consist essentially of the specified amino acid sequence or sequences described herein, such that other components, e.g., other amino acids, do not materially change the biological activity of the functional variant.

The CAR constructs of embodiments of the invention (including functional portions and functional variants) can be of any length, i.e., can comprise any number of amino acids, provided that the CAR constructs (or functional portions or functional variants thereof) retain their biological activity, e.g., the ability to specifically bind to antigen, detect diseased cells in a mammal, or treat or prevent disease in a mammal, etc. For example, the CAR can be about 50 to about 5000 amino acids long, such as 50, 70, 75, 100, 125, 150, 175, 200, 300, 400, 500, 600, 700, 800, 900, 1000 or more amino acids in length.

The CAR constructs of embodiments of the invention (including functional portions and functional variants of the invention) can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

The CAR constructs of embodiments of the invention (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

The CAR constructs of embodiments of the invention (including functional portions and functional variants thereof) can be obtained by methods known in the art. The CAR constructs may be made by any suitable method of making polypeptides or proteins, including de novo synthesis. Also, the CAR constructs can be recombinantly produced using the nucleic acids described herein using standard recombinant methods. See, for instance, Green et al., *Molecular Cloning: A Laboratory Manual,* 4th ed., Cold Spring Harbor Press, Cold Spring Harbor, NY 2012. Further, portions of some of the CAR constructs of the invention (including functional portions and functional variants thereof) can be isolated and/or purified from a source, such as a plant, a bacterium, an insect, a mammal, e.g., a rat, a human, etc. Methods of isolation and purification are well-known in the art. Alternatively, the CAR constructs described herein (including functional portions and functional variants thereof) can be commercially synthesized by companies, such as Synpep (Dublin, CA), Peptide Technologies Corp. (Gaithersburg, MD), and Multiple Peptide Systems (San Diego, CA). In this respect, the inventive CAR constructs can be synthetic, recombinant, isolated, and/or purified.

Another embodiment of the invention provides chimeric antigen receptor (CAR) amino acid construct comprising (a) two or more cleavable domains; (b) a first CAR comprising a first antigen binding domain, a first transmembrane domain, and a first intracellular T cell signaling domain; and (c) a second CAR comprising a second antigen binding domain, a second transmembrane domain, and a second intracellular T cell signaling domain; wherein the first and second CARs are linked through the two or more cleavable domains. In an embodiment, the two or more cleavable domains are immediately adjacent or have at least one linker between at least two cleavable domains. In an embodiment, there are exactly two cleavable domains.

Another embodiment of the invention provides a method of making a chimeric antigen receptor (CAR) amino acid construct, the method comprising designing two or more cleavable domains between (a) a first CAR comprising a first antigen binding domain, a first transmembrane domain, and a first intracellular T cell signaling domain; and (b) a second CAR comprising a second antigen binding domain, a second transmembrane domain, and a second intracellular T cell signaling domain; wherein the first and second CARs are linked through the two or more cleavable domains; and cloning into a plasmid a sequence comprising from N-tenninus to C-terminus the first CAR, the two or more cleavable domains, and the second CAR. In an embodiment, the two or more cleavable domains are immediately adjacent or have at least one linker between at least two cleavable domains. In an embodiment, there are exactly two cleavable domains.

Further provided by an embodiment of the invention is a nucleic acid comprising a nucleotide sequence encoding any of the CAR constructs described herein (including functional portions and functional variants thereof). The nucleic acids of the invention may comprise a nucleotide sequence encoding any of the leader sequences, antigen binding domains, transmembrane domains, linkers, and/or intracellular T cell signaling domains described herein.

In an embodiment, the nucleic acid comprises a nucleotide sequence that encodes any CAR construct described herein. In an embodiment of the invention, the nucleic acid may comprise, consist of, or consist essentially of, the nucleotide sequence of SEQ ID NO: 53 (an anti-CD19/anti-CD22 V1 CAR), SEQ ID NO: 54 (an anti-CD19/anti-CD22 V5 CAR), SEQ ID NO: 55 (an anti-CD19/anti-CD22 V6 CAR), SEQ ID NO: 56 (an anti-CD19/anti-CD22 V7 CAR), SEQ ID NO: 57 (an anti-CD19/anti-CD22 V8 CAR), SEQ ID NO: 71 (a TanCAR2), SEQ ID NO: 72 (a TanCAR3), SEQ ID NO: 73 (a TanCAR4), SEQ ID NO: 74 (a LoopCAR1), SEQ ID NO: 75 (a LoopCAR2), SEQ ID NO: 76 (a LoopCAR3), SEQ ID NO: 77 (a LoopCAR4), or SEQ ID NO: 78 (a LoopCAR5).

"Nucleic acid," as used herein, includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In some embodiments, the nucleic acid does not comprise any insertions, deletions, inversions, and/or substitutions. However, it may be suitable in some instances, as discussed herein, for the nucleic acid to comprise one or more insertions, deletions, inversions, and/or substitutions. In some embodiments, the nucleic acid may encode additional amino acid sequences that do not affect the function of the CAR construct and which may or may not be translated upon expression of the nucleic acid by a host cell.

The nucleic acids of an embodiment of the invention may be recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

A recombinant nucleic acid may be one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques, such as those described in Green et al., supra. The nucleic acids can be constructed based on chemical synthesis and/or enzymatic ligation reactions using procedures known in the art. See, for example, Green et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, CO) and Synthegen (Houston, TX).

The nucleic acid can comprise any isolated or purified nucleotide sequence which encodes any of the CAR constructs or functional portions or functional variants thereof. Alternatively, the nucleotide sequence can comprise a nucleotide sequence which is degenerate to any of the sequences or a combination of degenerate sequences.

An embodiment of the invention also provides an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions may hybridize under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive CAR constructs. It is generally appreciated that conditions can be rendered more stringent by the addition of increasing amounts of formamide.

The invention also provides a nucleic acid comprising a nucleotide sequence that is at least about 70% or more, e.g., about 80%, about 90%, about 91%, about 92%, about 93%, about 94%, about 95%, about 96%, about 97%, about 98%, or about 99% identical to any of the nucleic acids described herein.

In an embodiment, the nucleic acids of the invention can be incorporated into a recombinant expression vector. In this regard, an embodiment of the invention provides recombinant expression vectors comprising any of the nucleic acids of the invention. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring or non-naturally-occurring internucleotide linkages, or both types of linkages. Preferably, the non-naturally occurring or altered nucleotides or internucleotide linkages do not hinder the transcription or replication of the vector. An exemplary vector backbone is the lenti-vector backbone of SEQ ID NO: 58.

In an embodiment, the recombinant expression vector of the invention can be any suitable recombinant expression vector, and can be used to transform or transfect any suitable host cell. Suitable vectors include those designed for propagation and expansion or for expression or both, such as plasmids and viruses. The vector can be selected from the group consisting of the pUC series (Fermentas Life Sciences, Glen Burnie, MD), the pBluescript series (Stratagene, LaJolla, CA), the pET series (Novagen, Madison, WI), the pGEX series (Pharmacia Biotech, Uppsala, Sweden), and the pEX series (Clontech, Palo Alto, CA). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-Cl, pMAM, and pMAMneo (Clontech). The recombinant expression vector may be a viral vector, e.g., a retroviral vector or a lentiviral vector.

In an embodiment, the recombinant expression vectors of the invention can be prepared using standard recombinant DNA techniques described in, for example, Green et al., supra. Constructs of expression vectors, which are circular or linear, can be prepared to contain a replication system functional in a prokaryotic or eukaryotic host cell. Replication systems can be derived, e.g., from ColE1, 2μ plasmid, λ, SV40, bovine papilloma virus, and the like.

The recombinant expression vector may comprise regulatory sequences, such as transcription and translation initiation and termination codons, which are specific to the type of host cell (e.g., bacterium, fungus, plant, or animal) into which the vector is to be introduced, as appropriate, and taking into consideration whether the vector is DNA- or RNA-based. The recombinant expression vector may also comprise restriction sites to facilitate cloning.

The recombinant expression vector can include one or more marker genes, which allow for selection of transformed or transfected host cells. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the CAR construct (including functional portions and functional variants thereof), or to the nucleotide sequence which is complementary to or which hybridizes to the nucleotide sequence encoding the CAR construct. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, or a promoter found in the long-terminal repeat of the murine stem cell virus.

The inventive recombinant expression vectors can be designed for either transient expression, for stable expression, or for both. Also, the recombinant expression vectors can be made for constitutive expression or for inducible expression.

Further, the recombinant expression vectors can be made to include a suicide gene. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art and include, for example, the Herpes Simplex Virus (HSV) thymidine kinase (TK) gene, cytosine daminase, purine nucleoside phosphorylase, and nitroreductase.

Included in the scope of the invention are conjugates, e.g., bioconjugates, comprising any of the inventive CAR constructs (including any of the functional portions or variants thereof), nucleic acids, recombinant expression vectors, host cells, or populations of host cells. Conjugates, as well as methods of synthesizing conjugates in general, are known in the art.

An embodiment of the invention further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5α E. coli cells, Chinese hamster ovarian cells, monkey VERO cells, COS cells, HEK293 cells, and the like. For purposes of amplifying or replicating the recombinant expression vector, the host cell may be a prokaryotic cell, e.g., a DH5α cell. For purposes of producing a recombinant CAR construct, the host cell may be a mammalian cell. The host cell may be a human cell. While the host cell can be of any cell type, can originate from any type of tissue, and can be of any developmental stage, the host cell may be a peripheral blood lymphocyte (PBL) or a peripheral blood mononuclear cell (PBMC). The host cell may be a T cell or natural killer cell (NK cell).

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. The T cell may be a human T cell. The T cell may be a T cell isolated from a human. The T cell can be any type of T cell and can be of any developmental stage, including but not limited to, CD4$^+$/CD8$^+$ double positive T cells, CD4$^+$ helper T cells, e.g., Th$_1$ and Th$_2$ cells, CD8$^+$ T cells (e.g., cytotoxic T cells), tumor infiltrating cells, memory T cells, naïve T cells, and the like. The T cell may be a CD8$^+$ T cell or a CD4$^+$ T cell.

Also provided by an embodiment of the invention is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cell, a muscle cell, a brain cell, etc. Alternatively, the population of cells can be a substantially homogeneous population, in which the population comprises mainly host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

The inventive CAR constructs (including functional portions and variants thereof), nucleic acids, recombinant expression vectors, and host cells (including populations thereof), all of which are collectively referred to as "inventive CAR construct materials" hereinafter, can be isolated and/or purified. The term "isolated," as used herein, means having been removed from its natural environment. The term "purified" or "isolated" does not require absolute purity or isolation; rather, it is intended as a relative term. Thus, for example, a purified (or isolated) host cell preparation is one in which the host cell is more pure than cells in their natural environment within the body. Such host cells may be produced, for example, by standard purification techniques. In some embodiments, a preparation of a host cell is purified such that the host cell represents at least about 50%, for example at least about 70%, of the total cell content of the preparation. For example, the purity can be at least about 50%, can be greater than about 60%, about 70% or about 80%, or can be about 100%.

The inventive CAR construct materials can be formulated into a composition, such as a pharmaceutical composition. In this regard, an embodiment of the invention provides a pharmaceutical composition comprising any of the inventive CAR construct materials described herein and a pharmaceutically acceptable carrier. The inventive pharmaceutical compositions containing any of the inventive CAR construct materials can comprise more than one inventive CAR construct material, e.g., a CAR construct and a nucleic acid, or two or more different CAR constructs. Alternatively, the pharmaceutical composition can comprise an inventive CAR construct material in combination with other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc. In a preferred embodiment, the pharmaceutical composition comprises the inventive host cell or populations thereof.

With respect to pharmaceutical compositions, the pharmaceutically acceptable carrier can be any of those conventionally used and is limited only by chemico-physical considerations, such as solubility and lack of reactivity with the active agent(s), and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which has no detrimental side effects or toxicity under the conditions of use.

The choice of carrier will be determined in part by the particular inventive CAR construct material, as well as by the particular method used to administer the inventive CAR construct material. Accordingly, there are a variety of suitable formulations of the pharmaceutical composition of the invention. Methods for preparing administrable (e.g., parenterally administrable) compositions are known or apparent to those skilled in the art and are described in more detail in, for example, *Remington: The Science and Practice of Pharmacy*, Pharmaceutical Press; 22nd ed. (2012).

The inventive CAR construct materials may be administered in any suitable manner. Preferably, the inventive CAR construct materials are administered by injection, (e.g., subcutaneously, intravenously, intratumorally, intraarterially, intramuscularly, intradermally, interperitoneally, or intrathecally). Preferably, the inventive CAR construct materials are administered intravenously. A suitable pharmaceutically acceptable carrier for the inventive CAR construct material for injection may include any isotonic carrier such as, for example, normal saline (about 0.90% w/v of NaCl in water, about 300 mOsm/L NaCl in water, or about 9.0 g NaCl per liter of water), NORMOSOL R electrolyte solution (Abbott, Chicago, IL), PLASMA-LYTE A (Baxter, Deerfield, IL), about 5% dextrose in water, or Ringer's lactate. In an embodiment, the pharmaceutically acceptable carrier is supplemented with human serum albumen.

An "effective amount" or "an amount effective to treat" refers to a dose that is adequate to prevent or treat cancer in an individual. Amounts effective for a therapeutic or prophylactic use will depend on, for example, the stage and severity of the disease or disorder being treated, the age, weight, and general state of health of the patient, and the judgment of the prescribing physician. The size of the dose will also be determined by the active selected, method of administration, timing and frequency of administration, the existence, nature, and extent of any adverse side-effects that might accompany the administration of a particular active, and the desired physiological effect. It will be appreciated by one of skill in the art that various diseases or disorders could require prolonged treatment involving multiple administrations, perhaps using the inventive CAR construct materials in each or various rounds of administration. By way of example and not intending to limit the invention, when the inventive CAR construct material is a host cell, an exemplary dose of host cells may be a minimum of one million cells ($1 \times 10^6$ cells/dose).

For purposes of the invention, the amount or dose of the inventive CAR construct material administered should be sufficient to effect a therapeutic or prophylactic response in the subject or animal over a reasonable time frame. For example, the dose of the inventive CAR construct material should be sufficient to bind to antigen, or detect, treat or prevent cancer in a period of from about 2 hours or longer, e.g., about 12 to about 24 or more hours, from the time of administration. In certain embodiments, the time period could be even longer. The dose will be determined by the efficacy of the particular inventive CAR construct material and the condition of the animal (e.g., human), as well as the body weight of the animal (e.g., human) to be treated.

For purposes of the invention, an assay, which comprises, for example, comparing the extent to which target cells are lysed and/or IFN-γ is secreted by T cells expressing the released CARs of the inventive CAR construct upon administration of a given dose of such T cells to a mammal, among a set of mammals of which is each given a different dose of the T cells, could be used to determine a starting dose to be administered to a mammal. The extent to which target cells are lysed and/or IFN-γ is secreted upon administration of a certain dose can be assayed by methods known in the art.

When the inventive CAR construct materials are administered with one or more additional therapeutic agents, one or more additional therapeutic agents can be coadministered to the mammal. By "coadministering" is meant administering one or more additional therapeutic agents and the inventive CAR construct materials sufficiently close in time such that the inventive CAR construct materials can enhance the effect of one or more additional therapeutic agents, or vice versa. In this regard, the inventive CAR construct materials can be administered first and the one or more additional therapeutic agents can be administered second, or vice versa. Alternatively, the inventive CAR construct materials and the one or more additional therapeutic agents can be administered simultaneously. An exemplary therapeutic agent that can be coadministered with the CAR construct materials is IL-2. It is believed that IL-2 enhances the therapeutic effect of the inventive CAR construct materials.

It is contemplated that the inventive CAR construct materials can be used in methods of treating or preventing a disease in a mammal. Without being bound to a particular theory or mechanism, the inventive CAR constructs have biological activity, e.g., ability to release/cleave CARs that recognize antigen, e.g., one or both of CD19 and CD22, such that the released CARs, when expressed by a cell, are able to mediate an immune response against the cell expressing the antigen, e.g., one or both of CD19 and CD22. In this regard, an embodiment of the invention provides a method of treating or preventing cancer in a mammal, comprising administering to the mammal any of the CAR constructs, the nucleic acids, the recombinant expression vectors, the host cells, the population of cells, and/or the pharmaceutical compositions of the invention in an amount effective to treat or prevent cancer in the mammal.

An embodiment of the invention further comprises lymphodepleting the mammal prior to administering the inventive CAR construct materials. Examples of lymphodepletion include, but may not be limited to, nonmyeloablative lymphodepleting chemotherapy, myeloablative lymphodepleting chemotherapy, total body irradiation, etc.

For purposes of the inventive methods, wherein host cells or populations of cells are administered, the cells can be cells that are allogeneic or autologous to the mammal. Preferably, the cells are autologous to the mammal.

The mammal referred to herein can be any mammal. As used herein, the term "mammal" refers to any mammal, including, but not limited to, mammals of the order Rodentia, such as mice and hamsters, and mammals of the order Logomorpha, such as rabbits. The mammals may be from the order Carnivora, including Felines (cats) and Canines (dogs). The mammals may be from the order Artiodactyla, including Bovines (cows) and Swines (pigs) or of the order Perssodactyla, including Equines (horses). The mammals may be of the order Primates, Ceboids, or Simoids (monkeys) or of the order Anthropoids (humans and apes). Preferably, the mammal is a human.

With respect to the inventive methods of treatment, the cancer can be any cancer, including any of acute lymphocytic cancer, acute myeloid leukemia, alveolar rhabdomyosarcoma, bladder cancer (e.g., bladder carcinoma), bone cancer, brain cancer (e.g., medulloblastoma), breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia (CLL), chronic myeloid cancer, colon cancer, esophageal cancer, cervical cancer, fibrosarcoma, gastrointestinal carcinoid tumor, head and neck cancer (e.g., head and neck squamous cell carcinoma), Hodgkin lymphoma, hypopharynx cancer, kidney cancer, larynx cancer, leukemia, liquid tumors, liver cancer, lung cancer (e.g., non-small cell lung carcinoma), lymphoma, malignant mesothelioma, mastocytoma, melanoma, multiple myeloma, nasopharynx cancer, non-Hodgkin lymphoma, B-chronic lymphocytic leukemia, B-precursor acute lymphoblastic leukemia (B-ALL), pre-B cell precursor acute lymphoblastic leukemia (BCP-ALL), B cell lymphoma, hairy cell leukemia, acute lymphocytic leukemia (ALL), and Burkitt's lymphoma, ovarian cancer, pancreatic cancer, peritoneum, omentum, and mesentery cancer, pharynx cancer, prostate cancer, rectal cancer, renal cancer, skin cancer, small intestine cancer, soft tissue cancer, solid tumors, stomach cancer, testicular cancer, thyroid cancer, and ureter cancer. Preferably, the cancer is a hematological malignancy (e.g., leukemia or lymphoma, including but not limited to Hodgkin lymphoma, non-Hodgkin lymphoma, CLL, acute lymphocytic cancer, acute myeloid leukemia, B-chronic lymphocytic leukemia, hairy cell leukemia, acute lymphocytic leukemia (ALL) (also referred to as "acute lymphoblastic leukemia"), B-ALL, BCP-ALL, B cell lymphoma, and Burkitt's lymphoma). Preferably, the cancer is characterized by the expression of one or both of CD22 and CD19, and more preferably is a hematological malignancy that is characterized by the expression of one or both of CD19 and CD22.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof.

Another embodiment of the invention provides a use of the inventive CAR constructs, nucleic acids, recombinant expression vectors, host cells, populations of cells, or pharmaceutical compositions, for the treatment or prevention of cancer in a mammal.

Another embodiment of the invention provides a method of detecting the presence of cancer in a mammal, comprising: (a) contacting a sample comprising one or more cells from the mammal with the CAR constructs, the nucleic acids, the recombinant expression vectors, the host cells, the population of cells, or the pharmaceutical compositions of the invention, thereby forming a complex, (b) and detecting the complex, wherein detection of the complex is indicative of the presence of cancer in the mammal.

The sample may be obtained by any suitable method, e.g., biopsy or necropsy. A biopsy is the removal of tissue and/or cells from an individual. Such removal may be to collect tissue and/or cells from the individual in order to perform experimentation on the removed tissue and/or cells. This experimentation may include experiments to determine if the individual has and/or is suffering from a certain condition or disease-state. The condition or disease may be, e.g., cancer.

With respect to an embodiment of the inventive method of detecting the presence of cancer in a mammal, the sample comprising cells of the mammal can be a sample comprising whole cells, lysates thereof, or a fraction of the whole cell lysates, e.g., a nuclear or cytoplasmic fraction, a whole protein fraction, or a nucleic acid fraction. If the sample comprises whole cells, the cells can be any cells of the mammal, e.g., the cells of any organ or tissue, including blood cells or endothelial cells.

For purposes of the inventive detecting method, the contacting can take place in vitro or in vivo with respect to the mammal. Preferably, the contacting is in vitro.

Also, detection of the complex can occur through any number of ways known in the art. For instance, the inventive CAR constructs, nucleic acids, recombinant expression vectors, host cells, or populations of cells, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

Methods of testing a CAR for the ability to recognize target cells and for antigen specificity are known in the art. For instance, Clay et al., *J. Immunol.*, 163: 507-513 (1999), teaches methods of measuring the release of cytokines (e.g., interferon-γ, granulocyte/monocyte colony stimulating factor (GM-CSF), tumor necrosis factor a (TNF-α) or interleukin 2 (IL-2)). In addition, CAR function can be evaluated by measurement of cellular cytoxicity, as described in Zhao et al., *J. Immunol.*, 174: 4415-4423 (2005).

The following includes certain aspects of the invention.

1. A chimeric antigen receptor (CAR) amino acid construct comprising:
   (a) a cleavable domain;
   (b) a first CAR comprising
      a first antigen binding domain,
      a first transmembrane domain, and
      a first intracellular T cell signaling domain; and
   (c) a second CAR comprising
      a second antigen binding domain,
      a second transmembrane domain, and
      a second intracellular T cell signaling domain;
   wherein the first and second CARs are linked through the cleavable domain,
   wherein the first antigen binding domain comprises an antigen binding domain of the m971 antibody,
   wherein when the first CAR is cleaved from the construct, the first antigen binding domain has antigenic specificity for CD22.

2. The CAR construct according to aspect 1, wherein cleaving the cleavable domain releases the first and second CARs from the CAR construct.

3. The CAR construct according to aspect 1 or 2, wherein the first antigen binding domain comprises a heavy chain variable region comprising the amino acid sequences of SEQ ID NOs: 3-9 and a light chain variable region comprising the amino acid sequences of SEQ ID NOs: 11-17.

4. The CAR construct according to any one of aspects 1-3, wherein the first antigen binding domain comprises the amino acid sequences of SEQ ID NOs: 3-9 and 11-17.

5. The CAR construct according to any one of aspects 1-4, wherein, when the second CAR is cleaved from the construct, the second antigen binding domain has antigenic specificity for CD19.

6. The CAR construct according to any one of aspects 1-5, wherein the second antigen binding domain comprises an antigen binding domain of the FMC63 antibody.

7. The CAR construct according to any one of aspects 1-6, wherein the second antigen binding domain comprises a heavy chain variable region comprising the amino acid sequences of SEQ ID NOs: 31-37 and a light chain variable region comprising the amino acid sequences of SEQ ID NOs: 23-29.

8. The CAR construct according to any one of aspects 1-7, wherein the second antigen binding domain comprises the amino acid sequences of SEQ ID NO: 23-29 and 31-37.

9. A chimeric antigen receptor (CAR) amino acid construct comprising:
   (a) a cleavable domain;
   (b) a first CAR comprising
      a first antigen binding domain,
      a first transmembrane domain, and
      a first intracellular T cell signaling domain; and (c) a second CAR comprising
a second antigen binding domain,
a second transmembrane domain, and
a second intracellular T cell signaling domain;
wherein the first and second CARs are linked through the cleavable domain,
wherein the first antigen binding domain comprises an antigen binding domain of the FMC63 antibody,
wherein when the first CAR is cleaved from the construct, the first antigen binding domain has antigenic specificity for CD19.

10. The CAR construct according to aspect 9, wherein cleaving the cleavable domain releases the first and second CARs from the CAR construct.

11. The CAR construct according to aspect 9 or 10, wherein the first antigen binding domain comprises a heavy chain variable region comprising the amino acid sequences of SEQ ID NO: 31-37 and a light chain variable region comprising the amino acid sequences of SEQ ID NOs: 23-29.

12. The CAR construct according to any one of aspects 9-11, wherein the first antigen binding domain comprises the amino acid sequences of SEQ ID NOs: 23-29 and 31-37.

13. The CAR construct according to any one of aspects 9-12, wherein, when the second CAR is cleaved from the construct, the second antigen binding domain has antigenic specificity for CD22.

14. The CAR construct according to any one of aspects 1-13, wherein the first or second transmembrane domain comprises a CD8 transmembrane domain and a CD8 hinge domain.

15. The CAR construct according to aspect 14, wherein the CD8 transmembrane domain comprises the amino acid sequence of SEQ ID NO: 19 and the CD8 hinge domain comprises the amino acid sequence of SEQ ID NO: 18.

16. The CAR construct according to any one of aspects 1-15, wherein the first or second intracellular T cell signaling domain comprises a 4-1BB intracellular T cell signaling sequence.

17. The CAR construct according to aspect 16, wherein the 4-1BB intracellular T cell signaling sequence comprises the amino acid sequence of SEQ ID NO: 20.

18. The CAR construct according to any one of aspects 1-17, wherein the first or second intracellular T cell signaling domain comprises a CD3 zeta (ζ) intracellular T cell signaling sequence.

19. The CAR construct according to aspect 18, wherein the CD3ζ intracellular T cell signaling sequence comprises the amino acid sequence of SEQ ID NO: 21.

20. The CAR construct according to any one of aspects 1-19, wherein the cleavable domain is 2A or furin.

21. The CAR construct according to any one of aspects 1-20, wherein the CAR construct comprises exactly two CARs being the first and second CARs, respectively.

22. A chimeric antigen receptor (CAR) amino acid construct comprising the amino acid sequence of SEQ ID NO: 48, 49, 50, 51, or 52.

23. A chimeric antigen receptor (CAR) amino acid construct comprising an amino acid sequence having 90%, 91%, 92%, 93%, 94%, 95%, 96%, 97%, 98%, 99% or greater sequence identity (e.g., 100%) with any one of SEQ ID NOS: 63-70.

24. A chimeric antigen receptor (CAR) amino acid construct comprising:

(a) two or more cleavable domains;
(b) a first CAR comprising
a first antigen binding domain,
a first transmembrane domain, and
a first intracellular T cell signaling domain; and
(c) a second CAR comprising
a second antigen binding domain,
a second transmembrane domain, and
a second intracellular T cell signaling domain;
wherein the first and second CARs are linked through the two or more cleavable domains.

25. The CAR construct of aspect 24, wherein the two or more cleavable domains are immediately adjacent or have at least one linker between at least two cleavable domains.

26. The CAR construct of aspect 25 or 24, wherein there are exactly two cleavable domains.

27. A nucleic acid comprising a nucleotide sequence encoding the CAR construct of any one of aspects 1-26.

28. The nucleic acid according to aspect 27, comprising the nucleotide sequence of any one of SEQ ID NOs: 53-57 or 71-78.

29. A recombinant expression vector comprising the nucleic acid of aspect 27 or 28.

30. An isolated host cell comprising the recombinant expression vector of aspect 29.

31. A population of cells comprising at least one host cell of aspect 30.

32. A pharmaceutical composition comprising the CAR construct of any one of aspects 1-26, the nucleic acid of aspect 27 or 28, the recombinant expression vector of aspect 29, the host cell of aspect 30, or the population of cells of aspect 31, and a pharmaceutically acceptable carrier.

33. A method of detecting the presence of cancer in a mammal, comprising:
(a) contacting a sample comprising one or more cells from the mammal with the CAR construct of any one of aspects 1-26, the nucleic acid of aspect 27 or 28, the recombinant expression vector of aspect 29, the host cell of aspect 30, the population of cells of aspect 31, or the pharmaceutical composition of aspect 32, thereby forming a complex, and
(b) detecting the complex, wherein detection of the complex is indicative of the presence of cancer in the mammal.

34. The CAR construct of any one of aspects 1-26, the nucleic acid of aspect 27 or 28, the recombinant expression vector of aspect 29, the host cell of aspect 30, the population of cells of aspect 31, or the pharmaceutical composition of aspect 32 for use in the treatment or prevention of cancer in a mammal.

35. The CAR construct for the use of aspect 34, wherein the cancer is a hematological malignancy.

36. A method of making a chimeric antigen receptor (CAR) amino acid construct, the method comprising designing two or more cleavable domains between
(a) a first CAR comprising
a first antigen binding domain,
a first transmembrane domain, and
a first intracellular T cell signaling domain; and
(b) a second CAR comprising
a second antigen binding domain,
a second transmembrane domain, and
a second intracellular T cell signaling domain;
wherein the first and second CARs are linked through the two or more cleavable domains;
and cloning into a plasmid a sequence comprising from N-terminus to C-terminus the first CAR, the two or more cleavable domains, and the second CAR.

37. The method of aspect 36, wherein the two or more cleavable domains are immediately adjacent or have at least one linker between at least two cleavable domains.
38. The method of aspect 36 or 37, wherein there are exactly two cleavable domains.

The following examples further illustrate the invention but, of course, should not be construed as in any way limiting its scope.

Example 1

This example demonstrates generation of CAR constructs, CAR construct-encoding lentiviral vectors, and CAR-expressing T cells, in accordance with embodiments of the invention, as well as generation of other CARs for comparison.

The CAR constructs were synthesized by GENEWIZ (South Plainfield, NJ, USA) and then sub-cloned into the lenti-viral plasmid backbone between NhE1 and HincII sites.

CAR construct-encoding lentiviral vectors were produced by transient transfection of the 293T cell line. Briefly, 293T cells were plated into poly-D lysine coated 15 cm plates (BD Biosciences, San Jose, CA, USA). The following day, 293T cells were transfected using lipofectamine 3000 (Life Technologies, Calrsbad, CA, USA) with plasmids encoding the CAR construct along with packaging and envelope vectors (pMDLg/pRRE, pMD-2G, and pRSV-Rev). Lentiviral supernatants were collected 48-72 hours post-transfection, centrifuged at 3000 RPM for 10 minutes to remove cell debris, then stored at −80° C. Human PBMCs from normal donors were activated with a 1:1 ratio of CD3/CD28 microbeads (Life Technologies) in AIM-V media containing 40 IU/mL recombinant IL-2 (rhIL-2; Roche, Basel, Switzerland) for 24 hours. Activated T cells were resuspended at 2 million cells per 3 mL of lentiviral supernatant plus 1 mL of fresh AIM-V media with 10 μg/mL protamine sulfate and 100 IU/mL IL-2 and cultured in 6-well plates. Plates were centrifuged at 1000×g for 2 hours at 32° C. and then incubated at 37° C. overnight. A second transduction was performed the following day. On the third day, the CD3/CD28 beads were removed, and the cells were cultured at 300,000 cells/mL in AIM-V containing 100 IU/mL IL-2 with fresh IL2-containing media added every 2-3 days until harvest at day 8 or 9.

Vectors for the single anti-CD19 CAR, the single anti-CD22 CAR, and the bispecific LoopCAR6 were produced by transient transfection of the 293T lenti packaging cell line.

The sequence of the anti-CD19 CAR is below:

(SEQ ID NO: 59)
MLLLVTSLLLCELPHPAFLLIPDIQMTQTTSSLSASLGDRVTISCRASQD

ISKYLNWYQQKPDGTVKLLIYHTSRLHSGVPSRFSGSGSGTDYSLTISNL

EQEDIATYFCQQGNTLPYTFGGGTKLEITGSTSGSGKPGSGEGSTKGEVK

LQESGPGLVAPSQSLSVTCTVSGVSLPDYGVSWIRQPPRKGLEWLGVIWG

SETTYYNSALKSRLTIIKDNSKSQVFLKMNSLQTDDTAIYYCAKHYYYGG

SYAMDYWGQGTSVTVSSSGTTTPAPRPPTPAPTIASQPLSLRPEACRPAA

GGAVHTRGLDFACDIYIWAPLAGTCGVLLLSLVITLYCKRGRKKLLYIFK

QPFMRPVQTTQEEDGCSCRFPEEEEGGCELRVKFSRSADAPAYQQGQNQL

YNELNLGRREEYDVLDKRRGRDPEMGGKPRRKNPQEGLYNELQKDKMAEA

YSEIGMKGERRRGKGHDGLYQGLSTATKDTYDALHMQALPPR.

The sequence of the anti-CD22 CAR is below:

(SEQ ID NO: 60)
MLLLVTSLLLCELPHPAFLLIPQVQLQQSGPGLVKPSQTLSLTCAISGDS

VSSNSAAWNWIRQSPSRGLEWLGRTYYRSKWYNDYAVSVKSRITINPDTS

KNQFSLQLNSVTPEDTAVYYCAREVTGDLEDAFDIWGQGTMVTVSSGGGG

SDIQMTQSPSSLSASVGDRVTITCRASQTIWSYLNWYQQRPGKAPNLLIY

AASSLQSGVPSRFSGRGSGTDFTLTISSLQAEDFATYYCQQSYSIPQTFG

QGTKLEIKTSSGTTTPAPRPPTPAPTIASQPLSLRPEACRPAAGGAVHTR

GLDFACDIYIWAPLAGTCGVLLLSLVITLYCKRGRKKLLYIFKQPFMRPV

QTTQEEDGCSCRFPEEEEGGCELRVKFSRSADAPAYQQGQNQLYNELNLG

RREEYDVLDKRRGRDPEMGGKPRRKNPQEGLYNELQKDKMAEAYSEIGMK

GERRRGKGHDGLYQGLSTATKDTYDALHMQALPPR.

The LoopCAR6 is described in International Patent Publication No. WO 2016/149578 and has the following sequence:

(SEQ ID NO: 61)
MLLLVTSLLLCELPHPAFLLIPDIQMTQTTSSLSASLGDRVTISCRASQD

ISKYLNWYQQKPDGTVKLLIYHTSRLHSGVPSRFSGSGSGTDYSLTISNL

EQEDIATYFCQQGNTLPYTFGGGTKLEITGGGGSQVQLQQSGPGLVKPSQ

TLSLTCAISGDSVSSNSAAWNWIRQSPSRGLEWLGRTYYRSKWYNDYAVS

VKSRITINPDTSKNQFSLQLNSVTPEDTAVYYCAREVTGDLEDAFDIWGQ

GTMVTVSSGSTSGSGKPGSGEGSTKGDIQMTQSPSSLSASVGDRVTITCR

ASQTIWSYLNWYQQRPGKAPNLLIYAASSLQSGVPSRFSGRGSGTDFTLT

ISSLQAEDFATYYCQQSYSIPQTFGQGTKLEIKGGGGSEVKLQESGPGLV

APSQSLSVTCTVSGVSLPDYGVSWIRQPPRKGLEWLGVIWGSETTYYNSA

LKSRLTIIKDNSKSQVFLKMNSLQTDDTAIYYCAKHYYYGGSYAMDYWGQ

GTSVTVSSSGTTTPAPRPPTPAPTIASQPLSLRPEACRPAAGGAVHTRGL

DFACDIYIWAPLAGTCGVLLLSLVITLYCKRGRKKLLYIFKQPFMRPVQT

TQEEDGCSCRFPEEEEGGCELRVKFSRSADAPAYKQGQNQLYNELNLGRR

EEYDVLDKRRGRDPEMGGKPRRKNPQEGLYNELQKDKMAEAYSEIGMKGE

RRRGKGHDGLYQGLSTATKDTYDALHMQALPPR.

Example 2

This example demonstrates surface expression on human T cells of CARs, cleaved from a CAR construct, in accordance with embodiments of the invention, compared to other CARs.

Figure 2A:
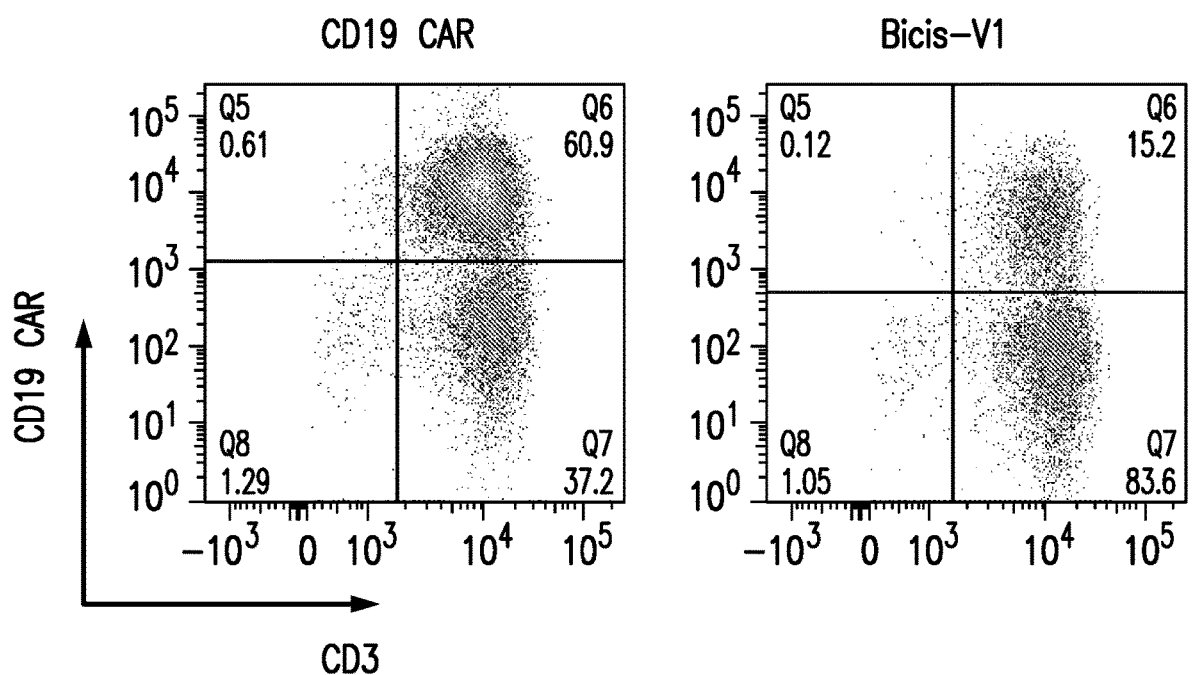
FIGS. 2A-2C present fluorescence-activated cell sorting dot plots comparing surface expression on human T cells of (2A) anti-CD19 CAR (the anti-CD19 CAR denoted as "CD19 CAR") and CD3 when the T cells are transduced with a vector encoding the single anti-CD19 CAR or the V1 CAR construct (also denoted as bicistronic-V1 or bicis-V1), (2B) anti-CD22 CAR (the anti-CD22 CAR denoted as "CD22 CAR") and CD3 when the T cells are transduced with a vector encoding the single anti-CD22 CAR or the V1 CAR construct, and (2C) anti-CD19 CAR and anti-CD22 CAR when the cells are transduced with a vector encoding the V1 CAR construct, in accordance with embodiments of the invention.
Figure 2B:
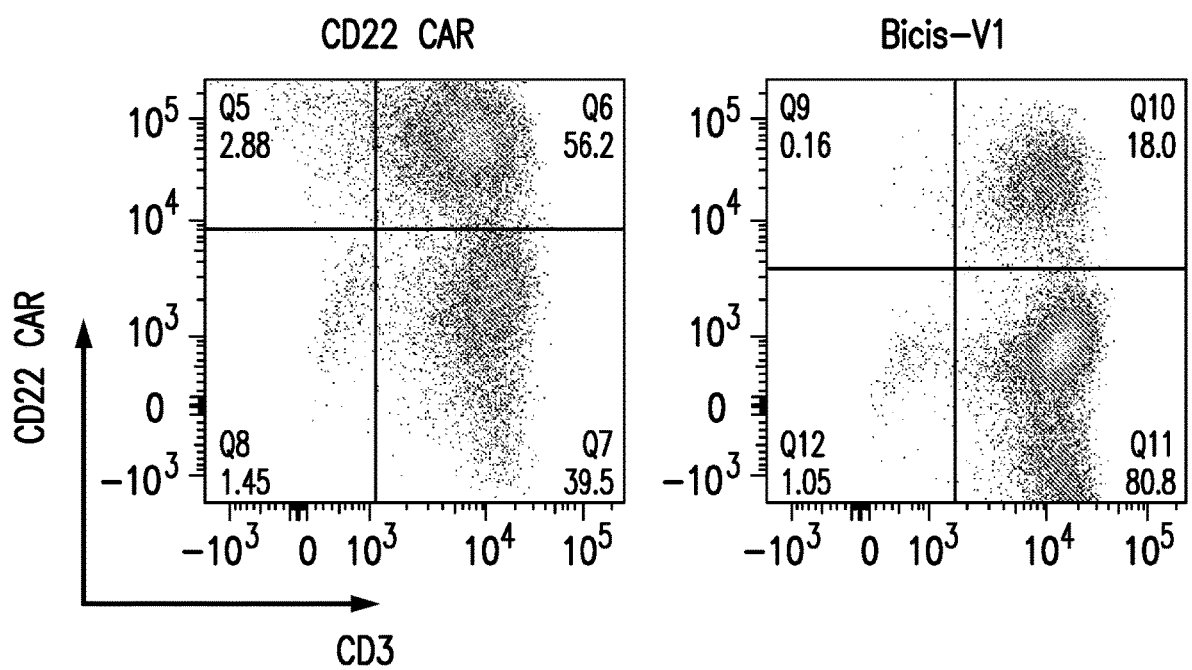
Figure 2C:
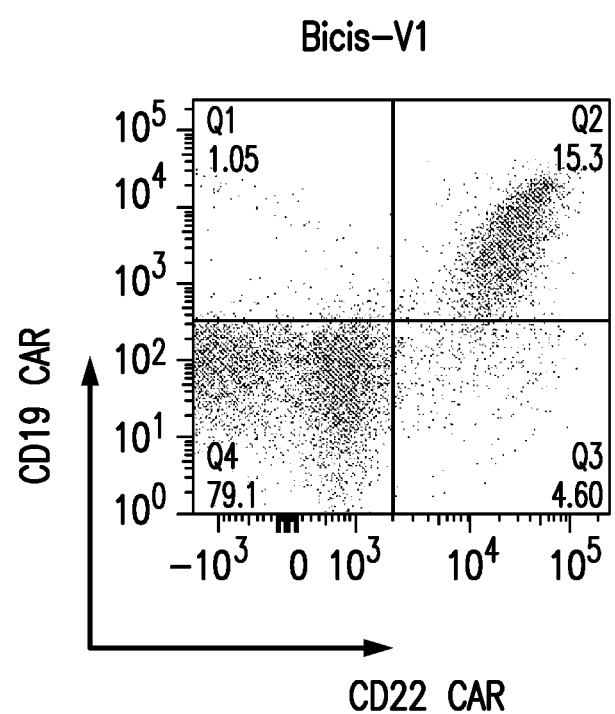

Surface expression of anti-CD19 CAR and anti-CD22 CAR on the V1 transduced T cells is about 15%, while the expression of the anti-CD19 CAR from a vector encoding only the single anti-CD19 CAR is 61% and expression of the anti-CD22 CAR from a vector encoding only the single anti-CD22 CAR is 56% (FIGS. 2A-2C).

Figure 3:
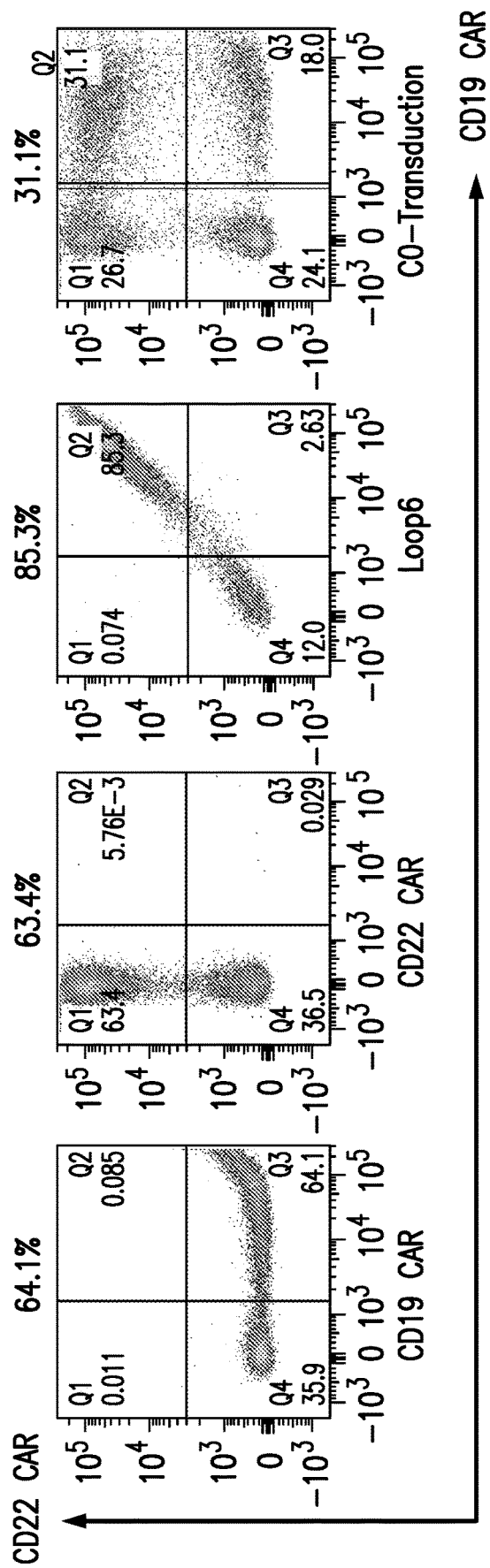
FIG. 3 presents fluorescence-activated cell sorting dot plots comparing surface expression of anti-CD19 CAR and anti-CD22 CAR on human T cells when transduced with a vector encoding the single anti-CD19 CAR, the single anti-CD22 CAR, the LoopCAR6, or co-transduced with separate vectors encoding the single anti-CD19 CAR and the single anti-CD22 CAR.

Human PBMCs from a healthy donor were activated with CD3/CD28 microbeads for 24 hours. Activated T cells were then transduced with vector individually or co-transduced with both the single anti-CD19 CAR and the single anti-CD22 CAR vectors together. Surface expression of the anti-CD19 CAR and the anti-CD22 CAR were analyzed on day 8. Cotransduced T cells had much lower expression of both anti-CD19 and anti-CD22 CARs compared to the bispecific LoopCAR6. The expression of anti-CD19 and anti-CD22 CARs on co-transduced T cells is not at an equal molar ratio. In contrast, the LoopCAR6 showed an almost 1:1 ratio in the expression of anti-CD19 and anti-CD22 CARs, which displays as a diagonal plot. See FIG. 3.

Figure 4:
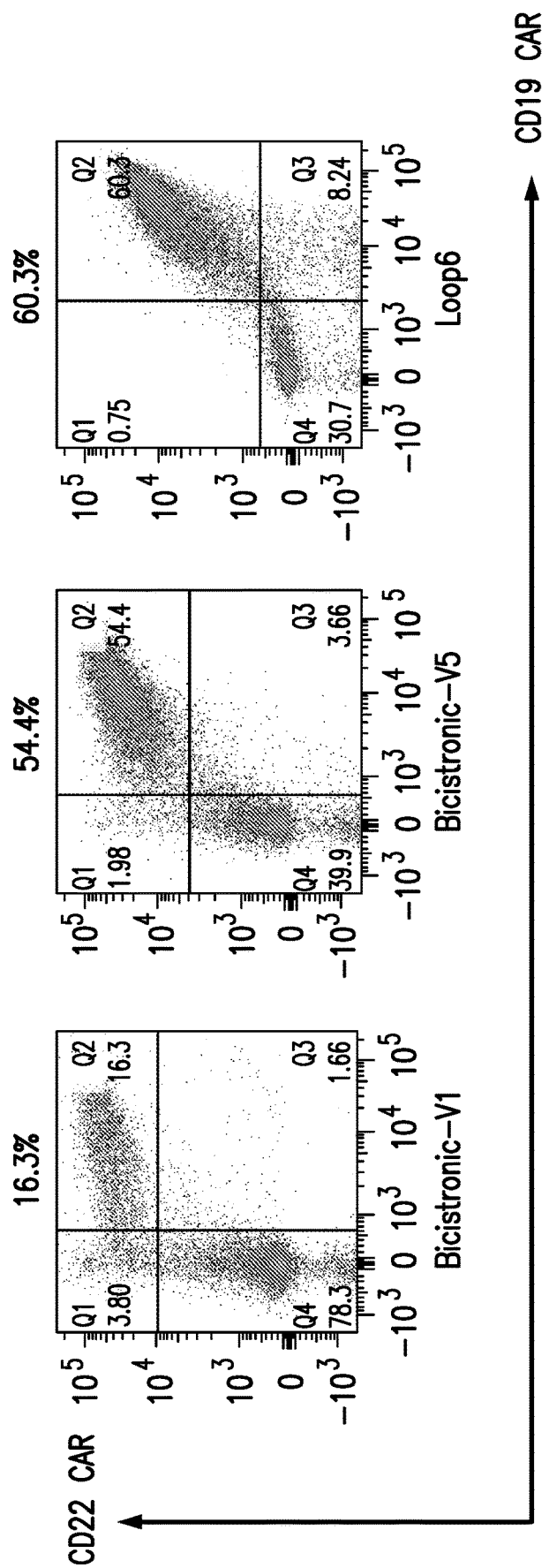
FIG. 4 presents fluorescence-activated cell sorting dot plots comparing surface expression of anti-CD19 CAR and anti-CD22 CAR on human T cells when transduced with a vector encoding the V1 CAR construct, the V5 CAR construct (also denoted as bicistronic-V5 or bicis-V5), or the LoopCAR6, in accordance with embodiments of the invention.

Vectors for the bispecific LoopCAR6 and V1 and V5 CARs were produced by transient transfection of the 293T lenti packaging cell line. Human PBMCs from a healthy donor were activated with CD3/CD28 microbeads for 24 hours. Activated T cells were then transduced with the vectors. Surface expression of anti-CD19 CAR and anti-CD22 CAR were analyzed on day 7 using flow cytometry. T cells transduced with a vector encoding the V5 CAR have higher cell surface expression of both the separated anti-CD19 CAR and the separated anti-CD22 CAR, as provided by cleavage of the CAR, than T cells transduced with a vector encoding the V1 CAR (FIG. 4).

Example 3

This example demonstrates in vitro activity of a CAR construct based on cytokine production, in accordance with embodiments of the invention, compared to other CARs.

Figure 5A:
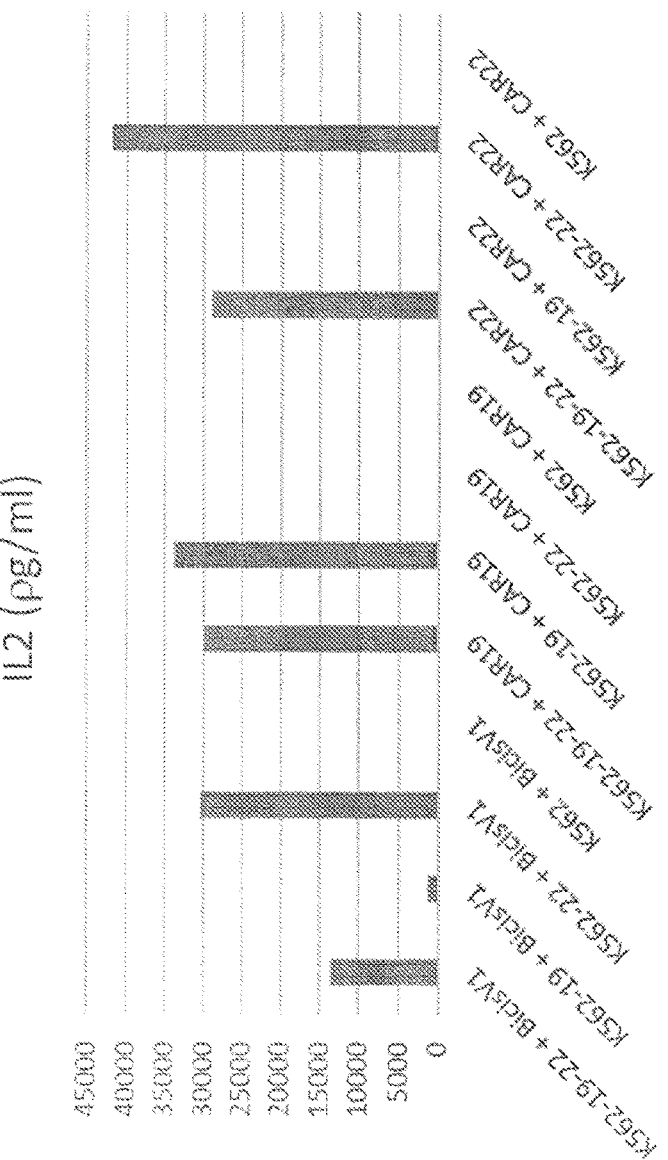

CAR-transduced T cells (1E5) were washed 3 times with 1×PBS and then co-incubated with an equal number of target cells in 200 ml RPMI media in 96-well plates in a 37° C. incubator for 15 to 20 hours. The target cells were K562 expressing CD19 or CD22 or both CD19 and CD22. K562 cells served as the negative control. The cytokine levels of the IL2 and IFNα in the culture supernatant were measured with an ELISA kit (R&D Systems, Minneapolis, MN, USA). All tests were set in triplicates. V1 CAR T cells made plenty of IL2 and IFNg when co-cultured with CD22 expression target cells, but made only low level of IL2 and IFNg when co-cultured with CD19 expression target cells (FIGS. 5A and 5B).

CML cell line K562 was artificially transduced with CD19 or CD22 or both to express the target antigens. K562 cells served as the negative control. 1E5 CAR T cells were washed 3 times and then co-incubated with 1E5 target cells in RPMI media at 37° C. After 14 hours, culture supernatant was harvested and the production of the cytokines was measured with ELISA kits. V5 makes the highest level of both IL2 and IFNg when co-incubated with target antigen expressed on K562 when compared with the bispecific LoopCAR6 and the anti-CD19 and anti-CD22 single CARs. V1 makes plenty of both IL2 and IFNg when co-incubated with target antigen expressed on K562 when compared with the bispecific LoopCAR6 and the anti-CD19 and anti-CD22 single CARs. See FIGS. 6A and 6B.

Figure 7A:
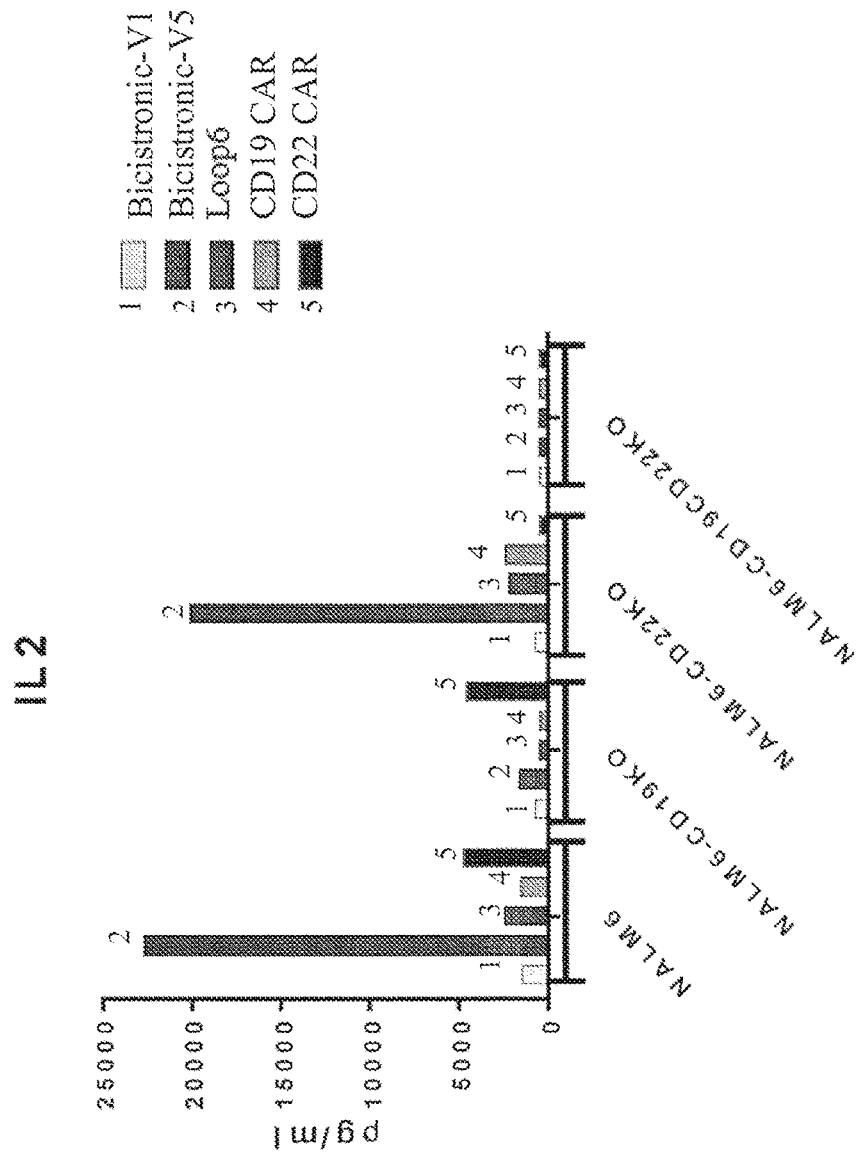
Figure 7B:
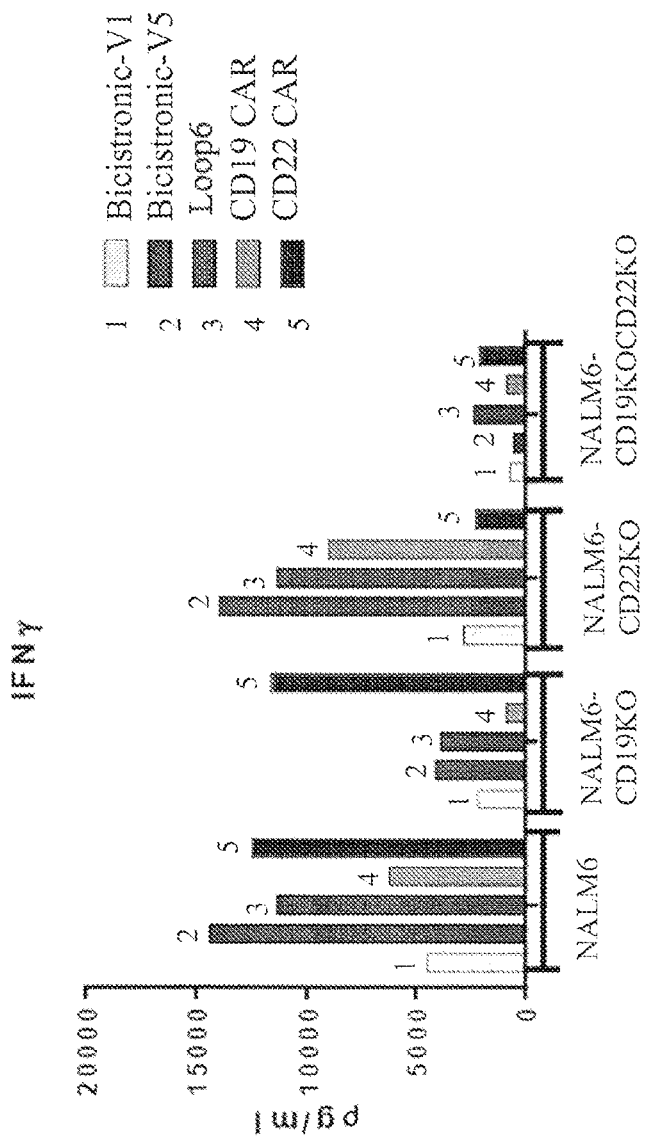

B cell leukemia cell line NALM6 expresses both CD19 and CD22 surface antigens. CD19 or CD22 was knocked out with CRISPR/Cas9 technology to eliminate the expression of these target antigens. NALM6 cells served as the positive control. 1E5 CAR T cells were washed 3 times and then co-incubated with 1E5 target cells in RPMI media at 37° C. After 14 hours, culture supernatant was harvested, and the production of the cytokines was measured with ELISA kits. V5 makes the highest level of both IL2 and IFNg when co-incubated with CD19 expressed on NALM6 when compared with the bispecific LoopCAR6 and the anti-CD19 and anti-CD22 single CARs. V5 makes lower amount of IL2 and IFNg when co-incubated with CD22 expressed on NALM6 when compared with the anti-CD22 single CARs. V1 makes small amount of IL2 and IFNg when co-incubated with target antigen expressed on NALM6 when compared with the V5 CAR. V1 makes comparable amount of IL2 and IFNg with bispecific LoopCAR6 and anti-CD19 and anti-CD22 single CARs. See FIGS. 7A and 7B.

Figure 8:
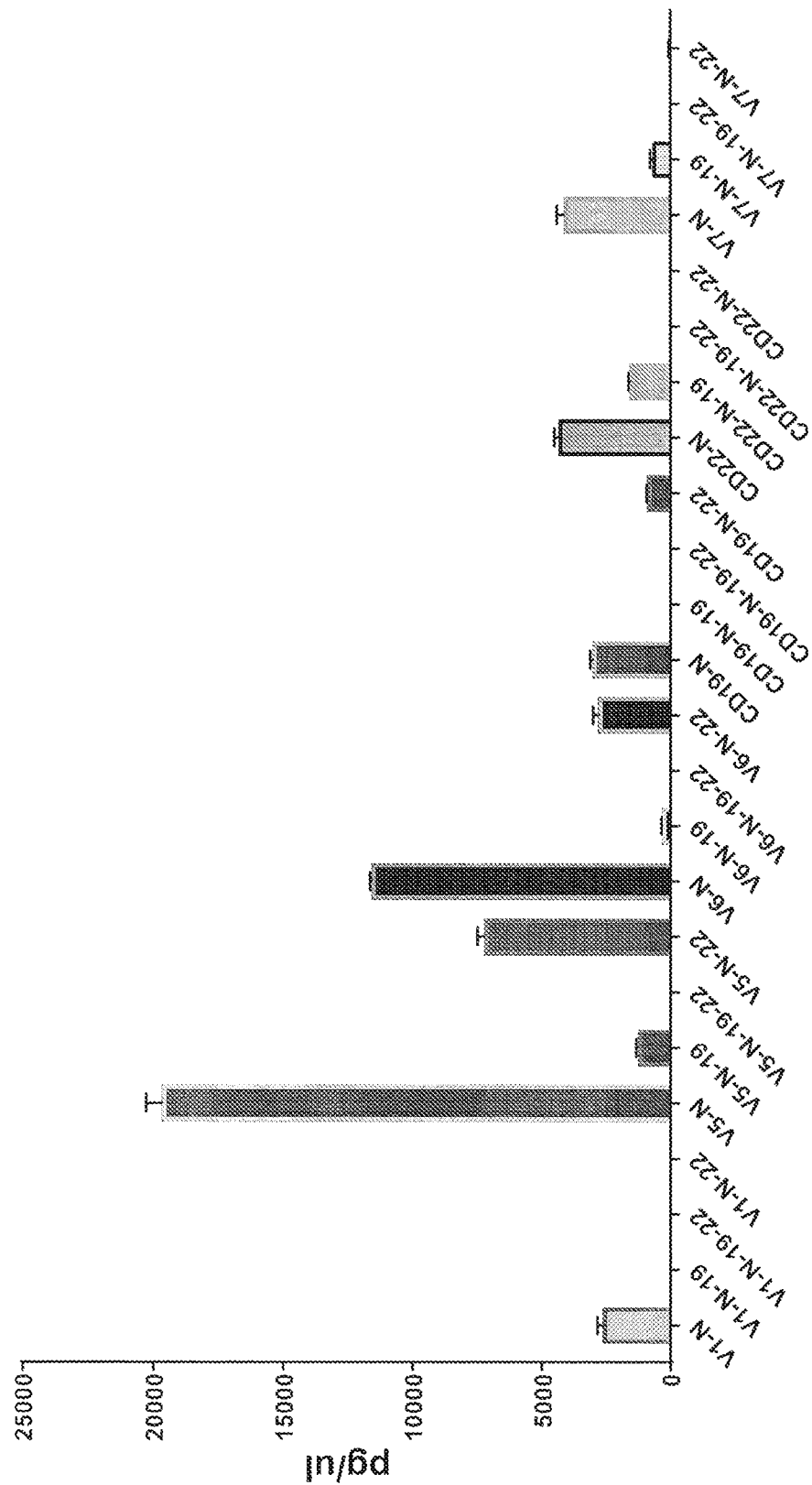

CAR T cells were co-incubated with NALM6 tumor cells for 18 hours, and the levels of IL2 production in the culture supernatant were measured by ELISA. As seen in FIG. 8, Bicis-V5 and Bicis-V6 may have a synergistic effect.

Example 4

This example demonstrates treatment of a Relapse Leukemic Model using a CAR construct, in accordance with embodiments of the invention, compared to other CARs.

Bioluminescent imaging was used to track leukemia progression in vivo. On day 0, 0.5 million of CD19KO NALM6 cells were mixed with an equal number of CD22KO NALM6 cells and injected into NSG mice. After 3 days, these mice were treated with 3 million CAR T cells or mock T cells.

Figure 9:
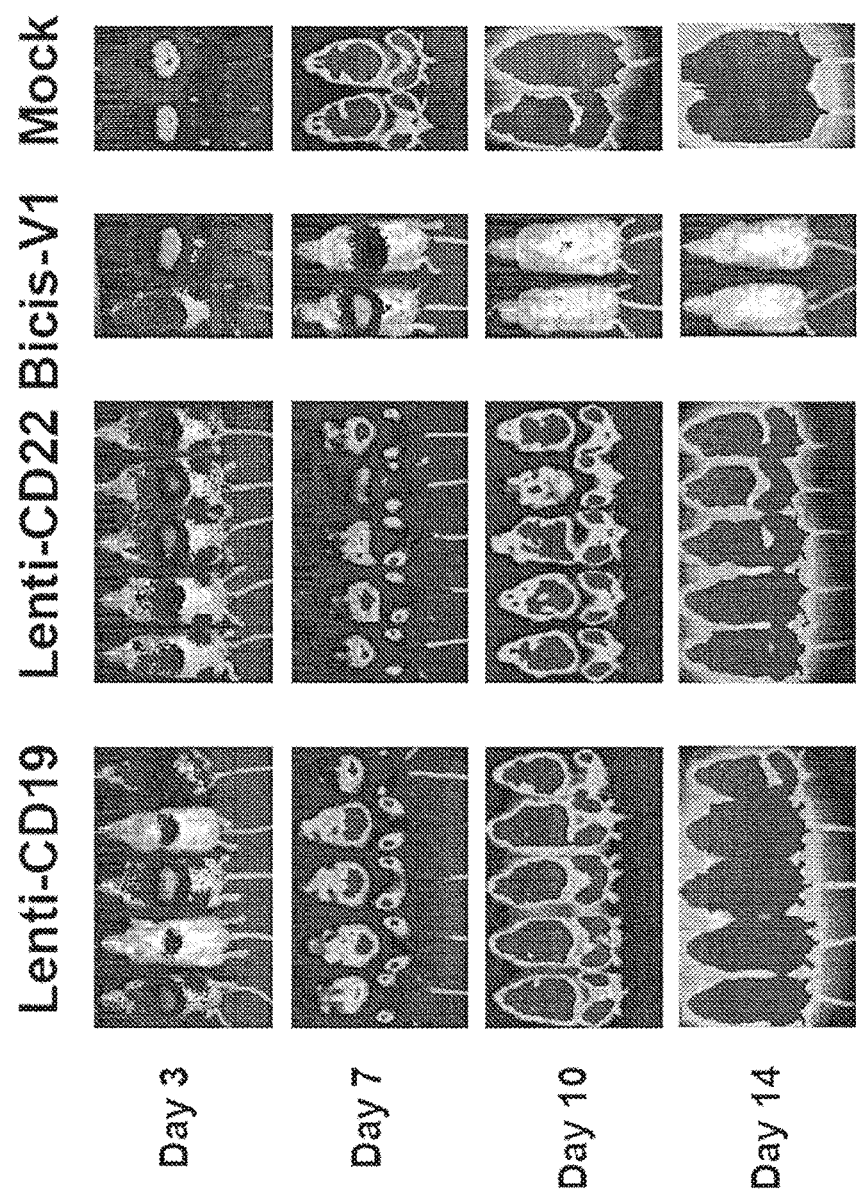
FIGS. 9-14 present bioluminescent imaging of leukemia progression in vivo after treatment using T cells transduced with a vector encoding the single anti-CD19 CAR, the single anti-CD22 CAR, the LoopCAR6, the V1 CAR construct, or the V5 CAR construct, compared to mock T cells (untransduced T cells), in accordance with embodiments of the invention. Bioluminescent intensity, as shown by increased levels of shading, represents tumor burden. "Lenti" indicates that the CAR has been designed and made within a lentiviral backbone.

Use of T cells transduced with a vector encoding the V1 CAR appeared to completely eradicate the leukemia while use of T cells transduced with a vector encoding either the single anti-CD19 CAR or the single anti-CD22 CAR failed to do so (FIG. 9).

The mice were euthanized on day 14. The bone marrow (BM) cells were stained with anti-CD19 or anti-CD22 antibody for the detection of leukemia, and also stained with CD22 Fc or anti-idiotype of CD19 for the detection of anti-CD22 CAR or anti-CD19 CAR, respectively.

There was no detectable level of leukemia in mice that were treated with T cells transduced with a vector encoding the V1 CAR, while there was a high tumor burden in mice that were treated with T cells transduced with a vector encoding either the single anti-CD19 CAR or the single anti-CD22 CAR. There was a high tumor burden in mice that were treated with mock T cells. V1 CART cells persisted up to day 14 in the BM compartment.

Figure 10:
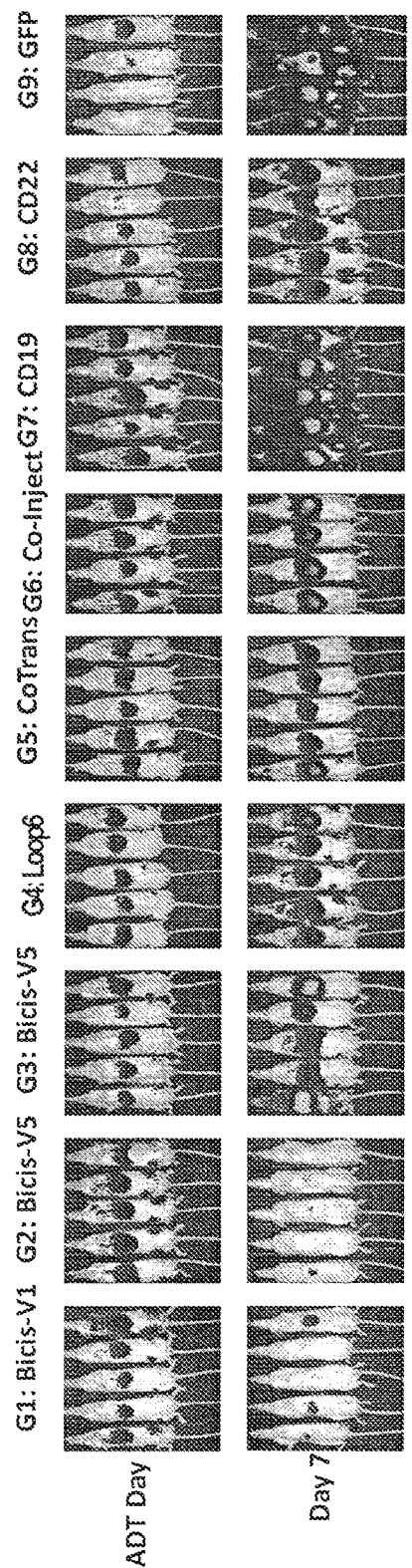

On day 0, NSG mice were injected with mixed leukemia cells (0.1E6 NALM6 and 0.1E6 NALM6-CD19$^-$ and 0.1E6 NALM6-CD22$^-$). On day 3, mice received 3E6 of CAR$^+$ T cells in all groups except group 2 (G2) with 6E6 CAR$^+$ T cells. Mice in group 5 (G5) received CD19 CAR and CD22 CAR co-transduced T cells. Mice in group 6 (G6) received co-administration of 3E6 of CD19 CAR and 3E6 of CD22 CARs. Mice in group 9 (G9) received Lenti-GFP$^+$ T cells and served as the negative control. Bioluminescent intensity represents tumor burden. The data suggests that at the same dose level of CAR T cells (3E6), Bicistronic-V1 CAR may be the most potent for reducing the leukemia in this relapse model (FIG. 10).

Example 5

This example demonstrates treatment of CD19$^-$ and CD22$^-$ leukemia using a CAR construct, in accordance with embodiments of the invention, compared to other CARs.

Bioluminescent imaging was used to track leukemia progression in vivo. On day 0, 0.5 million of CD19KO NALM6 cells were mixed with an equal number of CD22KO NALM6 cells and injected into NSG mice. After 3 days, these mice were treated with 3 million CAR T cells.

Figure 11:
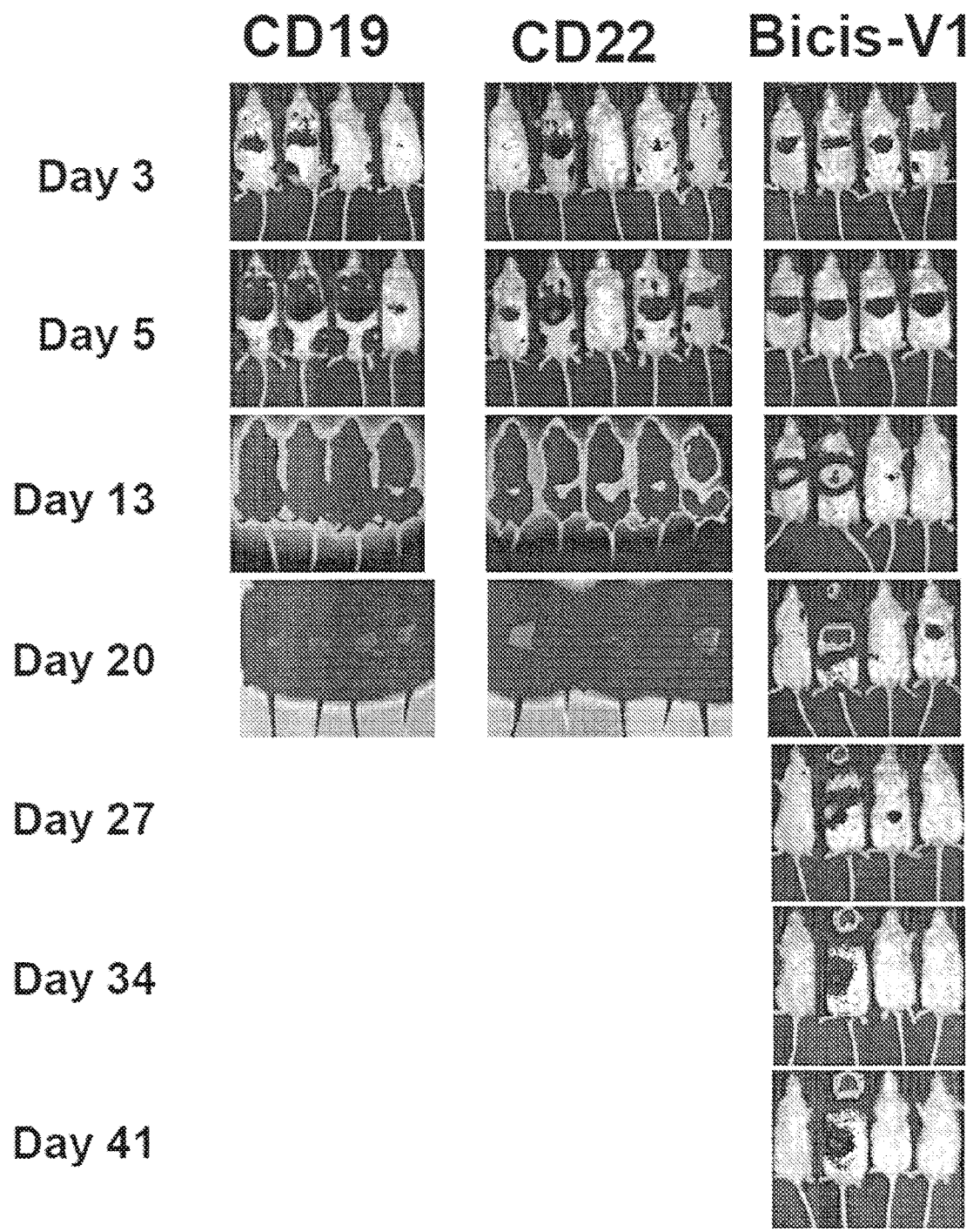

Use of T cells transduced with a vector encoding the V1 CAR almost cleared all of the leukemia, while use of T cells transduced with a vector encoding either the single anti-CD19 CAR or the single anti-CD22 CAR failed to do so (FIG. 11).

Figure 12:
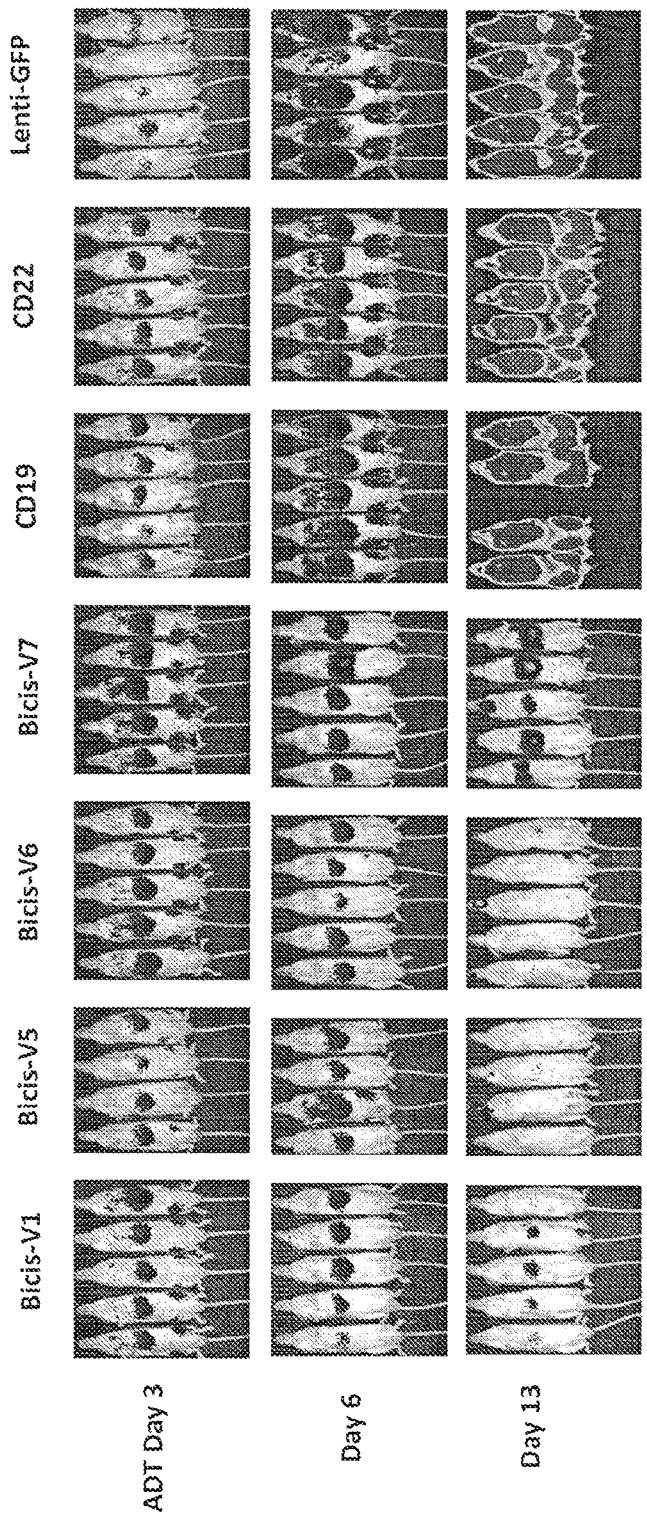

NSG mice were challenged with 1E5 cells of NALM6, 1E5 cells of NALM6-CD19KO and 1E5 CD22KO leukemia cells on day 0, and then received 3E6 of CAR+ T cells on day 3. Bioluminescent intensity represent tumor burden. The image indicates that the V1, V5, V6, and V7 CARs are efficient at reducing both $CD19^+$ $CD22^+$ leukemia and also CD19-negative and CD22-negative leukemic cells but the anti-CD19 or anti-CD22 single CARs failed to do so. FIG. 12.

Example 6

This example demonstrates treatment of leukemia with a CAR construct, in accordance with embodiments of the invention, compared to other CARs.

Figure 13:
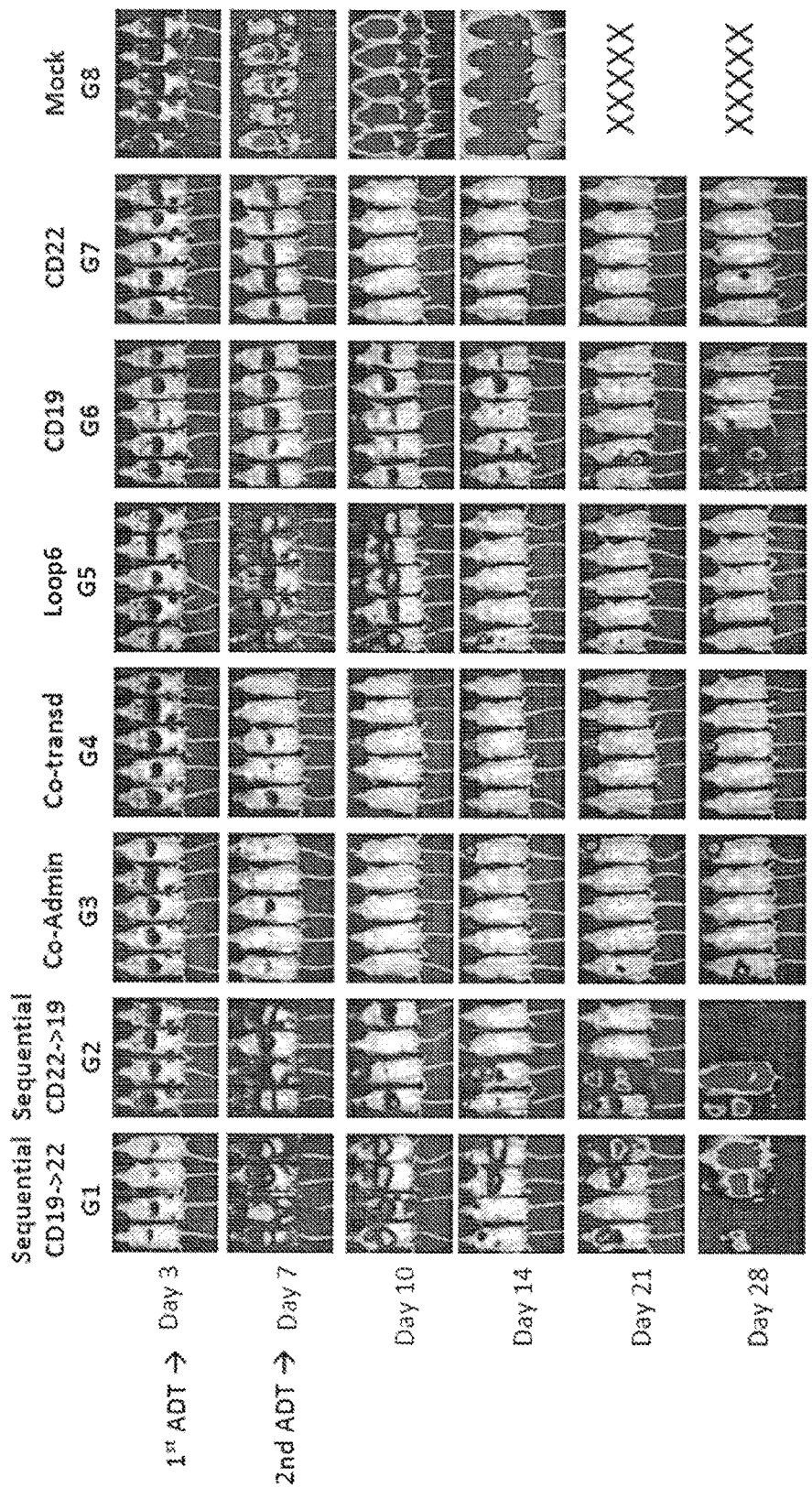

NSG mice were challenged with 1E6 of NALM6 leukemia cells on day 0. Mice in group 1 and group 2 (see FIG. 13 for mouse groups) received sequential treatment with 1E6 T cells transduced with a vector encoding the single anti-CD19 CAR or single anti-CD22 on day 3 and 3E6 T cells transduced with a vector encoding the other single CAR on day 7. Mice in group 3 received co-administration of a total of 6E6 CAR+ T cells with 3E6 T cells transduced with a vector encoding the single anti-CD19 CAR and 3E6 T cells transduced with a vector encoding the single anti-CD22 CAR on day 3. Mice in groups 4 to 7 received 3E6 of T cells transduced with a vector encoding the CARs indicated in FIG. 13 on day 3. Mice in group 4 received almost 10E6 of total CAR+ T cells due to the low expression on the co-transduced T cells. FIG. 13 demonstrates that simultaneously targeting of both CD19 and CD22 is better than sequential treatment with single targeting CARs.

Figure 14:
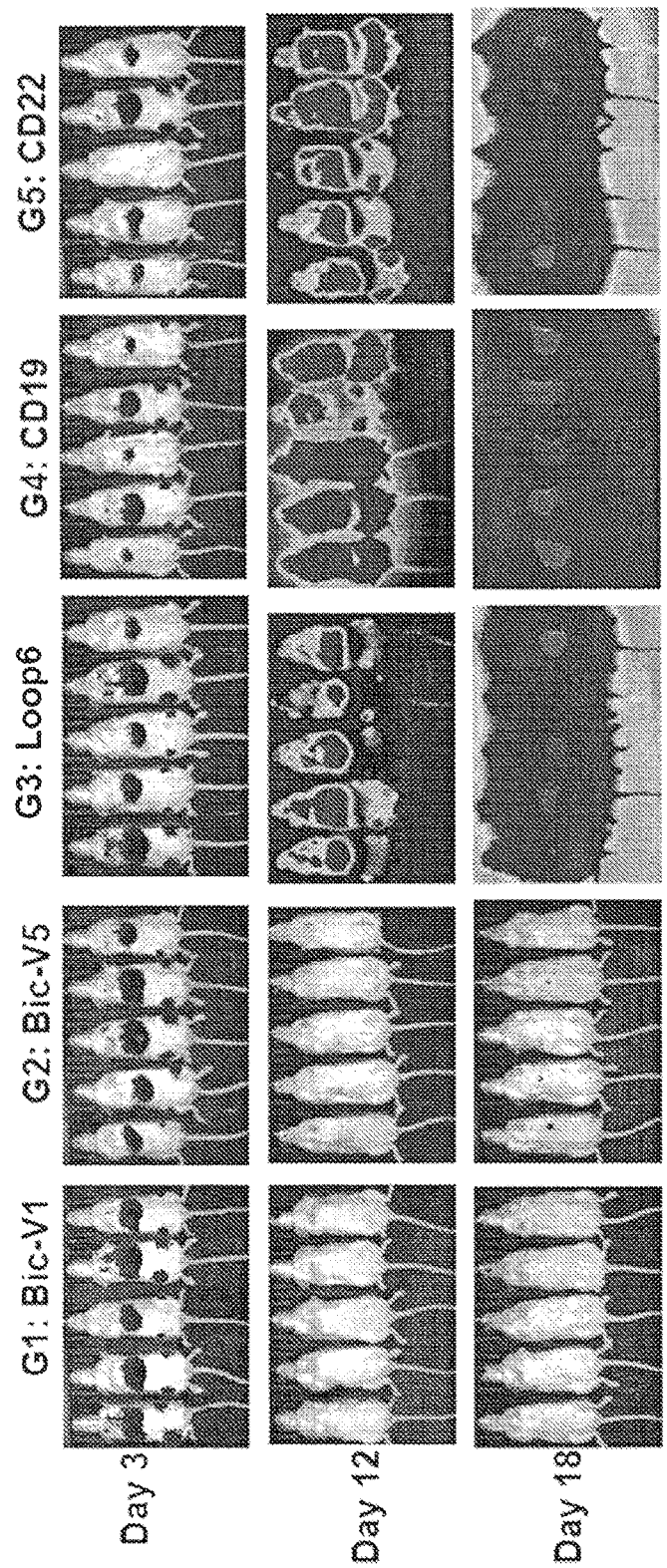

NSG mice were challenged with 0.25E6 of NALM6-CD19KO and 0.25E6 CD22KO leukemia cells on day 0. On day 3, NSG mice were injected with 3E6 CAR+ T cells. Use of T cells transduced with a vector encoding the V1 CAR and use of T cells transduced with a vector encoding the V5 CAR appear to completely eradicate both $CD19^-$ and $CD22^-$ leukemic cells (FIG. 14).

Example 7

This example demonstrates bispecific CARs, in accordance with embodiments of the invention.
Human Leukemia Samples Patient samples were screened for antigen expression via a NCI IRB approved screening protocol. Human ALL samples for xenograft generation were collected and stored after informed consent to an National Cancer Institute (NCI)-IRB approved tissue acquisition protocol. All research specimens from human subjects were obtained with informed consent in accordance with the Declaration of Helsinki.
Cell Lines and Culture Conditions The following leukemia cell lines were used: the erythroleukemia K562-CD22 (transduced with human CD22, GeneCopoeia, Cat: EX-Z9364-Lv151), K562-CD19 (transduced with human CD19), K562-CD19CD22 (transduced with both human CD19 and CD22), non-transduced K562 as a negative control; the B cell acute lymphoblastic leukemia lines NALM6, NALM6-GL (transduced with GFP and Luciferase) and REH-TSLPR-GL (Qin et al., Blood, 126: 629-39 (2015), incorporated by reference). Cell lines were cultured in media supplemented with 10% heat-inactivated FBS, 10 mM HEPES, 100 U/mL penicillin, 100 ug/mL streptomycin, and 2 mM L-glutamine (Invitrogen). The Lenti-X 293T lenti packaging cell line (Clontech. Cat #632180) was cultured in DMEM (Invitrogen) media.
Creation of the CD19neg and CD22neg Leukemia Relapse Model CRISPR Cas9 technology was used to edit Nalm6 to generate NALM6-CD19neg-GL (CRISPR CD19 on exon 3), NALM6-CD22neg-GL (CRISPR CD22 on exon 6). Lentiviral vectors for CRISPR/Cas9 gene editing of CD19 or CD22 on NALM6 was previously described (Fry et al., Nat. Med., 24: 20-28 (2018), incorporated by reference). Briefly, guide-RNAs were optimized by http://crispr. mit. edu/, cloned into LentiCRISPR v2 plasmid (Addgene Plasmid 52,961). Plasmids were then co-transfected with packaging plasmids and transformed into HEK293T cells. Two days later, supernatants were harvested, filtered, and concentrated. For viral transduction, $10^5$ NALM6 cells were incubated with 10 ml of concentrated viral supernatant for 2 days, followed by expansion in RPMI media. Cell phenotype was assessed by flow cytometry, followed by sorting of cells with phenotypic alterations and single-cell cloning. Sequencing was performed on single-cell clones to confirm genotypic alterations.
CAR Lentiviral Vector Production and T Cell Transduction Bivalent CAR constructs were designed and synthesized followed by cloning into lentiviral transfer plasmids. Bivalent CAR-encoding lentiviral vectors were produced by transient transfection of the Lenti-X 293T lenti packaging cell line. Briefly, lenti-X 293T cells were plated into poly-D lysine coated 15-cm plates (BD Biosciences). The following day, Lenti-X 293T cells were transfected using lipofectamine 3000 (Thermo Fisher Scientific) with plasmids encoding the CAR construct along with packaging and envelope vectors (pMDLg/pRRE, pMD-2G, and pRSV-Rev). Lentiviral supernatants were harvested at 24 and 48 hours post-transfection, centrifuged at 3000 RPM for 10 minutes to remove cell debris, frozen on dry ice and stored at −80° C. Human PBMCs from normal donors were obtained with an NIH-approved protocol and activated with a 1:3 ratio of CD3/CD28 microbeads (Dynabeads Human T-Expander CD3/CD28, Thermo Fisher Scientific, Cat #11141D) in AIM-V media containing 40 IU/mL recombinant IL-2 and 5% FBS for 24 hours. Activated T cells were resuspended at 2 million cells per 2 mL of lentiviral supernatant plus 1 mL of fresh AIM-V media with protamine sulfate at the final concentration of 10 ug/mL and 100 IU/mL IL-2 in 6-well plates. Plates were centrifuged at 1000×g for 2 hours at 32° C. and incubated overnight at 37° C. A second transduction was performed on the following day by repeating the same transduction procedure described above. The CD3/CD28 beads were removed on the third day following transduction, and the cells were cultured at 300,000 cells/mL in AIM-V containing 100 IU/mL IL2 with fresh IL2-containing media added every 2-3 days until harvest on day 8 or 9.
Flow Cytometry Analysis Surface expression of CD22 CAR-transduced T cells was determined by flow cytometry using a CD22-Fc (R&D Systems) followed by incubation with PE-F(ab)$_2$ or APC-F (ab)$_2$ specific for human IgG-Fc (Jackson ImmunoResearch Laboratories). Surface expression of CD19 CAR-transduced T cells was detected with anti-CD19 Idiotype or Recombinant Human CD19 Fc Chimera Protein (R&D Systems) conjugated with APC by using Lightning-Link APC Antibody Labeling Kit (Novus Biologicals). Expression of bivalent CARs was assessed using a combination of both detection reagents as indicated for individual figures. Expression of CD19 and CD22 on B-ALL lines were detected using the following anti-human antibodies: CD45-PerCP-Cy5.5 (eBioscience), CD19-Pacific Blue, CD19-APC-Cy7, CD10-PE-Cy7, and CD22-PE (Biolegend). T cells were characterized with the following antibodies: CD3-APC-Cy7, CD4-Pacific Blue, and CD8a-PE-Cy7 (BioLegend).

Incucyte Cytotoxicity Assay

5E4 of Target tumor cells in 100 ul of RPMI media were loaded into a 96-well plate (Corning® BioCoat™ Poly-L-Lysine 96-Well Clear TC-Treated Flat Bottom Assay Plate). An equal amount of CART cells were added into the designated well on the following day. An apoptosis marker (Essen BioScience) was diluted in 100 ul PBS and 1 ul of the diluent was added into each well. The plate was scanned for the GFP fluorescent expression to monitor apoptosis GFP-positive cell disappearance using an IncuCyte ZOOM® system every 30 minutes in a duration of 40 hours. The percentage of cell killing at each time point determined relative to baseline.

Analysis of Cytokine Production

Target tumor cells and transduced CAR positive T cells were washed 3 times with PBS and resuspend in RPMI at 1E6/ml. 100 ul of tumor cell suspension and 100 ul of CAR T cells suspension was loaded into each well of 96-well plate with T cell only and tumor cell only controls in duplicates or triplicates. After 18 hours at 37° C. incubator a culture supernatant was harvested for detection of the cytokines using either ELISA (R&D Biosciences) or a multiplex assay (Meso Scale Discovery).

In Vivo Studies

Animal experiments were carried out under protocols approved by the NCI Bethesda Animal Care and Use Committee. B-ALL cell lines and the xenografted human B-ALL specimens were IV injected into NSG mice (NOD.Cg-Prkdcscid112rgtm1 Wjl/SzJ, Jakcson Laboratories). For luciferase-expressing lines, leukemia was detected using the Xenogen IVIS Lumina (Caliper Life Sciences). Mice were injected intraperitoneally with 3 mg D-luciferin (Caliper Life Sciences) and were imaged 4 minutes later with an exposure time of 30 sec for NALM6 and 2 minutes for PDXs. Living Image Version 4.1 software (Caliper Life Sciences) was used to analyze the bioluminescent signal flux for each mouse as photons/s/cm$^2$/sr. Leukemia burden in non-luciferase expressing xenografts was measured by flow cytometry of peripheral blood, bone marrow, and spleen.

Patient-Derived Xenografts

The following primary samples were used for the generation of PDX models: CD19$^-$ ALL and the CD19$^+$ CD22$^{dim}$ (de novo relapse specimens ALL_H0113_post22_r (CAR3), ALL_H0090_post19_pd (HMB15). PDXs were created by injecting 1E6 to 10E6 of the patient ALL cells intravenously into NSG mice (NOD scid gamma, NOD.Cg-Prkdcscid Il2rgtmlWjl/SzJ; Jackson ImmunoResearch Laboratories). After 2 successful passages PDX lines were transduced with lenti-GFP-Luc virus and sorted for high expression of GFP and luciferase after the first and second passages. GFP-transduced PDX leukemia in vivo burden was assessed by weekly fluorescence imaging, and animals were treated with CAR T cells via tail vein injection once the human ALL was detectable by florescence imaging. Elutriated human lymphocytes from healthy donors were obtained from the Department of Transfusion Medicine at the National Institutes of Health (NIH) Clinical Center under an IRB-approved protocol. The human lymphocytes were cultured in AIM-V media.

Genomic Analysis of PDX Models

Nucleic acid extractions were performed on viably cryopreserved samples using Qiagen AllPrep micro kits per the manufactures protocol (Qiagen). DNA and RNA were quantified and assessed for quality using an Agilent 2100 Bio-Analyzer. Poly-adenylated RNA libraries were generated and sequenced using TruSeq 4.0 chemistry on a Hiseq2500 (Illumina) platform. Whole exome data was generated using Agilent SureSelect XT Human All Exon V5 and TruSeq V4 chemistry and sequenced to a median of 100× coverage using HiSeq 2500 (Illumina).

Whole-exome and RNA-sequencing data was mapped and analyzed using the CCR Collaborative Bioinformatics (CCBR) pipeline (https://bioinformatics. cancer. gov). Reads were aligned to reference genome Hg19. Somatic variant calling was performed using MuTect[20] and copy number alterations were analyzed using Nexus Copy Number Discovery Edition #9 (BioDiscovery). The integrity of the CD19 and CD22 gene was further interrogated by manual inspection using Integrative Genome Viewer (IGV). RNA sequencing reads for each sample were trimmed of their adapters and low quality bases using Trimmomatic software and alignment with reference human Hg 38 and Genecode V24 transcripts using STAR software.

Statistical Analysis

Statistics analysis were performed using Prism 7.0 software. Statistical significance was calculated using Mann Whitney test for patient CD19 and CD22 analyses.

Heterogeneous and Dynamic Expression of CD19 and CD22 on Pre-B ALL.

Figure 15:
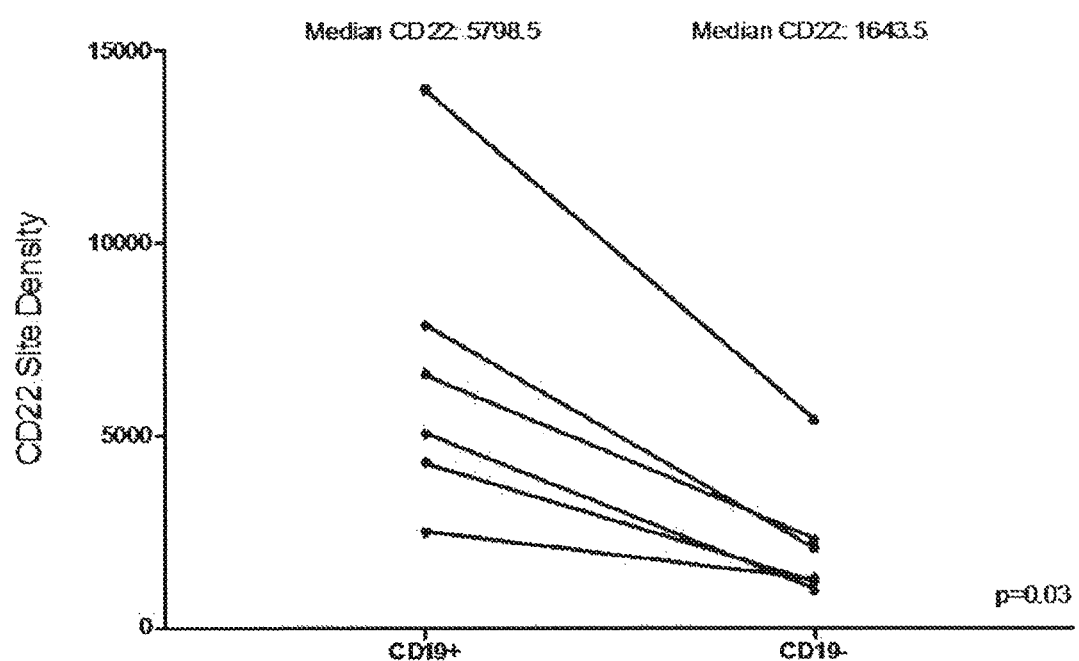
FIG. 15 is a line graph showing CD22 expression in patients prior to and after loss of CD19.
Figure 42:
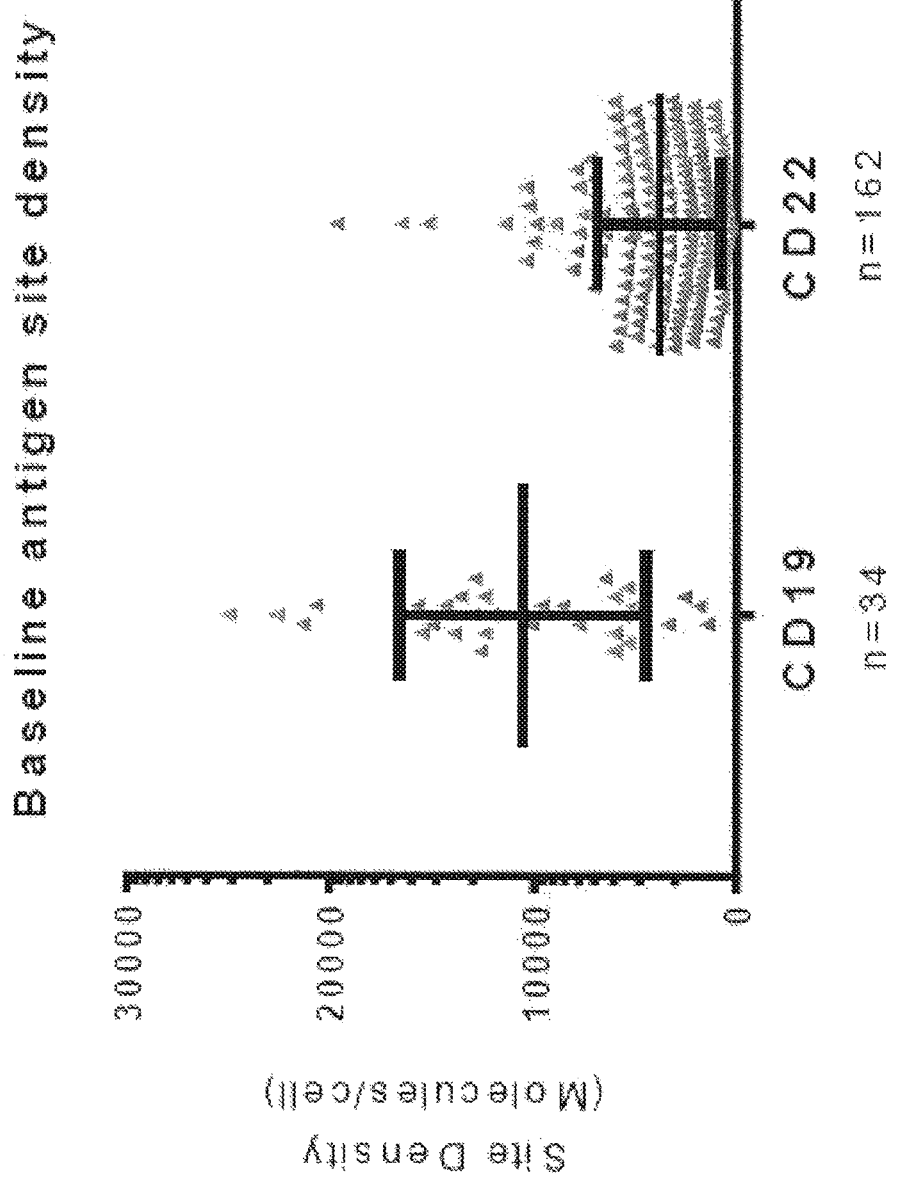
FIG. 42 is a graph showing site density, as described in Example 7.

Patient samples, primarily derived from patients with multiply relapsed disease, were evaluated for CD19 and CD22 expression. There was a broad range in expression of CD19 and CD22 prior to administration of immunotherapy (FIG. 42). CD19 epitope loss has been well-described following CD19-targeted immunotherapy. In a matched paired analysis, CD22 expression was evaluated in patients prior to and after loss of CD19 and demonstrated a consistent decrease in CD22 expression associated with CD19 loss, suggesting that single antigen loss may also broadly modulate antigen expression (FIG. 15). These results illustrate the challenges associated with single-antigen targeted immunotherapy.

Simultaneous Targeting of Both CD19 and CD22 is Superior to Sequential Treatment in Prevent Relapse or Disease Progression of Antigen Loss-Relapse Models.

Figure 16:
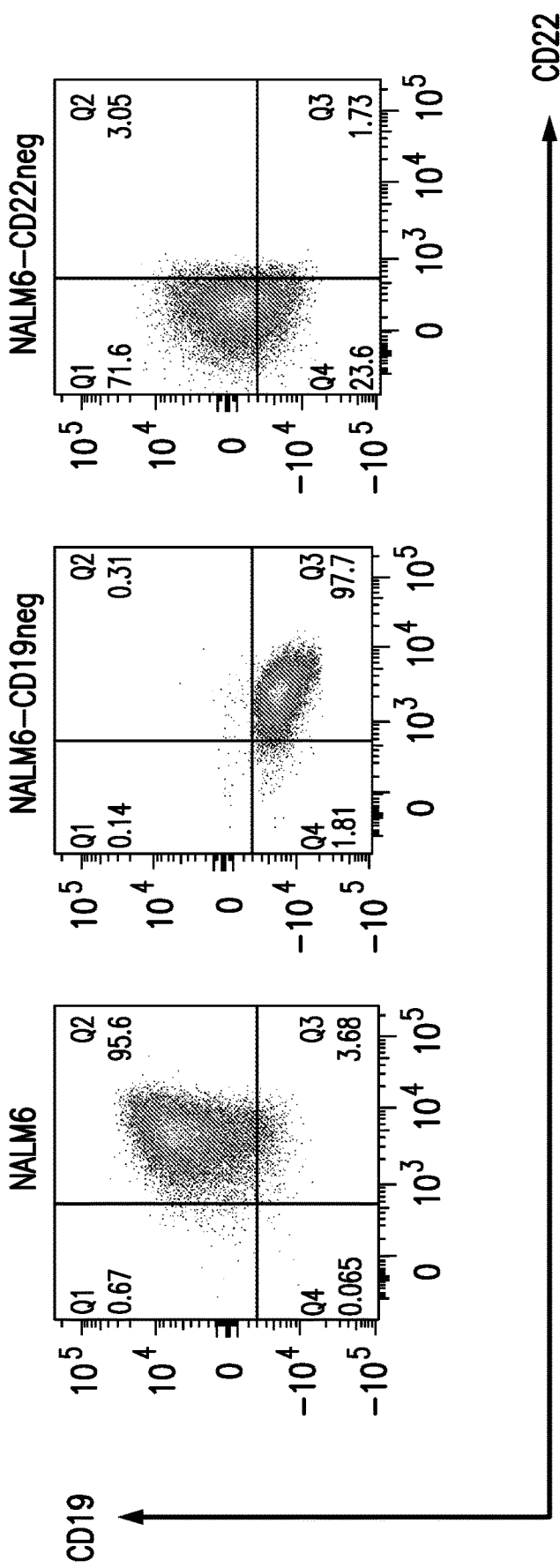
FIG. 16 is a dot plot showing CD19 and CD22 expression of CRISPR CD19neg and CD22neg leukemia lines vs parental NALM6 line.

To model the CD19 and CD22 relapse phenomenon seen in clinical trials, CRISPR/Cas9 gene editing was used to delete CD19 and/or CD22 from the pre-B ALL cell line NALM6 cell (FIG. 16) with certain data provided in Table 17.

TABLE 17

| | Diff in GeoMean CD22 | Diff in GeoMean CD19 |
|---|---|---|
| NALM6-CD19neg | 1909 | 0 |
| NALM6-CD22neg | 0 | 5779 |
| NALM6-GL | 3670 | 10733 |

Figure 17:
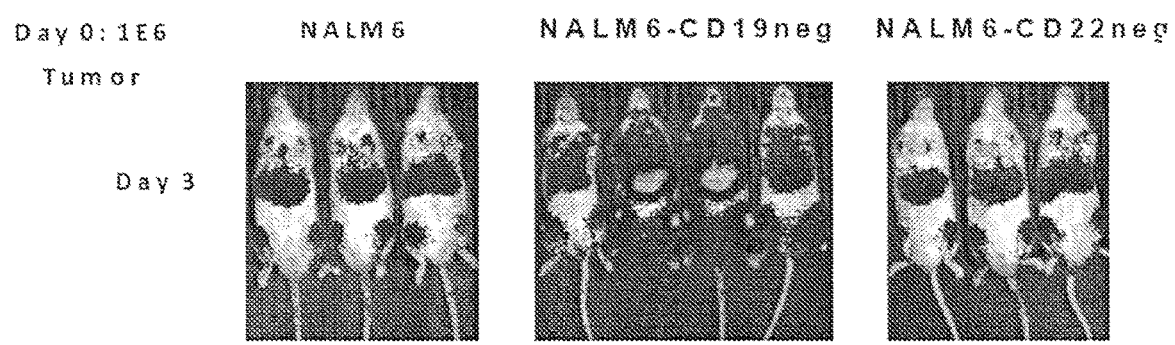
FIG. 17 presents images showing comparison of in vivo progression of CRISPR CD19neg and CD22neg leukemia cell vs parental NALM6 cell. Bioluminescent intensity, as shown by increased levels of shading, represents tumor burden.

After single cell cloning to ensure stability, both CRISPR-edited NALM6 lines and parental NALM6 all demonstrated disease progression when engrafted in NSG mice despite deletion of either B cell receptor-associated gene and loss of corresponding surface protein expression (FIG. 17).

Figure 18:
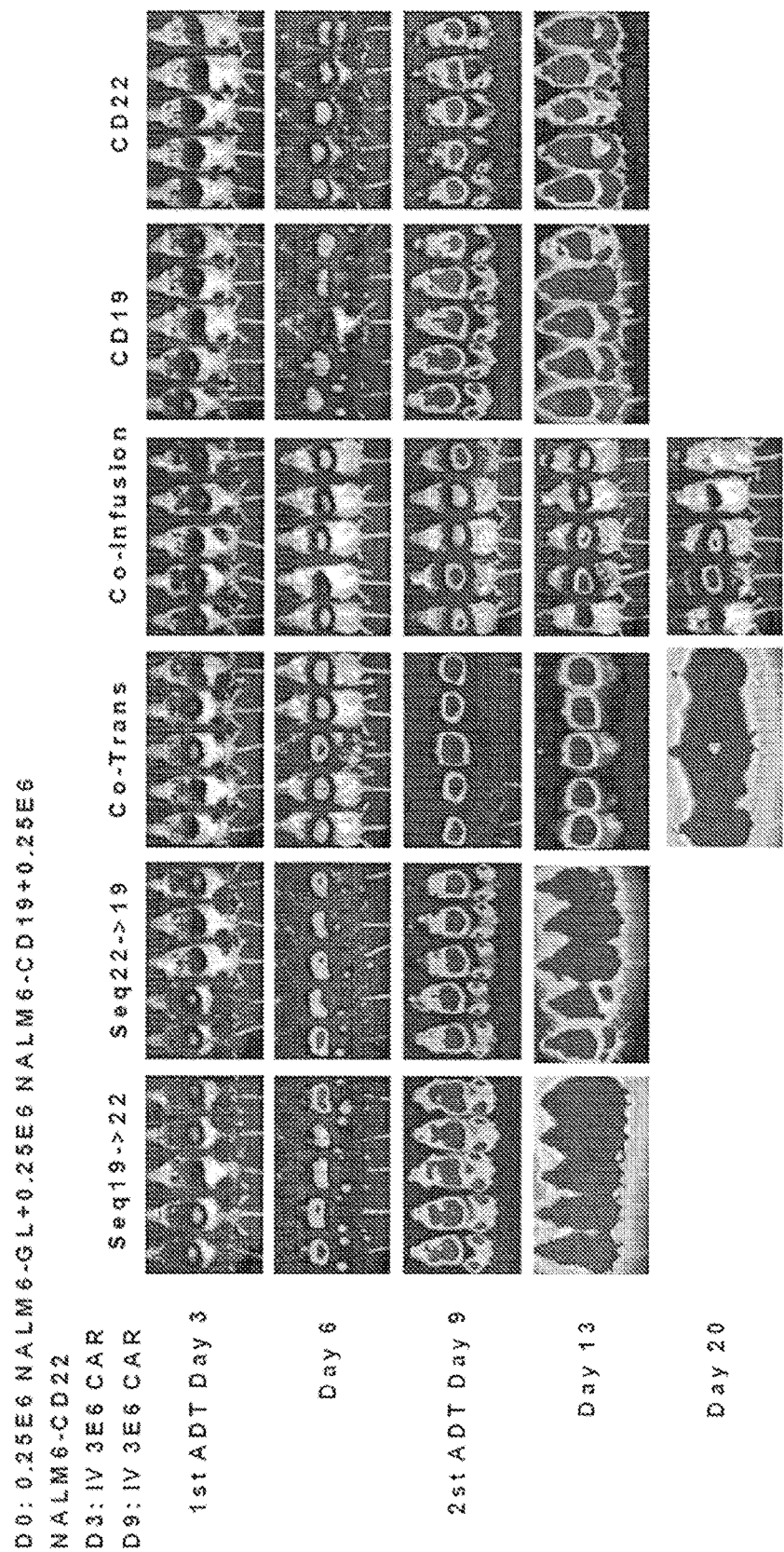
FIG. 18 presents images showing comparison of treatment methods using CARs as described herein. NSG mice were challenged with a mixture of 2.5E5 of NALM6 and NALM6-CD19neg and NALM6-CD22neg leukemia lines on day 0. Mice in the sequential treatment group received 3E6 CAR+ on day 3 and 3E6 CAR+ T cells on day 9. Mice in the co-injection group received a total of 6E6 CAR+ T cells with 3E6 of anti-CD19 CAR+ and 3E6 of anti-CD22 CAR+ T cells on day 3. Mice in the co-transduced group received 8E6 of total T cells which contain 3E6 of anti-CD19+ and 3E6 of anti-CD22+ CAR T cells. Mice in the CD19 or CD22 groups received 3E6 of CAR+ T cells. Bioluminescent intensity, as shown by increased levels of shading, represents tumor burden. Co-injection or co-transduction of anti-CD19 and anti-CD22 CAR suggest that simultaneously targeting on both CD19 and CD22 may reduce relapse of leukemia.

One approach to exert immunotherapeutic pressure on two antigens is via sequential infusion of anti-CD19-CAR T cells followed by anti-CD22 CAR T-cells or vice versa. To test this strategy, mice were injected with a mixture of CD19neg, CD22neg and parental NALM6 (CD19pos/CD22pos) ALL to simulate antigen-negative relapse. Administration of single antigen-specific CAR T cells resulted in recurrence of leukemia not expressing the targeted antigen, validating the relapse model (FIG. 18). Surprisingly, sequential infusion of curative doses of anti-CD19 and anti-CD22 CART separated by 6 days did not prevent ALL progression. Importantly, the relapse phenotype demonstrated redcued efficacy of the second CAR infusion. Simultaneous administration (co-infusion) of both anti-CD19 and anti-CD22 targeted CART was superior to sequential infusion but resulted in progression of CD19neg ALL still expressing CD22, suggesting that the anti-CD19 CAR may dominate.

Figure 19:
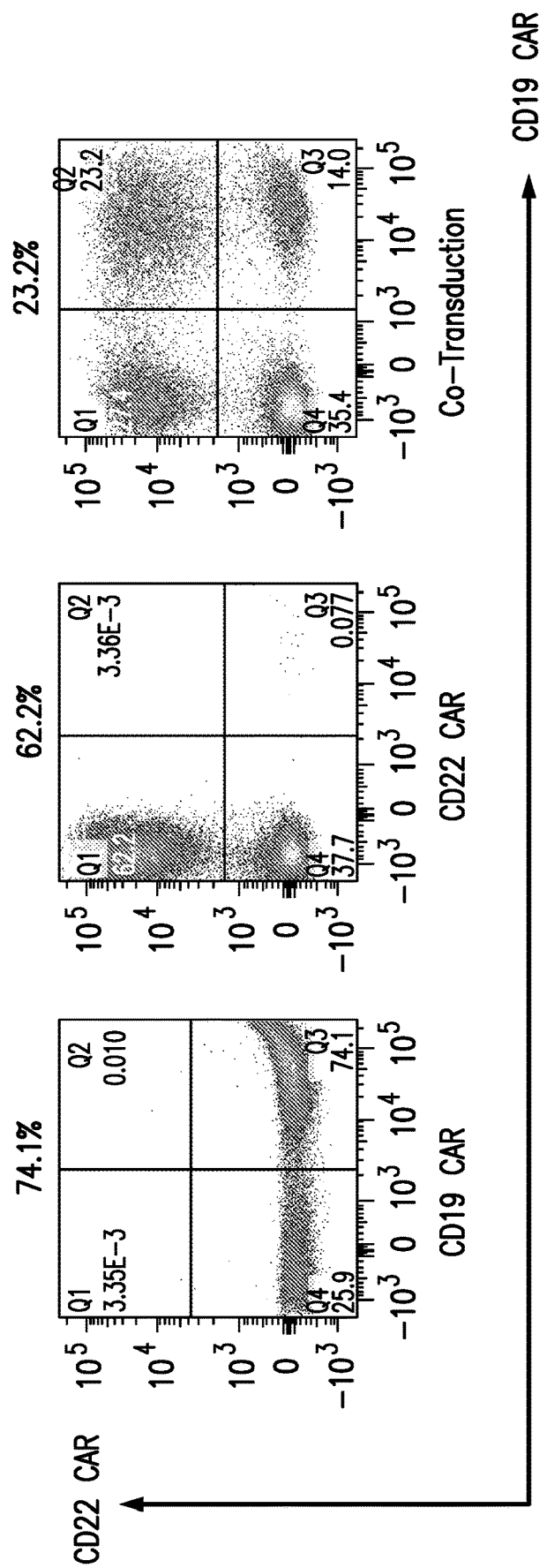
FIG. 19 is a dot plot showing comparison of single vector transduction vs co-transduction with anti-CD19 and anti-CD22 CAR constructs.
Figure 20:
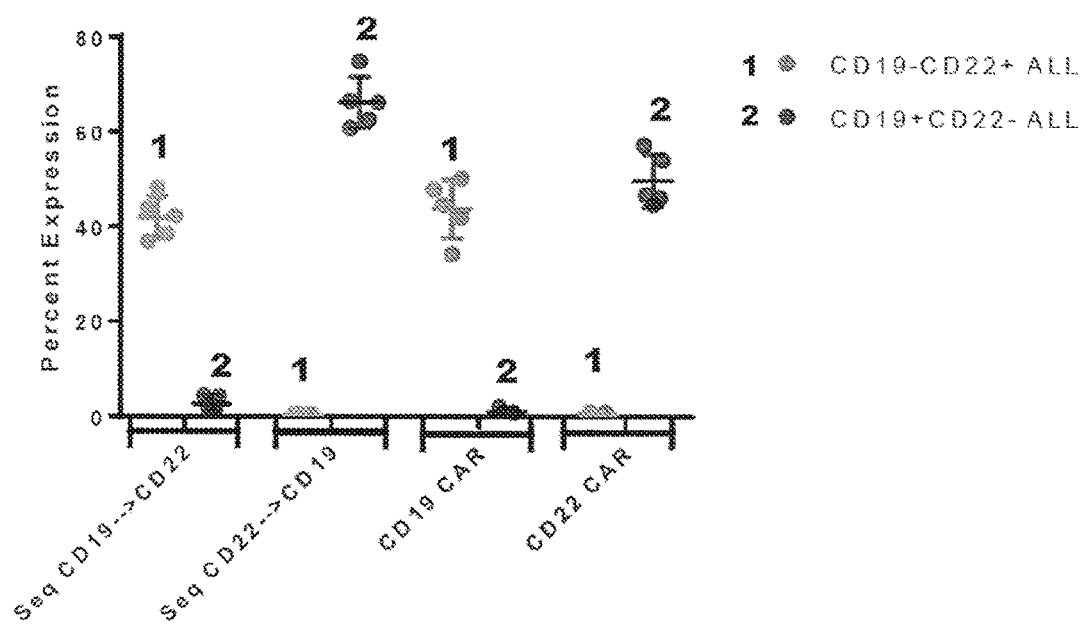
FIG. 20 is a graphic plot presentation of the leukemia phenotype post CAR treatment as described in Example 7.

Based on the apparent dominance of the anti-CD19 CAR when co-infused with the CD22 CAR, the next step was to introduce both the anti-CD19 and anti-CD22 CAR into the same T cell through co-transduction, generating a pool of T cells containing dually specific CAR T cells. However, co-transduction efficiency was consistently low, yielding only a quarter of the total T cell product expressing both anti-CD19 and anti-CD22 CAR (FIG. 19). Furthermore, the relapse phenotype (CD22+CD19neg and CD22negCD19neg, FIG. 20) suggests that again, the anti-CD19 CAR T cell may dominate when administered with T cells expressing both anti-CARs or the anti-CD22 CAR alone. Thus, based on the inefficiency of gene transfer by two vectors, the technical challenges and costs associated with managing two vectors as well as the possibility that inclusion of two single CAR expressing T cell may impair expansion of the dually specific T cell population, approaches were pursued to introduce dual-specificity from the same vector.

Development of the Bivalent CARs with Tandem Sequencing of scFv.

Figure 21:
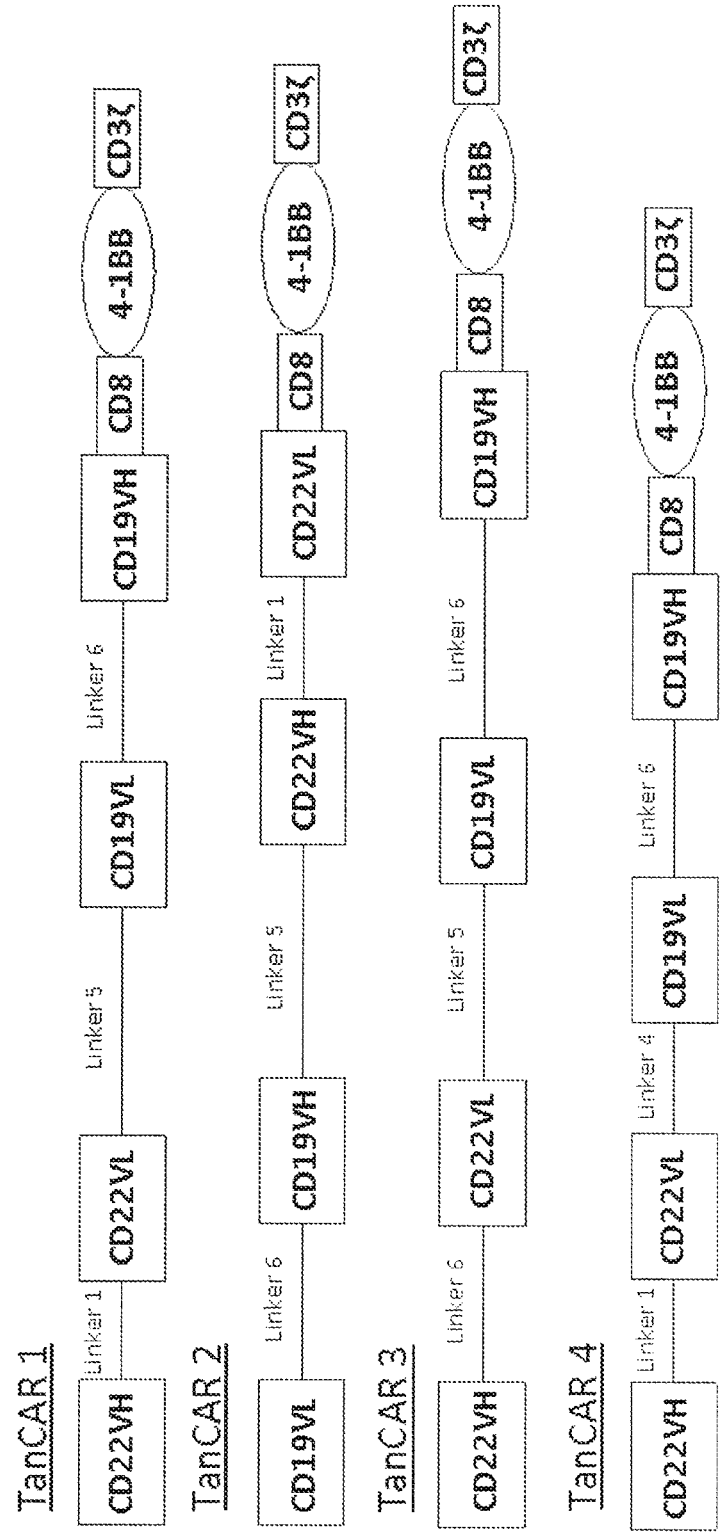
FIG. 21 diagrammatically presents TanCARs of Example 7, in accordance with embodiments of the invention.
Figure 22A:
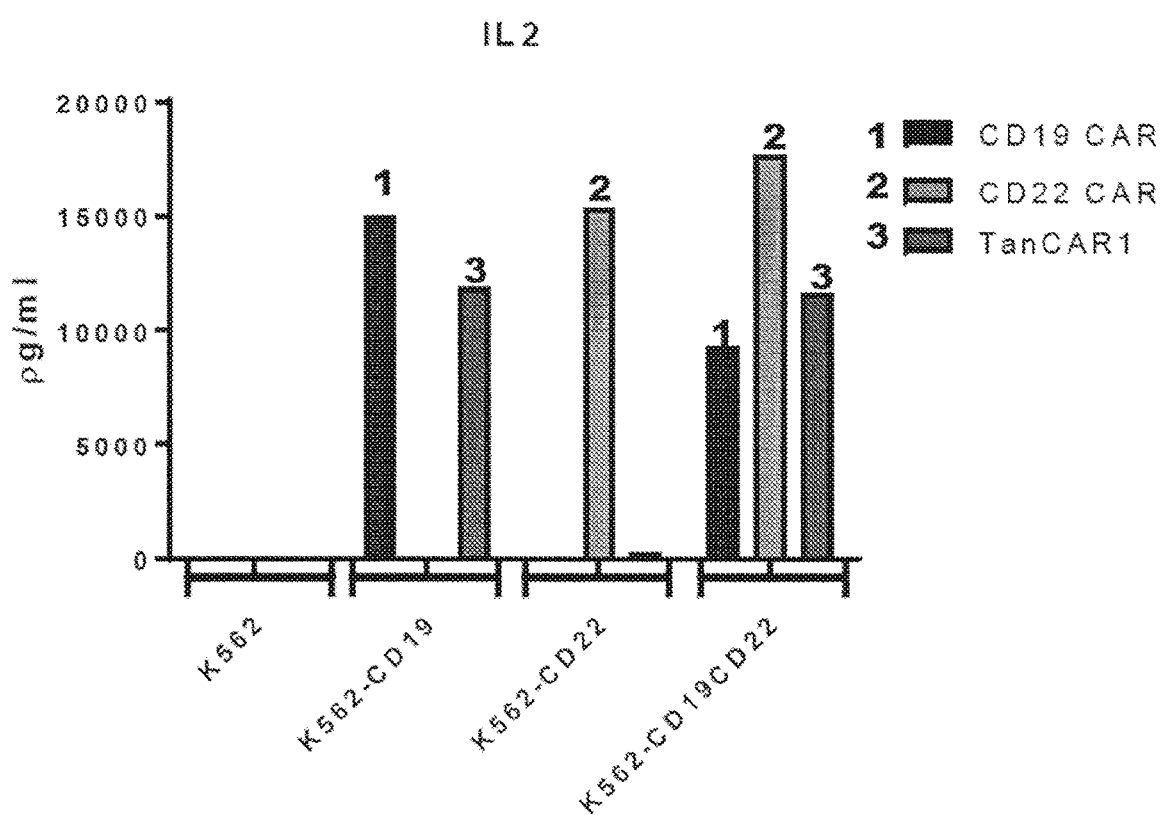
FIGS. 22A and 22B are bar graphs showing cytokine production of various CARs described herein with K562, K562-CD19, K562-CD22, and K562-CD19CD22 target cell lines, in accordance with embodiments of the invention.
Figure 22B:
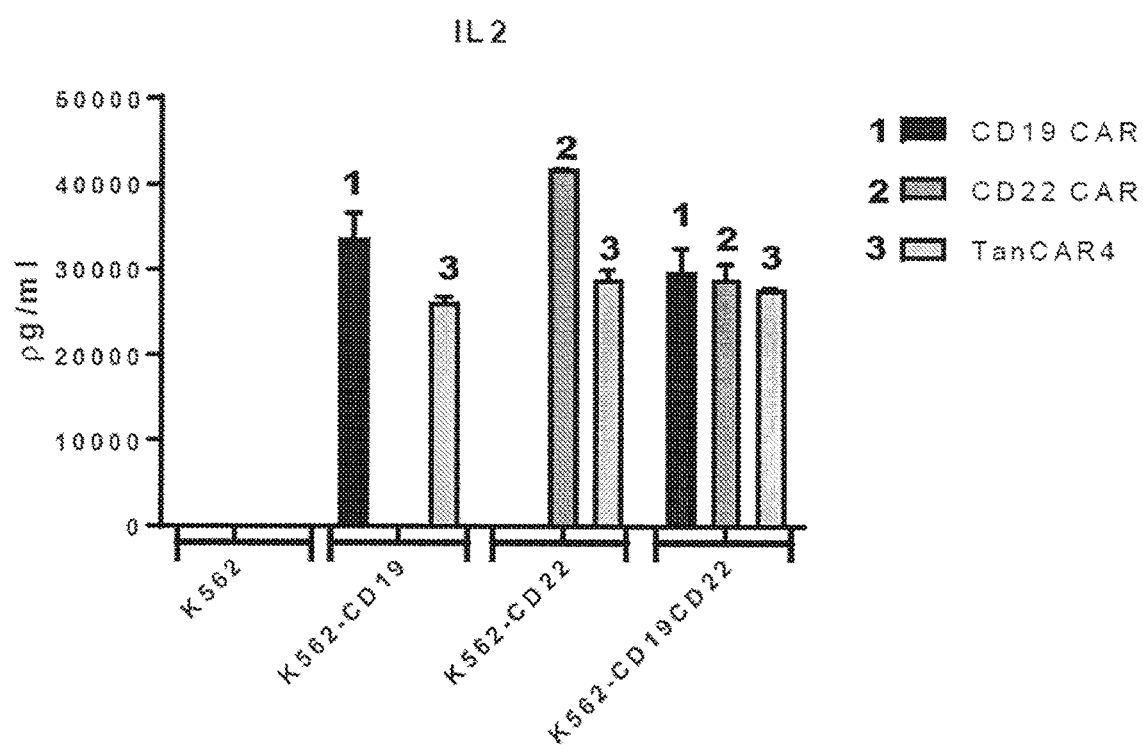
Figure 23A:
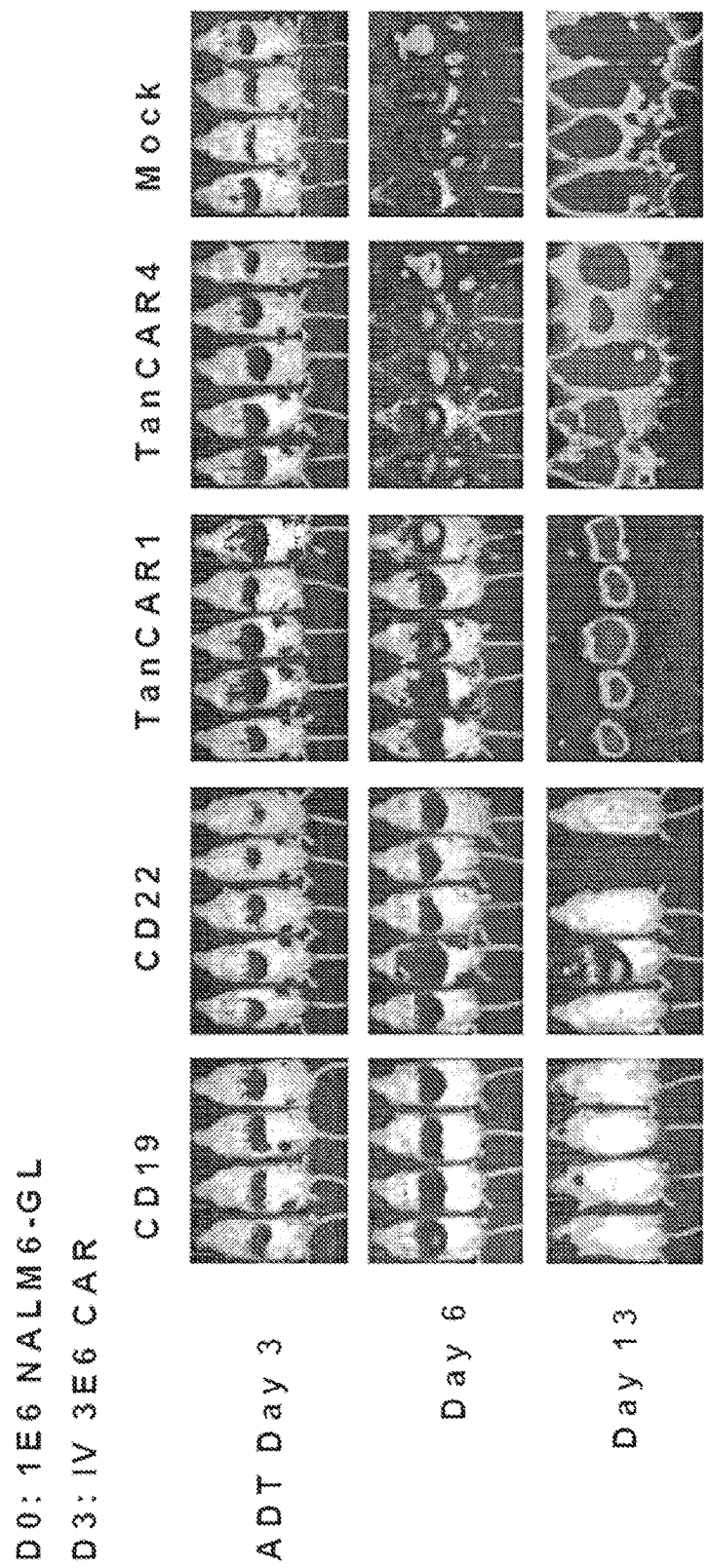
FIG. 23A presents images showing comparison of TanCAR1 and TanCAR4 on treatment of leukemia in vivo. NSG mice were challenged with 1E6 of luciferase-expressing NALM6 leukemia on day 0. On day 3, mice were IV injected with 3E6 of CAR expressing T cells. Bioluminescent intensity, as shown by increased levels of shading, represents tumor burden.
Figure 23B:
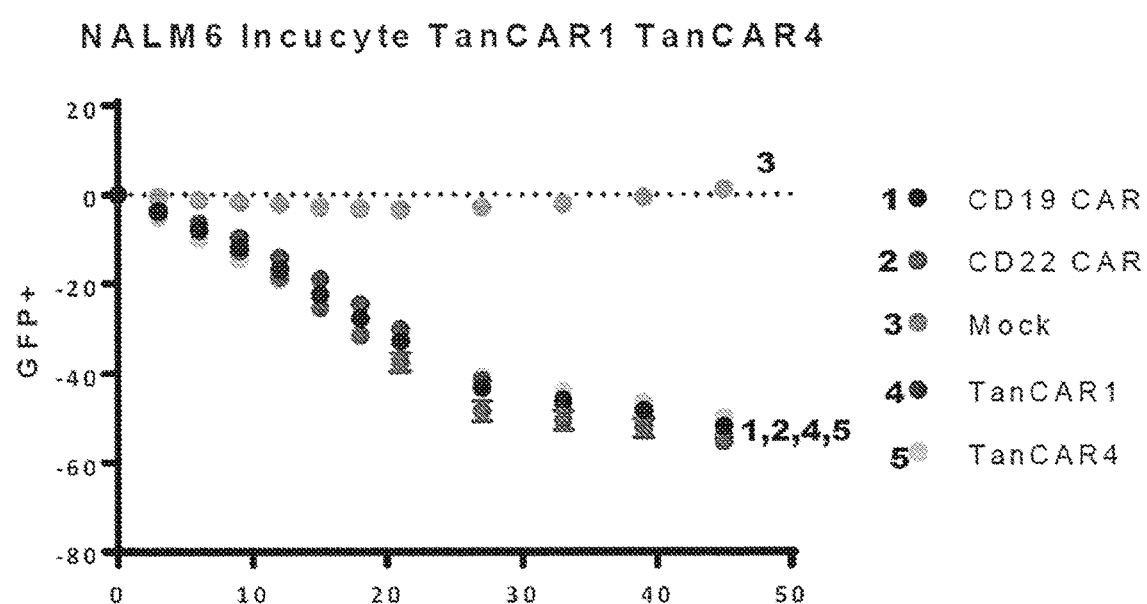
FIGS. 23B-23D present dot plots showing Incucyte killing assay with co-incubation of each CAR or mock T cell product, in accordance with embodiments of the invention.
Figure 23C:
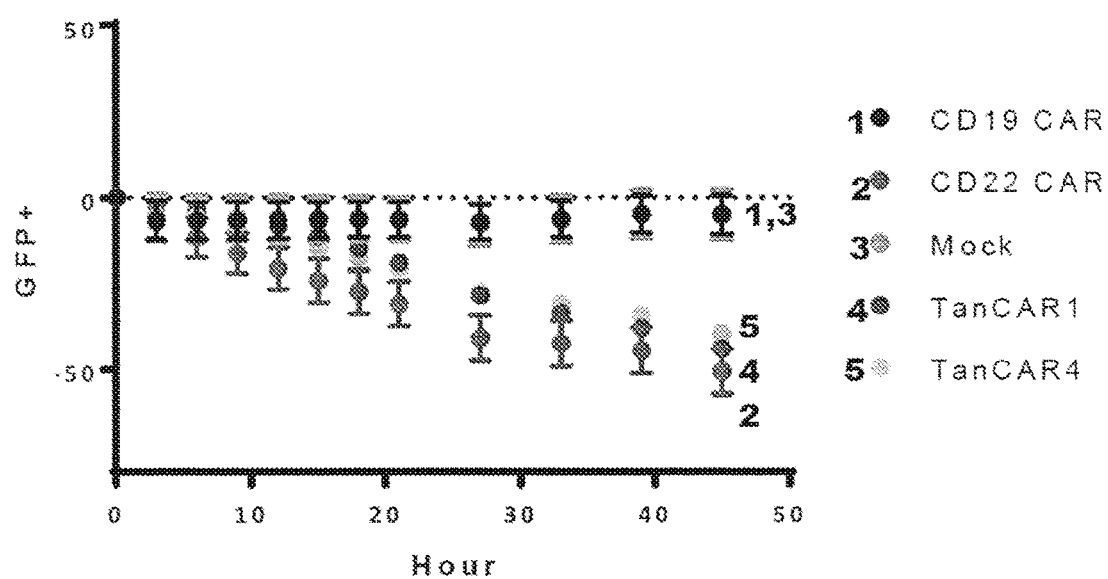
Figure 23D:
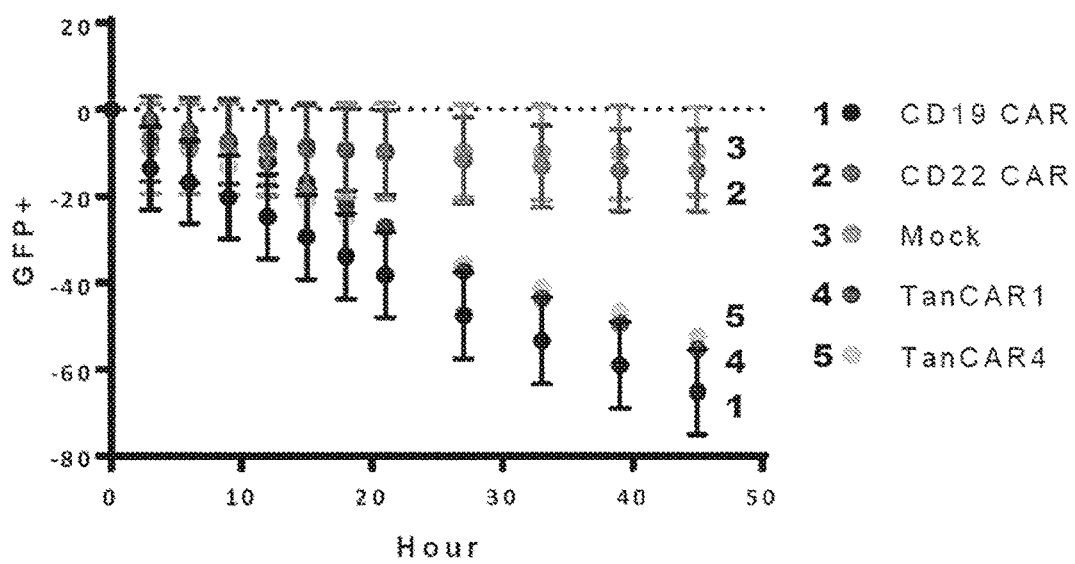

Bivalent CARs were generated by coupling two different scFv domains into a single CAR construct. The approach undertaken in constructing anti-CD19×anti-CD22 CARs was to place the heavy ($V_H$) and light chains ($V_L$) for each scFv (FMC63 for CD19 and m971 for CD22) in sequential order to make tandem CARs (TanCAR) as depicted in FIG. 21. For TanCAR1, the original linkers between the $V_H$ and $V_L$ from each single CAR were maintained and connected the two scFvs using a G(S)4×5 linker, a format that could be detected at a comparable level to single antigen targeted CARs on the cell surface following transduction. TanCAR1 is described in International Patent Publication No. WO 2016/149578. Importantly, all CAR-expressing T cells could be detected using anti-CD22 Fc fusion and anti-FMC63 idiotype. For TanCAR2 (SEQ ID NO: 63), the order of anti-CD19 and anti-CD22 scFv's were flipped, resulting in much lower detection on the surface. Despite good surface detection of TanCAR1 and comparable levels of IL2 production compared to mono-valent CD19 CART against CD19pos/CD22neg ALL, IL-2 production was extremely low when co-incubated with CD9neg/CD22pos ALL (FIGS. 22A and 22B). Given the extremely short linker (G4S) between the anti-CD22 $V_H$ and $V_L$, TanCAR3 (SEQ ID NO: 64) was constructed with increased linker length within the CD22 scFv, a format that abolished CD22 Fc and anti-idiotype binding (FIG. 21). For TanCAR4 (SEQ ID NO: 65), the short parental linker for the anti-CD22 scFv was maintained but the length of the linker was reduced between the anti-CD19 and anti-CD22 scFv. This resulted in CAR surface expression (anti-CD22 Fc and anti-FMC63 idiotype binding) and enhanced CD22-directed functionality compared to TanCAR1 as measured by the IL2 production against CD19−/CD22+ ALL (FIGS. 22A and 22B).

Cytotoxicity of TanCAR1 and TanCAR4 were further evaluated demonstrating comparable activity to CD19 and CD22 monovalent CARs. Despite in vitro activity, neither TanCAR1 nor TanCAR4 fully eradicated CD19posCD22pos ALL in vivo (FIGS. 23A-23D).

Development of the Bivalent CARs with Alternative Sequence of scFv Resulting in Loop Structure.

Figure 24:
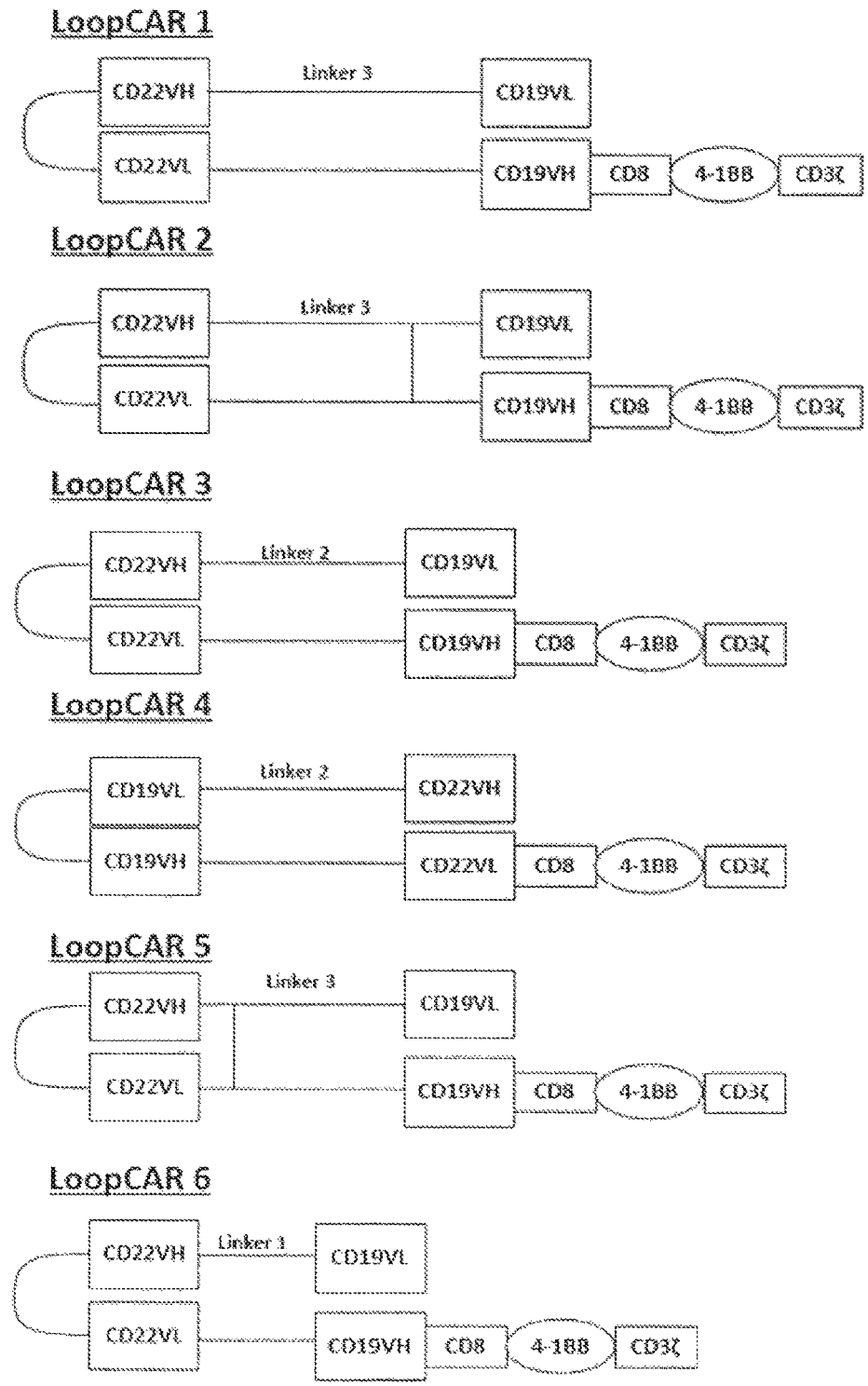
FIG. 24 diagrammatically presents LoopCARs of Example 7, in accordance with embodiments of the invention.
Figure 25A:
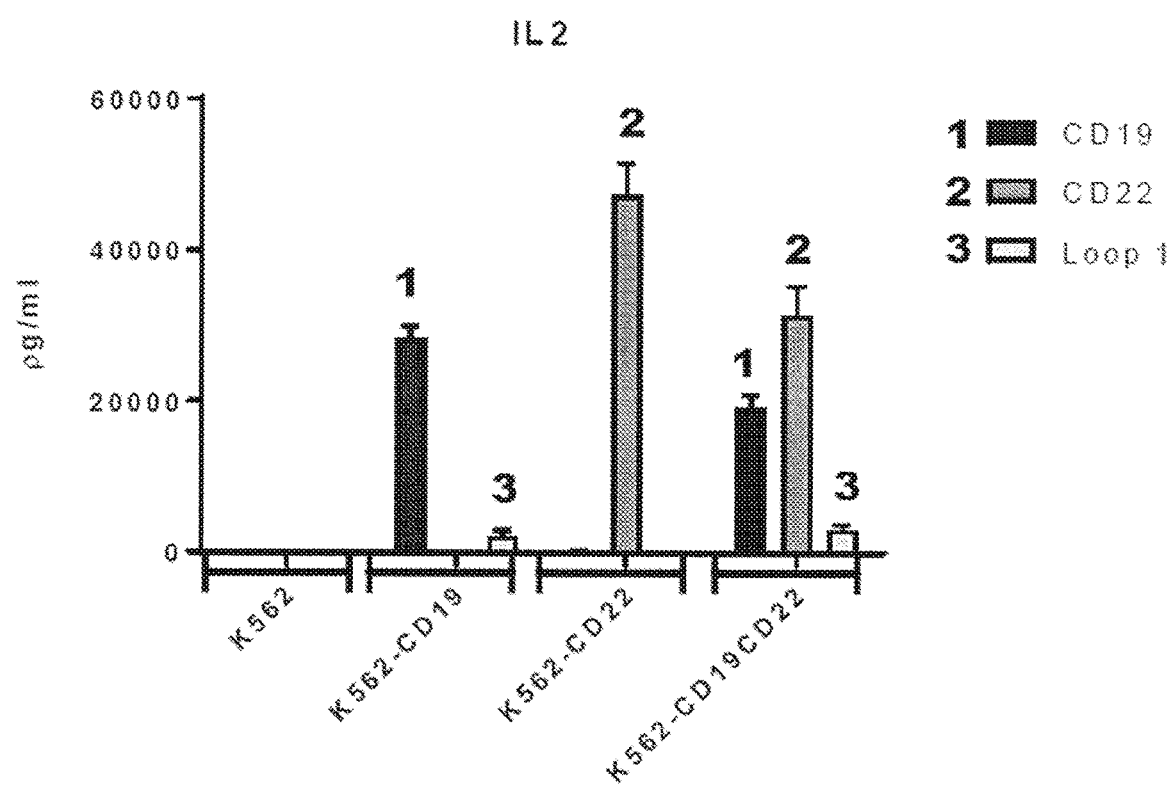
Figure 25B:
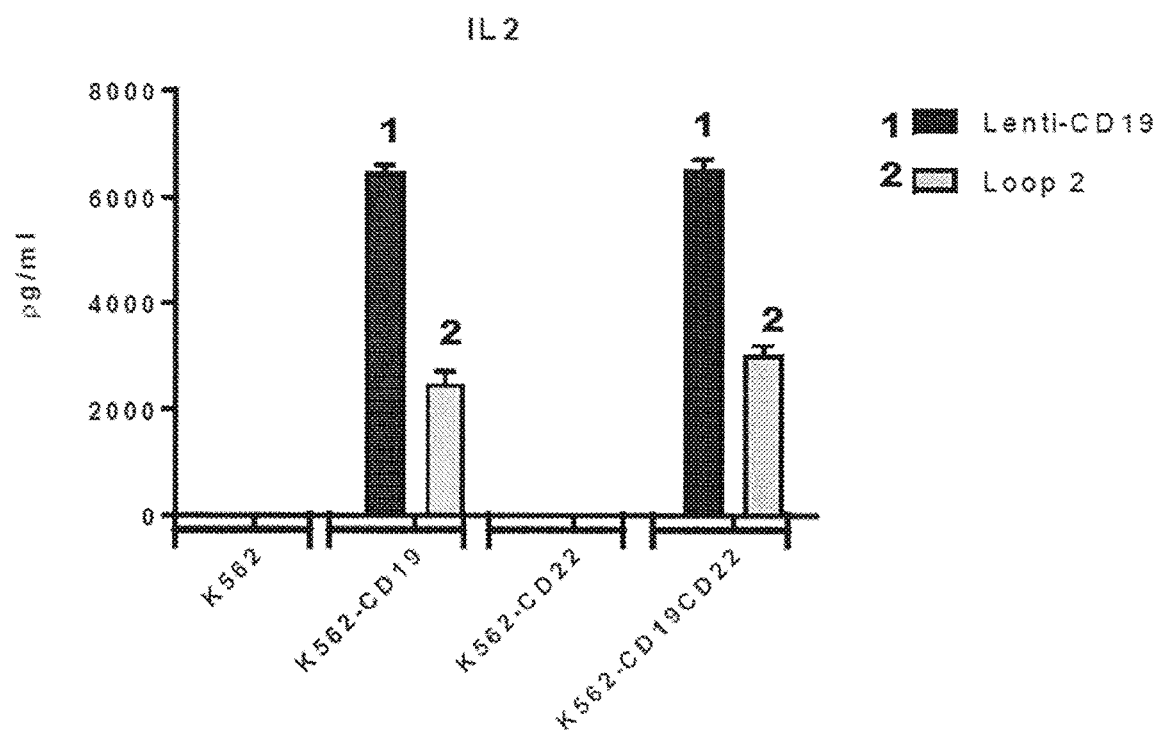

A series of bivalent CAR constructs were constructed (FIG. 24). Loop CARL (SEQ ID NO: 66) was constructed with the anti-CD22 scFv (maintaining the short linker) between the VH and VL of the anti-CD19 scFv, a format that could only be detected at low percentages on cell surface. For LoopCAR2 (SEQ ID NO: 67), the length of the linker was increased between anti-CD22 scFv in an attempt to facilitate folding of the loop structure, and the amino acid structure of the linker was slightly modified between the anti-CD19 variable chains and the anti-CD22 scFv to facilitate disulfide bond formation. This improved CAR surface detection. LoopCAR1 failed to generate IL-2 production against either CD19 or CD22. Despite improved surface detection and some IL-2 production against CD19, LoopCAR2 did not generate detectable IL-2 against CD22 antigen. See FIGS. 25A and 25B.

LoopCAR3 (SEQ ID NO: 68) was further modified to reduce the length of the linker between the anti-CD19 heavy chains and the anti-CD22 scFv, and the slightly longer linker was maintained between the $V_H$ and $V_L$ introduced in Loop2, resulting in improved IL-2 production against CD19neg/CD22pos ALL. For the next series of constructs, the anti-CD19 scFv was placed in a membrane distal location and between the variable chains of the anti-CD22 scFv. In LoopCAR4 (SEQ ID NO: 69), the linker between anti-CD19 scFv and the anti-CD22 scFv variable chains introduced in LoopCAR3 was maintained, resulting in high levels of CAR detection and superior IL2 production compared to any of the previous formats, suggesting the anti-CD22 scFv membrane proximal location may be optimal. Given that IL-2 production against CD19neg/CD22pos ALL was still inferior to the anti-CD22 monovalent CAR, LoopCAR5 (SEQ ID NO: 70) was modified to favor disulfide bond formation, a structure that did not improve cytokine production. See FIG. 25C.

Figure 26:
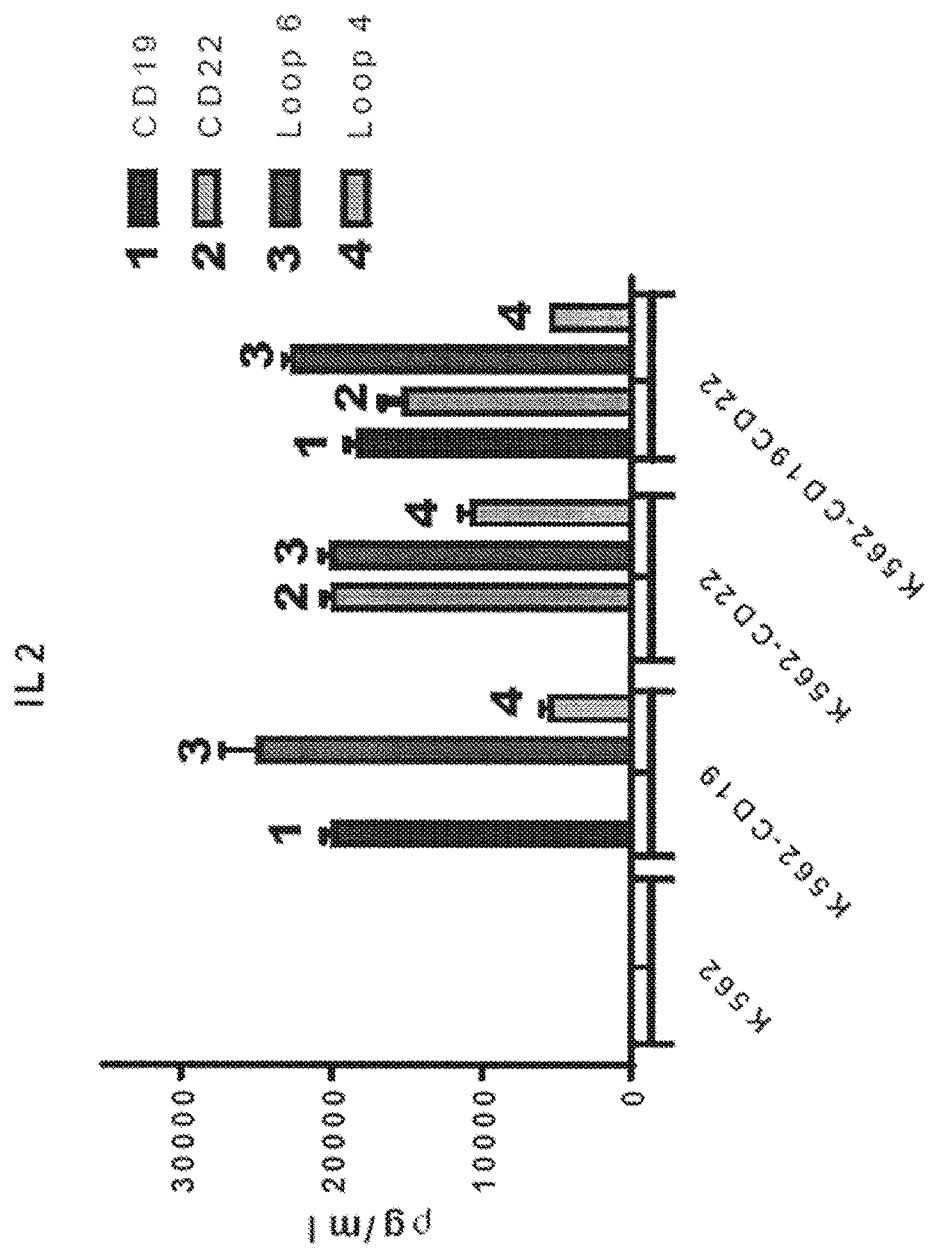
FIG. 26 is a bar graph showing cytokine production of various CARs with K562, K562-CD19, K562-CD22, and K562-CD19CD22 target cell lines, in accordance with embodiments of the invention.
Figure 27:
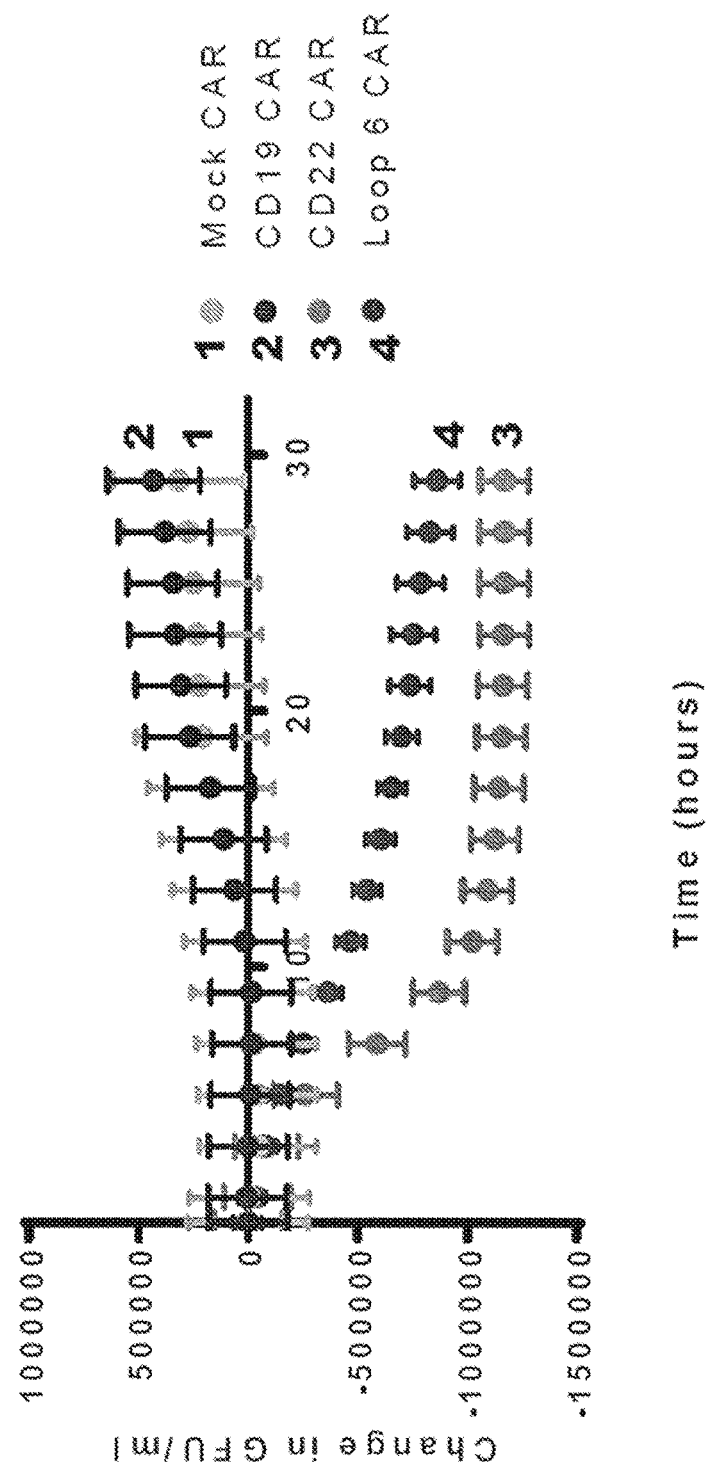
FIG. 27 is a dot plot showing Incucyte killing assay with co-incubation of each CAR or mock T cell product with 10:1 of NALM6: NALM6-CD19neg cells, in accordance with embodiments of the invention.
Figure 28:
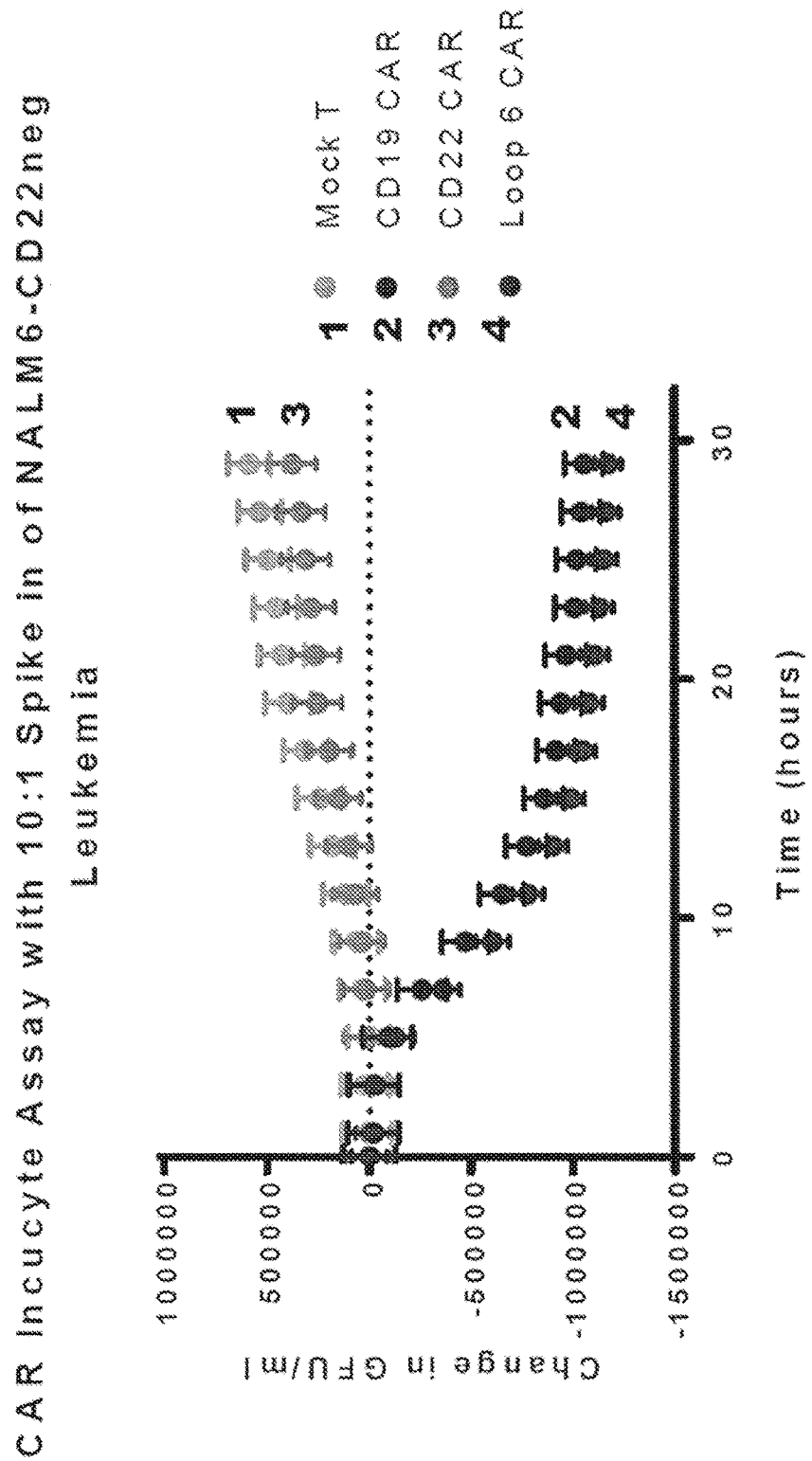
FIG. 28 is a dot plot showing Incucyte killing assay with co-incubation of each CAR or mock T cell product with 10:1 of NALM6: NALM6-CD22neg cells, in accordance with embodiments of the invention.
Figure 29A:
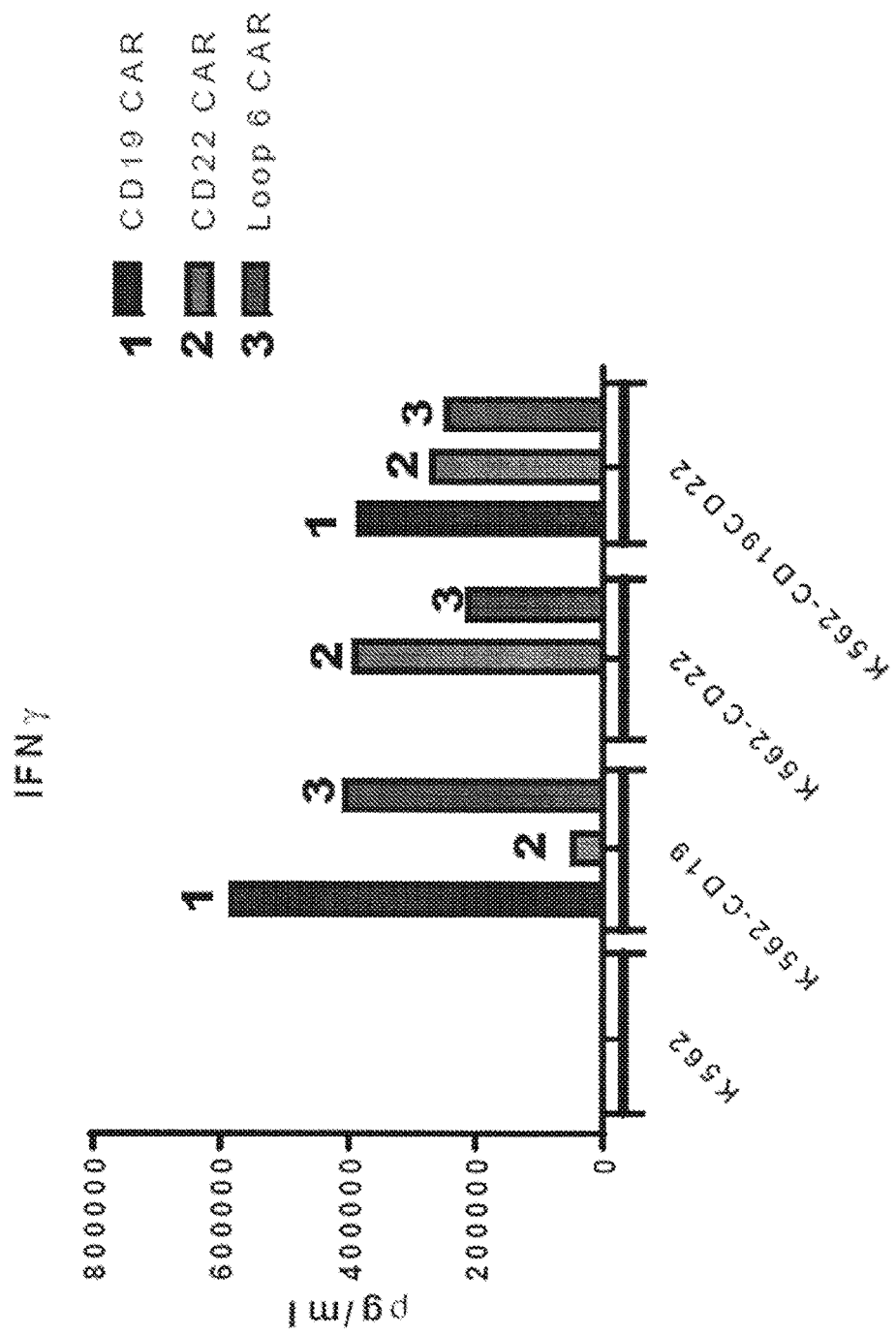
Figure 29C:
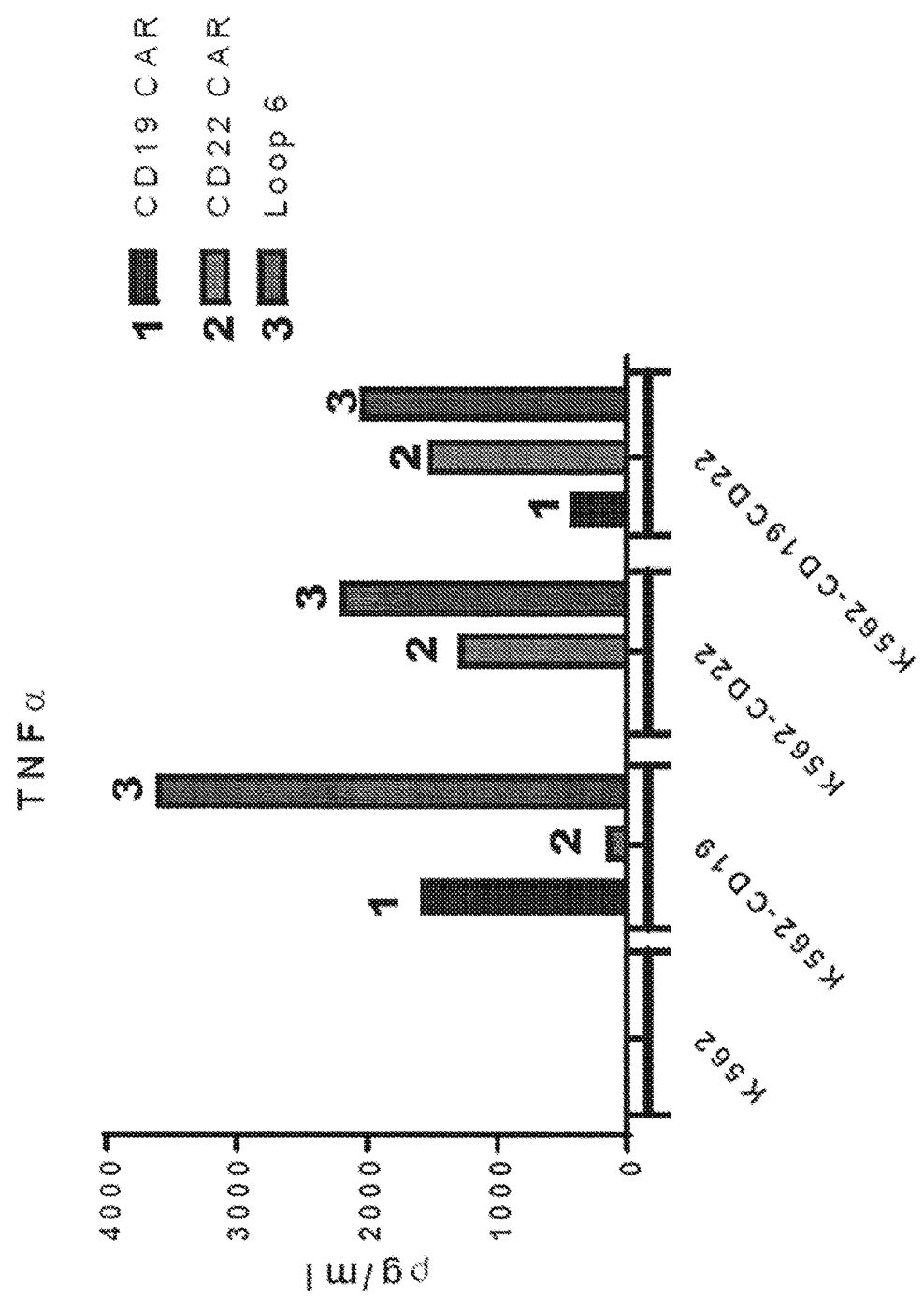
Figure 29E:
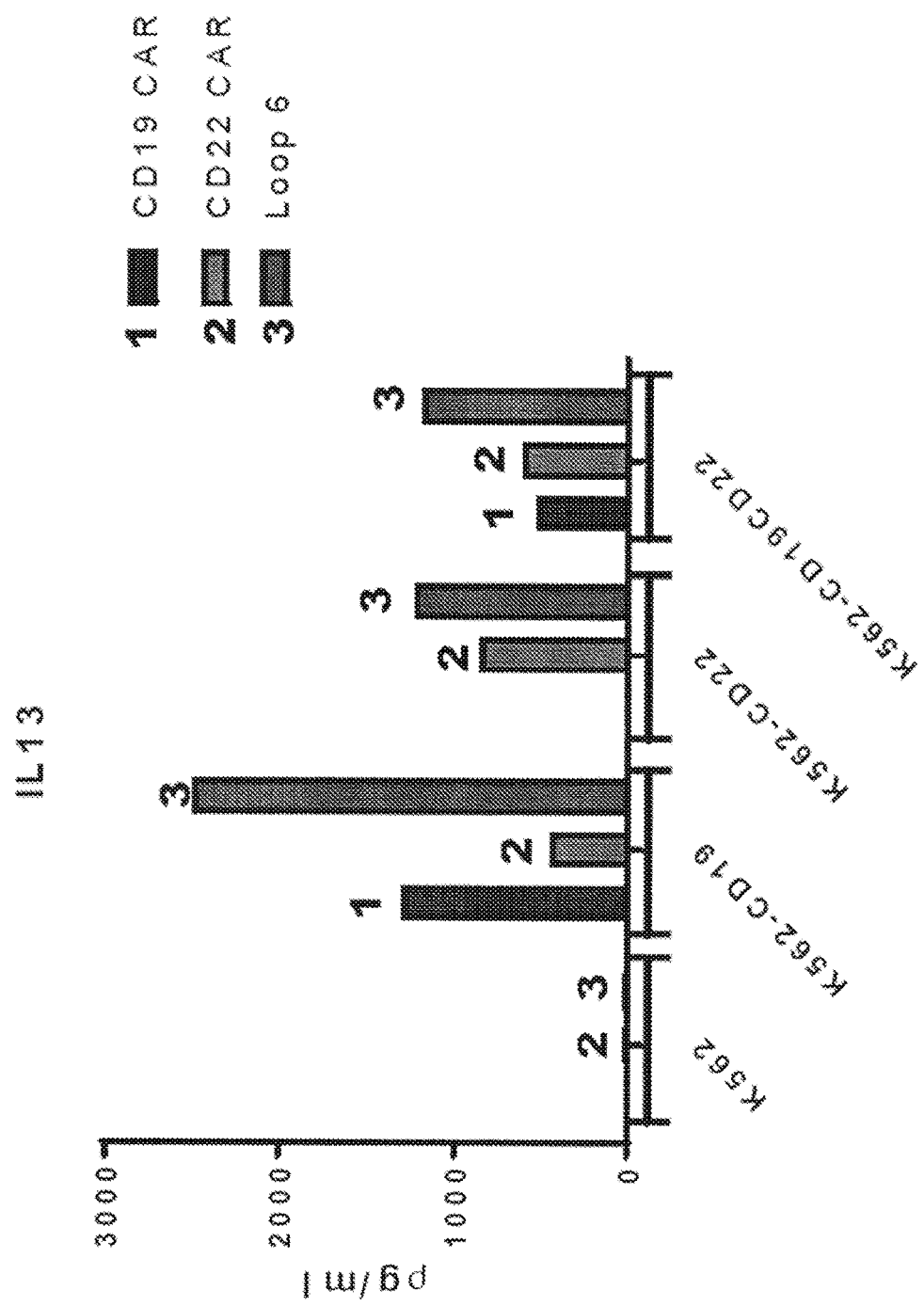
Figure 29F:
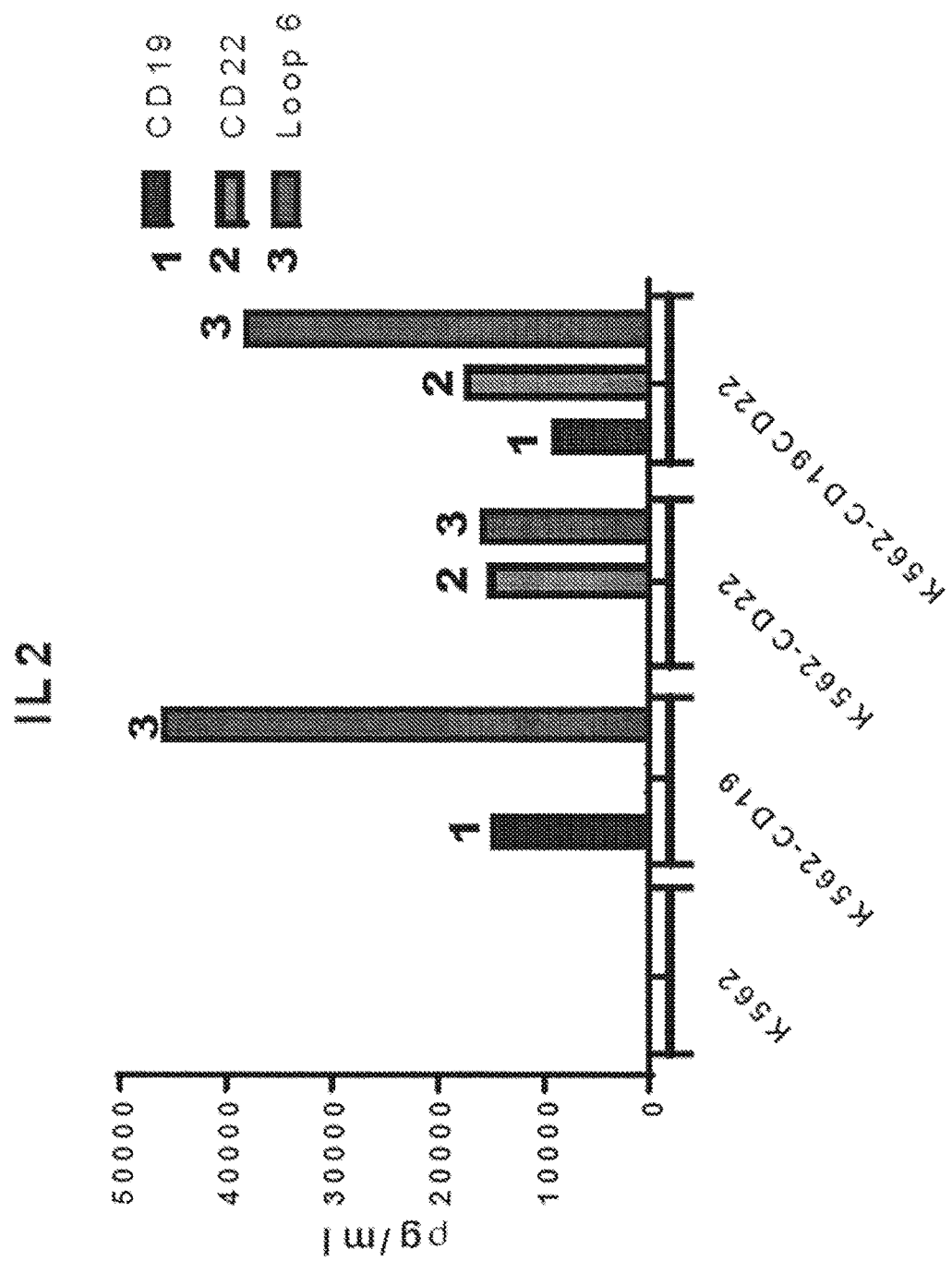

Finally, in LoopCAR6 (SEQ ID NO: 61), a shorter linker was incorporated between anti-CD19 scFv and anti-CD22 variable chains, which dramatically improved both CAR detection and IL-2 production against both CD19pos/CD22neg and CD19neg/CD22pos ALL (FIG. 26) as well as in vitro killing of single-antigen expressing ALL (FIGS. 27 and 28). Of note, the kinetics of killing of the CD19neg ALL by LoopCAR6 expressing T cells compared to anti-CD22 CAR expressing T cells suggested slightly less potency against CD22. LoopCAR6 produced multiple cytokines in response to both CD19 and CD22 (FIGS. 29A-29F) further confirming the potency and polyfunctionality of LoopCAR6 expressing T cells. Thus, the loop design may be optimal for bivalent CARs incorporating CD19×CD22 specificity, likely due to challenges maintaining CD22 binding. Amongst the multiple constructs designed and tested, Loop6 was identified as the most potent format and was further tested in in vivo models.

LoopCAR6 Efficiently Eradicates CD19posCD22Neg and CD19neg PDX.

Figure 30:
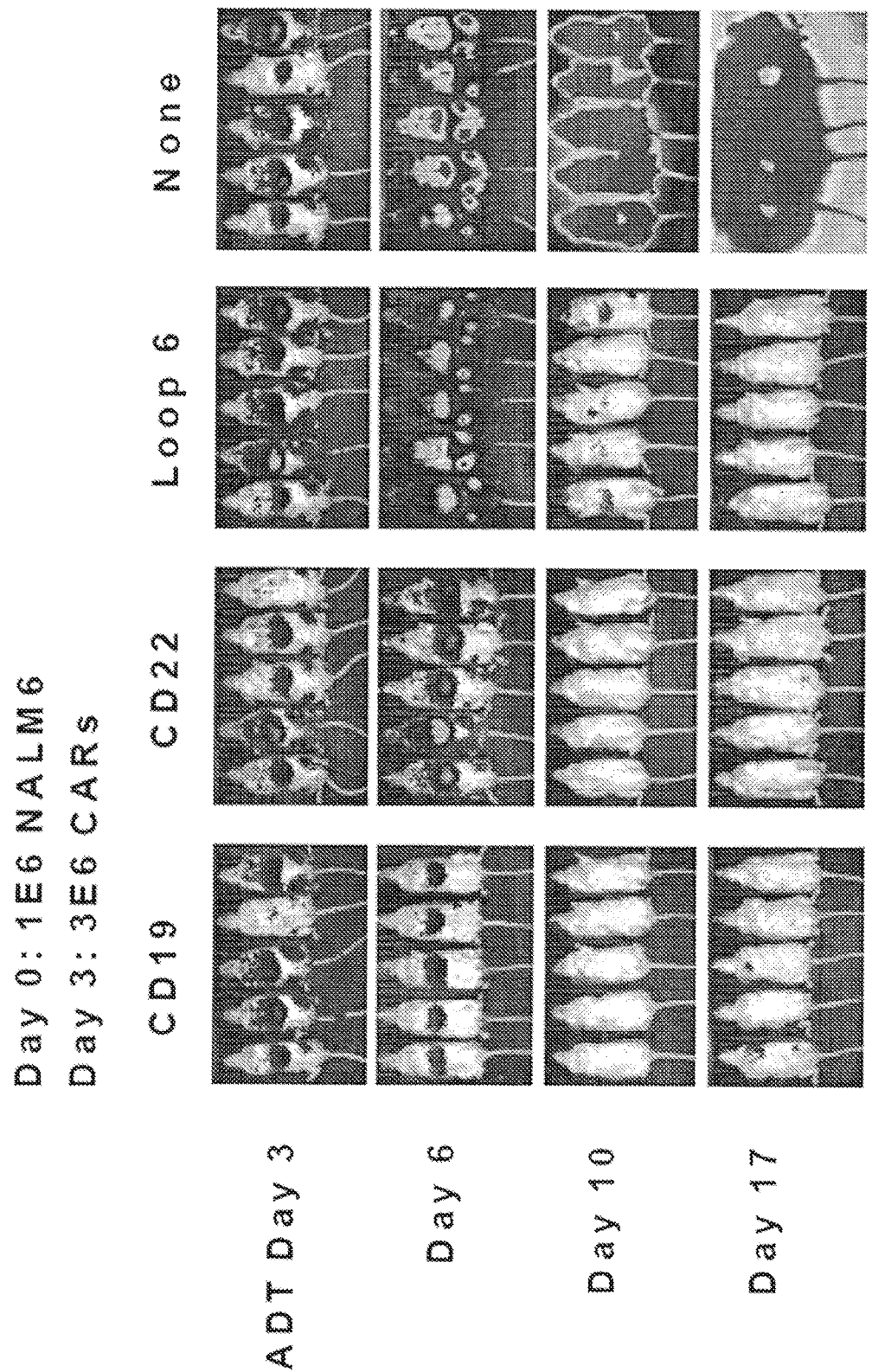
FIG. 30 presents images. NSG mice were challenged with 1E6 of luciferase-expressing NALM6 leukemia on day 0. On day 3, mice were IV injected with 3E6 of CAR expressing T cells. Bioluminescent intensity, as shown by increased levels of shading, represents tumor burden.
Figure 31:
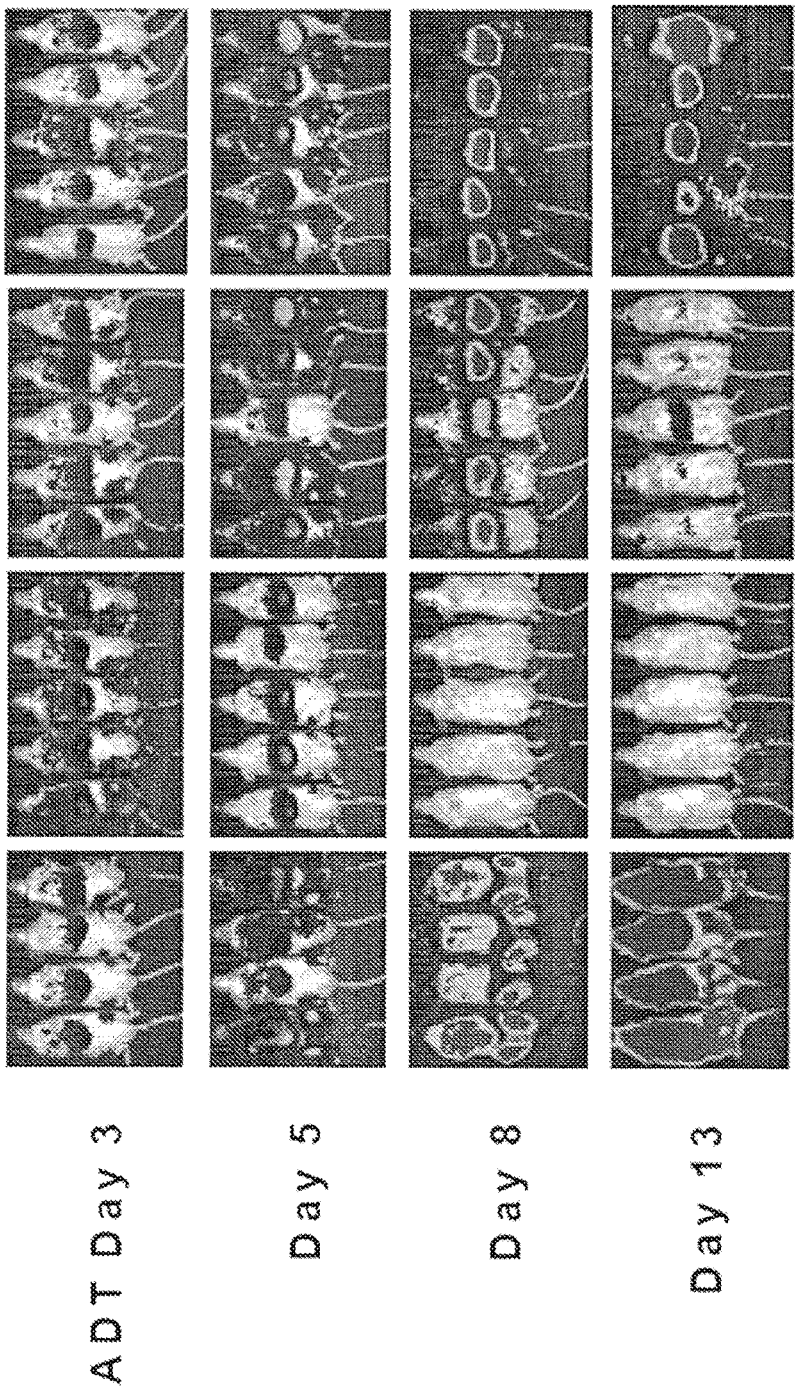
FIG. 31 presents images. NSG mice were challenged with 1E6 of luciferase-expressing NALM6 leukemia on day 0. On day 3, mice were IV injected with 9E6, 3E6 and 1E6 of Loop F CAR (which is also listed herein as LoopCAR6) expressing T cells. Bioluminescent intensity, as shown by increased levels of shading, represents tumor burden.
Figure 32:
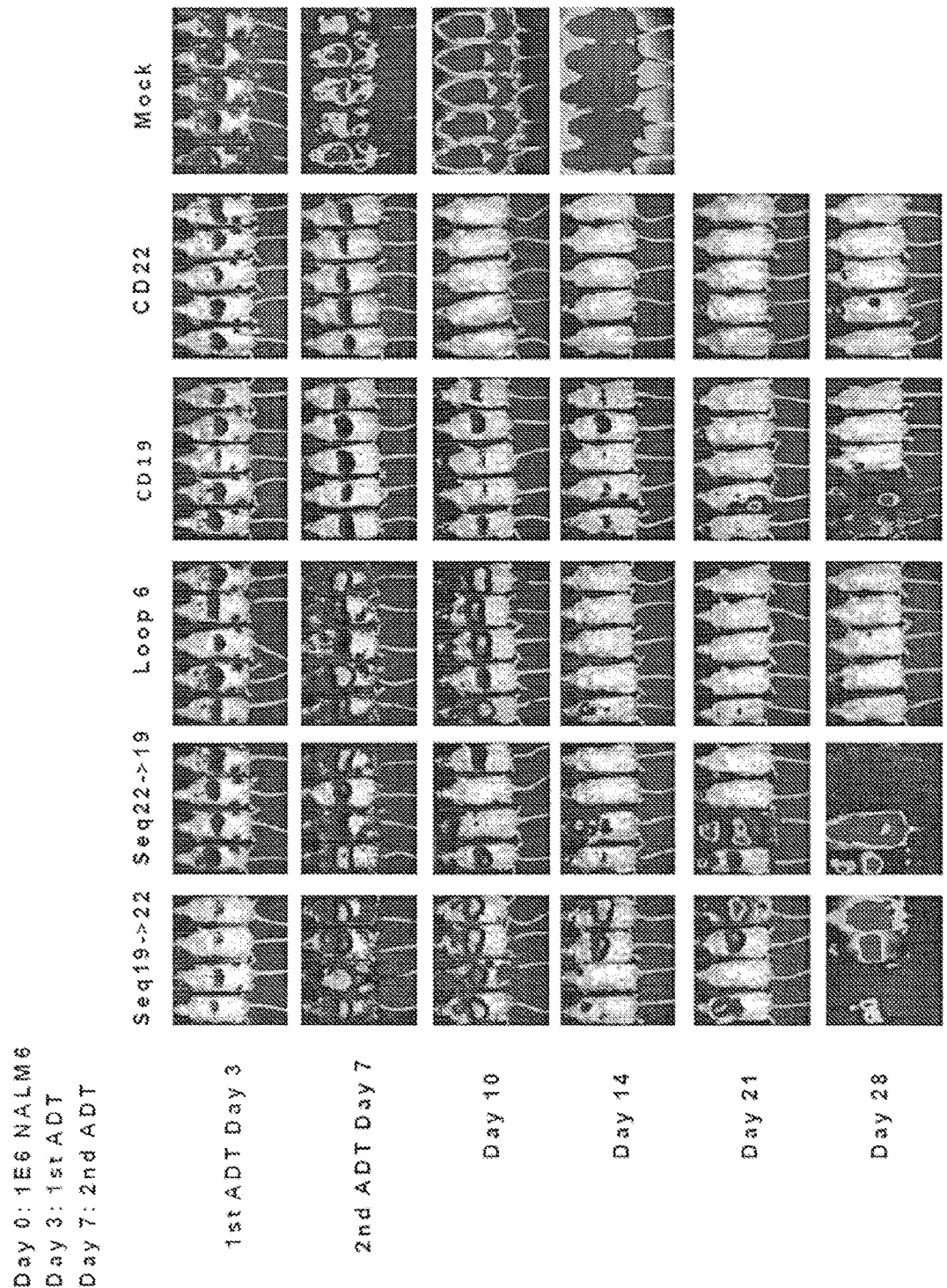
FIG. 32 presents images. NSG mice were challenged with 1E6 of NALM6 on day 0. The mice in sequential treatment group received 3E6 CAR+ on day 3 and 3E6 CAR$^P$ T cells on day 7. Mice in the co-injection group received a total of 6E6 CAR' T cells with 3E6 of anti-CD19 CAR' and 3E6 of anti-CD22 CAR+ T cells on day 3. Mice in the co-transduced group received 10E6 of total T cells which contain 3E6 of anti-CD19$^+$ and 3E6 of anti-CD22$^+$ CART cells. Mice in anti-CD19 or anti-CD22 groups received 3E6 of CAR$^+$ T cells. Co-injection or co-transduction of anti-CD19 and anti-CD22 CAR suggest that simultaneously targeting on both CD19 and CD22 may reduce relapse of leukemia. Bioluminescent intensity, as shown by increased levels of shading, represents tumor burden.

Next tested were LoopCAR6 on Nalm6 xenografts. LoopCAR6 at a dose of $8 \times 10^6$ appear to eradicate CD19pos/CD22pos Nalm6 (FIG. 30) and retained activity down to a dose of $3 \times 10^6$ (FIG. 31). LoopCAR6 was also superior to sequential infusion against CD19pos/CD22pos ALL (FIG. 32). However, at low doses, LoopCAR6 did not work as well against CD19neg/CD22pos leukemia, a cell line with lower expression of CD22 compared to parental NALM6 (FIG. 33A).

Figure 33B:
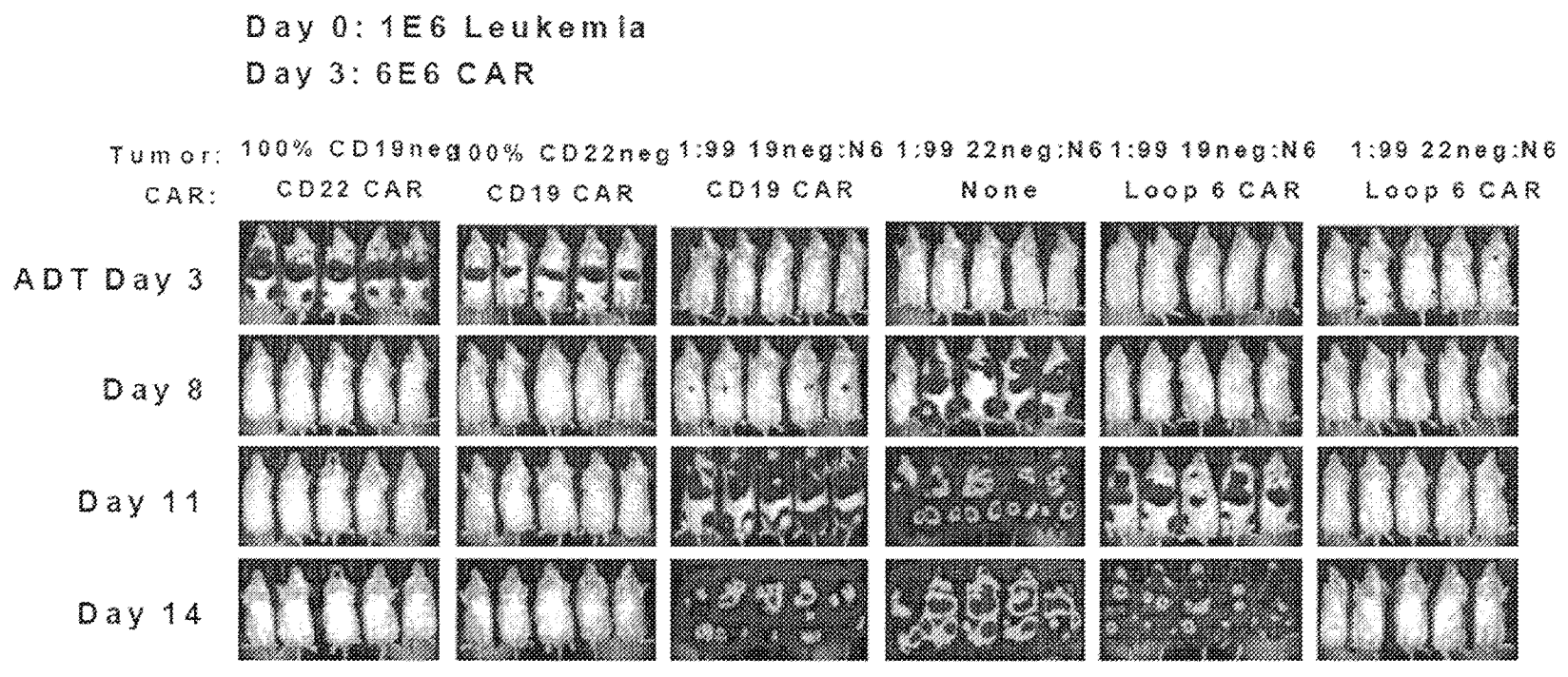

LoopCAR6 was further tested in a "spike in" relapse model in which the engrafted ALL inocula contained 1% CD19neg or CD22neg ALL with 99% CD19pos/CD22pos ALL, an assay that mimics relapse from a small, pre-existent clone. In this model, LoopCAR6 was comparable to anti-CD19 CAR at clearing CD22neg ALL, confirming the comparable potency of LoopCAR6 to the anti-CD19 monovalent CARs against CD19. However, in contrast to the anti-CD22 monovalent CAR, LoopCAR6 was unable to completely clear CD19neg/CD22pos ALL with low CD22 site density (FIG. 33B). Collectively, and as suggested by the kinetics of in vitro killing CD22-single expressing ALL (FIG. 27), the in vivo experiments suggest that LoopCAR6 has comparable potency to the anti-CD19 monovalent CAR against CD19 but is slightly less potent than the anti-CD22 monovalent CAR against CD22.

To further explore the in vivo activity of the LoopCAR6 in a clinically relevant model of anti-CD19 CAR resistance, two different patient-derived xenografts generated from de novo relapse specimens (HMB15; CD19pos/CD22pos and HMB28; CD19neg/CD22pos) were utilized. Whole-exome and transcriptome sequencing were performed to characterize the two PDX model systems. HMB15 harbors a translocation that results in an in-frame fusion oncogene between the N-terminus of MLL (exon 1-6) and C terminus of MLLT10. The CD19 and CD22 genomic locus is intact in this model. The HMB28 PDX primary oncogenic driver is a point mutation of KRAS G12D. In addition, this model harbors a premature stop codon in the CD19 (Table 18).

TABLE 18

| PDX Model | Primary Oncogene | CD19 | CD22 |
|---|---|---|---|
| HMB15 | MLL-MLLT10 fusion | Intact DNA and RNA | Intact DNA and RNA |
| HMB28 | KRAS G12D | W214 stop codon | Intact DNA and RNA |

Figure 34A:
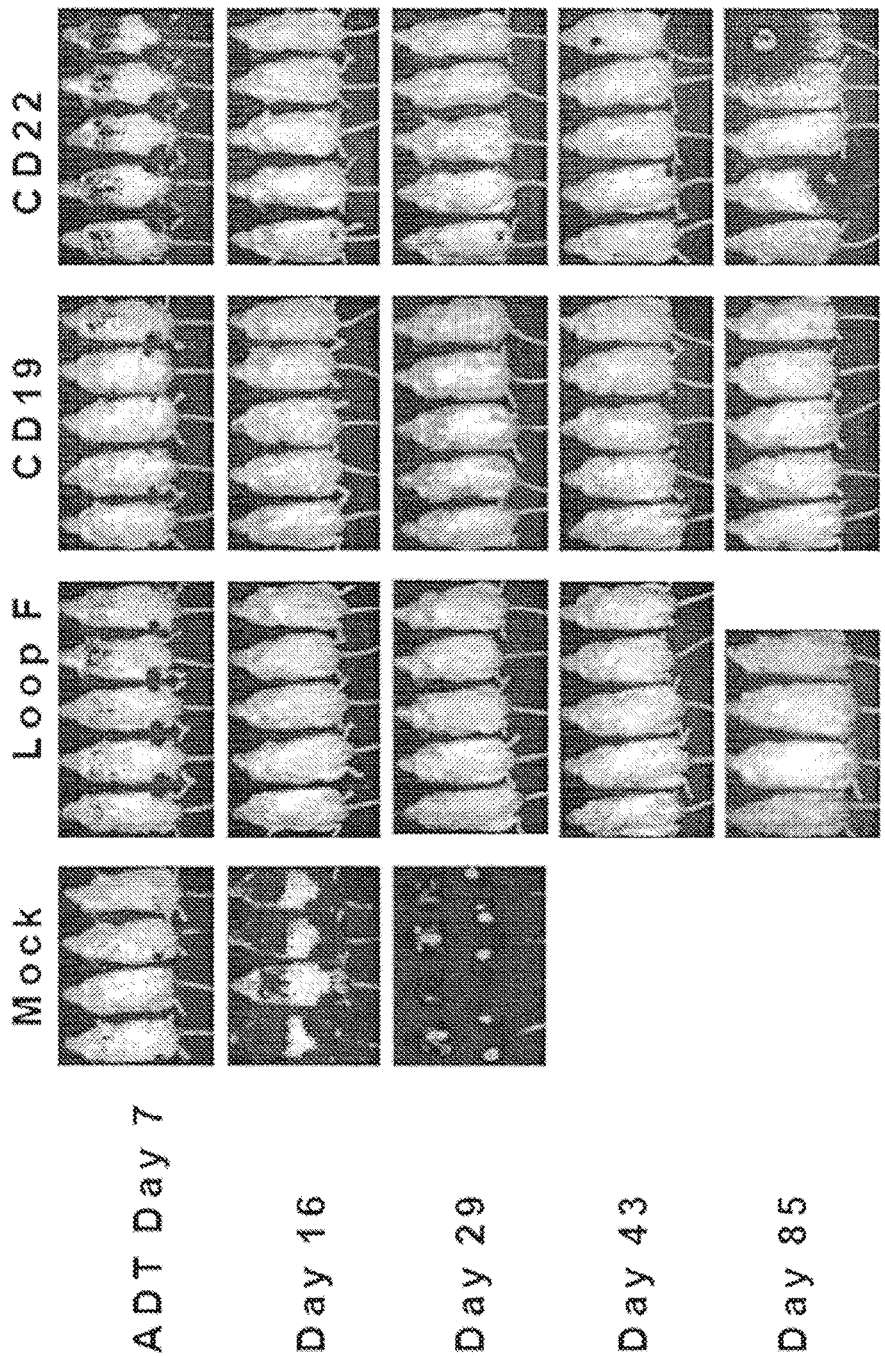
FIG. 34A presents images. NSG mice were challenged with 1E6 of NALM6 leukemia on day 0. Mice received treatment with 8E6 mock T, CD19, CD22 or Loop F CAR+ T cells on day 7. Bioluminescent intensity, as shown by increased levels of shading, represents tumor burden.
Figure 34B:
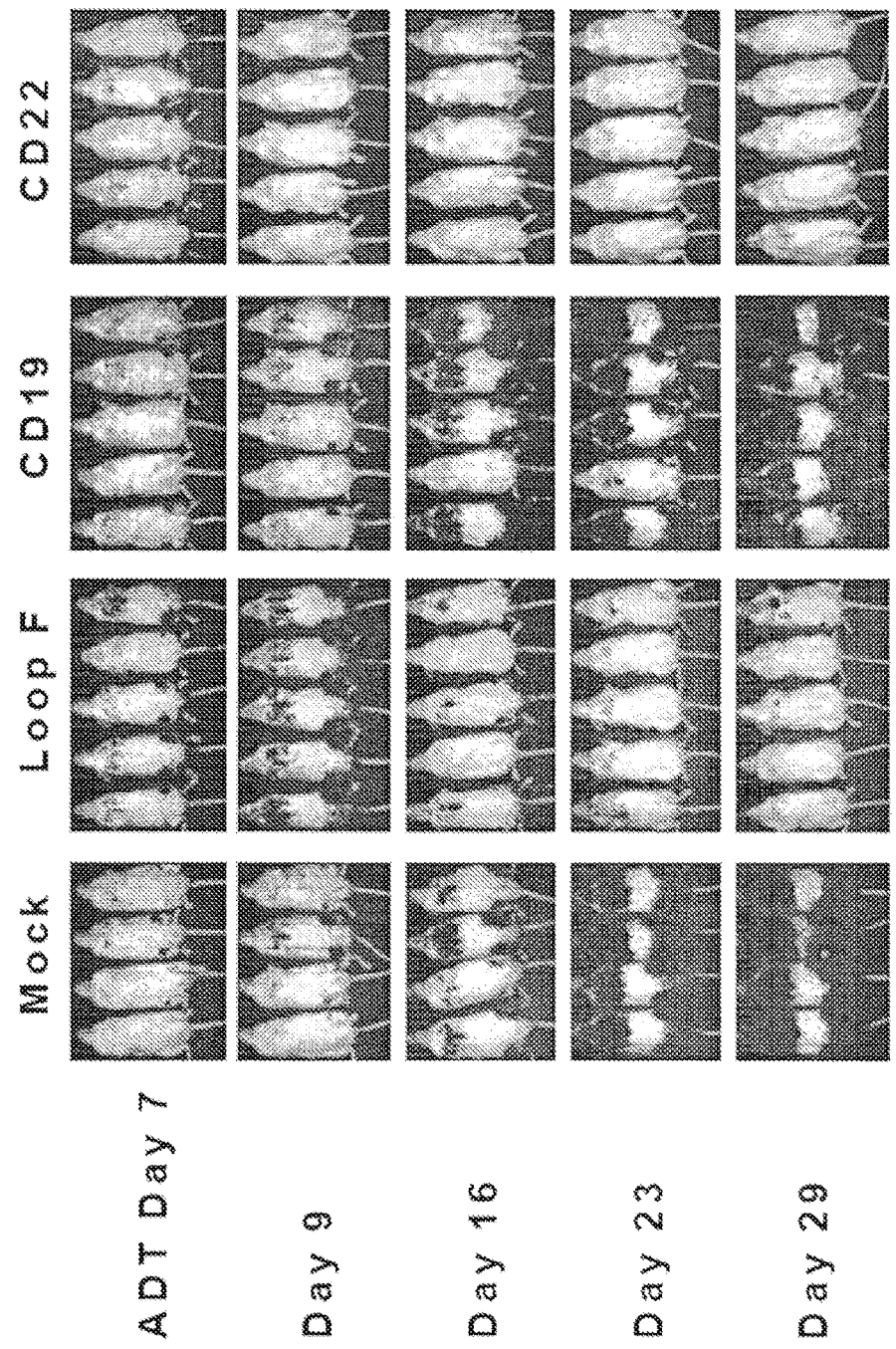
FIG. 34B presents images. NSG mice were challenged with 1E6 of NALM6 leukemia on day 0. Mice received treatment with 8E6 mock T, CD19, CD22 or Loop F CAR+ T cells on day 7. Bioluminescent intensity, as shown by increased levels of shading, represents tumor burden.

HMB15 appeared to be cleared by both monovalent CARs as well as LoopCAR6 (FIGS. 34A and 34B). HMB 28 was resistant to anti-CD19 monovalent CAR and therefore, a good model of anti-CD19 CAR resistance. Encouragingly, LoopCAR6 prevented progression in HMB28, indicating that LoopCAR6 may be effective at preventing anti-CD19 CAR resistance.

No Evidence for Off Target Activity of LoopCAR6.

Given the possibility of mispairing of two different $V_H$ and $V_L$ resulting in potential off tumor toxicity, functional screening of T cells expressing the LoopCAR6 was performed. LoopCAR6 T cells were co-incubated with human iPSC cell lines representing multiple normal tissues and IFNγ production was measured in the culture supernatant. IFNγ production was used to measure reactivity as all of the active CAR constructs developed induce IFNγ. NALM6 and REH-TSLPR, two separate ALL cell lines expressing both CD19 and CD22, were used as positive controls.

Figure 35A:
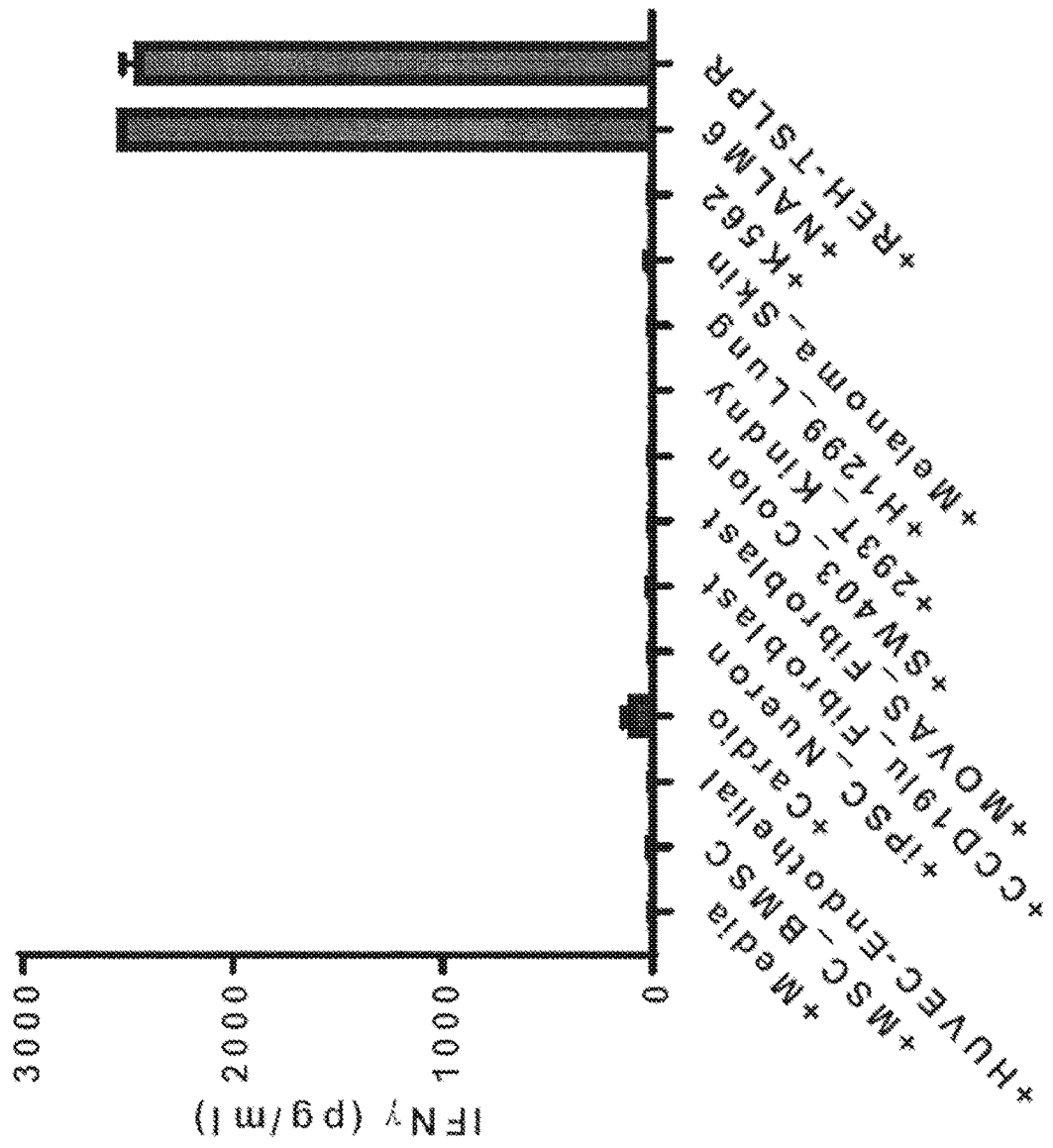
FIGS. 35A and 35B are bar graphs showing IFNα production of LoopCAR6, post co-incubated with various cell lines representing normal tissues, in accordance with embodiments of the invention.
Figure 35B:
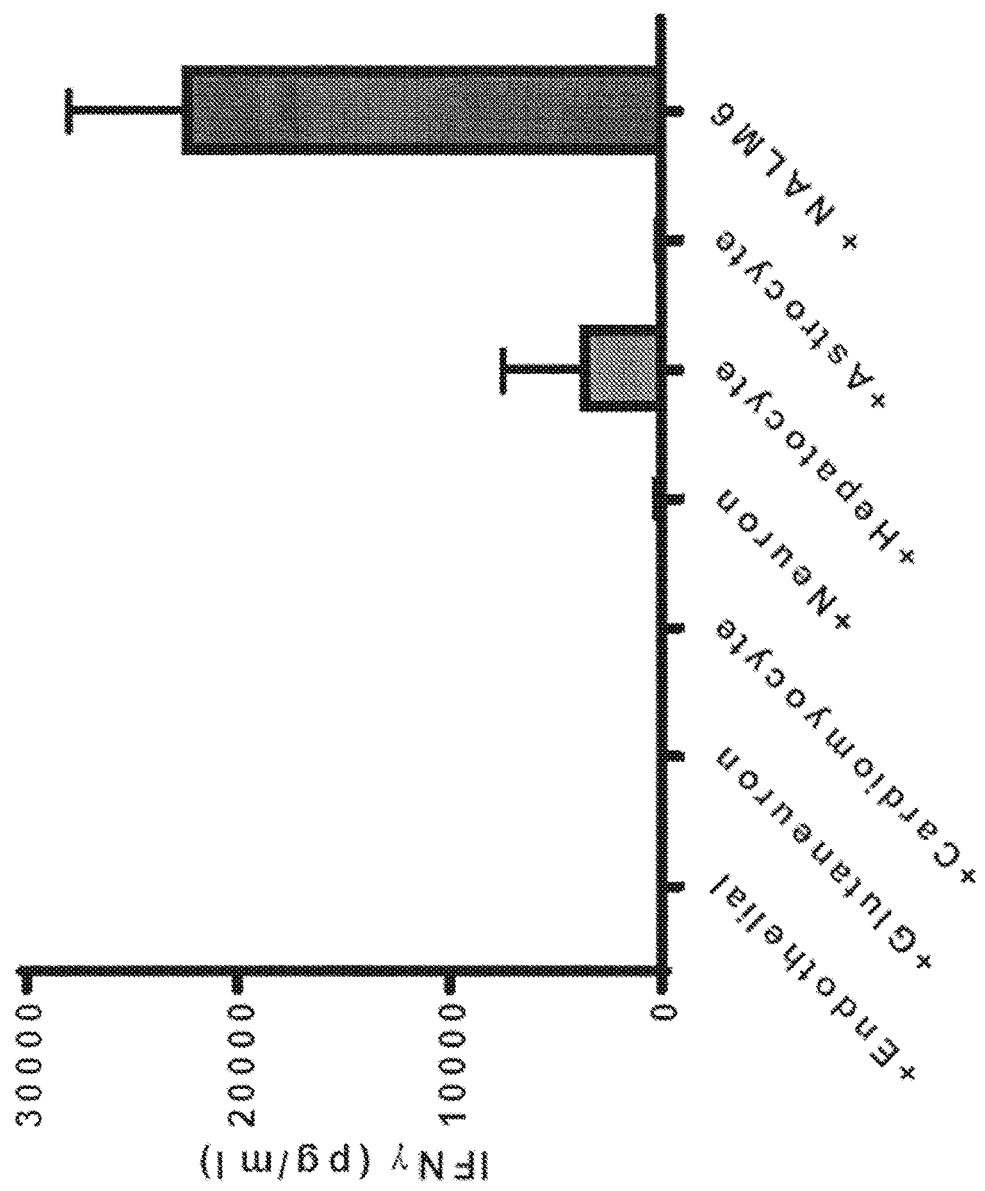

In this assay, LoopCAR6 induced IFNγ in T cells against both NALM6 and REH-TSLPR. IFNγ production was not detected in supernatants of by LoopCAR6-expressing T cells in the presence of any of the iPS cell lines (FIGS. 35A and 35B).

Table 19 presents a summary of results.

TABLE 19

| Construct | Surface Expression | In Vitro Efficacy | In Vivo Efficacy |
|---|---|---|---|
| TanCAR1 | 60% of both anti-CD19 and anti-CD22 | CD19 ++ CD22 | ++ |
| TanCAR2 | 29% anti-CD19 and anti-CD22 | CD19 + | + |
| TanCAR3 | None | | |
| TanCAR4 | 56% of both anti-CD19 and anti-CD22 | CD19 ++ CD22 ++ | +++ |
| LoopCAR1 | 19% of both anti-CD19 and anti-CD22 | CD19 + CD22 | |
| LoopCAR2 | 42% of both anti-CD19 and anti-CD22 | CD19 ++ CD22 | |
| LoopCAR3 | 24% of both anti-CD19 and anti-CD22 | CD19 ++ CD22 ++ | |
| LoopCAR4 | 63% of both anti-CD19 and anti-CD22 | CD19 ++ CD22 +++ | +++ |
| LoopCAR5 | 49% of both anti-CD19 and anti-CD22 | CD19 + CD22 | |
| LoopCAR6 | 82% of both anti-CD19 and anti-CD22 | CD19 +++ CD22 ++ | ++++ |

Example 8

This example demonstrates cleavable CARs, in accordance with embodiments of the invention.

Cell Lines and Culture Conditions

The following leukemia cell lines were used: the erythroleukemia K562-CD22 (transduced with human CD22, GeneCopoeia, Cat: EX-Z9364-Lv151), K562-CD19 (transduced with human CD19), K562-CD19CD22 (transduced with both human CD19 and CD22), non-transduced K562 as a negative control; the B cell acute lymphoblastic leukemia lines NALM6, NALM6-GL (transduced with GFP and Luciferase), NALM6-CD19⁻-GL (Crisper KO CD19 on exon 3), NALM6-CD22⁻-GL (Crisper KO CD22 on exon 6). Cell lines were cultured in media supplemented with 10% heat-inactivated FBS, 10 mM HEPES, 100 U/mL penicillin, 100 ug/mL streptomycin, and 2 mM L-glutamine (Invitrogen). The Lenti-X 293T lenti packaging cell line (Clontech. Cat #632180) was cultured in DMEM (Invitrogen) media.

Primary Human Leukemia Sample and Patient-Derived Xenografts

Human ALL (Acute Lymphoblastic Leukemia) samples were collected and stored after informed consent to an IRB-approved tissue acquisition protocol (Protocol number: 15-C-0029). All research specimens from human subjects were obtained with informed consent in accordance with the Declaration of Helsinki. The following primary samples were used: CD19⁻ ALL and the CD19⁺ CD22$^{dim}$ (de novo relapse specimens ALL_H0113_post22_r (CAR3), ALL_H0090_post19_pd (HMB15), were used for in vivo testing of the bispecific CAR constructs. PDX models were created by injecting 1E6 to 10E6 of the patient ALL cells intravenously into NSG mice (NOD scid gamma, NOD.Cg-Prkdcscid Il2rgtm1Wjl/SzJ; Jackson ImmunoResearch Laboratories). The PDX lines were transduced with lenti-GFP-Luc virus and sorted for the leukemia cell expressing GFP and luciferase after the first and second passages. For these studies, the secondary and later passages of the PDX were used for relapse and de novo ALL specimens, respectively. GFP-transduced PDX leukemia in vivo burden was assessed by weekly fluorescence imaging, and animals were treated with CAR T cells via tail vein injection once the human ALL was detectable by florescence imaging. Elutriated human lymphocytes from healthy donors were obtained from the Department of Transfusion Medicine at the National Institutes of Health (NIH) Clinical Center under an IRB-approved protocol. The human lymphocytes were cultured in AIM-V media.

Generating CD19 Negative or CD22 Negative Leukemia with CRISPR

Lentiviral vector for CRISPR knockout of the CD19 or CD22 on NALM6 were made. Briefly, guide-RNAs were optimized by http://crispr.mit.edu/, cloned into LentiCRISPR v2 plasmid (Addgene Plasmid 52,961). Plasmids were then co-transfected with packaging plasmids and transformed into HEK293T cells. Two days later, CRISPR supernatants were harvested, filtered, and concentrated. For viral transduction, $10^5$ NALM6 cells were incubated with 10 ml of concentrated viral supernatant for 2 days, followed by expansion in RPMI media. Cell phenotype was assessed by flow cytometry, followed by sorting of cells with phenotypic alterations and single-cell cloning. Sequencing was performed on single-cell clones to confirm genotypic alterations.

Making of Lenti-Viral CAR Constructs

CD19/CD22 bicistronic CARs were made with different pairings of the CD28 or 4-1BB costimulation domains in each CD19 and CD22 CAR and linked with a cleavable linker in between. Each CD19 and CD22 CAR has a leader sequence at the beginning, and followed with the CD19 or CD22 single chain variable fragment, then, either a CD8 transmembrane domain linked with 4-1BB and CD3 zeta domain, or a CD28 transmembrane domain linked with CD28 and CD3 zeta domain. These CARs were subcloned into an pELNS lenti vector backbone. All restriction enzymes were purchased from New England Biolabs. The sequence of all CAR constructs was confirmed by sequencing at Macrogen.

The CARs described in this Example are the following: 22-BB/19-28 (which is also listed herein as V5), 22-28/19-BB (which is also listed herein as V6), 22-BB/19-BB (which is also listed herein as V7), and 22-28/19-28 (which is also listed herein as V8).

CAR T-Cell Generation

The bicistronic CAR-encoding lentiviral vectors were produced by transient transfection of the Lenti-X 293T lenti packaging cell line. Briefly, lenti-X 293T cells were plated into poly-D lysine coated 15-cm plates (BD Biosciences). The following day, Lenti-X 293T cells were transfected using lipofectamine 3000 (Thermo Fisher Scientific) with plasmids encoding the CAR construct along with packaging and envelope vectors (pMDLg/pRRE, pMD-2G, and pRSV-Rev). Lentiviral supernatants were harvested at 24 and 48 hours post-transfection, centrifuged at 3000 RPM for 10 minutes to remove cell debris, frozen on dry ice and stored at −80° C. Human PBMCs from normal donors were obtained with an NIH-approved protocol and activated with a 1:3 ratio of CD3/CD28 microbeads (Dynabeads Human T-Expander CD3/CD28, Thermo Fisher Scientific, Cat #11141D) in AIM-V media containing 40 IU/mL recombinant IL-2 and 5% FBS for 24 hours. Activated T cells were resuspended at 2 million cells per 2 mL of lentiviral supernatant plus 1 mL of fresh AIM-V media with 10 mg/mL protamine sulfate and 100 IU/mL IL-2 in 6-well plates. Plates were centrifuged at 1000×g for 2 hours at 32° C. and incubated overnight at 37° C. A second transduction was performed on the following day by repeating the same transduction procedure described above. The CD3/CD28 beads were removed on the third day following transduction, and the cells were cultured at 300,000 cells/mL in AIM-V containing 100 IU/mL IL2 with fresh IL2-containing media added every 2-3 days until harvest on day 8 or 9.

Flow Cytometry

Surface expression of CD22 CAR-transduced T cells was determined by flow cytometry using a CD22-Fc (R&D Systems) followed by incubation with PE-F(ab)$_2$ or APC-F (ab)$_2$ specific for human IgG-Fc (Jackson ImmunoResearch Laboratories). Surface expression of CD19 CAR-transduced T cells was detected with anti-CD19 Idiotype or Recombinant Human CD19 Fc Chimera Protein (R&D Systems) conjugated with APC by using Lightning-Link APC Antibody Labeling Kit (Novus Biologicals). Expression of CD19, CD22 on B-ALL lines were detected using the following anti-human antibodies: CD45-PerCP-Cy5.5 (eBioscience), CD19-Pacific Blue, CD19-APC-Cy7, CD10-PE-Cy7, and CD22-PE (Biolegend). T cells were characterized with the following antibodies: CD3-APC-Cy7, CD4-Pacific Blue, and CD8a-PE-Cy7 (BioLegend).

Cytotoxicity Assay

5E4 of Target tumor cells in 100 ul of RPMI media were loaded into a 96-well plate (Corning® BioCoat™ Poly-L-Lysine 96-Well Clear TC-Treated Flat Bottom Assay Plate). An equal amount of CAR T cells were added into the designated well on the following day. The initial incucyte apoptosis marker (Essen BioScience) was diluted in 100 ul PBS and 1ul of the diluent was added into each well. The plate was scanned for the GFP and or RFP fluorescent expression to monitor the cell apoptosis using an IncuCyte ZOOM® system every 30 minutes in a duration of 40 hours. The percentage of cell killing at each time point was baseline-corrected.

Analysis of Cytokine Production

Target tumor cell and transduced CAR positive T cells were washed 3 times with 1×PBS and resuspend in RPMI at 1E6/ml. 100 ul of tumor cells with 100 ul of CAR positive T cells were loaded into each well of a 96-well plate. T cell only and tumor cell only controls were set up. All tests were performed in duplicate or triplicate. Cells were incubated for 18 hours at 37° C. and 120 ul of the culture supernatant was harvested for detection of cytokine production. Cytokine levels in supernatants were measured using either ELISA kits (R&D Systems) or a multiplex assay (Meso Scale Discovery).

RNAseq Analysis

NALM6 and CAR T cells were resuspended at 1E6/ml. 5E5 of NALM6 was co-incubated with 5E5 CAR+ T cells in 10 ml of AIMV with 40 U of IL2 culture media in 25 ml culture flasks for 24 hours in duplicate or triplicate. NALM6 with CD19 microbeads were removed with an LD column. Total effluent was collected and the cells pelleted down by centrifuge at 1200 rpm for 6 minutes. tRNA was extracted immediately with RNAeasy Plus Mini Kit. RNA samples were sent to the NIH core facility for analysis. The RNA quality was evaluated with TapeStation Analysis Software (Agilent Technologies). The RNAseq was generated with NextSeq FASTQ by TruSeq LT assay.

Bioenergetic Analyses

For the glycolysis stress test, the CAR T cells were suspended in serum-free unbuffered DMEM medium (Sigma-Aldrich) supplemented with L-glutamine (200 mM) and NaCl (143 mM). 0.6 mL of a 0.5% Phenol Red solution (SigmaP0290) was added for a final concentration of 3 mg/L and adjust the pH to 7.35+/−0.05. CAR T Cells were plated onto Seahorse cell plates (3E5 cells per well), coated with Cell-Tak (Corning) to facilitate T cell attachment. Briefly, the cartridges were hydrated the day before the assay. On the day of the assay, the plates were coated with Cell-Tak and the cells were seeded in the Cell-Tak coated plates and placed on the XF24 Analyzer for the assay. The detailed procedure is as the following. The assay cartridge was initially hydrated with XF calibrant solution at 200 ul/well, hydro booster was added, and warped in parafilm, and the sensor cartridge was placed on top of utility plate, and incubated at 37° C. without $CO_2$ for overnight. The cell culture plate was then coated with Cell-Tak as follows: For 1 plate, 46 μl of Cell-Tak was diluted in 204 μl TC water and 1 ml of $NaHCO_3$. The mixer was dispensed 50 μl in each well and the plate was incubated at room temperature for at least 20 minutes. After removing the Cell-Tak solution, 250 ml of TC water was used to wash each well. CAR T cells (3E5/well) were plated in 158 μl assay media. The cell culture plate was then spun at 450 rpm for 1 sec at slow acceleration and no deceleration, and then the plate was reversed in orientation and spun at 650 rpm for 1 sec at slow acceleration and no deceleration. The plate was then incubated at 37° C. 0% $CO_2$ for 25-30 minutes. After 25-30 minutes incubation, added 158 ul of warm assay medium slowly and gently to the top of each well along the side of the wall using a manual P200 pipettor. The cell plates were incubated for 15-25 minutes. After 15-25 minutes, the plates were placed on XF24 Analyzer (after calibration finished). The XF assay were executed. Solution was injected sequentially through three ports: Port A: glucose 80 mM (96 μl of the stock solution in 3 ml assay media). Port B: oligomycin 18 μM (10.8 μl of the stock solution in 3 ml assay media). Port C: 2DG use stock solution. Glycolysis stress test was performed by measuring ECAR (mpH/min) at steady state after the cartridge ports were loaded with 75 μl of drug solution. For the mitochondrial stress test, CAR T cells were suspended in serum-free unbuffered DMEM medium with D-glucose (25 mM), and sodium pyruvate (1 mM). Mitochondrial stress test was performed similarly as the above by measuring OCR (pmol/min) at steady state and after sequential injection of oligomycin (0.5 μM), FCCP (0.5 μM), rotenone (1 μM) and antimycin A (1 μM) (Sigma-Aldrich). Experiments with the Seahorse system utilized the following assay conditions: 2 minutes mixture; 2 minutes wait; and 3 minutes measurement.

Fluorescence Microscopy Imaging and Analysis

T cells were co-transduced to express CAR-Cerulean or CAR-mCherry fusion proteins. CAR positive T cells were sorted and stained with the lipophilic tracer-DiD Membrane dye (Life Technologies) and with the LIVE/DEAD Fixable Blue Dead Cell (Life Technologies) in PBS. Cells were then washed and mounted. The images were acquired with a Zeiss Apotome fitted with an AxioCam MRm camera, using a Zeiss plan apochromat 20× objective. The exposure setting was the same for the entire experiment. ImageJ software was used for data analysis. Dead cells were excluded. The DiD membrane stain was used to identifying for each cell. The dimension and the maximum intensity of the Cerulean (CFP) positive or mCherry positive region were counted. Only a maximum intensity greater than one was counted. The threshold for the DiD stain was set at 10% of maximum pixel intensity. The threshold for the Cerulean channel and mCherry channel was set at 20% of maximum pixel intensity.

In Vivo Experiments

Animal experiments were carried out under protocols approved by the NCI Bethesda Animal Care and Use Committee. B-ALL cell lines and the xenografted human B-ALL specimens were IV injected into NSG mice. For luciferase-expressing lines, leukemia was detected using the Xenogen IVIS Lumina (Caliper Life Sciences). NSG were injected intraperitoneally with 3 mg D-luciferin (Caliper Life Sciences) and were imaged 4 minutes later with an exposure time of 30 sec for NALM6 cell and 2 minutes for PDXs. Living Image Version 4.1 software (Caliper Life Sciences) was used to analyze the bioluminescent signal flux for each mouse as photons/s/$cm^2$/sr. Leukemia burden in non-luciferase expressing xenografts was measured by flow cytometry of peripheral blood, bone marrow, and spleen.

Statistical Analysis

Statistics analysis were performed using Prism 7.0 software. The plots are presented as mean+/−SD. Statistical Significance of all data was calculated using Mann Whitney test for patient CD19 and CD22 analyses.

Development of a Bicistronic CAR

When tested in the extremely aggressive relapse model with low dose of CAR, bivalent LoopCAR6 does not completely eradicate $CD19^{neg}$ and $CD22^{neg}$ Leukemia. After testing 11 different forms of bivalent CAR, it was found that it is difficult to reserve the CD22 activity in the bivalent form.

Figure 36:
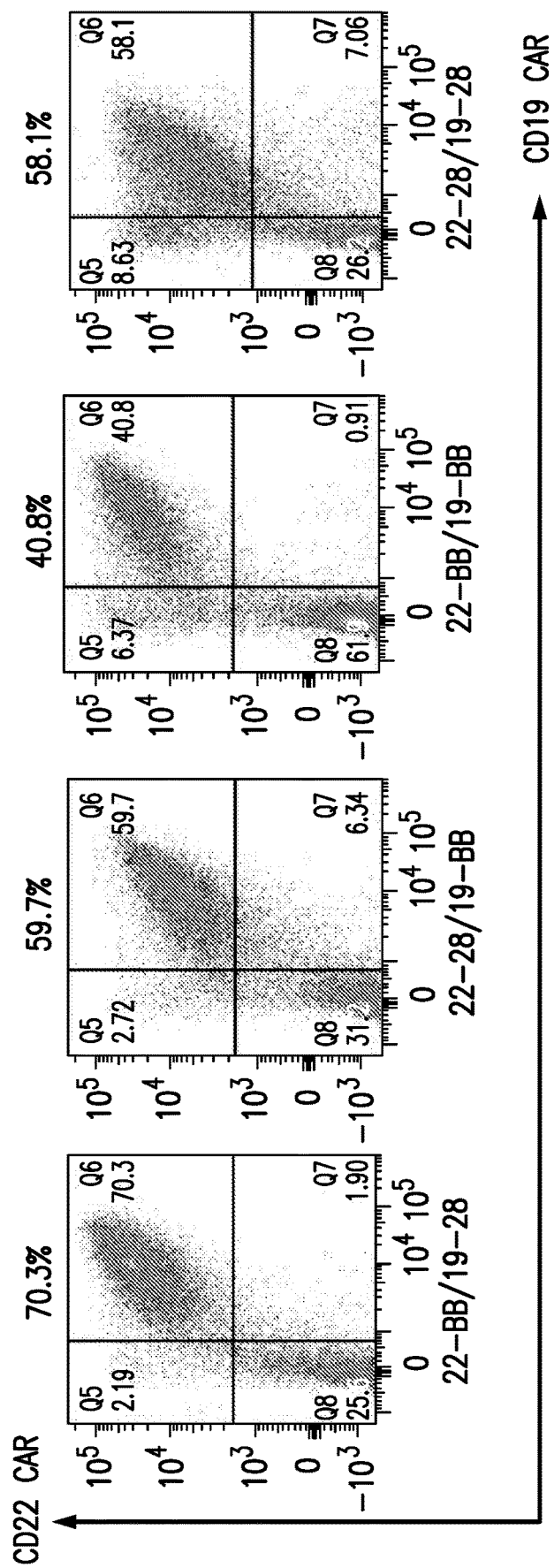
FIG. 36 is a dot plot showing human PBMC surface expression of the CD19 CAR and CD22 CAR analyzed on day 8.

Bicistronic CAR expression was determined by flow cytometry to confirm expression of the biscitronic construct. As indicated in FIG. 36, upon protein translation, bicistronic CD19 CAR and CD22 CAR became two separate fragments and eventually expressed as two CARs on the cell surface. The clustering of cells in the fourth quadrant indicated an equal molar expression of CD19 and CD22 CAR on the cell surface. It was found that the CAR with a 22-BB/19-28 expression system had the highest rate of double positive cells with 70.3% positive cells. The lowest levels of dual expression were associated with those that either double BB or double 28 with 40.8% and 58.1%, respectively. When the costimulatory domains were switched, around 10% expression was lost in the double positive population.

Bicistronic CARs with the Combination of 4-1BB and CD28 have Superior Function In Vitro Compared with Bivalent and Other Bicistronic CARs It has been previously reported that co-stimulation endo domain CD28 and 4-1BB has different effects on the immunomodulation of the CAR function. To elucidate the sensitivity of the single targeting CAR constructs, each CAR-T cell was co-cultured with leukemia expressing cognate antigens at various densities, and the IL-2 level was measured in the 18 hr co-culture supernatant. Target antigen density makes as high as 10-fold differences in cytokine production, and CD22 CAR is especially sensitive to the target density (FIG. 37A). The co-stimulation domain also contributes to the difference in cytokine production but the difference attributable to co-stimulation domain was modest compared to the impact of the target antigen density.

Figure 37B:
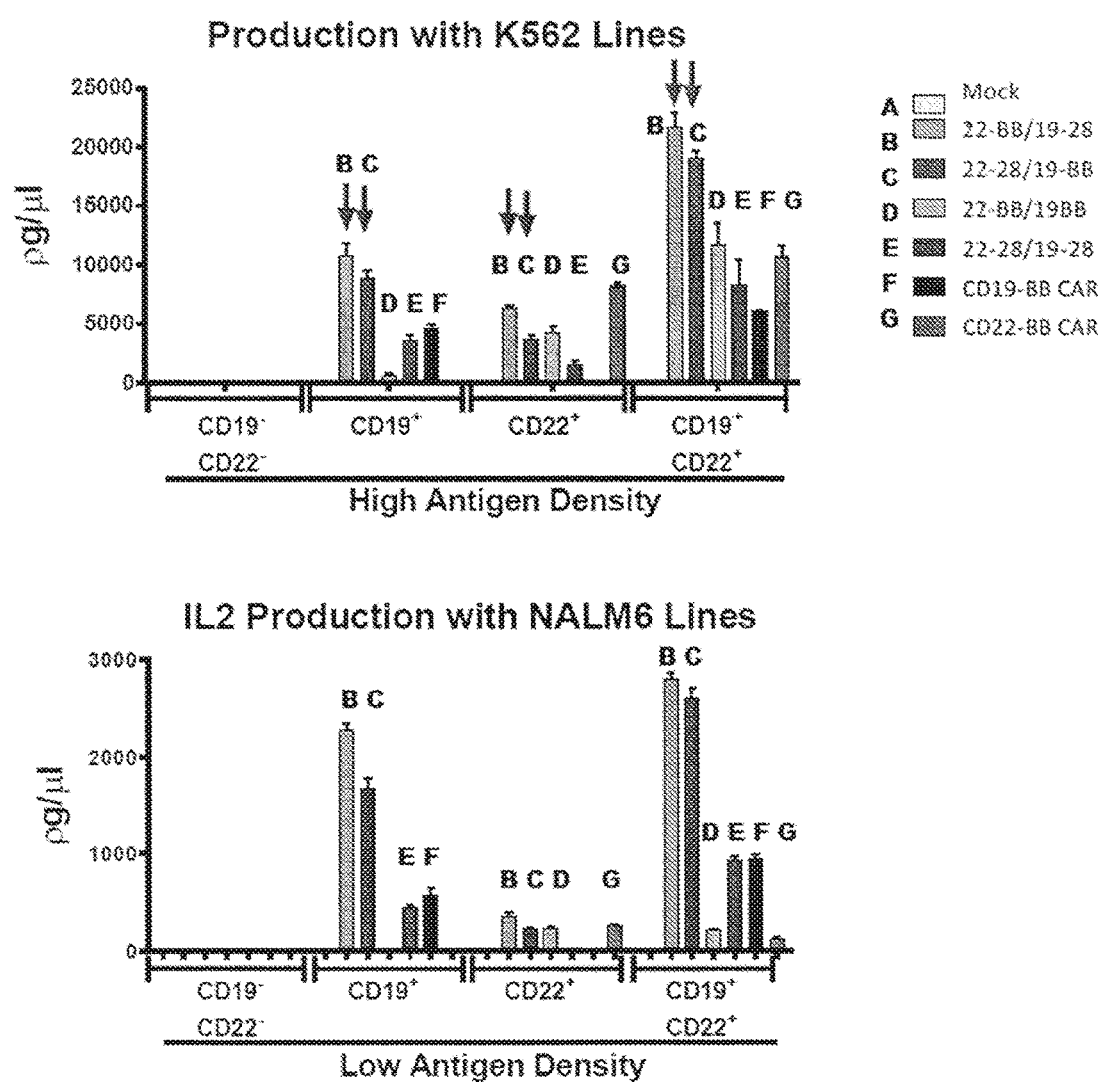
Figure 37D:
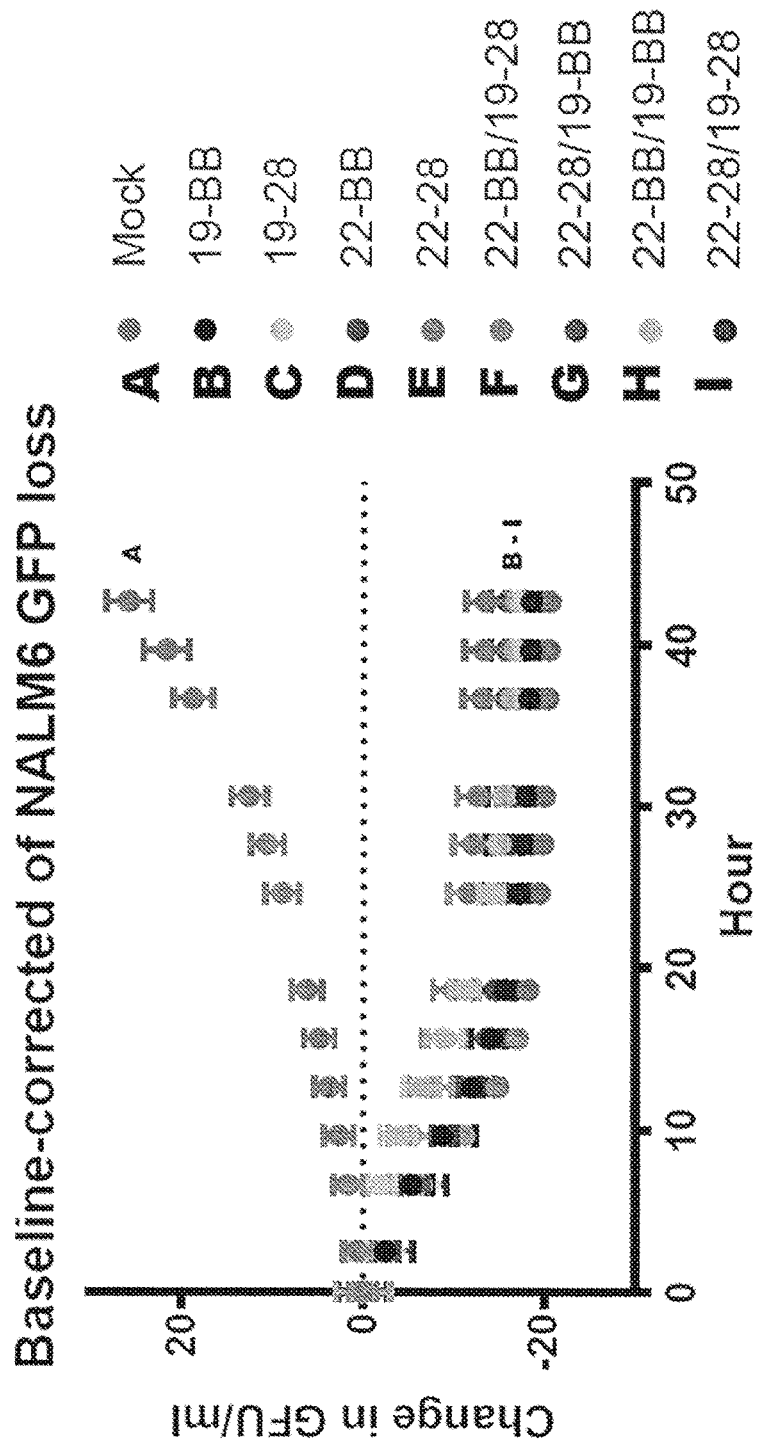
Figure 37E:
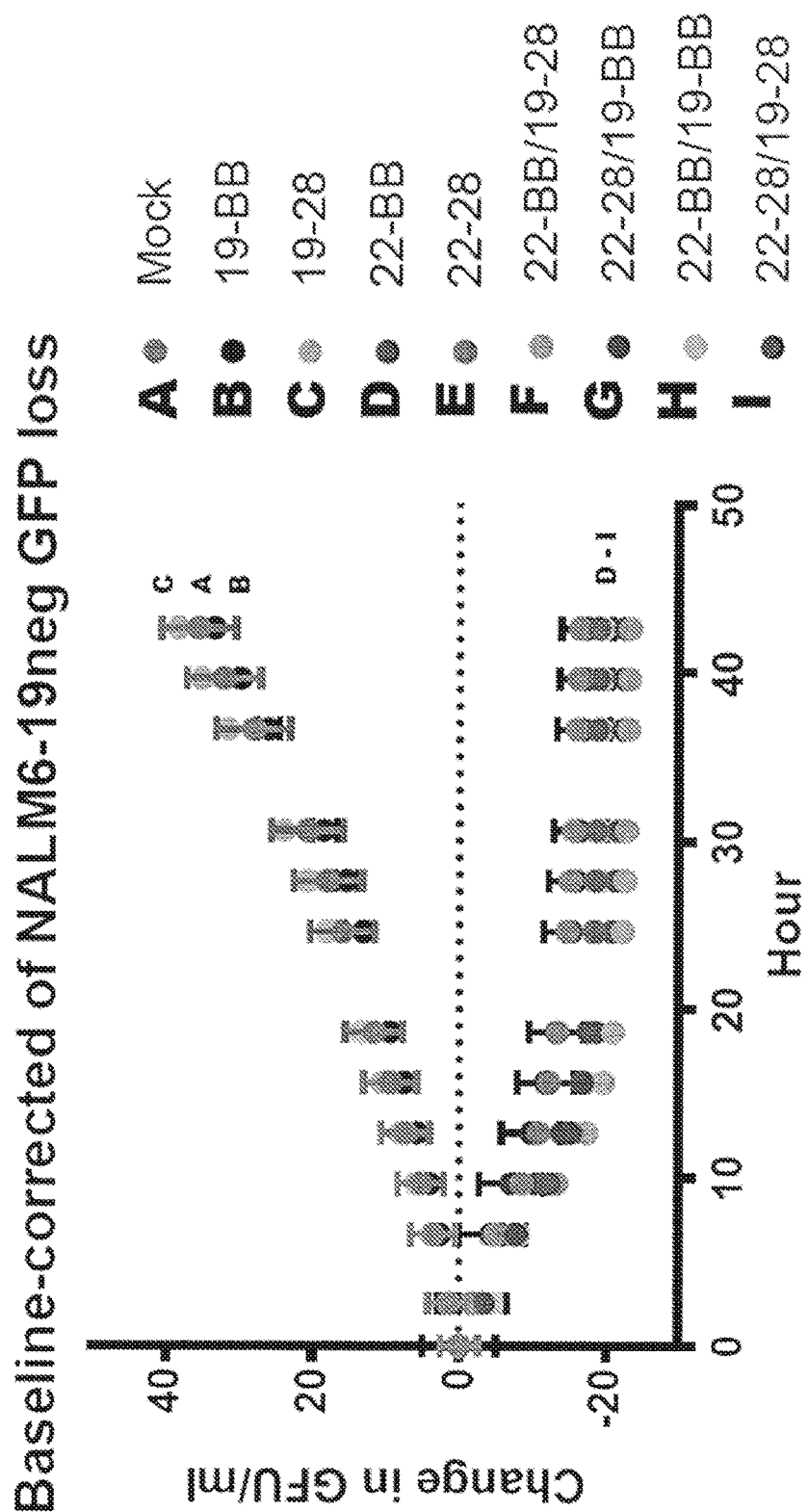
Figure 37F:
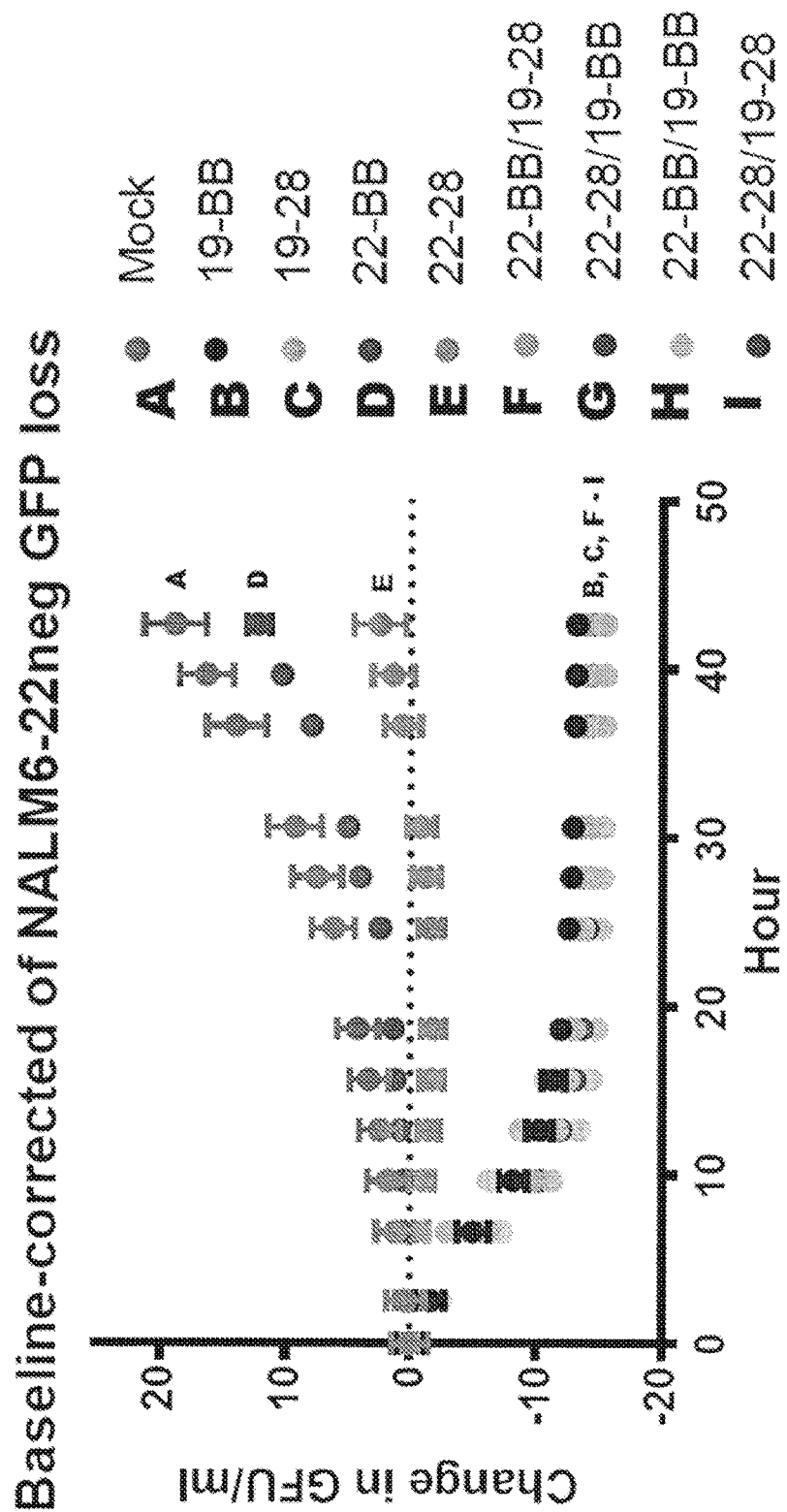
Figure 37G:
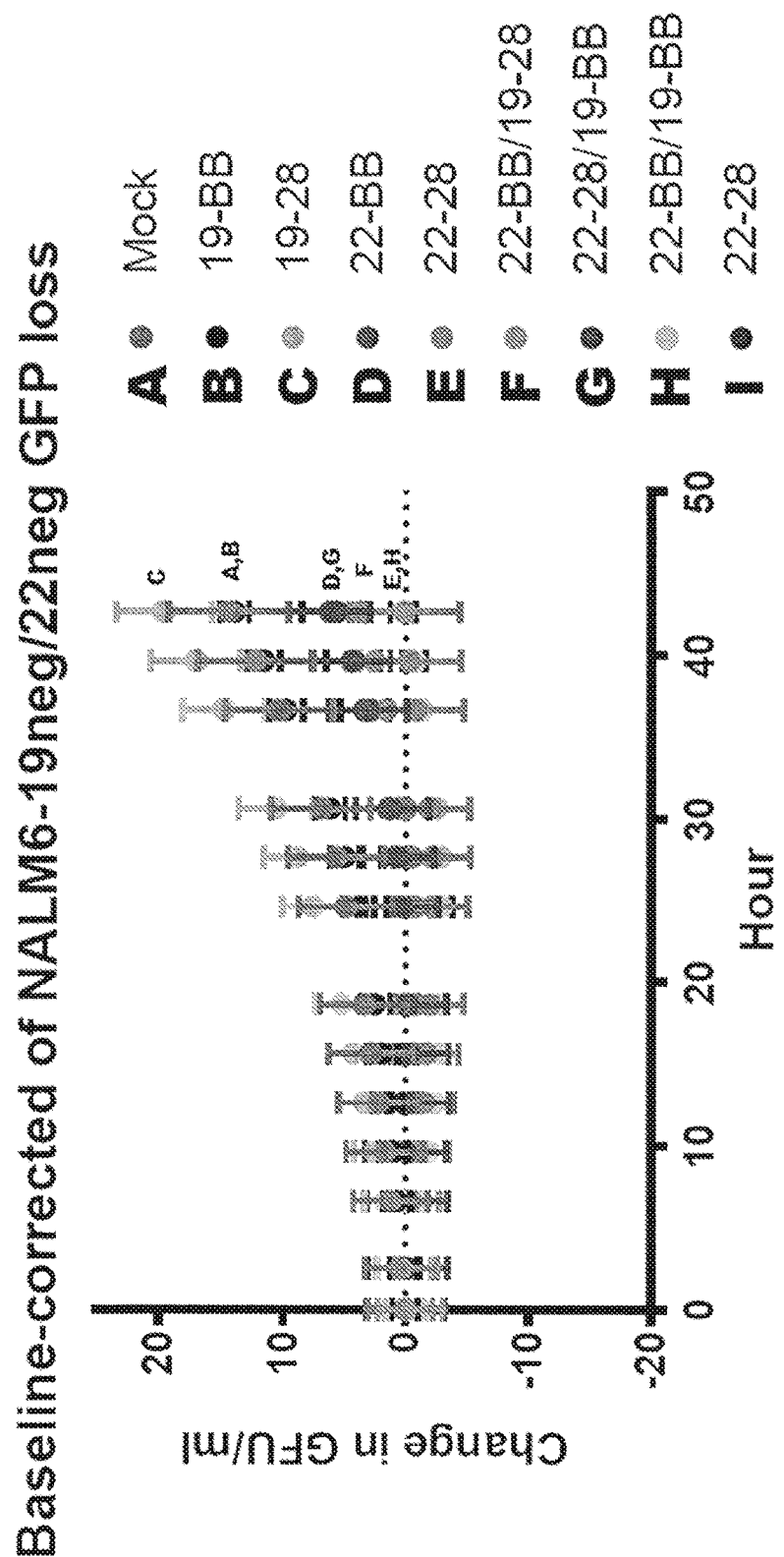

Next, bicistronic CARs, having different pairings of the co-stimulation domains, were incubated with K562 and NALM6 derived cells to determine if antigen density would affect cytokine production. The bicistronic CARs with the combination of both CD28 and 4-1BB co-stimulation domain produce more cytokines than the one with only CD28 or 4-1BB co-stimulation domain or the single targeting CAR (FIG. 37B). Antigen density again had the highest impact on the cytokine production of the CAR T cells. 22-BB/19-28 makes slightly more cytokines than the 22-28/19-BB CAR. 22-BB/19-28 CAR also made more cytokines than the CD19/CD22 bivalent CAR (FIG. 37C). All the bicistronic CARs demonstrated effective killing of the target cell lines (FIG. 37D-37G).

Figure 38:
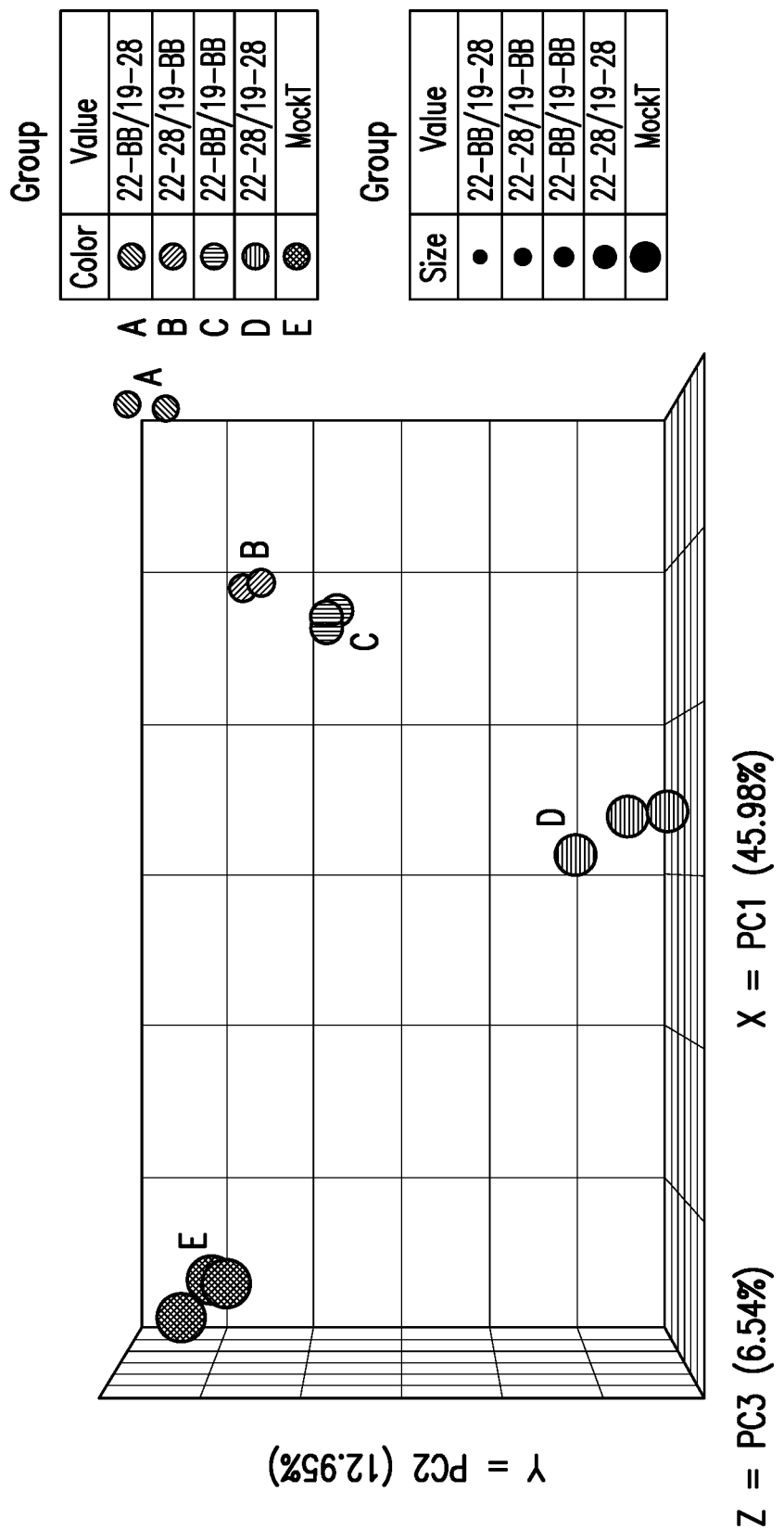
FIG. 38: RNAseq analysis demonstrates unique gene expression associated with different pairing of costimulatory domain. Bicistronic CAR T cells were co-incubated with an equal number of NALM6 for 24 hours in AMV media. NALM6 cells were removed with magnetic beads, and TRNA was extracted immediately and used for RNAseq analysis. The PCA plot indicates distinct gene expression profiles associated with different pairing of the costimulation domain.

RNAseq Analysis Demonstrates Unique Gene Expression Associated with Different Pairing of Costimulatory Domain RNAseq analysis was performed to interrogate the biological pathways associated with the different co-stimulation domain combinations. The bicistronic CARs were co-incubated with CD19$^+$ CD22$^+$ NALM6 cells, and extracted total RNA for the RNAseq analysis. The PCA indicates that the different combinations are associated with distinct gene expression profile (FIG. 38).

Figure 39A:
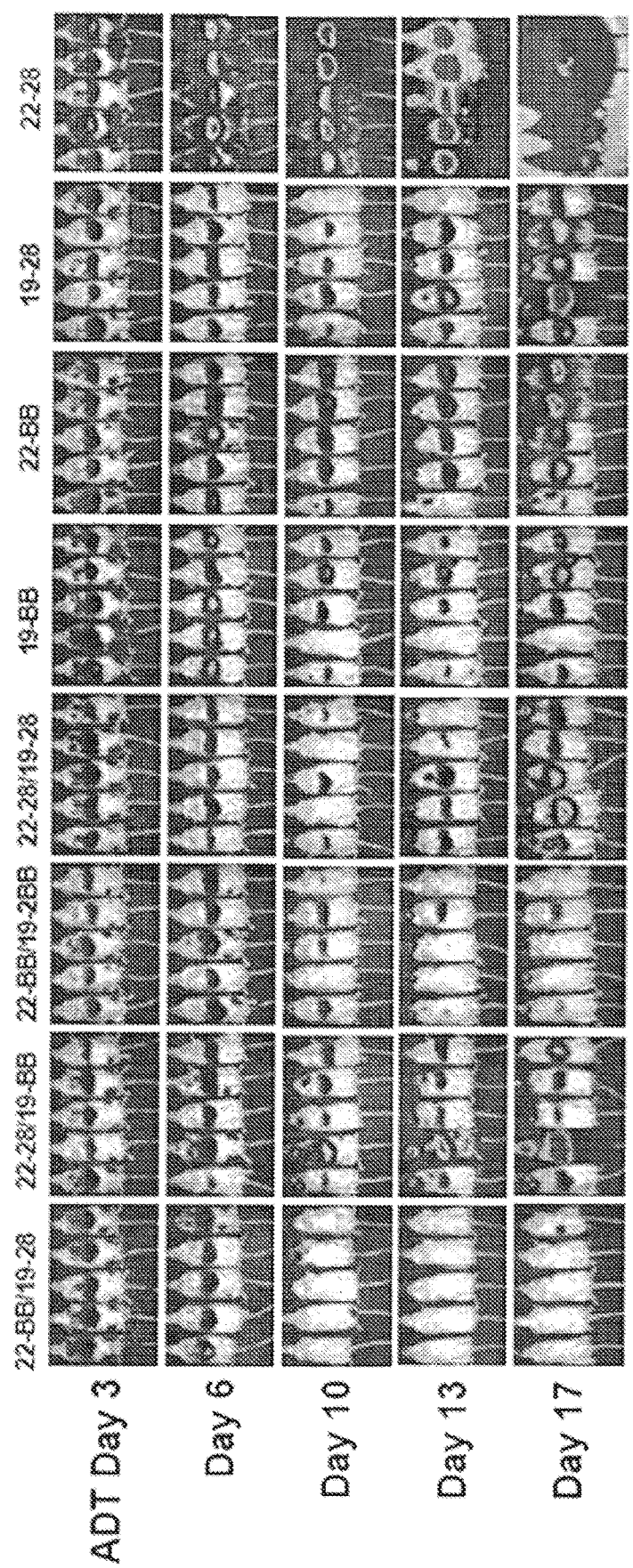
FIGS. 39A and 39B present images. Bioluminescent intensity, as shown by increased levels of shading, represents tumor burden.

Bicistronic CAR Efficiently Reduces Both CD19$^+$ CD22$^+$ Leukemia, and CD19$^{neg}$ or CD22$^{neg}$ Leukemia Blast CD19$^+$ CD22$^+$ NALM6 line was used to test the in vivo activity of the bicistronic CARs. CD19 and CD22 CAR with CD28 or 4-1BB single CARs were used as the controls. As indicated in FIG. 39, in general, bicistronic CARs are better than the single targeting CARs. Different pairings of CD28 and 4-1BB costimulation induce different rate of tumor elimination; 22-BB/19-28 is the best one at eliminating the leukemia blast.

Figure 39B:
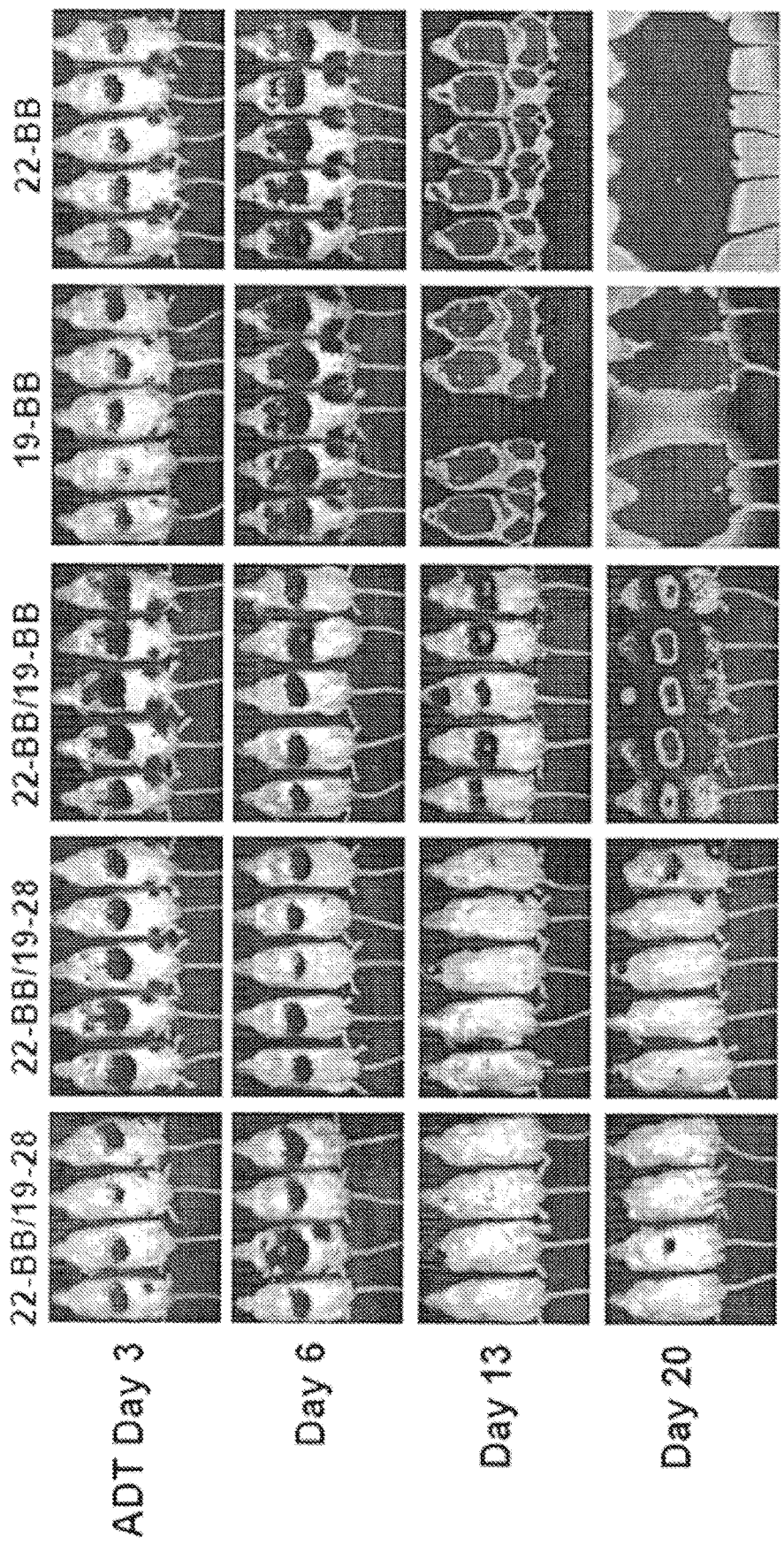

CD19$^{neg}$ and CD22low blast have been observed in relapsed patients. To simulate this clinic situation, the CRISPR Cas9 technology was used to generate CD19$^{neg}$ and CD22$^{neg}$ leukemia lines with NALM6 cell. A mixture of the CD19$^{neg}$, CD22$^{neg}$, and parental NALM6 cells were injected into immunodeficient NSG to create an aggressive xenograft model to simulate the clinical relapse situation. Three bicistronic CARs were compared to the CD19 and CD22 single targeting CARs (FIG. 39B). Single targeting CARs were not able to prevent the leukemia progression. Bicistronic CARs with both CD28 and 4-1BB had very potent activity on clearing the leukemia.

Figure 40:
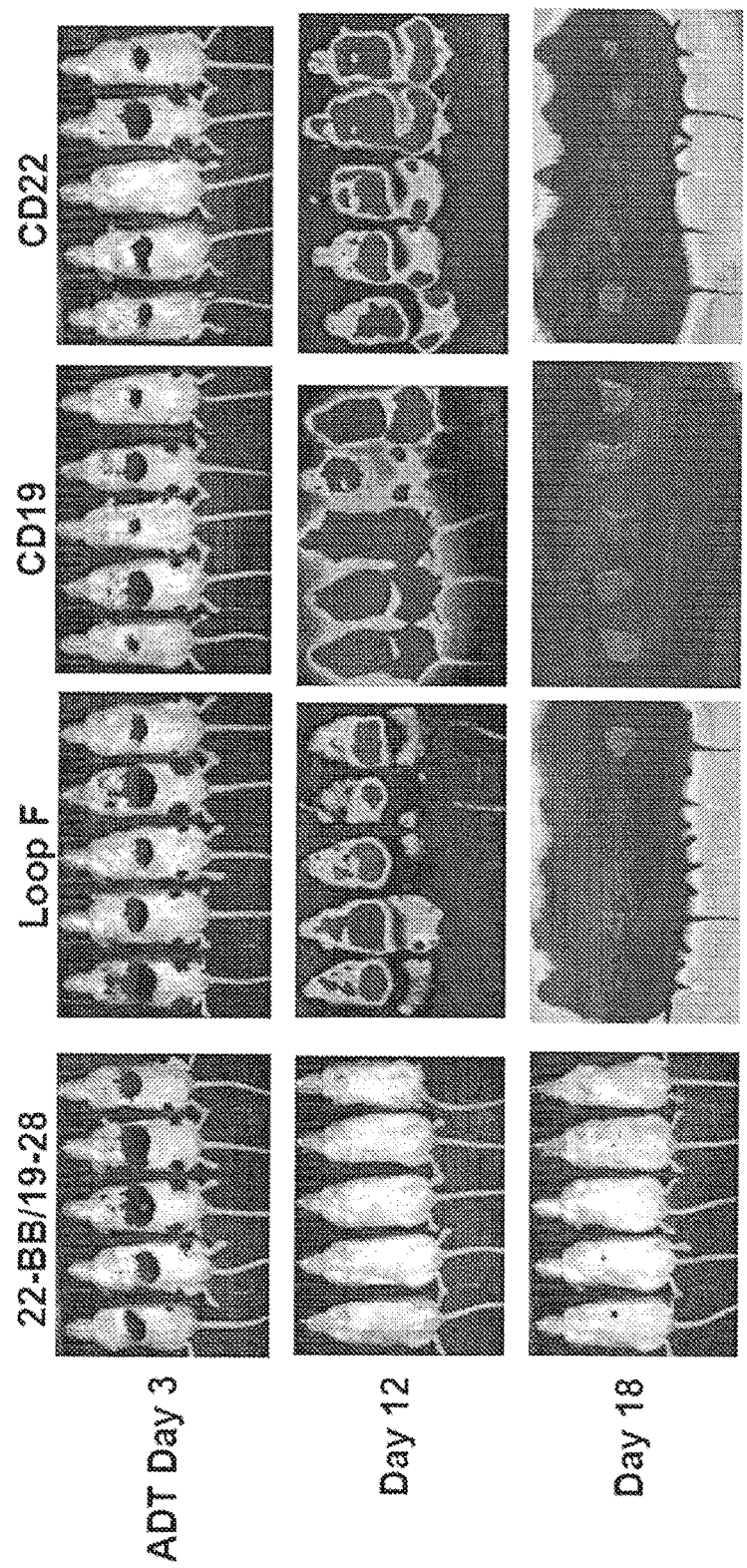
FIG. 40: NSG mice were challenged with 2.5E5 of luciferase-expressing NALM6-CD19$^{neg}$, and NALM6-CD22$^{neg}$ leukemia cells on day 0. On day 3, mice were IV injected with 3E6 of CAR expressing T cells. Bioluminescent intensity, as shown by increased levels of shading, represents tumor burden.

Further comparison was made with the bicistronic CAR and the bivalent CAR in vivo with the mixed CD19$^{neg}$ and CD22$^{neg}$ leukemia (FIG. 40). The bicistronic CAR is superior to the bivalent CARs in reducing the CD19$^{neg}$ and CD22$^{neg}$ leukemia.

Potent Activities of Bicistronic CAR

Figure 41:
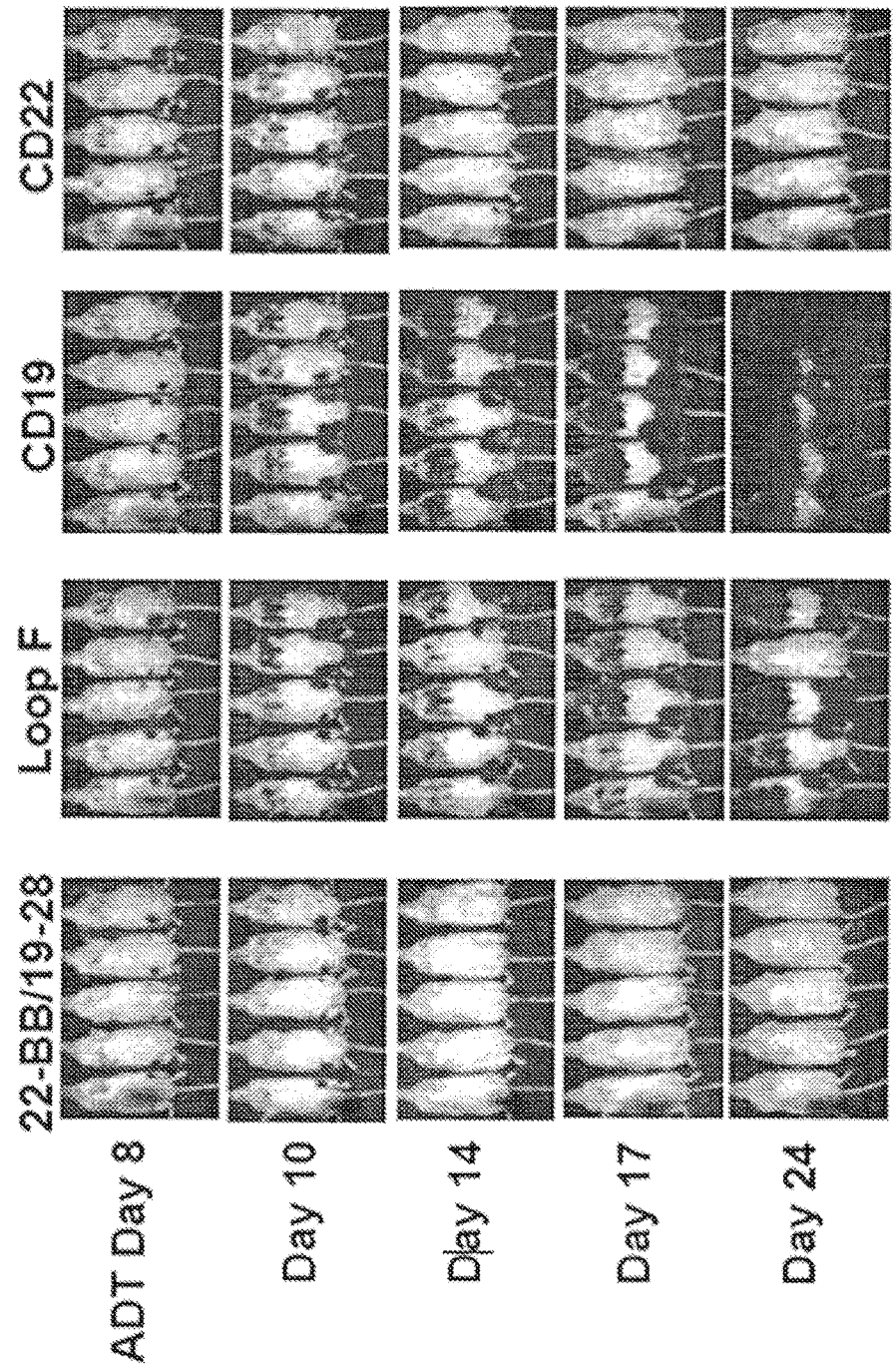
FIG. 41: NSG mice were IV injected with luciferase-expressing HMB28 Patient derived ALL xenograft (CD19$^{neg}$ CD22+, 1×10$^6$). On day 8, mice were injected with 3E6 CAR expressing T cells as indicated in the figure. Bioluminescent intensity, as shown by increased levels of shading, represents tumor burden.

A bicistronic CAR was testedusing the clinically relevant CD19$^{neg}$ PDX model (HMB28). Leukemia for the PDX model was derived from a patient who was previously treated with CD19 CAR and relapsed with CD19 negative leukemia relapse, subsequently treated with anti-CD22 CAR-T cells, which failed to clear leukemia due to an emergence of CD22-low expressing blast. Bicistronic CAR can completely eradicate the CD19 negative leukemia blast (FIG. 41).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A chimeric antigen receptor (CAR) amino acid construct comprising:
   (a) two or more cleavable domains;
   (b) a first CAR comprising
      a first antigen binding domain,
      a first transmembrane domain, and
      a first intracellular T cell signaling domain; and
   (c) a second CAR comprising
      a second antigen binding domain,
      a second transmembrane domain, and
      a second intracellular T cell signaling domain;
   wherein the first and second CARs are linked through the two or more cleavable domains, and
   (i) wherein the first antigen binding domain comprises the heavy chain variable region CDR sequences of SEQ ID NOS: 4, 6, and 8 and the light chain variable region CDR sequences of SEQ ID NOS: 12, 14 and 16, and wherein when the first CAR is cleaved from the construct, the first antigen binding domain has antigenic specificity for CD22; or
   (ii) wherein the first antigen binding domain comprises the light chain variable region CDR sequences of SEQ ID NOS: 24, 26, and 28, and the heavy chain variable region CDR sequences of SEQ ID NOS: 32, 34 and 36, and
   wherein when the first CAR is cleaved from the construct, the first antigen binding domain has antigenic specificity for CD19.

2. The CAR construct according to claim 1, wherein the first antigen binding domain comprises the heavy chain variable region CDR sequences of SEQ ID NOS: 4, 6, and 8, and the light chain variable region CDR sequences of SEQ ID NOS: 12, 14, and 16.

3. The CAR construct according to claim 1, wherein the first antigen binding domain comprises the light chain variable region CDR sequences of SEQ ID NOS: 24, 26, and 28, and the heavy chain variable region CDR sequences of SEQ ID NOS: 32, 34, and 36.

4. The CAR construct according to claim 2, wherein the second antigen binding domain comprises the light chain variable region CDR sequences of SEQ ID NOS: 24, 26, and 28, and the heavy chain variable region CDR sequences of SEQ ID NOS: 32, 34, and 36.

5. The CAR construct according to claim 4, wherein the first or second transmembrane domain comprises a CD8 transmembrane domain and a CD8 hinge domain, and wherein the CD8 transmembrane domain comprises the amino acid sequence of IYIWAPLAGTCGVLLLSLVIT-LYC (SEQ ID NO: 191 and the CD8 hinge domain comprises the amino acid sequence of TSTTTPAPRPPTPAP-TIASQPLSLRPEACRPAAGGAVHTRGLDFACD (SEQ ID NO: 18), SGTTTPAPRPPTPAPTIASQPLSLRPEACR-PAAGGAVHTRGLDFACD (SEQ ID NO: 86), or TTTPA-PRPPTPAPTIASQPLSLRPEACRPAAGGAVHTRGLD-FACD of SEQ ID NO: 18.

6. The CAR construct according to claim 4, wherein the first or second intracellular T cell signaling domain comprises a 4-1BB intracellular T cell signaling sequence, and wherein the 4-1BB intracellular T cell signaling sequence comprises the amino acid sequence of SEQ ID NO: 20.

7. The CAR construct according to claim 4, wherein the first or second intracellular T cell signaling domain comprises a CD3 zeta (ζ) intracellular T cell signaling sequence, and wherein the CD3ζ intracellular T cell signaling sequence comprises the amino acid sequence of SEQ ID NO: 21.

8. The CAR construct according to claim 4, wherein the two or more cleavable domains comprise a 2A cleavable domain and/or a furin cleavable domain.

9. The CAR construct according to claim 4, wherein the CAR construct comprises exactly two CARs being the first and second CARs.

10. The CAR construct according to claim 1, wherein the CAR comprises an amino acid sequence having 90% or greater sequence identity with, or comprising, any one of SEQ ID NOS: 49, 50, 51, or 52.

11. The CAR construct according to claim 1, wherein there are exactly two cleavable domains.

12. A nucleic acid comprising a nucleotide sequence encoding the CAR amino acid construct according to claim 11.

13. An isolated host cell comprising a recombinant expression vector comprising the nucleic acid according to claim 12.

14. A pharmaceutical composition comprising a population of cells comprising at least one host cell of claim 13, and a pharmaceutically acceptable carrier.

15. A method of treating cancer in a mammal, the method comprising administering to the mammal a population of cells comprising at least one host cell of claim 13 in an amount effective to treat cancer in the mammal.

16. The method of claim 15, wherein the cancer is a hematological malignancy.

17. The CAR construct according to claim 1, wherein the CAR comprises the amino acid sequence of SEQ ID NO: 49.

18. The CAR construct according to claim 1, wherein the CAR comprises the amino acid sequence of SEQ ID NO: 50.

19. The CAR construct according to claim 1, wherein the CAR comprises the amino acid sequence of SEQ ID NO: 51.

20. The CAR construct according to claim 1, wherein the CAR comprises the amino acid sequence of SEQ ID NO: 52.

* * * * *

SEQUENCE LISTING

```
<160> NUMBER OF SEQ ID NOS: 88

<210> SEQ ID NO 1
<211> LENGTH: 1
<212> TYPE: PRT
<213> ORGANISM: Artificial Sequence
<220> FEATURE:
<223> OTHER INFORMATION: synthetic

<400> SEQUENCE: 1

Met
1
```

```
<210> SEQ ID NO 2
<211> LENGTH: 21
<212> TYPE: PRT
<213> ORGANISM: Artificial Sequence
<220> FEATURE:
<223> OTHER INFORMATION: synthetic

<400> SEQUENCE: 2

Leu Leu Leu Val Thr Ser Leu Leu Leu Cys Glu Leu Pro His Pro Ala
1               5                   10                  15

Phe Leu Leu Ile Pro
            20

<210> SEQ ID NO 3
<211> LENGTH: 25
<212> TYPE: PRT
<213> ORGANISM: Artificial Sequence
<220> FEATURE:
<223> OTHER INFORMATION: synthetic

<400> SEQUENCE: 3

Gln Val Gln Leu Gln Gln Ser Gly Pro Gly Leu Val Lys Pro Ser Gln
1               5                   10                  15

Thr Leu Ser Leu Thr Cys Ala Ile Ser
            20                  25

<210> SEQ ID NO 4
<211> LENGTH: 10
<212> TYPE: PRT
<213> ORGANISM: Artificial Sequence
<220> FEATURE:
<223> OTHER INFORMATION: synthetic

<400> SEQUENCE: 4

Gly Asp Ser Val Ser Ser Asn Ser Ala Ala
1               5                   10

<210> SEQ ID NO 5
<211> LENGTH: 17
<212> TYPE: PRT
<213> ORGANISM: Artificial Sequence
<220> FEATURE:
<223> OTHER INFORMATION: synthetic

<400> SEQUENCE: 5

Trp Asn Trp Ile Arg Gln Ser Pro Ser Arg Gly Leu Glu Trp Leu Gly
1               5                   10                  15

Arg

<210> SEQ ID NO 6
<211> LENGTH: 9
<212> TYPE: PRT
<213> ORGANISM: Artificial Sequence
<220> FEATURE:
<223> OTHER INFORMATION: synthetic

<400> SEQUENCE: 6

Thr Tyr Tyr Arg Ser Lys Trp Tyr Asn
1               5

<210> SEQ ID NO 7
<211> LENGTH: 38
<212> TYPE: PRT
<213> ORGANISM: Artificial Sequence
<220> FEATURE:
```

-continued

<223> OTHER INFORMATION: synthetic

<400> SEQUENCE: 7

Asp Tyr Ala Val Ser Val Lys Ser Arg Ile Thr Ile Asn Pro Asp Thr
1               5                   10                  15

Ser Lys Asn Gln Phe Ser Leu Gln Leu Asn Ser Val Thr Pro Glu Asp
            20                  25                  30

Thr Ala Val Tyr Tyr Cys
        35

<210> SEQ ID NO 8
<211> LENGTH: 14
<212> TYPE: PRT
<213> ORGANISM: Artificial Sequence
<220> FEATURE:
<223> OTHER INFORMATION: synthetic

<400> SEQUENCE: 8

Ala Arg Glu Val Thr Gly Asp Leu Glu Asp Ala Phe Asp Ile
1               5                   10

<210> SEQ ID NO 9
<211> LENGTH: 11
<212> TYPE: PRT
<213> ORGANISM: Artificial Sequence
<220> FEATURE:
<223> OTHER INFORMATION: synthetic

<400> SEQUENCE: 9

Trp Gly Gln Gly Thr Met Val Thr Val Ser Ser
1               5                   10

<210> SEQ ID NO 10
<211> LENGTH: 5
<212> TYPE: PRT
<213> ORGANISM: Artificial Sequence
<220> FEATURE:
<223> OTHER INFORMATION: synthetic

<400> SEQUENCE: 10

Gly Gly Gly Gly Ser
1               5

<210> SEQ ID NO 11
<211> LENGTH: 26
<212> TYPE: PRT
<213> ORGANISM: Artificial Sequence
<220> FEATURE:
<223> OTHER INFORMATION: synthetic

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Arg Ala Ser
            20                  25

<210> SEQ ID NO 12
<211> LENGTH: 6
<212> TYPE: PRT
<213> ORGANISM: Artificial Sequence
<220> FEATURE:
<223> OTHER INFORMATION: synthetic

<400> SEQUENCE: 12

Gln Thr Ile Trp Ser Tyr

<210> SEQ ID NO 13
<211> LENGTH: 17
<212> TYPE: PRT
<213> ORGANISM: Artificial Sequence
<220> FEATURE:
<223> OTHER INFORMATION: synthetic

<400> SEQUENCE: 13

Leu Asn Trp Tyr Gln Gln Arg Pro Gly Lys Ala Pro Asn Leu Leu Ile
1               5                   10                  15

Tyr

<210> SEQ ID NO 14
<211> LENGTH: 3
<212> TYPE: PRT
<213> ORGANISM: Artificial Sequence
<220> FEATURE:
<223> OTHER INFORMATION: synthetic

<400> SEQUENCE: 14

Ala Ala Ser
1

<210> SEQ ID NO 15
<211> LENGTH: 36
<212> TYPE: PRT
<213> ORGANISM: Artificial Sequence
<220> FEATURE:
<223> OTHER INFORMATION: synthetic

<400> SEQUENCE: 15

Ser Leu Gln Ser Gly Val Pro Ser Arg Phe Ser Gly Arg Gly Ser Gly
1               5                   10                  15

Thr Asp Phe Thr Leu Thr Ile Ser Ser Leu Gln Ala Glu Asp Phe Ala
            20                  25                  30

Thr Tyr Tyr Cys
        35

<210> SEQ ID NO 16
<211> LENGTH: 9
<212> TYPE: PRT
<213> ORGANISM: Artificial Sequence
<220> FEATURE:
<223> OTHER INFORMATION: synthetic

<400> SEQUENCE: 16

Gln Gln Ser Tyr Ser Ile Pro Gln Thr
1               5

<210> SEQ ID NO 17
<211> LENGTH: 10
<212> TYPE: PRT
<213> ORGANISM: Artificial Sequence
<220> FEATURE:
<223> OTHER INFORMATION: synthetic

<400> SEQUENCE: 17

Phe Gly Gln Gly Thr Lys Leu Glu Ile Lys
1               5                   10

<210> SEQ ID NO 18
<211> LENGTH: 47
<212> TYPE: PRT

```
<213> ORGANISM: Artificial Sequence
<220> FEATURE:
<223> OTHER INFORMATION: synthetic

<400> SEQUENCE: 18

Thr Ser Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Cys Arg Pro Ala
                20                  25                  30

Ala Gly Gly Ala Val His Thr Arg Gly Leu Asp Phe Ala Cys Asp
            35                  40                  45

<210> SEQ ID NO 19
<211> LENGTH: 24
<212> TYPE: PRT
<213> ORGANISM: Artificial Sequence
<220> FEATURE:
<223> OTHER INFORMATION: synthetic

<400> SEQUENCE: 19

Ile Tyr Ile Trp Ala Pro Leu Ala Gly Thr Cys Gly Val Leu Leu Leu
1               5                   10                  15

Ser Leu Val Ile Thr Leu Tyr Cys
                20

<210> SEQ ID NO 20
<211> LENGTH: 42
<212> TYPE: PRT
<213> ORGANISM: Artificial Sequence
<220> FEATURE:
<223> OTHER INFORMATION: synthetic

<400> SEQUENCE: 20

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
                20                  25                  30

Pro Glu Glu Glu Glu Gly Gly Cys Glu Leu
            35                  40

<210> SEQ ID NO 21
<211> LENGTH: 112
<212> TYPE: PRT
<213> ORGANISM: Artificial Sequence
<220> FEATURE:
<223> OTHER INFORMATION: synthetic

<400> SEQUENCE: 21

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
```

<210> SEQ ID NO 22
<211> LENGTH: 22
<212> TYPE: PRT
<213> ORGANISM: Artificial Sequence
<220> FEATURE:
<223> OTHER INFORMATION: synthetic

<400> SEQUENCE: 22

Gly Ser Gly Glu Gly Arg Gly Ser Leu Leu Thr Cys Gly Asp Val Glu
1               5                   10                  15

Glu Asn Pro Gly Pro Arg
            20

<210> SEQ ID NO 23
<211> LENGTH: 26
<212> TYPE: PRT
<213> ORGANISM: Artificial Sequence
<220> FEATURE:
<223> OTHER INFORMATION: synthetic

<400> SEQUENCE: 23

Asp Ile Gln Met Thr Gln Thr Thr Ser Ser Leu Ser Ala Ser Leu Gly
1               5                   10                  15

Asp Arg Val Thr Ile Ser Cys Arg Ala Ser
            20                  25

<210> SEQ ID NO 24
<211> LENGTH: 6
<212> TYPE: PRT
<213> ORGANISM: Artificial Sequence
<220> FEATURE:
<223> OTHER INFORMATION: synthetic

<400> SEQUENCE: 24

Gln Asp Ile Ser Lys Tyr
1               5

<210> SEQ ID NO 25
<211> LENGTH: 17
<212> TYPE: PRT
<213> ORGANISM: Artificial Sequence
<220> FEATURE:
<223> OTHER INFORMATION: synthetic

<400> SEQUENCE: 25

Leu Asn Trp Tyr Gln Gln Lys Pro Asp Gly Thr Val Lys Leu Leu Ile
1               5                   10                  15

Tyr

<210> SEQ ID NO 26
<211> LENGTH: 3
<212> TYPE: PRT
<213> ORGANISM: Artificial Sequence
<220> FEATURE:
<223> OTHER INFORMATION: synthetic

<400> SEQUENCE: 26

His Thr Ser
1

<210> SEQ ID NO 27
<211> LENGTH: 36
<212> TYPE: PRT

```
<213> ORGANISM: Artificial Sequence
<220> FEATURE:
<223> OTHER INFORMATION: synthetic

<400> SEQUENCE: 27

Arg Leu His Ser Gly Val Pro Ser Arg Phe Ser Gly Ser Gly
1               5                   10                  15

Thr Asp Tyr Ser Leu Thr Ile Ser Asn Leu Glu Gln Glu Asp Ile Ala
            20                  25                  30

Thr Tyr Phe Cys
        35

<210> SEQ ID NO 28
<211> LENGTH: 9
<212> TYPE: PRT
<213> ORGANISM: Artificial Sequence
<220> FEATURE:
<223> OTHER INFORMATION: synthetic

<400> SEQUENCE: 28

Gln Gln Gly Asn Thr Leu Pro Tyr Thr
1               5

<210> SEQ ID NO 29
<211> LENGTH: 10
<212> TYPE: PRT
<213> ORGANISM: Artificial Sequence
<220> FEATURE:
<223> OTHER INFORMATION: synthetic

<400> SEQUENCE: 29

Phe Gly Gly Gly Thr Lys Leu Glu Ile Thr
1               5                   10

<210> SEQ ID NO 30
<211> LENGTH: 18
<212> TYPE: PRT
<213> ORGANISM: Artificial Sequence
<220> FEATURE:
<223> OTHER INFORMATION: synthetic

<400> SEQUENCE: 30

Gly Ser Thr Ser Gly Ser Gly Lys Pro Gly Ser Gly Glu Gly Ser Thr
1               5                   10                  15

Lys Gly

<210> SEQ ID NO 31
<211> LENGTH: 25
<212> TYPE: PRT
<213> ORGANISM: Artificial Sequence
<220> FEATURE:
<223> OTHER INFORMATION: synthetic

<400> SEQUENCE: 31

Glu Val Lys Leu Gln Glu Ser Gly Pro Gly Leu Val Ala Pro Ser Gln
1               5                   10                  15

Ser Leu Ser Val Thr Cys Thr Val Ser
            20                  25

<210> SEQ ID NO 32
<211> LENGTH: 8
<212> TYPE: PRT
<213> ORGANISM: Artificial Sequence
<220> FEATURE:
<223> OTHER INFORMATION: synthetic
```

<400> SEQUENCE: 32

Gly Val Ser Leu Pro Asp Tyr Gly
1               5

<210> SEQ ID NO 33
<211> LENGTH: 17
<212> TYPE: PRT
<213> ORGANISM: Artificial Sequence
<220> FEATURE:
<223> OTHER INFORMATION: synthetic

<400> SEQUENCE: 33

Val Ser Trp Ile Arg Gln Pro Pro Arg Lys Gly Leu Glu Trp Leu Gly
1               5                   10                  15

Val

<210> SEQ ID NO 34
<211> LENGTH: 7
<212> TYPE: PRT
<213> ORGANISM: Artificial Sequence
<220> FEATURE:
<223> OTHER INFORMATION: synthetic

<400> SEQUENCE: 34

Ile Trp Gly Ser Glu Thr Thr
1               5

<210> SEQ ID NO 35
<211> LENGTH: 38
<212> TYPE: PRT
<213> ORGANISM: Artificial Sequence
<220> FEATURE:
<223> OTHER INFORMATION: synthetic

<400> SEQUENCE: 35

Tyr Tyr Asn Ser Ala Leu Lys Ser Arg Leu Thr Ile Ile Lys Asp Asn
1               5                   10                  15

Ser Lys Ser Gln Val Phe Leu Lys Met Asn Ser Leu Gln Thr Asp Asp
                20                  25                  30

Thr Ala Ile Tyr Tyr Cys
            35

<210> SEQ ID NO 36
<211> LENGTH: 14
<212> TYPE: PRT
<213> ORGANISM: Artificial Sequence
<220> FEATURE:
<223> OTHER INFORMATION: synthetic

<400> SEQUENCE: 36

Ala Lys His Tyr Tyr Tyr Gly Gly Ser Tyr Ala Met Asp Tyr
1               5                   10

<210> SEQ ID NO 37
<211> LENGTH: 11
<212> TYPE: PRT
<213> ORGANISM: Artificial Sequence
<220> FEATURE:
<223> OTHER INFORMATION: synthetic

<400> SEQUENCE: 37

Trp Gly Gln Gly Thr Ser Val Thr Val Ser Ser
1               5                   10

<210> SEQ ID NO 38
<211> LENGTH: 12
<212> TYPE: PRT
<213> ORGANISM: Artificial Sequence
<220> FEATURE:
<223> OTHER INFORMATION: synthetic

<400> SEQUENCE: 38

Arg Lys Arg Arg Gly Ser Gly Thr Pro Asp Pro Trp
1               5                   10

<210> SEQ ID NO 39
<211> LENGTH: 24
<212> TYPE: PRT
<213> ORGANISM: Artificial Sequence
<220> FEATURE:
<223> OTHER INFORMATION: synthetic

<400> SEQUENCE: 39

Gly Ser Gly Ala Thr Asn Phe Ser Leu Leu Lys Gln Ala Gly Asp Val
1               5                   10                  15

Glu Glu Asn Pro Gly Pro Leu Glu
            20

<210> SEQ ID NO 40
<211> LENGTH: 44
<212> TYPE: PRT
<213> ORGANISM: Artificial Sequence
<220> FEATURE:
<223> OTHER INFORMATION: synthetic

<400> SEQUENCE: 40

Thr Ser Ala Ala Ala Ile Glu Val Met Tyr Pro Pro Pro Tyr Leu Asp
1               5                   10                  15

Asn Glu Lys Ser Asn Gly Thr Ile Ile His Val Lys Gly Lys His Leu
            20                  25                  30

Cys Pro Ser Pro Leu Phe Pro Gly Pro Ser Lys Pro
        35                  40

<210> SEQ ID NO 41
<211> LENGTH: 27
<212> TYPE: PRT
<213> ORGANISM: Artificial Sequence
<220> FEATURE:
<223> OTHER INFORMATION: synthetic

<400> SEQUENCE: 41

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 42
<211> LENGTH: 41
<212> TYPE: PRT
<213> ORGANISM: Artificial Sequence
<220> FEATURE:
<223> OTHER INFORMATION: synthetic

<400> SEQUENCE: 42

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
         35                  40

<210> SEQ ID NO 43
<211> LENGTH: 21
<212> TYPE: PRT
<213> ORGANISM: Artificial Sequence
<220> FEATURE:
<223> OTHER INFORMATION: synthetic

<400> SEQUENCE: 43

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 44
<211> LENGTH: 22
<212> TYPE: PRT
<213> ORGANISM: Artificial Sequence
<220> FEATURE:
<223> OTHER INFORMATION: synthetic

<400> SEQUENCE: 44

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 45
<211> LENGTH: 23
<212> TYPE: PRT
<213> ORGANISM: Artificial Sequence
<220> FEATURE:
<223> OTHER INFORMATION: synthetic

<400> SEQUENCE: 45

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 46
<211> LENGTH: 25
<212> TYPE: PRT
<213> ORGANISM: Artificial Sequence
<220> FEATURE:
<223> OTHER INFORMATION: synthetic

<400> SEQUENCE: 46

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25

<210> SEQ ID NO 47
<211> LENGTH: 4
<212> TYPE: PRT
<213> ORGANISM: Artificial Sequence
<220> FEATURE:
<223> OTHER INFORMATION: synthetic

<400> SEQUENCE: 47

Arg Lys Arg Arg

```
<210> SEQ ID NO 48
<211> LENGTH: 997
<212> TYPE: PRT
<213> ORGANISM: Artificial Sequence
<220> FEATURE:
<223> OTHER INFORMATION: synthetic

<400> SEQUENCE: 48
```

| | | | | | | | | | | | | | | |
|---|---|---|---|---|---|---|---|---|---|---|---|---|---|---|
|Met|Leu|Leu|Leu|Val|Thr|Ser|Leu|Leu|Cys|Glu|Leu|Pro|His|Pro|
|1| | | |5| | | | |10| | | | |15|

| | | | | | | | | | | | | | | |
|---|---|---|---|---|---|---|---|---|---|---|---|---|---|---|
|Ala|Phe|Leu|Leu|Ile|Pro|Gln|Val|Gln|Leu|Gln|Gln|Ser|Gly|Pro|Gly|
| | | |20| | | |25| | | | |30| | |

Leu Val Lys Pro Ser Gln Thr Leu Ser Leu Thr Cys Ala Ile Ser Gly
            35                  40                  45

Asp Ser Val Ser Ser Asn Ser Ala Ala Trp Asn Trp Ile Arg Gln Ser
        50                  55                  60

Pro Ser Arg Gly Leu Glu Trp Leu Gly Arg Thr Tyr Tyr Arg Ser Lys
65                  70                  75                  80

Trp Tyr Asn Asp Tyr Ala Val Ser Val Lys Ser Arg Ile Thr Ile Asn
                85                  90                  95

Pro Asp Thr Ser Lys Asn Gln Phe Ser Leu Gln Leu Asn Ser Val Thr
            100                 105                 110

Pro Glu Asp Thr Ala Val Tyr Tyr Cys Ala Arg Glu Val Thr Gly Asp
        115                 120                 125

Leu Glu Asp Ala Phe Asp Ile Trp Gly Gln Gly Thr Met Val Thr Val
130                 135                 140

Ser Ser Gly Gly Gly Gly Ser Asp Ile Gln Met Thr Gln Ser Pro Ser
145                 150                 155                 160

Ser Leu Ser Ala Ser Val Gly Asp Arg Val Thr Ile Thr Cys Arg Ala
                165                 170                 175

Ser Gln Thr Ile Trp Ser Tyr Leu Asn Trp Tyr Gln Gln Arg Pro Gly
            180                 185                 190

Lys Ala Pro Asn Leu Leu Ile Tyr Ala Ala Ser Ser Leu Gln Ser Gly
        195                 200                 205

Val Pro Ser Arg Phe Ser Gly Arg Gly Ser Gly Thr Asp Phe Thr Leu
210                 215                 220

Thr Ile Ser Ser Leu Gln Ala Glu Asp Phe Ala Thr Tyr Tyr Cys Gln
225                 230                 235                 240

Gln Ser Tyr Ser Ile Pro Gln Thr Phe Gly Gln Gly Thr Lys Leu Glu
                245                 250                 255

Ile Lys Thr Ser Thr Thr Thr Pro Ala Pro Arg Pro Pro Thr Pro Ala
            260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
290                 295                 300

Asp Ile Tyr Ile Trp Ala Pro Leu Ala Gly Thr Cys Gly Val Leu Leu
305                 310                 315                 320

Leu Ser Leu Val Ile Thr Leu Tyr Cys Lys Arg Gly Arg Lys Lys Leu
                325                 330                 335

Leu Tyr Ile Phe Lys Gln Pro Phe Met Arg Pro Val Gln Thr Thr Gln
            340                 345                 350

Glu Glu Asp Gly Cys Ser Cys Arg Phe Pro Glu Glu Glu Glu Gly Gly

```
                355                 360                 365
Cys Glu Leu Arg Val Lys Phe Ser Arg Ser Ala Asp Ala Pro Ala Tyr
    370                 375                 380
Gln Gly Gln Asn Gln Leu Tyr Asn Glu Leu Asn Leu Gly Arg Arg
385                 390                 395                 400
Glu Glu Tyr Asp Val Leu Asp Lys Arg Gly Arg Asp Pro Glu Met
                405                 410                 415
Gly Gly Lys Pro Arg Arg Lys Asn Pro Gln Glu Gly Leu Tyr Asn Glu
            420                 425                 430
Leu Gln Lys Asp Lys Met Ala Glu Ala Tyr Ser Glu Ile Gly Met Lys
        435                 440                 445
Gly Glu Arg Arg Arg Gly Lys Gly His Asp Gly Leu Tyr Gln Gly Leu
    450                 455                 460
Ser Thr Ala Thr Lys Asp Thr Tyr Asp Ala Leu His Met Gln Ala Leu
465                 470                 475                 480
Pro Pro Arg Gly Ser Gly Glu Gly Arg Gly Ser Leu Leu Thr Cys Gly
                485                 490                 495
Asp Val Glu Glu Asn Pro Gly Pro Arg Met Leu Leu Leu Val Thr Ser
            500                 505                 510
Leu Leu Leu Cys Glu Leu Pro His Pro Ala Phe Leu Leu Ile Pro Asp
        515                 520                 525
Ile Gln Met Thr Gln Thr Thr Ser Ser Leu Ser Ala Ser Leu Gly Asp
    530                 535                 540
Arg Val Thr Ile Ser Cys Arg Ala Ser Gln Asp Ile Ser Lys Tyr Leu
545                 550                 555                 560
Asn Trp Tyr Gln Gln Lys Pro Asp Gly Thr Val Lys Leu Leu Ile Tyr
                565                 570                 575
His Thr Ser Arg Leu His Ser Gly Val Pro Ser Arg Phe Ser Gly Ser
            580                 585                 590
Gly Ser Gly Thr Asp Tyr Ser Leu Thr Ile Ser Asn Leu Glu Gln Glu
        595                 600                 605
Asp Ile Ala Thr Tyr Phe Cys Gln Gln Gly Asn Thr Leu Pro Tyr Thr
    610                 615                 620
Phe Gly Gly Gly Thr Lys Leu Glu Ile Thr Gly Ser Thr Ser Gly Ser
625                 630                 635                 640
Gly Lys Pro Gly Ser Gly Glu Gly Ser Thr Lys Gly Glu Val Lys Leu
                645                 650                 655
Gln Glu Ser Gly Pro Gly Leu Val Ala Pro Ser Gln Ser Leu Ser Val
            660                 665                 670
Thr Cys Thr Val Ser Gly Val Ser Leu Pro Asp Tyr Gly Val Ser Trp
        675                 680                 685
Ile Arg Gln Pro Pro Arg Lys Gly Leu Glu Trp Leu Gly Val Ile Trp
    690                 695                 700
Gly Ser Glu Thr Thr Tyr Tyr Asn Ser Ala Leu Lys Ser Arg Leu Thr
705                 710                 715                 720
Ile Ile Lys Asp Asn Ser Lys Ser Gln Val Phe Leu Lys Met Asn Ser
                725                 730                 735
Leu Gln Thr Asp Asp Thr Ala Ile Tyr Tyr Cys Ala Lys His Tyr Tyr
            740                 745                 750
Tyr Gly Gly Ser Tyr Ala Met Asp Tyr Trp Gly Gln Gly Thr Ser Val
        755                 760                 765
Thr Val Ser Ser Ser Gly Thr Thr Pro Ala Pro Arg Pro Pro Thr
    770                 775                 780
```

```
Pro Ala Pro Thr Ile Ala Ser Gln Pro Leu Ser Leu Arg Pro Glu Ala
785                 790                 795                 800

Cys Arg Pro Ala Ala Gly Gly Ala Val His Thr Arg Gly Leu Asp Phe
            805                 810                 815

Ala Cys Asp Ile Tyr Ile Trp Ala Pro Leu Ala Gly Thr Cys Gly Val
            820                 825                 830

Leu Leu Leu Ser Leu Val Ile Thr Leu Tyr Cys Lys Arg Gly Arg Lys
            835                 840                 845

Lys Leu Leu Tyr Ile Phe Lys Gln Pro Phe Met Arg Pro Val Gln Thr
            850                 855                 860

Thr Gln Glu Glu Asp Gly Cys Ser Cys Arg Phe Pro Glu Glu Glu Glu
865                 870                 875                 880

Gly Gly Cys Glu Leu Arg Val Lys Phe Ser Arg Ser Ala Asp Ala Pro
            885                 890                 895

Ala Tyr Gln Gln Gly Gln Asn Gln Leu Tyr Asn Glu Leu Asn Leu Gly
            900                 905                 910

Arg Arg Glu Glu Tyr Asp Val Leu Asp Lys Arg Arg Gly Arg Asp Pro
            915                 920                 925

Glu Met Gly Gly Lys Pro Arg Arg Lys Asn Pro Gln Glu Gly Leu Tyr
            930                 935                 940

Asn Glu Leu Gln Lys Asp Lys Met Ala Glu Ala Tyr Ser Glu Ile Gly
945                 950                 955                 960

Met Lys Gly Glu Arg Arg Arg Gly Lys Gly His Asp Gly Leu Tyr Gln
            965                 970                 975

Gly Leu Ser Thr Ala Thr Lys Asp Thr Tyr Asp Ala Leu His Met Gln
            980                 985                 990

Ala Leu Pro Pro Arg
            995

<210> SEQ ID NO 49
<211> LENGTH: 1008
<212> TYPE: PRT
<213> ORGANISM: Artificial Sequence
<220> FEATURE:
<223> OTHER INFORMATION: synthetic

<400> SEQUENCE: 49

Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Pro Gly Leu
            20                  25                  30

Val Lys Pro Ser Gln Thr Leu Ser Leu Thr Cys Ala Ile Ser Gly Asp
            35                  40                  45

Ser Val Ser Ser Asn Ser Ala Ala Trp Asn Trp Ile Arg Gln Ser Pro
    50                  55                  60

Ser Arg Gly Leu Glu Trp Leu Gly Arg Thr Tyr Tyr Arg Ser Lys Trp
65              70                  75                  80

Tyr Asn Asp Tyr Ala Val Ser Val Lys Ser Arg Ile Thr Ile Asn Pro
            85                  90                  95

Asp Thr Ser Lys Asn Gln Phe Ser Leu Gln Leu Asn Ser Val Thr Pro
            100                 105                 110

Glu Asp Thr Ala Val Tyr Tyr Cys Ala Arg Glu Val Thr Gly Asp Leu
            115                 120                 125

Glu Asp Ala Phe Asp Ile Trp Gly Gln Gly Thr Met Val Thr Val Ser
            130                 135                 140
```

```
Ser Gly Gly Gly Gly Ser Asp Ile Gln Met Thr Gln Ser Pro Ser Ser
145                 150                 155                 160

Leu Ser Ala Ser Val Gly Asp Arg Val Thr Ile Thr Cys Arg Ala Ser
            165                 170                 175

Gln Thr Ile Trp Ser Tyr Leu Asn Trp Tyr Gln Gln Arg Pro Gly Lys
        180                 185                 190

Ala Pro Asn Leu Leu Ile Tyr Ala Ala Ser Ser Leu Gln Ser Gly Val
    195                 200                 205

Pro Ser Arg Phe Ser Gly Arg Gly Ser Gly Thr Asp Phe Thr Leu Thr
210                 215                 220

Ile Ser Ser Leu Gln Ala Glu Asp Phe Ala Thr Tyr Tyr Cys Gln Gln
225                 230                 235                 240

Ser Tyr Ser Ile Pro Gln Thr Phe Gly Gln Gly Thr Lys Leu Glu Ile
            245                 250                 255

Lys Ser Gly Thr Thr Thr Pro Ala Pro Arg Pro Pro Thr Pro Ala Pro
        260                 265                 270

Thr Ile Ala Ser Gln Pro Leu Ser Leu Arg Pro Glu Ala Cys Arg Pro
    275                 280                 285

Ala Ala Gly Gly Ala Val His Thr Arg Gly Leu Asp Phe Ala Cys Asp
290                 295                 300

Ile Tyr Ile Trp Ala Pro Leu Ala Gly Thr Cys Gly Val Leu Leu Leu
305                 310                 315                 320

Ser Leu Val Ile Thr Leu Tyr Cys Lys Arg Gly Arg Lys Lys Leu Leu
            325                 330                 335

Tyr Ile Phe Lys Gln Pro Phe Met Arg Pro Val Gln Thr Thr Gln Glu
        340                 345                 350

Glu Asp Gly Cys Ser Cys Arg Phe Pro Glu Glu Glu Glu Gly Gly Cys
            355                 360                 365

Glu Leu Arg Val Lys Phe Ser Arg Ser Ala Asp Ala Pro Ala Tyr Gln
        370                 375                 380

Gln Gly Gln Asn Gln Leu Tyr Asn Glu Leu Asn Leu Gly Arg Arg Glu
385                 390                 395                 400

Glu Tyr Asp Val Leu Asp Lys Arg Arg Gly Arg Asp Pro Glu Met Gly
            405                 410                 415

Gly Lys Pro Arg Arg Lys Asn Pro Gln Glu Gly Leu Tyr Asn Glu Leu
        420                 425                 430

Gln Lys Asp Lys Met Ala Glu Ala Tyr Ser Glu Ile Gly Met Lys Gly
        435                 440                 445

Glu Arg Arg Arg Gly Lys Gly His Asp Gly Leu Tyr Gln Gly Leu Ser
450                 455                 460

Thr Ala Thr Lys Asp Thr Tyr Asp Ala Leu His Met Gln Ala Leu Pro
465                 470                 475                 480

Pro Arg Arg Lys Arg Arg Gly Ser Gly Thr Pro Asp Pro Trp Gly Ser
            485                 490                 495

Gly Ala Thr Asn Phe Ser Leu Leu Lys Gln Ala Gly Asp Val Glu Glu
        500                 505                 510

Asn Pro Gly Pro Leu Glu Met Glu Phe Gly Leu Ser Trp Leu Phe Leu
        515                 520                 525

Val Ala Ile Leu Lys Gly Val Gln Cys Ser Arg Asp Ile Gln Met Thr
530                 535                 540

Gln Thr Thr Ser Ser Leu Ser Ala Ser Leu Gly Asp Arg Val Thr Ile
545                 550                 555                 560
```

```
Ser Cys Arg Ala Ser Gln Asp Ile Ser Lys Tyr Leu Asn Trp Tyr Gln
            565                 570                 575

Gln Lys Pro Asp Gly Thr Val Lys Leu Leu Ile Tyr His Thr Ser Arg
        580                 585                 590

Leu His Ser Gly Val Pro Ser Arg Phe Ser Gly Ser Gly Ser Gly Thr
            595                 600                 605

Asp Tyr Ser Leu Thr Ile Ser Asn Leu Glu Gln Glu Asp Ile Ala Thr
        610                 615                 620

Tyr Phe Cys Gln Gln Gly Asn Thr Leu Pro Tyr Thr Phe Gly Gly Gly
625                 630                 635                 640

Thr Lys Leu Glu Ile Thr Gly Ser Thr Ser Gly Ser Gly Lys Pro Gly
            645                 650                 655

Ser Gly Glu Gly Ser Thr Lys Gly Glu Val Lys Leu Gln Glu Ser Gly
            660                 665                 670

Pro Gly Leu Val Ala Pro Ser Gln Ser Leu Ser Val Thr Cys Thr Val
            675                 680                 685

Ser Gly Val Ser Leu Pro Asp Tyr Gly Val Ser Trp Ile Arg Gln Pro
            690                 695                 700

Pro Arg Lys Gly Leu Glu Trp Leu Gly Val Ile Trp Gly Ser Glu Thr
705                 710                 715                 720

Thr Tyr Tyr Asn Ser Ala Leu Lys Ser Arg Leu Thr Ile Ile Lys Asp
            725                 730                 735

Asn Ser Lys Ser Gln Val Phe Leu Lys Met Asn Ser Leu Gln Thr Asp
            740                 745                 750

Asp Thr Ala Ile Tyr Tyr Cys Ala Lys His Tyr Tyr Gly Gly Ser
            755                 760                 765

Tyr Ala Met Asp Tyr Trp Gly Gln Gly Thr Ser Val Thr Val Ser Ser
        770                 775                 780

Thr Ser Ala Ala Ala Ile Glu Val Met Tyr Pro Pro Pro Tyr Leu Asp
785                 790                 795                 800

Asn Glu Lys Ser Asn Gly Thr Ile Ile His Val Lys Gly Lys His Leu
            805                 810                 815

Cys Pro Ser Pro Leu Phe Pro Gly Pro Ser Lys Pro Phe Trp Val Leu
            820                 825                 830

Val Val Val Gly Gly Val Leu Ala Cys Tyr Ser Leu Leu Val Thr Val
            835                 840                 845

Ala Phe Ile Ile Phe Trp Val Arg Ser Lys Arg Ser Arg Leu Leu His
        850                 855                 860

Ser Asp Tyr Met Asn Met Thr Pro Arg Arg Pro Gly Pro Thr Arg Lys
865                 870                 875                 880

His Tyr Gln Pro Tyr Ala Pro Pro Arg Asp Phe Ala Ala Tyr Arg Ser
            885                 890                 895

Arg Val Lys Phe Ser Arg Ser Ala Asp Ala Pro Ala Tyr Gln Gln Gly
            900                 905                 910

Gln Asn Gln Leu Tyr Asn Glu Leu Asn Leu Gly Arg Arg Glu Glu Tyr
        915                 920                 925

Asp Val Leu Asp Lys Arg Arg Gly Arg Asp Pro Glu Met Gly Gly Lys
        930                 935                 940

Pro Arg Arg Lys Asn Pro Gln Glu Gly Leu Tyr Asn Glu Leu Gln Lys
945                 950                 955                 960

Asp Lys Met Ala Glu Ala Tyr Ser Glu Ile Gly Met Lys Gly Glu Arg
            965                 970                 975

Arg Arg Gly Lys Gly His Asp Gly Leu Tyr Gln Gly Leu Ser Thr Ala
```

```
                980               985               990
Thr Lys Asp Thr Tyr Asp Ala Leu  His Met Gln Ala Leu  Pro Pro Arg
            995                 1000                1005

<210> SEQ ID NO 50
<211> LENGTH: 1008
<212> TYPE: PRT
<213> ORGANISM: Artificial Sequence
<220> FEATURE:
<223> OTHER INFORMATION: synthetic

<400> SEQUENCE: 50

Met Ala Leu Pro Val Thr Ala Leu Leu Pro Leu Ala Leu Leu Leu
1               5                   10                  15

His Ala Ala Arg Pro Gln Val Gln Leu Gln Gln Ser Gly Pro Gly Leu
                20                  25                  30

Val Lys Pro Ser Gln Thr Leu Ser Leu Thr Cys Ala Ile Ser Gly Asp
            35                  40                  45

Ser Val Ser Ser Asn Ser Ala Ala Trp Asn Trp Ile Arg Gln Ser Pro
50                  55                  60

Ser Arg Gly Leu Glu Trp Leu Gly Arg Thr Tyr Tyr Arg Ser Lys Trp
65                  70                  75                  80

Tyr Asn Asp Tyr Ala Val Ser Val Lys Ser Arg Ile Thr Ile Asn Pro
                85                  90                  95

Asp Thr Ser Lys Asn Gln Phe Ser Leu Gln Leu Asn Ser Val Thr Pro
            100                 105                 110

Glu Asp Thr Ala Val Tyr Tyr Cys Ala Arg Glu Val Thr Gly Asp Leu
        115                 120                 125

Glu Asp Ala Phe Asp Ile Trp Gly Gln Gly Thr Met Val Thr Val Ser
    130                 135                 140

Ser Gly Gly Gly Gly Ser Asp Ile Gln Met Thr Gln Ser Pro Ser Ser
145                 150                 155                 160

Leu Ser Ala Ser Val Gly Asp Arg Val Thr Ile Thr Cys Arg Ala Ser
                165                 170                 175

Gln Thr Ile Trp Ser Tyr Leu Asn Trp Tyr Gln Gln Arg Pro Gly Lys
            180                 185                 190

Ala Pro Asn Leu Leu Ile Tyr Ala Ala Ser Ser Leu Gln Ser Gly Val
        195                 200                 205

Pro Ser Arg Phe Ser Gly Arg Gly Ser Gly Thr Asp Phe Thr Leu Thr
    210                 215                 220

Ile Ser Ser Leu Gln Ala Glu Asp Phe Ala Thr Tyr Tyr Cys Gln Gln
225                 230                 235                 240

Ser Tyr Ser Ile Pro Gln Thr Phe Gly Gln Gly Thr Lys Leu Glu Ile
                245                 250                 255

Lys Ser Gly Ala Ala Ala Ile Glu Val Met Tyr Pro Pro Pro Tyr Leu
            260                 265                 270

Asp Asn Glu Lys Ser Asn Gly Thr Ile Ile His Val Lys Gly Lys His
        275                 280                 285

Leu Cys Pro Ser Pro Leu Phe Pro Gly Pro Ser Lys Pro Phe Trp Val
    290                 295                 300

Leu Val Val Val Gly Gly Val Leu Ala Cys Tyr Ser Leu Leu Val Thr
305                 310                 315                 320

Val Ala Phe Ile Ile Phe Trp Val Arg Ser Lys Arg Ser Arg Leu Leu
                325                 330                 335

His Ser Asp Tyr Met Asn Met Thr Pro Arg Arg Pro Gly Pro Thr Arg
```

```
                    340                 345                 350
Lys His Tyr Gln Pro Tyr Ala Pro Pro Arg Asp Phe Ala Ala Tyr Arg
            355                 360                 365

Ser Arg Val Lys Phe Ser Arg Ser Ala Asp Ala Pro Ala Tyr Gln Gln
        370                 375                 380

Gly Gln Asn Gln Leu Tyr Asn Glu Leu Asn Leu Gly Arg Arg Glu Glu
385                 390                 395                 400

Tyr Asp Val Leu Asp Lys Arg Gly Arg Asp Pro Glu Met Gly Gly
                405                 410                 415

Lys Pro Arg Arg Lys Asn Pro Gln Glu Gly Leu Tyr Asn Glu Leu Gln
            420                 425                 430

Lys Asp Lys Met Ala Glu Ala Tyr Ser Glu Ile Gly Met Lys Gly Glu
        435                 440                 445

Arg Arg Arg Gly Lys Gly His Asp Gly Leu Tyr Gln Gly Leu Ser Thr
    450                 455                 460

Ala Thr Lys Asp Thr Tyr Asp Ala Leu His Met Gln Ala Leu Pro Pro
465                 470                 475                 480

Arg Arg Lys Arg Arg Gly Ser Gly Thr Pro Asp Pro Trp Gly Ser Gly
                485                 490                 495

Ala Thr Asn Phe Ser Leu Leu Lys Gln Ala Gly Asp Val Glu Glu Asn
            500                 505                 510

Pro Gly Pro Leu Glu Met Glu Phe Gly Leu Ser Trp Leu Phe Leu Val
        515                 520                 525

Ala Ile Leu Lys Gly Val Gln Cys Ser Arg Asp Ile Gln Met Thr Gln
    530                 535                 540

Thr Thr Ser Ser Leu Ser Ala Ser Leu Gly Asp Arg Val Thr Ile Ser
545                 550                 555                 560

Cys Arg Ala Ser Gln Asp Ile Ser Lys Tyr Leu Asn Trp Tyr Gln Gln
                565                 570                 575

Lys Pro Asp Gly Thr Val Lys Leu Leu Ile Tyr His Thr Ser Arg Leu
            580                 585                 590

His Ser Gly Val Pro Ser Arg Phe Ser Gly Ser Gly Ser Gly Thr Asp
        595                 600                 605

Tyr Ser Leu Thr Ile Ser Asn Leu Glu Gln Glu Asp Ile Ala Thr Tyr
    610                 615                 620

Phe Cys Gln Gln Gly Asn Thr Leu Pro Tyr Thr Phe Gly Gly Gly Thr
625                 630                 635                 640

Lys Leu Glu Ile Thr Gly Ser Thr Ser Gly Ser Gly Lys Pro Gly Ser
                645                 650                 655

Gly Glu Gly Ser Thr Lys Gly Glu Val Lys Leu Gln Glu Ser Gly Pro
            660                 665                 670

Gly Leu Val Ala Pro Ser Gln Ser Leu Ser Val Thr Cys Thr Val Ser
        675                 680                 685

Gly Val Ser Leu Pro Asp Tyr Gly Val Ser Trp Ile Arg Gln Pro Pro
    690                 695                 700

Arg Lys Gly Leu Glu Trp Leu Gly Val Ile Trp Gly Ser Glu Thr Thr
705                 710                 715                 720

Tyr Tyr Asn Ser Ala Leu Lys Ser Arg Leu Thr Ile Ile Lys Asp Asn
                725                 730                 735

Ser Lys Ser Gln Val Phe Leu Lys Met Asn Ser Leu Gln Thr Asp Asp
            740                 745                 750

Thr Ala Ile Tyr Tyr Cys Ala Lys His Tyr Tyr Gly Gly Ser Tyr
        755                 760                 765
```

Ala Met Asp Tyr Trp Gly Gln Gly Thr Ser Val Thr Val Ser Ser Thr
770                 775                 780

Ser Thr Thr Thr Pro Ala Pro Arg Pro Pro Thr Pro Ala Pro Thr Ile
785                 790                 795                 800

Ala Ser Gln Pro Leu Ser Leu Arg Pro Glu Ala Cys Arg Pro Ala Ala
            805                 810                 815

Gly Gly Ala Val His Thr Arg Gly Leu Asp Phe Ala Cys Asp Ile Tyr
            820                 825                 830

Ile Trp Ala Pro Leu Ala Gly Thr Cys Gly Val Leu Leu Leu Ser Leu
            835                 840                 845

Val Ile Thr Leu Tyr Cys Lys Arg Gly Arg Lys Lys Leu Leu Tyr Ile
            850                 855                 860

Phe Lys Gln Pro Phe Met Arg Pro Val Gln Thr Thr Gln Glu Glu Asp
865                 870                 875                 880

Gly Cys Ser Cys Arg Phe Pro Glu Glu Glu Glu Gly Gly Cys Glu Leu
            885                 890                 895

Arg Val Lys Phe Ser Arg Ser Ala Asp Ala Pro Ala Tyr Gln Gln Gly
            900                 905                 910

Gln Asn Gln Leu Tyr Asn Glu Leu Asn Leu Gly Arg Arg Glu Glu Tyr
            915                 920                 925

Asp Val Leu Asp Lys Arg Arg Gly Arg Asp Pro Glu Met Gly Gly Lys
930                 935                 940

Pro Arg Arg Lys Asn Pro Gln Glu Gly Leu Tyr Asn Glu Leu Gln Lys
945                 950                 955                 960

Asp Lys Met Ala Glu Ala Tyr Ser Glu Ile Gly Met Lys Gly Glu Arg
            965                 970                 975

Arg Arg Gly Lys Gly His Asp Gly Leu Tyr Gln Gly Leu Ser Thr Ala
            980                 985                 990

Thr Lys Asp Thr Tyr Asp Ala Leu His Met Gln Ala Leu Pro Pro Arg
            995                 1000                1005

<210> SEQ ID NO 51
<211> LENGTH: 1009
<212> TYPE: PRT
<213> ORGANISM: Artificial Sequence
<220> FEATURE:
<223> OTHER INFORMATION: synthetic

<400> SEQUENCE: 51

Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Pro Gly Leu
            20                  25                  30

Val Lys Pro Ser Gln Thr Leu Ser Leu Thr Cys Ala Ile Ser Gly Asp
        35                  40                  45

Ser Val Ser Ser Asn Ser Ala Ala Trp Asn Trp Ile Arg Gln Ser Pro
    50                  55                  60

Ser Arg Gly Leu Glu Trp Leu Gly Arg Thr Tyr Tyr Arg Ser Lys Trp
65                  70                  75                  80

Tyr Asn Asp Tyr Ala Val Ser Val Lys Ser Arg Ile Thr Ile Asn Pro
                85                  90                  95

Asp Thr Ser Lys Asn Gln Phe Ser Leu Gln Leu Asn Ser Val Thr Pro
            100                 105                 110

Glu Asp Thr Ala Val Tyr Tyr Cys Ala Arg Glu Val Thr Gly Asp Leu
        115                 120                 125

```
Glu Asp Ala Phe Asp Ile Trp Gly Gln Gly Thr Met Val Thr Val Ser
        130                 135                 140

Ser Gly Gly Gly Gly Ser Asp Ile Gln Met Thr Gln Ser Pro Ser Ser
145                 150                 155                 160

Leu Ser Ala Ser Val Gly Asp Arg Val Thr Ile Thr Cys Arg Ala Ser
            165                 170                 175

Gln Thr Ile Trp Ser Tyr Leu Asn Trp Tyr Gln Gln Arg Pro Gly Lys
        180                 185                 190

Ala Pro Asn Leu Leu Ile Tyr Ala Ala Ser Ser Leu Gln Ser Gly Val
    195                 200                 205

Pro Ser Arg Phe Ser Gly Arg Gly Ser Gly Thr Asp Phe Thr Leu Thr
210                 215                 220

Ile Ser Ser Leu Gln Ala Glu Asp Phe Ala Thr Tyr Tyr Cys Gln Gln
225                 230                 235                 240

Ser Tyr Ser Ile Pro Gln Thr Phe Gly Gln Gly Thr Lys Leu Glu Ile
            245                 250                 255

Lys Ser Gly Thr Thr Thr Pro Ala Pro Arg Pro Pro Thr Pro Ala Pro
        260                 265                 270

Thr Ile Ala Ser Gln Pro Leu Ser Leu Arg Pro Glu Ala Cys Arg Pro
    275                 280                 285

Ala Ala Gly Gly Ala Val His Thr Arg Gly Leu Asp Phe Ala Cys Asp
290                 295                 300

Ile Tyr Ile Trp Ala Pro Leu Ala Gly Thr Cys Gly Val Leu Leu Leu
305                 310                 315                 320

Ser Leu Val Ile Thr Leu Tyr Cys Lys Arg Gly Arg Lys Lys Leu Leu
            325                 330                 335

Tyr Ile Phe Lys Gln Pro Phe Met Arg Pro Val Gln Thr Thr Gln Glu
        340                 345                 350

Glu Asp Gly Cys Ser Cys Arg Phe Pro Glu Glu Glu Glu Gly Gly Cys
            355                 360                 365

Glu Leu Arg Val Lys Phe Ser Arg Ser Ala Asp Ala Pro Ala Tyr Gln
370                 375                 380

Gln Gly Gln Asn Gln Leu Tyr Asn Glu Leu Asn Leu Gly Arg Arg Glu
385                 390                 395                 400

Glu Tyr Asp Val Leu Asp Lys Arg Arg Gly Arg Asp Pro Glu Met Gly
            405                 410                 415

Gly Lys Pro Arg Arg Lys Asn Pro Gln Glu Gly Leu Tyr Asn Glu Leu
        420                 425                 430

Gln Lys Asp Lys Met Ala Glu Ala Tyr Ser Glu Ile Gly Met Lys Gly
    435                 440                 445

Glu Arg Arg Arg Gly Lys Gly His Asp Gly Leu Tyr Gln Gly Leu Ser
450                 455                 460

Thr Ala Thr Lys Asp Thr Tyr Asp Ala Leu His Met Gln Ala Leu Pro
465                 470                 475                 480

Pro Arg Arg Lys Arg Gly Ser Gly Thr Pro Asp Pro Trp Gly Ser
            485                 490                 495

Gly Ala Thr Asn Phe Ser Leu Leu Lys Gln Ala Gly Asp Val Glu Glu
        500                 505                 510

Asn Pro Gly Pro Leu Glu Met Glu Phe Gly Leu Ser Trp Leu Phe Leu
    515                 520                 525

Val Ala Ile Leu Lys Gly Val Gln Cys Ser Arg Asp Ile Gln Met Thr
530                 535                 540
```

```
Gln Thr Thr Ser Ser Leu Ser Ala Ser Leu Gly Asp Arg Val Thr Ile
545                 550                 555                 560

Ser Cys Arg Ala Ser Gln Asp Ile Ser Lys Tyr Leu Asn Trp Tyr Gln
            565                 570                 575

Gln Lys Pro Asp Gly Thr Val Lys Leu Leu Ile Tyr His Thr Ser Arg
        580                 585                 590

Leu His Ser Gly Val Pro Ser Arg Phe Ser Gly Ser Gly Ser Gly Thr
    595                 600                 605

Asp Tyr Ser Leu Thr Ile Ser Asn Leu Glu Gln Glu Asp Ile Ala Thr
610                 615                 620

Tyr Phe Cys Gln Gln Gly Asn Thr Leu Pro Tyr Thr Phe Gly Gly Gly
625                 630                 635                 640

Thr Lys Leu Glu Ile Thr Gly Ser Thr Ser Gly Ser Gly Lys Pro Gly
            645                 650                 655

Ser Gly Glu Gly Ser Thr Lys Gly Glu Val Lys Leu Gln Glu Ser Gly
        660                 665                 670

Pro Gly Leu Val Ala Pro Ser Gln Ser Leu Ser Val Thr Cys Thr Val
    675                 680                 685

Ser Gly Val Ser Leu Pro Asp Tyr Gly Val Ser Trp Ile Arg Gln Pro
690                 695                 700

Pro Arg Lys Gly Leu Glu Trp Leu Gly Val Ile Trp Gly Ser Glu Thr
705                 710                 715                 720

Thr Tyr Tyr Asn Ser Ala Leu Lys Ser Arg Leu Thr Ile Ile Lys Asp
            725                 730                 735

Asn Ser Lys Ser Gln Val Phe Leu Lys Met Asn Ser Leu Gln Thr Asp
        740                 745                 750

Asp Thr Ala Ile Tyr Tyr Cys Ala Lys His Tyr Tyr Gly Gly Ser
    755                 760                 765

Tyr Ala Met Asp Tyr Trp Gly Gln Gly Thr Ser Val Thr Val Ser Ser
770                 775                 780

Thr Ser Thr Thr Thr Pro Ala Pro Arg Pro Pro Thr Pro Ala Pro Thr
785                 790                 795                 800

Ile Ala Ser Gln Pro Leu Ser Leu Arg Pro Glu Ala Cys Arg Pro Ala
            805                 810                 815

Ala Gly Gly Ala Val His Thr Arg Gly Leu Asp Phe Ala Cys Asp Ile
        820                 825                 830

Tyr Ile Trp Ala Pro Leu Ala Gly Thr Cys Gly Val Leu Leu Leu Ser
    835                 840                 845

Leu Val Ile Thr Leu Tyr Cys Lys Arg Gly Arg Lys Lys Leu Leu Tyr
850                 855                 860

Ile Phe Lys Gln Pro Phe Met Arg Pro Val Gln Thr Thr Gln Glu Glu
865                 870                 875                 880

Asp Gly Cys Ser Cys Arg Phe Pro Glu Glu Glu Glu Gly Gly Cys Glu
            885                 890                 895

Leu Arg Val Lys Phe Ser Arg Ser Ala Asp Ala Pro Ala Tyr Gln Gln
        900                 905                 910

Gly Gln Asn Gln Leu Tyr Asn Glu Leu Asn Leu Gly Arg Arg Glu Glu
    915                 920                 925

Tyr Asp Val Leu Asp Lys Arg Gly Arg Asp Pro Glu Met Gly Gly
930                 935                 940

Lys Pro Arg Arg Lys Asn Pro Gln Glu Gly Leu Tyr Asn Glu Leu Gln
945                 950                 955                 960

Lys Asp Lys Met Ala Glu Ala Tyr Ser Glu Ile Gly Met Lys Gly Glu
```

965                 970                 975
Arg Arg Arg Gly Lys Gly His Asp Gly Leu Tyr Gln Gly Leu Ser Thr
                980                 985                 990

Ala Thr Lys Asp Thr Tyr Asp Ala Leu His Met Gln Ala Leu Pro Pro
            995                 1000                1005

Arg

<210> SEQ ID NO 52
<211> LENGTH: 1007
<212> TYPE: PRT
<213> ORGANISM: Artificial Sequence
<220> FEATURE:
<223> OTHER INFORMATION: synthetic

<400> SEQUENCE: 52

Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Pro Gly Leu
            20                  25                  30

Val Lys Pro Ser Gln Thr Leu Ser Leu Thr Cys Ala Ile Ser Gly Asp
        35                  40                  45

Ser Val Ser Ser Asn Ser Ala Ala Trp Asn Trp Ile Arg Gln Ser Pro
    50                  55                  60

Ser Arg Gly Leu Glu Trp Leu Gly Arg Thr Tyr Tyr Arg Ser Lys Trp
65                  70                  75                  80

Tyr Asn Asp Tyr Ala Val Ser Val Lys Ser Arg Ile Thr Ile Asn Pro
                85                  90                  95

Asp Thr Ser Lys Asn Gln Phe Ser Leu Gln Leu Asn Ser Val Thr Pro
            100                 105                 110

Glu Asp Thr Ala Val Tyr Tyr Cys Ala Arg Glu Val Thr Gly Asp Leu
        115                 120                 125

Glu Asp Ala Phe Asp Ile Trp Gly Gln Gly Thr Met Val Thr Val Ser
    130                 135                 140

Ser Gly Gly Gly Gly Ser Asp Ile Gln Met Thr Gln Ser Pro Ser Ser
145                 150                 155                 160

Leu Ser Ala Ser Val Gly Asp Arg Val Thr Ile Thr Cys Arg Ala Ser
                165                 170                 175

Gln Thr Ile Trp Ser Tyr Leu Asn Trp Tyr Gln Gln Arg Pro Gly Lys
            180                 185                 190

Ala Pro Asn Leu Leu Ile Tyr Ala Ala Ser Ser Leu Gln Ser Gly Val
        195                 200                 205

Pro Ser Arg Phe Ser Gly Arg Gly Ser Gly Thr Asp Phe Thr Leu Thr
    210                 215                 220

Ile Ser Ser Leu Gln Ala Glu Asp Phe Ala Thr Tyr Tyr Cys Gln Gln
225                 230                 235                 240

Ser Tyr Ser Ile Pro Gln Thr Phe Gly Gln Gly Thr Lys Leu Glu Ile
                245                 250                 255

Lys Ser Gly Ala Ala Ala Ile Glu Val Met Tyr Pro Pro Pro Tyr Leu
            260                 265                 270

Asp Asn Glu Lys Ser Asn Gly Thr Ile Ile His Val Lys Gly Lys His
        275                 280                 285

Leu Cys Pro Ser Pro Leu Phe Pro Gly Pro Ser Lys Pro Phe Trp Val
    290                 295                 300

Leu Val Val Val Gly Gly Val Leu Ala Cys Tyr Ser Leu Leu Val Thr
305                 310                 315                 320

```
Val Ala Phe Ile Ile Phe Trp Val Arg Ser Lys Arg Leu Leu
            325                 330                 335

His Ser Asp Tyr Met Asn Met Thr Pro Arg Arg Pro Gly Pro Thr Arg
            340                 345                 350

Lys His Tyr Gln Pro Tyr Ala Pro Pro Arg Asp Phe Ala Ala Tyr Arg
            355                 360                 365

Ser Arg Val Lys Phe Ser Arg Ser Ala Asp Ala Pro Ala Tyr Gln Gln
        370                 375                 380

Gly Gln Asn Gln Leu Tyr Asn Glu Leu Asn Leu Gly Arg Arg Glu Glu
385                 390                 395                 400

Tyr Asp Val Leu Asp Lys Arg Arg Gly Arg Asp Pro Glu Met Gly Gly
                405                 410                 415

Lys Pro Arg Arg Lys Asn Pro Gln Glu Gly Leu Tyr Asn Glu Leu Gln
                420                 425                 430

Lys Asp Lys Met Ala Glu Ala Tyr Ser Glu Ile Gly Met Lys Gly Glu
            435                 440                 445

Arg Arg Arg Gly Lys Gly His Asp Gly Leu Tyr Gln Gly Leu Ser Thr
        450                 455                 460

Ala Thr Lys Asp Thr Tyr Asp Ala Leu His Met Gln Ala Leu Pro Pro
465                 470                 475                 480

Arg Arg Lys Arg Arg Gly Ser Gly Thr Pro Asp Pro Trp Gly Ser Gly
                485                 490                 495

Ala Thr Asn Phe Ser Leu Leu Lys Gln Ala Gly Asp Val Glu Glu Asn
            500                 505                 510

Pro Gly Pro Leu Glu Met Glu Phe Gly Leu Ser Trp Leu Phe Leu Val
            515                 520                 525

Ala Ile Leu Lys Gly Val Gln Cys Ser Arg Asp Ile Gln Met Thr Gln
        530                 535                 540

Thr Thr Ser Ser Leu Ser Ala Ser Leu Gly Asp Arg Val Thr Ile Ser
545                 550                 555                 560

Cys Arg Ala Ser Gln Asp Ile Ser Lys Tyr Leu Asn Trp Tyr Gln Gln
                565                 570                 575

Lys Pro Asp Gly Thr Val Lys Leu Leu Ile Tyr His Thr Ser Arg Leu
            580                 585                 590

His Ser Gly Val Pro Ser Arg Phe Ser Gly Ser Gly Ser Gly Thr Asp
        595                 600                 605

Tyr Ser Leu Thr Ile Ser Asn Leu Glu Gln Glu Asp Ile Ala Thr Tyr
        610                 615                 620

Phe Cys Gln Gln Gly Asn Thr Leu Pro Tyr Thr Phe Gly Gly Gly Thr
625                 630                 635                 640

Lys Leu Glu Ile Thr Gly Ser Thr Ser Gly Ser Gly Lys Pro Gly Ser
                645                 650                 655

Gly Glu Gly Ser Thr Lys Gly Glu Val Lys Leu Gln Glu Ser Gly Pro
            660                 665                 670

Gly Leu Val Ala Pro Ser Gln Ser Leu Ser Val Thr Cys Thr Val Ser
        675                 680                 685

Gly Val Ser Leu Pro Asp Tyr Gly Val Ser Trp Ile Arg Gln Pro Pro
        690                 695                 700

Arg Lys Gly Leu Glu Trp Leu Gly Val Ile Trp Gly Ser Glu Thr Thr
705                 710                 715                 720

Tyr Tyr Asn Ser Ala Leu Lys Ser Arg Leu Thr Ile Ile Lys Asp Asn
                725                 730                 735
```

| | | | | | | | | | | | |
|---|---|---|---|---|---|---|---|---|---|---|---|
|Ser|Lys|Ser|Gln|Val|Phe|Leu|Lys|Met|Asn|Ser|Leu|Gln|Thr|Asp|Asp|
| | | |740| | | |745| | | |750|

Ser Lys Ser Gln Val Phe Leu Lys Met Asn Ser Leu Gln Thr Asp Asp
                740                 745                 750

Thr Ala Ile Tyr Tyr Cys Ala Lys His Tyr Tyr Gly Gly Ser Tyr
            755                 760             765

Ala Met Asp Tyr Trp Gly Gln Gly Thr Ser Val Thr Val Ser Ser Thr
        770                 775                 780

Ser Ala Ala Ala Ile Glu Val Met Tyr Pro Pro Tyr Leu Asp Asn
785             790                 795                 800

Glu Lys Ser Asn Gly Thr Ile Ile His Val Lys Gly Lys His Leu Cys
                805                 810                 815

Pro Ser Pro Leu Phe Pro Gly Pro Ser Lys Pro Phe Trp Val Leu Val
                820                 825                 830

Val Val Gly Gly Val Leu Ala Cys Tyr Ser Leu Leu Val Thr Val Ala
                835                 840                 845

Phe Ile Ile Phe Trp Val Arg Ser Lys Arg Ser Arg Leu Leu His Ser
850                 855                 860

Asp Tyr Met Asn Met Thr Pro Arg Arg Pro Gly Pro Thr Arg Lys His
865                 870                 875                 880

Tyr Gln Pro Tyr Ala Pro Pro Arg Asp Phe Ala Ala Tyr Arg Ser Arg
                885                 890                 895

Val Lys Phe Ser Arg Ser Ala Asp Ala Pro Ala Tyr Gln Gln Gly Gln
                900                 905                 910

Asn Gln Leu Tyr Asn Glu Leu Asn Leu Gly Arg Arg Glu Glu Tyr Asp
                915                 920                 925

Val Leu Asp Lys Arg Arg Gly Arg Asp Pro Glu Met Gly Gly Lys Pro
930                 935                 940

Arg Arg Lys Asn Pro Gln Glu Gly Leu Tyr Asn Glu Leu Gln Lys Asp
945                 950                 955                 960

Lys Met Ala Glu Ala Tyr Ser Glu Ile Gly Met Lys Gly Glu Arg Arg
                965                 970                 975

Arg Gly Lys Gly His Asp Gly Leu Tyr Gln Gly Leu Ser Thr Ala Thr
                980                 985                 990

Lys Asp Thr Tyr Asp Ala Leu His Met Gln Ala Leu Pro Pro Arg
                995                 1000                1005

<210> SEQ ID NO 53
<211> LENGTH: 2994
<212> TYPE: DNA
<213> ORGANISM: Artificial Sequence
<220> FEATURE:
<223> OTHER INFORMATION: synthetic

<400> SEQUENCE: 53

```
atgctgctgc tcgtgacatc tctgctgctg tgcgagctgc ccacccgc ctttctgctg      60 attcctcagg tgcagctgca gcagtctggc cctggcctcg tgaagcctag ccagaccctg    120
agcctgacct gtgccatcag cggcgatagc gtgtccagca atagcgccgc ctggaactgg    180
atcagacaga gccctagcag aggcctggaa tggctgggcc ggacctacta ccggtccaag    240
tggtacaacg actacgccgt gtccgtgaag tcccggatca ccatcaaccc cgacaccagc    300
aagaaccagt tctccctgca gctgaacagc gtgaccccg aggataccgc cgtgtactac    360
tgcgccagag aagtgaccgg cgacctggaa gatgccttcg acatctgggg ccagggcaca    420
atggtcaccg tgtctagcgg aggcggcgga agcgacatcc agatgacaca gagcccccagc   480 tccctgagcg ccagcgtggg agacagagtg accatcacct gtcgggccag ccagaccatc    540
```

-continued

```
tggtcctacc tgaactggta tcagcagcgg cctggcaagg cccccaacct gctgatctat    600
gccgccagct cactgcagag cggcgtgccc agcagatttt ccggcagagg cagcggcacc    660
gacttcaccc tgacaatcag ttccctgcag gccgaggact cgccaccta ctactgccag    720
cagagctaca gcatccccca gaccttcggc caggggacca agctggaaat caagactagt    780
accaccaccc ctgcccctag acctcccacc ccagcccaa caattgccag ccagcctctg    840
tctctgcggc ccgaagcttg tagacctgct gccggcggag ccgtgcacac cagaggactg    900
gatttcgcct gcgacatcta catctgggcc cctctggccg gcacatgtgg cgtgctgctg    960
ctgagcctgg tcatcaccct gtactgcaag cggggcagaa agaagctgct gtacatcttc   1020
aagcagccct tcatgcggcc cgtgcagacc acacaggaag aggacggctg cagctgccgg   1080
ttccctgagg aagaagaagg cggctgcgaa ctgagagtga agttcagcag aagcgccgac   1140
gcccctgcct accagcaggg ccagaaccag ctgtacaacg agctgaacct gggcagacgg   1200
gaagagtacg acgtgctgga caagcggaga ggcagagatc ccgagatggg cggcaagccc   1260
agacggaaga atccccagga aggcctgtat aacgaactgc agaaagacaa gatggccgag   1320
gcctacagcg agatcggaat gaagggcgag cggagaagag gcaagggcca cgatggcctg   1380
taccagggcc tgagcaccgc caccaaggac acctacgatg ccctgcacat gcaggccctg   1440
cctccaagag gcagcggaga gggcagaggc agcctgctga cctgcgggga cgtggaagag   1500
aacccaggcc ccagaatgct gctcctggtc acctctctgc tgctgtgcga gctgccccac   1560
cccgcctttc tgctgatccc cgacatccag atgacccaga ccaccagcag cctgagcgcc   1620
agcctgggcg atagagtgac catcagctgc agagccagcc aggacatcag caagtacctg   1680
aactggtatc agcagaaacc cgatggcacc gtgaaactgc tgatctacca caccagcaga   1740
ctgcacagcg gcgtgcccag cagatttttct ggcagcggct ccggaccgga ctacagcctg   1800
accatctcca acctggaaca ggaagatatc gctacctact tctgtcagca aggcaacacc   1860
ctgccctaca ccttcggcgg aggcaccaag ctggaaatca ccggcagcac aagcggctct   1920
ggcaagcctg gatctggcga gggctctacc aagggcgaag tgaagctgca ggaaagcggc   1980
cctggactgg tggcccccatc tcagagcctg tccgtgacct gtaccgtgtc cggcgtgtcc   2040
ctgcccgatt atggcgtgtc ctggatccgg cagcctccca gaaagggcct ggaatggctg   2100
ggcgtgatct ggggcagcga gacaacctac tacaacagcg ccctgaagtc ccggctgacc   2160
atcatcaagg acaactccaa gagccaggtg ttcctgaaga tgaactccct gcagaccgac   2220
gacaccgcca tctactactg cgccaagcac tactactacg gcggcagcta cgccatggac   2280
tactggggcc agggcaccag cgtgaccgtg tcatcttccg gaaccacgac gccagcgccg   2340
cgaccaccaa caccggcgcc caccatcgcg tcgcagcccc tgtccctgcg cccagaggcg   2400
tgccggccag cggcgggggg cgcagtgcac acgagggggc tggacttcgc ctgtgatatc   2460
tacatctggg cgcccttggc cgggacttgt ggggtccttc tcctgtcact ggttatcacc   2520
ctttactgca acgggcag aaagaaactc ctgtatatat tcaaacaacc atttatgaga    2580
ccagtacaaa ctactcaaga ggaagatggc tgtagctgcc gatttccaga agaagaagaa   2640
ggaggatgtg aactgagagt gaagttcagc aggagcgcag acgcccccgc gtaccaacag   2700
ggccagaacc agctctataa cgagctcaat ctaggacgaa gagaggagta cgatgttttg   2760
gacaagagac gtggccggga ccctgagatg ggggaaagc cgagaaggaa gaaccctcag   2820
gaaggcctgt acaatgaact gcagaaagat aagatggcgg aggcctacag tgagattggg   2880
atgaaaggcg agcgccggag gggcaagggg cacgatggcc tttaccaggg tctcagtaca   2940
```
gccaccaagg acacctacga cgcccttcac atgcaggccc tgcccctcg ctaa        2994

<210> SEQ ID NO 54
<211> LENGTH: 3027
<212> TYPE: DNA
<213> ORGANISM: Artificial Sequence
<220> FEATURE:
<223> OTHER INFORMATION: synthetic

<400> SEQUENCE: 54
atggctctgc ctgtgacagc tctgctgctg cctctggccc tgctgctcca tgctgctaga      60
cctcaggtgc agctccagca gtctggccca ggactggtca agcctagcca gaccctgagc     120
ctgacctgcg ccatcagcgg cgacagcgtg tcctctaaca gcgccgcctg aactggatc     180 agacagagcc ccagcagagg cctggaatgg ctgggccgga cctactaccg gtccaagtgg     240
tacaacgact acgccgtgtc cgtgaagtcc ggatcacca tcaacccga caccagcaag     300 aaccagttct ccctgcagct gaacagcgtg accctgagg acaccgccgt gtactactgc     360
gccagagaag tgaccggcga cctggaagat gccttcgaca tctggggcca gggcaccatg     420
gtcaccgtgt ctagcggagg cggcggaagc gacatccaga tgacccagag ccctagctcc     480
ctgagcgcca gcgtgggcga cagagtgacc atcacctgtc gggccagcca gaccatctgg     540
tcctacctga attggtatca gcagcggcca ggcaaggccc ctaacctgct gatctatgcc     600
gccagcagcc tgcagagcgg cgtgccaagc agattctctg gcagaggctc cggcaccgac     660
ttcaccctga caatcagttc cctgcaggcc gaggacttcg ccacctacta ctgccagcag     720
tcctacagca tccctcagac cttcggccag gggaccaagc tggaaatcaa gtccggaacc     780
accacccccg cccctaggcc tcccacacct gcccccacaa tcgcctccca gcctctcagc     840
ctgaggcctg aagcttgcag gccgctgcc ggaggagctg tccataccag gggactcgac     900
ttcgcctgcg acatttacat ttgggcccct ctggctggaa cctgcggagt cctgctgctg     960
tccctggtga tcacactgta ctgtaagagg ggcagaaaga agctgctcta catcttcaag    1020
cagcccttta tgagacccgt gcagacaacc caggaggaag acggatgcag ctgcaggttc    1080
cctgaggagg aggagggcgg ctgcgaactg agggtgaagt tcagcaggag cgccgacgcc    1140
cccgcttatc aacagggcca gaaccagctg tacaacgagc tgaacctcgg cagaagagag    1200
gagtatgacg tgctggacaa gaggaggggc agggaccctg agatgggcgg caagcctaga    1260
agaaagaacc cccaggaagg cctctacaac gaactgcaga ggacaagat ggccgaggcc    1320 tacagcgaga tcggcatgaa aggcgagaga aggaggggaa agggacatga cggcctgtac    1380
cagggactct ccacagccac caaggacacc tacgatgccc tgcacatgca ggctctgccc    1440
cctagaagga agaagaagag ctctggtacc cccgatcctt ggggaagcgg cgctaccaac    1500
ttctccctgc tcaagcaggc tggcgatgtg gaggagaacc ccggccccct cgagatggag    1560
tttgggctga gctggctgtt cctggtggcc atcctcaagg gcgtgcagtg ctccagggac    1620
atccagatga cccagaccac aagcagcctg agcgcttccc tcggcgacag ggtgaccatc    1680
tcctgtagag cctcccaaga catctccaag tacctgaact ggtaccagca gaaacccgac    1740
ggcaccgtga agctgctgat ctaccacacc agcaggctgc attccggcgt gccctccaga    1800
ttttccggca gcggctctgg taccgactac agcctcacca tcagcaactt agaacaggag    1860
gacatcgcca catatttctg ccaacaggga aacacactcc cctatacctt cggcggcggc    1920
acaaagttag aaatcaccgg ctcccacatcc ggcagcggaa aacctggttc tggcgagggc    1980

-continued

| | |
|---|---|
| agcaccaagg gcgaagtgaa gctgcaggaa agcggacctg actggtcgc tcccagccag | 2040 |
| agcctcagcg tgacctgtac agtgagcggc gtgagcctgc ctgattacgg cgtgagctgg | 2100 |
| attagacagc ctcccaggaa gggcttagaa tggctcggcg tgatttgggg cagcgagaca | 2160 |
| acctactata acagcgccct gaagagcagg ctcaccatta tcaaggacaa cagcaaatcc | 2220 |
| caggtcttcc tgaagatgaa cagcctccag accgacgaca ccgccatcta ctactgcgcc | 2280 |
| aagcactact attatggcgg ctcctacgcc atggactact ggggccaggg caccagcgtg | 2340 |
| acagtgagct ccactagtgc cgccgctatc gaagtgatgt accctcctcc ctacctggac | 2400 |
| aacgagaagt ccaacggcac catcatccac gtgaagggca agcacctgtg ccccagccct | 2460 |
| ctgttccctg gccctagcaa gccttttctgg gtgctggtgg tcgtgggcgg cgtgctggcc | 2520 |
| tgttactctc tgctggtcac agtggccttc atcatctttt gggtccgaag caagcggagc | 2580 |
| cggctgctgc acagcgacta catgaacatg accctcgga ggccaggccc caccagaaag | 2640 |
| cactaccagc cctacgcccc tccccgggac tttgccgcct atcggagccg cgtgaagttc | 2700 |
| tccagatccg ctgatgctcc cgcttatcag caggggcaga atcagctcta taatgaactg | 2760 |
| aatctggggc ggagagagga atacgacgtc ctcgataaga ggcgcggcag ggaccctgag | 2820 |
| atgggaggaa aacctcggag aaaaaaccct caggaagggc tctacaacga gctgcagaaa | 2880 |
| gataagatgg ctgaagctta ctccgaaatt gggatgaagg gtgaaaggcg gaggggcaaa | 2940 |
| ggacacgacg gactgtatca gggactgtcc acagccacaa agataccta tgacgcactc | 3000 |
| catatgcagg ctctccccacc cagatga | 3027 |

<210> SEQ ID NO 55
<211> LENGTH: 3024
<212> TYPE: DNA
<213> ORGANISM: Artificial Sequence
<220> FEATURE:
<223> OTHER INFORMATION: synthetic

<400> SEQUENCE: 55

| | |
|---|---|
| atggctctgc ctgtgacagc tctgctgctg cctctggccc tgctgctcca tgctgctaga | 60 |
| cctcaggtgc agctccagca gtctggccca ggactggtca agcctagcca gaccctgagc | 120 |
| ctgacctgcg ccatcagcgg cgacagcgtg tcctctaaca gcgccgcctg gaactggatc | 180 |
| agacagagcc ccagcagagg cctggaatgg ctgggccgga cctactaccg gtccaagtgg | 240 |
| tacaacgact acgccgtgtc cgtgaagtcc cggatcacca tcaaccccga caccagcaag | 300 |
| aaccagttct ccctgcagct gaacagcgtg acccctgagg acaccgccgt gtactactgc | 360 |
| gccagagaag tgaccggcga cctggaagat gccttcgaca tctggggcca gggcaccatg | 420 |
| gtcaccgtgt ctagcggagg cggcggaagc gacatccaga tgacccagag ccctagctcc | 480 |
| ctgagcgcca gcgtgggcga cagagtgacc atcacctgtc gggccagcca gaccatctgg | 540 |
| tcctacctga attggtatca gcagcggcca ggcaaggccc ctaacctgct gatctatgcc | 600 |
| gccagcagcc tgcagagcgg cgtgccaagc agattctctg gcagaggctc cggcaccgac | 660 |
| ttcaccctga caatcagttc cctgcaggcc gaggacttcg ccacctacta ctgccagcag | 720 |
| tcctacagca tccctcagac cttcggccag gggaccaagc tggaaatcaa gtccggagcc | 780 |
| gctgctattg aagtgatgta ccccccccc tacctggata cgagaagtc caacggcacc | 840 |
| atcatccacg tgaagggaaa gcatctgtgt cccagccctc tgttcccgg acccagcaag | 900 |
| cccttctggg tcctcgtcgt cgtgggaggc gtgctggcct gctacagcct gctggtcacc | 960 |
| gtcgccttca tcatcttctg ggtgaggtcc aagaggagca gactgctgca cagcgattac | 1020 |

```
atgaacatga ccccccagaag gcctggacct accagaaagc actaccagcc ttatgctcct   1080
cccagagact ttgccgccta cagatccaga gtgaagttta gcaggagcgc tgatgccccc   1140
gcctatcagc agggccagaa ccagctctac aacgagctga acctgggcag aagggaggaa   1200
tatgatgtgc tggacaagag aagaggcagg acccccgaga tgggcggcaa gcctaggagg   1260
aaaaatcctc aagagggcct gtacaacgag ctccaaaagg ataagatggc cgaggcctat   1320
tccgagatcg gcatgaaagg cgagaggaga agggaaaagg acacgacgg cctgtatcaa   1380
ggcctgtcca cagccaccaa agacacctat gatgccctgc acatgcaggc tctgcctcct   1440
aggaggaaga ggaggggttc tggcacaccc gaccctggg gttctggtgc caccaacttc   1500
tccctgctga acaggccgg agacgtcgaa gagaatcctg accctcga gatggagttt    1560
ggactgtcct ggctgtttct cgtcgccatc ctgaaaggcg tgcaatgctc cagagacatc   1620
caaatgaccc agacaacatc ctccctcagc gccagcctgg gcgacagagt gaccatttcc   1680
tgcagagctt cccaggacat cagcaagtac ctgaactggt atcagcagaa gcccgacggc   1740
accgtgaagc tcctcatcta tcacaccagc aggctccatt ccggcgtgcc tagcaggttc   1800
agcggaagcg gcagcggaac cgactactcc ctgaccatca gcaatttaga acaagaggat   1860
atcgccacct acttttgcca gcagggaaac acactgcctt cacctttgg cggcggcacc   1920
aaactggaga ttacaggttc tacctccggc agcggcaaac ccggaagcgg cgagggcagc   1980
acaaagggag aagtcaaact gcaggagagc ggccctggac tggtggctcc tagccagtcc   2040
ctgtccgtga cctgcacagt gagcggagtc agcctgcctg attacggcgt cagctggatt   2100
aggcagcccc ccagaaaggg actggagtgg ctcggcgtga tttgggctc cgaaaccacc   2160
tactacaact ccgctctgaa gagcaggctg accatcatta agataactc caagtcccag   2220
gtgttcctga agatgaactc cctgcagaca gatgacaccg ccatctatta ctgcgccaag   2280
cactactact acgaggcag ctacgccatg gattactggg gccagggcac ctccgtgacc   2340
gtgtccagca ctagtaccac aaccccctgct cctagacccc ctacacctgc ccccaccatt   2400
gccagccagc cctgtccct gaggcctgaa gcctgcagac ccgctgctgg aggagctgtg   2460
cacaccaggg gactggactt cgcctgcgac atctacatct gggccccct ggccggaacc   2520
tgtggcgtgc tgctgctgag cctggtcatc acactgtact gcaagagggg caggaaaaag   2580
ctgctctaca tcttcaagca gccttttcatg aggcctgtcc agacaaccca agaggaggat   2640
ggctgcagct gtaggttccc tgaggaggag aaggcggct gcgagctcag agtgaaattc   2700
agcagatccg ctgatgctcc cgcttaccag cagggacaga accagctgta taacgaactg   2760
aatctgggaa ggagggagga atacgacgtg ctggataaaa ggaggggacg tgatcctgaa   2820
atgggaggca agcccagaag aaaaaatccc caggaggc tgtataatga gctccagaaa   2880
gacaagatgg ccgaagccta ctccgagatt ggcatgaaag gagagagaag gagaggcaaa   2940
ggccatgatg gcctctacca gggcctgtcc accgctacaa aggacaccta cgacgccctc   3000
catatgcagg ccctgccccc cagg                                           3024
```

<210> SEQ ID NO 56
<211> LENGTH: 3027
<212> TYPE: DNA
<213> ORGANISM: Artificial Sequence
<220> FEATURE:
<223> OTHER INFORMATION: synthetic

<400> SEQUENCE: 56

-continued

| | |
|---|---|
| atggctctgc ctgtgacagc tctgctgctg cctctggccc tgctgctcca tgctgctaga | 60 |
| cctcaggtgc agctccagca gtctggccca ggactggtca agcctagcca gaccctgagc | 120 |
| ctgacctgcg ccatcagcgg cgacagcgtg tcctctaaca gcgccgcctg gaactggatc | 180 |
| agacagagcc ccagcagagg cctggaatgg ctgggccgga cctactaccg gtccaagtgg | 240 |
| tacaacgact acgccgtgtc cgtgaagtcc cggatcacca tcaaccccga caccagcaag | 300 |
| aaccagttct ccctgcagct gaacagcgtg acccctgagg acaccgccgt gtactactgc | 360 |
| gccagagaag tgaccggcga cctggaagat gccttcgaca tctggggcca gggcaccatg | 420 |
| gtcaccgtgt ctagcggagg cggcggaagc gacatccaga tgacccagag ccctagctcc | 480 |
| ctgagcgcca gcgtgggcga cagagtgacc atcacctgtc gggccagcca gaccatctgg | 540 |
| tcctacctga attggtatca gcagcggcca ggcaaggccc ctaacctgct gatctatgcc | 600 |
| gccagcagcc tgcagagcgg cgtgccaagc agattctctg gcagaggctc cggcaccgac | 660 |
| ttcaccctga caatcagttc cctgcaggcc gaggacttcg ccacctacta ctgccagcag | 720 |
| tcctacagca tccctcagac cttcggccag gggaccaagc tggaaatcaa gtccggaacc | 780 |
| accaccccg cccctaggcc tcccacacct gcccccacaa tcgcctccca gcctctcagc | 840 |
| ctgaggcctg aagcttgcag gcccgctgcc ggaggagctg tccataccag gggactcgac | 900 |
| ttcgcctgcg acatttacat ttgggcccct ctggctggaa cctgcggagt cctgctgctg | 960 |
| tccctggtga tcacactgta ctgtaagagg ggcagaaaga agctgctcta catcttcaag | 1020 |
| cagcccttta tgagacccgt gcagacaacc caggaggaag acggatgcag ctgcaggttc | 1080 |
| cctgaggagg aggagggcgg ctgcgaactg agggtgaagt tcagcaggag cgccgacgcc | 1140 |
| cccgcttatc aacagggcca gaaccagctg tacaacgagc tgaacctcgg cagaagagag | 1200 |
| gagtatgacg tgctggacaa gaggaggggc agggaccctg agatgggcgg caagcctaga | 1260 |
| agaaagaacc cccaggaagg cctctacaac gaactgcaga aggacaagat ggccgaggcc | 1320 |
| tacagcgaga tcggcatgaa aggcgagaga aggaggggaa agggacatga cggcctgtac | 1380 |
| cagggactct ccacagccac caaggacacc tacgatgccc tgcacatgca ggctctgccc | 1440 |
| cctagaagga agaagaggg ctctggtacc cccgatcctt ggggaagcgg cgctaccaac | 1500 |
| ttctccctgc tcaagcaggc tggcgatgtg gaggagaacc ccggccccct cgagatggag | 1560 |
| tttgactgt cctggctgtt ctcgtcgcc atcctgaaag gcgtgcaatg ctccagagac | 1620 |
| atccaaatga cccagacaac atcctccctc agcgccagcc tgggcgacag agtgaccatt | 1680 |
| tcctgcagag cttcccagga catcagcaag tacctgaact ggtatcagca gaagcccgac | 1740 |
| ggcaccgtga agctcctcat ctatcacacc agcaggctcc attccggcgt gcctagcagg | 1800 |
| ttcagcggaa gcggcagcgg aaccgactac tccctgacca tcagcaattt agaacaagag | 1860 |
| gatatcgcca cctactttg ccagcaggga aacacactgc cttacacctt tggcggcggc | 1920 |
| accaaactgg agattacagg ttctacctcc ggcagcggca aacccggaag cggcgagggc | 1980 |
| agcacaaagg gagaagtcaa actgcaggag agcggccctg actggtggc tcctagccag | 2040 |
| tccctgtccg tgacctgcac agtgagcgga gtcagcctgc ctgattacgg cgtcagctgg | 2100 |
| attaggcagc cccccagaaa gggactggag tggctcggcg tgatttgggg ctccgaaacc | 2160 |
| acctactaca actccgctct gaagagcagg ctgaccatca ttaaagataa ctccaagtcc | 2220 |
| caggtgttcc tgaagatgaa ctccctgcag acagatgaca ccgccatcta ttactgcgcc | 2280 |
| aagcactact actacggagg cagctacgcc atgattact ggggcaggg cacctccgtg | 2340 |
| accgtgtcca gcactagtac cacaacccct gctcctagac ccctacacc tgcccccacc | 2400 |

```
attgccagcc agccctgtc cctgaggcct gaagcctgca gacccgctgc tggaggagct    2460
gtgcacacca ggggactgga cttcgcctgc gacatctaca tctgggcccc cctggccgga    2520
acctgtggcg tgctgctgct gagcctggtc atcacactgt actgcaagag gggcaggaaa    2580
aagctgctct acatcttcaa gcagcctttc atgaggcctg tccagacaac ccaagaggag    2640
gatggctgca gctgtaggtt ccctgaggag gaggaaggcg gctgcgagct cagagtgaaa    2700
ttcagcagat ccgctgatgc tcccgcttac cagcagggac agaaccagct gtataacgaa    2760
ctgaatctgg aaggaggga ggaatacgac gtgctggata aaggaggg acgtgatcct    2820 gaaatgggag gcaagcccag aagaaaaaat ccccaggagg gcctgtataa tgagctccag    2880
aaagacaaga tggccgaagc ctactccgag attggcatga aggagagag aaggagaggc    2940 aaaggccatg atggcctcta ccagggcctg tccaccgcta caaggacac ctacgacgcc    3000 ctccatatgc aggccctgcc ccccagg                                       3027
```

<210> SEQ ID NO 57  
<211> LENGTH: 3021  
<212> TYPE: DNA  
<213> ORGANISM: Artificial Sequence  
<220> FEATURE:  
<223> OTHER INFORMATION: synthetic

<400> SEQUENCE: 57

```
atggctctgc ctgtgacagc tctgctgctg cctctggccc tgctgctcca tgctgctaga      60
cctcaggtgc agctccagca gtctggccca ggactggtca agcctagcca gaccctgagc     120
ctgacctgcg ccatcagcgg cgacagcgtg tcctctaaca gcgccgcctg gaactggatc     180
agacagagcc ccagcagagg cctggaatgg ctgggccgga cctactaccg gtccaagtgg     240
tacaacgact acgccgtgtc cgtgaagtcc cggatcacca tcaaccccga caccagcaag     300
aaccagttct ccctgcagct gaacagcgtg accctgagg acaccgccgt gtactactgc     360
gccagagaag tgaccggcga cctggaagat gccttcgaca tctggggcca gggcaccatg     420
gtcaccgtgt ctagcggagg cggcggaagc gacatccaga tgacccagag ccctagctcc     480
ctgagcgcca gcgtgggcga cagagtgacc atcacctgtc gggccagcca gaccatctgg     540
tcctacctga attggtatca gcagcggcca ggcaaggccc ctaacctgct gatctatgcc     600
gccagcagcc tgcagagcgg cgtgccaagc agattctctg gcagaggctc cggcaccgac     660
ttcaccctga caatcagttc cctgcaggcc gaggacttcg ccacctacta ctgccagcag     720
tcctacagca tccctcagac cttcggccag ggaccaagc tggaaatcaa gtccggagcc     780
gctgctattg aagtgatgta ccccccccc tacctggata cgagaagtc caacggcacc     840 atcatccacg tgaagggaaa gcatctgtgt cccagccctc tgttccccgg acccagcaag     900
cccttctggg tcctcgtcgt cgtgggaggc gtgctggcct gctacagcct gctggtcacc     960
gtcgccttca tcatcttctg ggtgaggtcc aagaggagca gactgctgca cagcgattac    1020
atgaacatga cccccagaag gcctggacct accagaaagc actaccagcc ttatgctcct    1080
cccagagact ttgccgccta cagatccaga gtgaagtta gcaggagcgc tgatgccccc    1140
gcctatcagc agggccagaa ccagctctac aacgagctga acctgggcag aagggaggaa    1200
tatgatgtgc tggacaagag aagaggcagg gaccccgaga tgggcggcaa gcctaggagg    1260
aaaaatcctc aagagggcct gtacaacgag ctccaaaagg ataagatggc cgaggcctat    1320
tccgagatcg gcatgaaagg cgagaggaga agggaaagg gacacgacgg cctgtatcaa    1380
```

| | |
|---|---|
| ggcctgtcca cagccaccaa agacacctat gatgccctgc acatgcaggc tctgcctcct | 1440 |
| aggaggaaga ggaggggttc tggcacaccc gacccttggg gttctggtgc caccaacttc | 1500 |
| tccctgctga acaggccgg agacgtcgaa gagaatcctg acccctcga gatggagttt | 1560 |
| ggcctgagct ggctgttcct ggtggccatc ctcaagggcg tgcagtgctc cagggacatc | 1620 |
| cagatgaccc agaccacaag cagcctgagc gcttccctcg gcgacagggt gaccatctcc | 1680 |
| tgtagagcct cccaagacat ctccaagtac ctgaactggt accagcagaa acccgacggc | 1740 |
| accgtgaagc tgctgatcta ccacaccagc aggctgcatt ccggcgtgcc ctccagattt | 1800 |
| tccggcagcg gctctggtac cgactacagc ctcaccatca gcaacttaga acaggaggac | 1860 |
| atcgccacat atttctgcca acagggaaac acactcccct ataccttcgg cggcggcaca | 1920 |
| aagttagaaa tcaccggctc cacatccggc agcggaaaac ctggttctgg cgagggcagc | 1980 |
| accaagggcg aagtgaagct gcaggaaagc ggacctggac tggtcgctcc cagccagagc | 2040 |
| ctcagcgtga cctgtacagt gagcggcgtg agcctgcctg attacggcgt gagctggatt | 2100 |
| agacagcctc ccaggaaggg cttagaatgg ctcgcgtga tttggggcag cgagacaacc | 2160 |
| tactataaca gcgccctgaa gagcaggctc accattatca aggacaacag caaatcccag | 2220 |
| gtcttcctga agatgaacag cctccagacc gacgacaccg ccatctacta ctgcgccaag | 2280 |
| cactactatt atggcggctc ctacgccatg gactactggg gccagggcac cagcgtgaca | 2340 |
| gtgagctcca ctagtgccgc cgctatcgaa gtgatgtacc ctcctccta cctggacaac | 2400 |
| gagaagtcca acggcaccat catccacgtg aagggcaagc acctgtgccc cagccctctg | 2460 |
| ttccctggcc ctagcaagcc tttctgggtg ctggtggtcg tgggcggcgt gctggcctgt | 2520 |
| tactctctgc tggtcacagt ggccttcatc atcttttggg tccgaagcaa gcggagccgg | 2580 |
| ctgctgcaca cgcactacat gaacatgacc cctcggaggc caggccccac cagaaagcac | 2640 |
| taccagcct acgcccctcc ccgggacttt gccgctatc ggagccgcgt gaagttctcc | 2700 |
| agatccgctg atgctcccgc ttatcagcag ggcagaatc agctctataa tgaactgaat | 2760 |
| ctggggcgga gagaggaata cgacgtcctc gataagaggc gcggcaggga ccctgagatg | 2820 |
| ggaggaaaac ctcggagaaa aaaccctcag gaagggctct acaacgagct gcagaaagat | 2880 |
| aagatggctg aagcttactc cgaaattggg atgaagggtg aaaggcggag ggcaaagga | 2940 |
| cacgacggac tgtatcaggg actgtccaca gccacaaaag atacctatga cgcactccat | 3000 |
| atgcaggctc tcccacccag a | 3021 |

<210> SEQ ID NO 58
<211> LENGTH: 7691
<212> TYPE: DNA
<213> ORGANISM: Artificial Sequence
<220> FEATURE:
<223> OTHER INFORMATION: synthetic

<400> SEQUENCE: 58

| | |
|---|---|
| gacaatcaac ctctggatta caaaatttgt gaaagattga ctggtattct taactatgtt | 60 |
| gctcctttta cgctatgtgg atacgctgct ttaatgcctt tgtatcatgc tattgcttcc | 120 |
| cgtatggctt tcattttctc ctccttgtat aaatcctggt tgctgtctct ttatgaggag | 180 |
| ttgtggcccg ttgtcaggca acgtggcgtg gtgtgcactg tgtttgctga cgcaaccccc | 240 |
| actggttggg gcattgccac cacctgtcag ctcctttccg ggactttcgc tttccccctc | 300 |
| cctattgcca cggcggaact catcgccgcc tgccttgccc gctgctggac aggggctcgg | 360 |
| ctgttgggca ctgacaattc cgtggtgttg tcggggaagc tgacgtcctt tccatggctg | 420 |

-continued

```
ctcgcctgtg ttgccacctg gattctgcgc gggacgtcct tctgctacgt cccttcggcc      480
ctcaatccag cggaccttcc ttcccgcggc ctgctgccgg ctctgcggcc tcttccgcgt      540
cttcgccttc gccctcagac gagtcggatc tccctttggg ccgcctcccc gcctggaatt      600
cgagctcggt acctttaaga ccaatgactt acaaggcagc tgtagatctt agccactttt      660
taaaagaaaa gggggactg aagggctaa ttcactccca acgaagacaa gatctgcttt       720
ttgcttgtac tgggtctctc tggttagacc agatctgagc ctgggagctc tctggctaac      780
tagggaaccc actgcttaag cctcaataaa gcttgccttg agtgcttcaa gtagtgtgtg      840
cccgtctgtt gtgtgactct ggtaactaga tccctcag acccttttag tcagtgtgga       900
aaatctctag cagtagtagt tcatgtcatc ttattattca gtatttataa cttgcaaaga      960
aatgaatatc agagagtgag aggaacttgt ttattgcagc ttataatggt acaaataaa      1020 gcaatagcat cacaaatttc acaaataaag cattttttc actgcattct agttgtggtt     1080
tgtccaaact catcaatgta tcttatcatg tctggctcta gctatcccgc ccctaactcc     1140
gcccagttcc gcccattctc cgccccatgg ctgactaatt ttttttattt atgcagaggc     1200
cgaggccgcc tcggcctctg agctattcca gaagtagtga ggaggctttt ttggaggcct     1260
aggcttttgc gtcgagacgt acccaattcg ccctatagtg agtcgtatta cgcgcgctca     1320
ctggccgtcg ttttacaacg tcgtgactgg gaaaaccctg gcgttaccca acttaatcgc     1380
cttgcagcac atccccctt cgccagctgg cgtaatagcg aagaggcccg caccgatcgc     1440
ccttcccaac agttgcgcag cctgaatggc gaatgggacg cgccctgtag cggcgcatta     1500
agcgcggcgg gtgtggtggt tacgcgcagc gtgaccgcta cacttgccag cgccctagcg     1560
cccgctcctt tcgctttctt cccttccttt ctcgccacgt tcgccggctt tccccgtcaa     1620
gctctaaatc gggggctccc tttagggttc cgatttagtg ctttacggca cctcgacccc     1680
aaaaaacttg attagggtga tggttcacgt agtgggccat cgccctgata acggttttt     1740 cgcccttga cgttggagtc cacgttcttt aatagtggac tcttgttcca aactggaaca     1800
acactcaacc ctatctcggt ctattctttt gatttataag ggattttgcc gatttcggcc     1860
tattggttaa aaaatgagct gatttaacaa aaatttaacg cgaattttaa caaaatatta     1920
acgcttacaa tttaggtggc acttttcggg gaaatgtgcg cggaaccct atttgtttat     1980 ttttctaaat acattcaaat atgtatccgc tcatgagaca ataaccctga taatgcttc     2040 aataatattg aaaaaggaag agtatgagta ttcaacattt ccgtgtcgcc cttattccct     2100
tttttgcggc attttgcctt cctgtttttg ctcacccaga aacgctggtg aaagtaaaag     2160
atgctgaaga tcagttgggt gcacgagtgg gttacatcga actggatctc aacagcggta     2220
agatccttga gagttttcgc cccgaagaac gttttccaat gatgagcact tttaaagttc     2280
tgctatgtgg cgcggtatta tcccgtattg acgccgggca agagcaactc ggtcgccgca     2340
tacactattc tcagaatgac ttggttgagt actcaccagt cacagaaaag catcttacgg     2400
atggcatgac agtaagagaa ttatgcagtg ctgccataac catgagtgat aacactgcgg     2460
ccaacttact tctgacaacg atcggaggac cgaaggagct aaccgctttt ttgcacaaca     2520
tgggggatca tgtaactcgc cttgatcgtt gggaaccgga gctgaatgaa gccataccaa     2580
acgacgagcg tgacaccacg atgcctgtag caatggcaac aacgttgcgc aaactattaa     2640
ctggcgaact acttactcta gcttcccggc aacaattaat agactggatg gaggcggata     2700
aagttgcagg accacttctg cgctcggccc ttccggctgg ctggtttatt gctgataaat     2760
```

```
ctggagccgg tgagcgtggg tctcgcggta tcattgcagc actggggcca gatggtaagc    2820
cctcccgtat cgtagttatc tacacgacgg ggagtcaggc aactatggat gaacgaaata    2880
gacagatcgc tgagataggt gcctcactga ttaagcattg gtaactgtca gaccaagttt    2940
actcatatat actttagatt gatttaaaac ttcattttta atttaaaagg atctaggtga    3000
agatcctttt tgataatctc atgaccaaaa tcccttaacg tgagttttcg ttccactgag    3060
cgtcagaccc cgtagaaaag atcaaaggat cttcttgaga tcctttttt ctgcgcgtaa    3120 tctgctgctt gcaaacaaaa aaaccaccgc taccagcggt ggtttgtttg ccggatcaag    3180
agctaccaac tcttttccg aaggtaactg gcttcagcag agcgcagata ccaaatactg    3240
ttcttctagt gtagccgtag ttaggccacc acttcaagaa ctctgtagca ccgcctacat    3300
acctcgctct gctaatcctg ttaccagtgg ctgctgccag tggcgataag tcgtgtctta    3360
ccgggttgga ctcaagacga tagttaccgg ataaggcgca gcggtcgggc tgaacggggg    3420
gttcgtgcac acagcccagc ttggagcgaa cgacctacac cgaactgaga tacctacagc    3480
gtgagctatg agaaagcgcc acgcttcccg aagggagaaa ggcggacagg tatccggtaa    3540
gcggcagggt cggaacagga gagcgcacga gggagcttcc agggggaaac gcctggtatc    3600
tttatagtcc tgtcgggttt cgccacctct gacttgagcg tcgatttttg tgatgctcgt    3660
caggggggcg gagcctatgg aaaaacgcca gcaacgcggc ctttttacgg ttcctggcct    3720
tttgctggcc ttttgctcac atgttctttc ctgcgttatc ccctgattct gtggataacc    3780
gtattaccgc ctttgagtga gctgataccg ctcgccgcag ccgaacgacc gagcgcagcg    3840
agtcagtgag cgaggaagcg gaagagcgcc caatacgcaa accgcctctc cccgcgcgtt    3900
ggccgattca ttaatgcagc tggcacgaca ggtttcccga ctggaaagcg ggcagtgagc    3960
gcaacgcaat taatgtgagt tagctcactc attaggcacc ccaggcttta cactttatgc    4020
ttccggctcg tatgttgtgt ggaattgtga gcggataaca atttcacaca ggaaacagct    4080
atgaccatga ttacgccaag cgcgcaatta accctcacta aagggaacaa agctggagc    4140 tgcaagctta atgtagtctt atgcaatact cttgtagtct tgcaacatgg taacgatgag    4200
ttagcaacat gccttacaag gagagaaaaa gcaccgtgca tgccgattgg tggaagtaag    4260
gtggtacgat cgtgccttat taggaaggca acagacgggt ctgacatgga ttggacgaac    4320
cactgaattg ccgcattgca gagatattgt atttaagtgc ctagctcgat acataaacgg    4380
gtctctctgg ttagaccaga tctgagcctg ggagctctct ggctaactag ggaacccact    4440
gcttaagcct caataaagct tgccttgagt gcttcaagta gtgtgtgccc gtctgttgtg    4500
tgactctggt aactagagat ccctcagacc cttttagtca gtgtggaaaa tctctagcag    4560
tggcgcccga acaggggactt gaaagcgaaa gggaaaccag aggagctctc tcgacgcagg    4620
actcggcttg ctgaagcgcg cacggcaaga ggcgaggggc ggcgactggt gagtacgcca    4680
aaaattttga ctagcggagg ctagaaggag agagatgggt gcgagagcgt cagtattaag    4740
cgggggagaa ttagatcgcg atgggaaaaa attcggttaa ggccaggggg aagaaaaaa    4800 tataaattaa aacatatagt atgggcaagc agggagctag aacgattcgc agttaatcct    4860
ggcctgttag aaacatcaga aggctgtaga caaatactgg gacagctaca accatccctt    4920
cagacaggat cagaagaact agatcatta tataatacag tagcaaccct ctattgtgtg    4980
catcaaagga tagagataaa agacaccaag gaagctttag acaagataga ggaagagcaa    5040
aacaaaagta agaccaccgc acagcaagcg gccgctgatc ttcagacctg gaggaggaga    5100
tatgagggac aattggagaa gtgaattata taaatataaa gtagtaaaaa ttgaaccatt    5160
```

```
aggagtagca cccaccaagg caaagagaag agtggtgcag agagaaaaaa gagcagtggg    5220
aataggagct ttgttccttg ggttcttggg agcagcagga agcactatgg gcgcagcgtc    5280
aatgacgctg acggtacagg ccagacaatt attgtctggt atagtgcagc agcagaacaa    5340
tttgctgagg gctattgagg cgcaacagca tctgttgcaa ctcacagtct ggggcatcaa    5400
gcagctccag gcaagaatcc tggctgtgga agataccta aaggatcaac agctcctggg    5460
gatttggggt tgctctggaa aactcatttg caccactgct gtgccttgga atgctagttg    5520
gagtaataaa tctctggaac agatttggaa tcacacgacc tggatggagt gggacagaga    5580
aattaacaat tacacaagct taatacactc cttaattgaa gaatcgcaaa accagcaaga    5640
aaagaatgaa caagaattat tggaattaga taaatgggca gtttgtggaa attggtttaa    5700
cataacaaat tggctgtggt atataaaatt attcataatg atagtaggag gcttggtagg    5760
tttaagaata gtttttgctg tactttctat agtgaataga gttaggcagg gatattcacc    5820
attatcgttt cagacccacc tcccaacccc gaggggaccc gacaggcccg aaggaataga    5880
agaagaaggt ggagagagag acagagacag atccattcga ttagtgaacg gatctcgacg    5940
gtatcgatta gactgtagcc caggaatatg gcagctagat tgtacacatt tagaaggaaa    6000
agttatcttg gtagcagttc atgtagccag tggatatata gaagcagaag taattccagc    6060
agagacaggg caagaaacag catacttcct cttaaaatta gcaggaagat ggccagtaaa    6120
aacagtacat acagacaatg gcagcaattt caccagtact acagttaagg ccgcctgttg    6180
gtgggcgggg atcaagcagg aatttggcat tccctacaat ccccaaagtc aaggagtaat    6240
agaatctatg aataaagaat taagaaaat tataggacag gtaagagatc aggctgaaca    6300
tcttaagaca gcagtacaaa tggcagtatt catccacaat tttaaaagaa aaggggggat    6360 tggggggta cagtgcaggg gaaagaatag tagacataat agcaacagac atacaaacta    6420
aagaattaca aaaacaaatt acaaaaattc aaaattttcg ggtttattac agggacagca    6480
gagatccagt ttggctgcat acgcgtcgtg aggctccggt gcccgtcagt gggcagagcg    6540
cacatcgccc acagtccccg agaagttggg gggaggggtc ggcaattgaa ccggtgccta    6600
gagaaggtgg cgcggggtaa actgggaaag tgatgtcgtg tactggctcc gccttttcc    6660 cgagggtggg ggagaaccgt atataagtgc agtagtcgcc gtgaacgttc tttttcgcaa    6720
cgggtttgcc gccagaacac aggtaagtgc cgtgtgtggt tcccgcgggc ctggcctctt    6780
tacgggttat ggcccttgcg tgccttgaat tacttccacc tggctgcagt acgtgattct    6840
tgatcccgag cttcgggttg gaagtgggtg ggagagttcg aggccttgcg cttaaggagc    6900
cccttcgcct cgtgcttgag ttgaggcctg gcctgggcgc tggggccgcc gcgtgcgaat    6960
ctggtggcac cttcgcgcct gtctcgctgc tttcgataag tctctagcca tttaaaattt    7020
ttgatgacct gctgcgacgc ttttttttctg gcaagatagt cttgtaaatg cgggccaaga    7080
tctgcacact ggtatttcgg ttttggggc cgcgggcggc gacggggccc gtgcgtccca    7140
gcgcacatgt tcggcgaggc ggggcctgcg agcgcggcca ccgagaatcg gacggggta    7200 gtctcaagct ggccggcctg ctctggtgcc tggcctcgcg ccgccgtgta tcgccccgcc    7260
ctgggcggca aggctggccc ggtcggcacc agttgcgtga gcggaaagat ggccgcttcc    7320
cggccctgct gcagggagct caaaatggag gacgcggcgc tcgggagagc gggcgggtga    7380
gtcacccaca caaaggaaaa gggccttttcc gtcctcagcc gtcgcttcat gtgactccac    7440
tgagtaccgg gcgccgtcca ggcacctcga ttagttctcg tgcttttgga gtacgtcgtc    7500
```

```
tttaggttgg ggggaggggt tttatgcgat ggagtttccc cacactgagt gggtggagac    7560
tgaagttagg ccagcttggc acttgatgta attctccttg gaatttgccc tttttgagtt    7620
tggatcttgg ttcattctca agcctcagac agtggttcaa agttttttc ttccatttca     7680 ggtgtcgtga g                                                          7691
```

```
<210> SEQ ID NO 59
<211> LENGTH: 492
<212> TYPE: PRT
<213> ORGANISM: Artificial Sequence
<220> FEATURE:
<223> OTHER INFORMATION: synthetic

<400> SEQUENCE: 59
```

```
Met Leu Leu Leu Val Thr Ser Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Ser Thr Ser Gly Ser Gly Lys Pro Gly Ser Gly Glu Gly Ser
    130                 135                 140

Thr Lys Gly Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
                165                 170                 175

Pro Asp Tyr Gly Val Ser Trp Ile Arg Gln Pro Pro Arg Lys Gly Leu
            180                 185                 190

Glu Trp Leu Gly Val Ile Trp Gly Ser Glu Thr Thr Tyr Tyr Asn Ser
        195                 200                 205

Ala Leu Lys Ser Arg Leu Thr Ile Ile Lys Asp Asn Ser Lys Ser Gln
    210                 215                 220

Val Phe Leu Lys Met Asn Ser Leu Gln Thr Asp Asp Thr Ala Ile Tyr
225                 230                 235                 240

Tyr Cys Ala Lys His Tyr Tyr Tyr Gly Gly Ser Tyr Ala Met Asp Tyr
                245                 250                 255

Trp Gly Gln Gly Thr Ser Val Thr Val Ser Ser Gly Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
```

|   |   | 325 |   |   |   | 330 |   |   |   | 335 |   |

Tyr Cys Lys Arg Gly Arg Lys Lys Leu Leu Tyr Ile Phe Lys Gln Pro
                340                 345                 350

Phe Met Arg Pro Val Gln Thr Thr Gln Glu Glu Asp Gly Cys Ser Cys
                355                 360                 365

Arg Phe Pro Glu Glu Glu Gly Gly Cys Glu Leu Arg Val Lys Phe
            370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
                420                 425                 430

Asn Pro Gln Glu Gly Leu Tyr Asn Glu Leu Gln Lys Asp Lys Met Ala
                435                 440                 445

Glu Ala Tyr Ser Glu Ile Gly Met Lys Gly Glu Arg Arg Arg Gly Lys
                450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490

<210> SEQ ID NO 60
<211> LENGTH: 485
<212> TYPE: PRT
<213> ORGANISM: Artificial Sequence
<220> FEATURE:
<223> OTHER INFORMATION: synthetic

<400> SEQUENCE: 60

Met Leu Leu Leu Val Thr Ser Leu Leu Leu Cys Glu Leu Pro His Pro
1               5                   10                  15

Ala Phe Leu Leu Ile Pro Gln Val Gln Leu Gln Gln Ser Gly Pro Gly
                20                  25                  30

Leu Val Lys Pro Ser Gln Thr Leu Ser Leu Thr Cys Ala Ile Ser Gly
                35                  40                  45

Asp Ser Val Ser Ser Asn Ser Ala Ala Trp Asn Trp Ile Arg Gln Ser
            50                  55                  60

Pro Ser Arg Gly Leu Glu Trp Leu Gly Arg Thr Tyr Tyr Arg Ser Lys
65              70                  75                  80

Trp Tyr Asn Asp Tyr Ala Val Ser Val Lys Ser Arg Ile Thr Ile Asn
                85                  90                  95

Pro Asp Thr Ser Lys Asn Gln Phe Ser Leu Gln Leu Asn Ser Val Thr
                100                 105                 110

Pro Glu Asp Thr Ala Val Tyr Tyr Cys Ala Arg Glu Val Thr Gly Asp
                115                 120                 125

Leu Glu Asp Ala Phe Asp Ile Trp Gly Gln Gly Thr Met Val Thr Val
            130                 135                 140

Ser Ser Gly Gly Gly Gly Ser Asp Ile Gln Met Thr Gln Ser Pro Ser
145                 150                 155                 160

Ser Leu Ser Ala Ser Val Gly Asp Arg Val Thr Ile Thr Cys Arg Ala
                165                 170                 175

Ser Gln Thr Ile Trp Ser Tyr Leu Asn Trp Tyr Gln Gln Arg Pro Gly
                180                 185                 190

Lys Ala Pro Asn Leu Leu Ile Tyr Ala Ala Ser Ser Leu Gln Ser Gly

```
            195                 200                 205
Val Pro Ser Arg Phe Ser Gly Arg Gly Ser Gly Thr Asp Phe Thr Leu
210                 215                 220

Thr Ile Ser Ser Leu Gln Ala Glu Asp Phe Ala Thr Tyr Tyr Cys Gln
225                 230                 235                 240

Gln Ser Tyr Ser Ile Pro Gln Thr Phe Gly Gln Gly Thr Lys Leu Glu
                245                 250                 255

Ile Lys Thr Ser Ser Gly Thr Thr Thr Pro Ala Pro Arg Pro Pro Thr
            260                 265                 270

Pro Ala Pro Thr Ile Ala Ser Gln Pro Leu Ser Leu Arg Pro Glu Ala
                275                 280                 285

Cys Arg Pro Ala Ala Gly Gly Ala Val His Thr Arg Gly Leu Asp Phe
290                 295                 300

Ala Cys Asp Ile Tyr Ile Trp Ala Pro Leu Ala Gly Thr Cys Gly Val
305                 310                 315                 320

Leu Leu Leu Ser Leu Val Ile Thr Leu Tyr Cys Lys Arg Gly Arg Lys
                325                 330                 335

Lys Leu Leu Tyr Ile Phe Lys Gln Pro Phe Met Arg Pro Val Gln Thr
                340                 345                 350

Thr Gln Glu Glu Asp Gly Cys Ser Cys Arg Phe Pro Glu Glu Glu Glu
                355                 360                 365

Gly Gly Cys Glu Leu Arg Val Lys Phe Ser Arg Ser Ala Asp Ala Pro
370                 375                 380

Ala Tyr Gln Gln Gly Gln Asn Gln Leu Tyr Asn Glu Leu Asn Leu Gly
385                 390                 395                 400

Arg Arg Glu Glu Tyr Asp Val Leu Asp Lys Arg Arg Gly Arg Asp Pro
                405                 410                 415

Glu Met Gly Gly Lys Pro Arg Arg Lys Asn Pro Gln Glu Gly Leu Tyr
            420                 425                 430

Asn Glu Leu Gln Lys Asp Lys Met Ala Glu Ala Tyr Ser Glu Ile Gly
                435                 440                 445

Met Lys Gly Glu Arg Arg Arg Gly Lys Gly His Asp Gly Leu Tyr Gln
            450                 455                 460

Gly Leu Ser Thr Ala Thr Lys Asp Thr Tyr Asp Ala Leu His Met Gln
465                 470                 475                 480

Ala Leu Pro Pro Arg
            485

<210> SEQ ID NO 61
<211> LENGTH: 733
<212> TYPE: PRT
<213> ORGANISM: Artificial Sequence
<220> FEATURE:
<223> OTHER INFORMATION: synthetic

<400> SEQUENCE: 61

Met Leu Leu Leu Val Thr Ser Leu Leu Cys Glu Leu Pro His Pro
1               5                   10                  15

Ala Phe Leu Leu Ile Pro Asp Ile Gln Met Thr Gln Thr Thr Ser Ser
                20                  25                  30

Leu Ser Ala Ser Leu Gly Asp Arg Val Thr Ile Ser Cys Arg Ala Ser
                35                  40                  45

Gln Asp Ile Ser Lys Tyr Leu Asn Trp Tyr Gln Gln Lys Pro Asp Gly
            50                  55                  60

Thr Val Lys Leu Leu Ile Tyr His Thr Ser Arg Leu His Ser Gly Val
```

```
                65                  70                  75                  80
        Pro Ser Arg Phe Ser Gly Ser Gly Ser Gly Thr Asp Tyr Ser Leu Thr
                            85                  90                  95
        Ile Ser Asn Leu Glu Gln Glu Asp Ile Ala Thr Tyr Phe Cys Gln Gln
                        100                 105                 110
        Gly Asn Thr Leu Pro Tyr Thr Phe Gly Gly Gly Thr Lys Leu Glu Ile
                    115                 120                 125
        Thr Gly Gly Gly Gly Ser Gln Val Gln Leu Gln Gln Ser Gly Pro Gly
                130                 135                 140
        Leu Val Lys Pro Ser Gln Thr Leu Ser Leu Thr Cys Ala Ile Ser Gly
        145                 150                 155                 160
        Asp Ser Val Ser Ser Asn Ser Ala Ala Trp Asn Trp Ile Arg Gln Ser
                        165                 170                 175
        Pro Ser Arg Gly Leu Glu Trp Leu Gly Arg Thr Tyr Tyr Arg Ser Lys
                    180                 185                 190
        Trp Tyr Asn Asp Tyr Ala Val Ser Val Lys Ser Arg Ile Thr Ile Asn
                195                 200                 205
        Pro Asp Thr Ser Lys Asn Gln Phe Ser Leu Gln Leu Asn Ser Val Thr
            210                 215                 220
        Pro Glu Asp Thr Ala Val Tyr Tyr Cys Ala Arg Glu Val Thr Gly Asp
        225                 230                 235                 240
        Leu Glu Asp Ala Phe Asp Ile Trp Gly Gln Gly Thr Met Val Thr Val
                        245                 250                 255
        Ser Ser Gly Ser Thr Ser Gly Ser Gly Lys Pro Gly Ser Gly Glu Gly
                    260                 265                 270
        Ser Thr Lys Gly Asp Ile Gln Met Thr Gln Ser Pro Ser Ser Leu Ser
                275                 280                 285
        Ala Ser Val Gly Asp Arg Val Thr Ile Thr Cys Arg Ala Ser Gln Thr
            290                 295                 300
        Ile Trp Ser Tyr Leu Asn Trp Tyr Gln Gln Arg Pro Gly Lys Ala Pro
        305                 310                 315                 320
        Asn Leu Leu Ile Tyr Ala Ala Ser Ser Leu Gln Ser Gly Val Pro Ser
                        325                 330                 335
        Arg Phe Ser Gly Arg Gly Ser Gly Thr Asp Phe Thr Leu Thr Ile Ser
                    340                 345                 350
        Ser Leu Gln Ala Glu Asp Phe Ala Thr Tyr Tyr Cys Gln Gln Ser Tyr
                355                 360                 365
        Ser Ile Pro Gln Thr Phe Gly Gln Gly Thr Lys Leu Glu Ile Lys Gly
            370                 375                 380
        Gly Gly Gly Ser Glu Val Lys Leu Gln Glu Ser Gly Pro Gly Leu Val
        385                 390                 395                 400
        Ala Pro Ser Gln Ser Leu Ser Val Thr Cys Thr Val Ser Gly Val Ser
                        405                 410                 415
        Leu Pro Asp Tyr Gly Val Ser Trp Ile Arg Gln Pro Pro Arg Lys Gly
                    420                 425                 430
        Leu Glu Trp Leu Gly Val Ile Trp Gly Ser Glu Thr Thr Tyr Tyr Asn
                435                 440                 445
        Ser Ala Leu Lys Ser Arg Leu Thr Ile Ile Lys Asp Asn Ser Lys Ser
            450                 455                 460
        Gln Val Phe Leu Lys Met Asn Ser Leu Gln Thr Asp Asp Thr Ala Ile
        465                 470                 475                 480
        Tyr Tyr Cys Ala Lys His Tyr Tyr Tyr Gly Gly Ser Tyr Ala Met Asp
                        485                 490                 495
```

```
Tyr Trp Gly Gln Gly Thr Ser Val Thr Val Ser Ser Ser Gly Thr Thr
                500                 505                 510

Thr Pro Ala Pro Arg Pro Pro Thr Pro Ala Pro Thr Ile Ala Ser Gln
            515                 520                 525

Pro Leu Ser Leu Arg Pro Glu Ala Cys Arg Pro Ala Ala Gly Gly Ala
        530                 535                 540

Val His Thr Arg Gly Leu Asp Phe Ala Cys Asp Ile Tyr Ile Trp Ala
545                 550                 555                 560

Pro Leu Ala Gly Thr Cys Gly Val Leu Leu Leu Ser Leu Val Ile Thr
                565                 570                 575

Leu Tyr Cys Lys Arg Gly Arg Lys Lys Leu Leu Tyr Ile Phe Lys Gln
            580                 585                 590

Pro Phe Met Arg Pro Val Gln Thr Thr Gln Glu Glu Asp Gly Cys Ser
        595                 600                 605

Cys Arg Phe Pro Glu Glu Glu Gly Gly Cys Glu Leu Arg Val Lys
            610                 615                 620

Phe Ser Arg Ser Ala Asp Ala Pro Ala Tyr Lys Gln Gly Gln Asn Gln
625                 630                 635                 640

Leu Tyr Asn Glu Leu Asn Leu Gly Arg Arg Glu Glu Tyr Asp Val Leu
                645                 650                 655

Asp Lys Arg Arg Gly Arg Asp Pro Glu Met Gly Gly Lys Pro Arg Arg
            660                 665                 670

Lys Asn Pro Gln Glu Gly Leu Tyr Asn Glu Leu Gln Lys Asp Lys Met
        675                 680                 685

Ala Glu Ala Tyr Ser Glu Ile Gly Met Lys Gly Glu Arg Arg Arg Gly
690                 695                 700

Lys Gly His Asp Gly Leu Tyr Gln Gly Leu Ser Thr Ala Thr Lys Asp
705                 710                 715                 720

Thr Tyr Asp Ala Leu His Met Gln Ala Leu Pro Pro Arg
                725                 730

<210> SEQ ID NO 62
<211> LENGTH: 20
<212> TYPE: PRT
<213> ORGANISM: Artificial Sequence
<220> FEATURE:
<223> OTHER INFORMATION: synthetic

<400> SEQUENCE: 62

Ala Leu Pro Val Thr Ala Leu Leu Leu Pro Leu Ala Leu Leu Leu His
1               5                   10                  15

Ala Ala Arg Pro
            20

<210> SEQ ID NO 63
<211> LENGTH: 751
<212> TYPE: PRT
<213> ORGANISM: Artificial Sequence
<220> FEATURE:
<223> OTHER INFORMATION: Synthetic

<400> SEQUENCE: 63

Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
```

-continued

```
                35                  40                  45
Gln Asp Ile Ser Lys Tyr Leu Asn Trp Tyr Gln Gln Lys Pro Asp Gly
         50                  55                  60
Thr Val Lys Leu Leu Ile Tyr His Thr Ser Arg Leu His Ser Gly Val
 65                  70                  75                  80
Pro Ser Arg Phe Ser Gly Ser Gly Ser Gly Thr Asp Tyr Ser Leu Thr
                 85                  90                  95
Ile Ser Asn Leu Glu Gln Glu Asp Ile Ala Thr Tyr Phe Cys Gln Gln
            100                 105                 110
Gly Asn Thr Leu Pro Tyr Thr Phe Gly Gly Gly Thr Lys Leu Glu Ile
            115                 120                 125
Thr Gly Ser Thr Ser Gly Ser Gly Lys Pro Gly Ser Gly Glu Gly Ser
            130                 135                 140
Thr Lys Gly Glu Val Lys Leu Gln Glu Ser Gly Pro Gly Leu Val Ala
145                 150                 155                 160
Pro Ser Gln Ser Leu Ser Val Thr Cys Thr Val Ser Gly Val Ser Leu
                165                 170                 175
Pro Asp Tyr Gly Val Ser Trp Ile Arg Gln Pro Pro Arg Lys Gly Leu
            180                 185                 190
Glu Trp Leu Gly Val Ile Trp Gly Ser Glu Thr Thr Tyr Tyr Asn Ser
            195                 200                 205
Ala Leu Lys Ser Arg Leu Thr Ile Ile Lys Asp Asn Ser Lys Ser Gln
            210                 215                 220
Val Phe Leu Lys Met Asn Ser Leu Gln Thr Asp Asp Thr Ala Ile Tyr
225                 230                 235                 240
Tyr Cys Ala Lys His Tyr Tyr Gly Gly Ser Tyr Ala Met Asp Tyr
                245                 250                 255
Trp Gly Gln Gly Thr Ser Val Thr Val Ser Ser Gly Gly Gly Gly Ser
            260                 265                 270
Gly Gly Gly Gly Ser Gly Gly Gly Ser Gly Gly Gly Gly Ser Gly
            275                 280                 285
Gly Gly Gly Ser Gln Val Gln Leu Gln Gln Ser Gly Pro Gly Leu Val
            290                 295                 300
Lys Pro Ser Gln Thr Leu Ser Leu Thr Cys Ala Ile Ser Gly Asp Ser
305                 310                 315                 320
Val Ser Ser Asn Ser Ala Ala Trp Asn Trp Ile Arg Gln Ser Pro Ser
                325                 330                 335
Arg Gly Leu Glu Trp Leu Gly Arg Thr Tyr Tyr Arg Ser Lys Trp Tyr
            340                 345                 350
Asn Asp Tyr Ala Val Ser Val Lys Ser Arg Ile Thr Ile Asn Pro Asp
            355                 360                 365
Thr Ser Lys Asn Gln Phe Ser Leu Gln Leu Asn Ser Val Thr Pro Glu
            370                 375                 380
Asp Thr Ala Val Tyr Tyr Cys Ala Arg Glu Val Thr Gly Asp Leu Glu
385                 390                 395                 400
Asp Ala Phe Asp Ile Trp Gly Gln Gly Thr Met Val Thr Val Ser Ser
                405                 410                 415
Gly Gly Gly Gly Ser Asp Ile Gln Met Thr Gln Ser Pro Ser Ser Leu
            420                 425                 430
Ser Ala Ser Val Gly Asp Arg Val Thr Ile Thr Cys Arg Ala Ser Gln
            435                 440                 445
Thr Ile Trp Ser Tyr Leu Asn Trp Tyr Gln Gln Arg Pro Gly Lys Ala
            450                 455                 460
```

```
Pro Asn Leu Leu Ile Tyr Ala Ala Ser Ser Leu Gln Ser Gly Val Pro
465                 470                 475                 480

Ser Arg Phe Ser Gly Arg Gly Ser Gly Thr Asp Phe Thr Leu Thr Ile
            485                 490                 495

Ser Ser Leu Gln Ala Glu Asp Phe Ala Thr Tyr Tyr Cys Gln Gln Ser
                500                 505                 510

Tyr Ser Ile Pro Gln Thr Phe Gly Gln Gly Thr Lys Leu Glu Ile Lys
            515                 520                 525

Thr Thr Thr Pro Ala Pro Arg Pro Pro Thr Pro Ala Pro Thr Ile Ala
        530                 535                 540

Ser Gln Pro Leu Ser Leu Arg Pro Glu Ala Cys Arg Pro Ala Ala Gly
545                 550                 555                 560

Gly Ala Val His Thr Arg Gly Leu Asp Phe Ala Cys Asp Ile Tyr Ile
                565                 570                 575

Trp Ala Pro Leu Ala Gly Thr Cys Gly Val Leu Leu Leu Ser Leu Val
            580                 585                 590

Ile Thr Leu Tyr Cys Lys Arg Gly Arg Lys Lys Leu Leu Tyr Ile Phe
                595                 600                 605

Lys Gln Pro Phe Met Arg Pro Val Gln Thr Thr Gln Glu Glu Asp Gly
        610                 615                 620

Cys Ser Cys Arg Phe Pro Glu Glu Glu Gly Gly Cys Glu Leu Arg
625                 630                 635                 640

Val Lys Phe Ser Arg Ser Ala Asp Ala Pro Ala Tyr Lys Gln Gly Gln
                645                 650                 655

Asn Gln Leu Tyr Asn Glu Leu Asn Leu Gly Arg Arg Glu Glu Tyr Asp
            660                 665                 670

Val Leu Asp Lys Arg Arg Gly Arg Asp Pro Glu Met Gly Gly Lys Pro
        675                 680                 685

Arg Arg Lys Asn Pro Gln Glu Gly Leu Tyr Asn Glu Leu Gln Lys Asp
690                 695                 700

Lys Met Ala Glu Ala Tyr Ser Glu Ile Gly Met Lys Gly Glu Arg Arg
705                 710                 715                 720

Arg Gly Lys Gly His Asp Gly Leu Tyr Gln Gly Leu Ser Thr Ala Thr
                725                 730                 735

Lys Asp Thr Tyr Asp Ala Leu His Met Gln Ala Leu Pro Pro Arg
            740                 745                 750

<210> SEQ ID NO 64
<211> LENGTH: 766
<212> TYPE: PRT
<213> ORGANISM: Artificial Sequence
<220> FEATURE:
<223> OTHER INFORMATION: Synthetic

<400> SEQUENCE: 64

Met Leu Leu Leu Val Thr Ser Leu Leu Leu Cys Glu Leu Pro His Pro
1               5                   10                  15

Ala Phe Leu Leu Ile Pro Gln Val Gln Leu Gln Gln Ser Gly Pro Gly
            20                  25                  30

Leu Val Lys Pro Ser Gln Thr Leu Ser Leu Thr Cys Ala Ile Ser Gly
        35                  40                  45

Asp Ser Val Ser Ser Asn Ser Ala Ala Trp Asn Trp Ile Arg Gln Ser
    50                  55                  60

Pro Ser Arg Gly Leu Glu Trp Leu Gly Arg Thr Tyr Tyr Arg Ser Lys
65                  70                  75                  80
```

```
Trp Tyr Asn Asp Tyr Ala Val Ser Val Lys Ser Arg Ile Thr Ile Asn
                85                  90                  95

Pro Asp Thr Ser Lys Asn Gln Phe Ser Leu Gln Leu Asn Ser Val Thr
            100                 105                 110

Pro Glu Asp Thr Ala Val Tyr Tyr Cys Ala Arg Glu Val Thr Gly Asp
            115                 120                 125

Leu Glu Asp Ala Phe Asp Ile Trp Gly Gln Gly Thr Met Val Thr Val
        130                 135                 140

Ser Ser Gly Ser Thr Ser Gly Ser Gly Lys Pro Gly Ser Gly Glu Gly
145                 150                 155                 160

Ser Thr Lys Gly Asp Ile Gln Met Thr Gln Ser Pro Ser Ser Leu Ser
                165                 170                 175

Ala Ser Val Gly Asp Arg Val Thr Ile Thr Cys Arg Ala Ser Gln Thr
            180                 185                 190

Ile Trp Ser Tyr Leu Asn Trp Tyr Gln Gln Arg Pro Gly Lys Ala Pro
        195                 200                 205

Asn Leu Leu Ile Tyr Ala Ala Ser Ser Leu Gln Ser Gly Val Pro Ser
        210                 215                 220

Arg Phe Ser Gly Arg Gly Ser Gly Thr Asp Phe Thr Leu Thr Ile Ser
225                 230                 235                 240

Ser Leu Gln Ala Glu Asp Phe Ala Thr Tyr Tyr Cys Gln Gln Ser Tyr
                245                 250                 255

Ser Ile Pro Gln Thr Phe Gly Gln Gly Thr Lys Leu Glu Ile Lys Gly
                260                 265                 270

Gly Gly Gly Ser Gly Gly Gly Ser Gly Gly Gly Ser Gly Gly Gly Gly
                275                 280                 285

Gly Gly Ser Gly Gly Gly Ser Asp Ile Gln Met Thr Gln Thr Thr
        290                 295                 300

Ser Ser Leu Ser Ala Ser Leu Gly Asp Arg Val Thr Ile Ser Cys Arg
305                 310                 315                 320

Ala Ser Gln Asp Ile Ser Lys Tyr Leu Asn Trp Tyr Gln Gln Lys Pro
                325                 330                 335

Asp Gly Thr Val Lys Leu Leu Ile Tyr His Thr Ser Arg Leu His Ser
            340                 345                 350

Gly Val Pro Ser Arg Phe Ser Gly Ser Gly Ser Gly Thr Asp Tyr Ser
            355                 360                 365

Leu Thr Ile Ser Asn Leu Glu Gln Glu Asp Ile Ala Thr Tyr Phe Cys
        370                 375                 380

Gln Gln Gly Asn Thr Leu Pro Tyr Thr Phe Gly Gly Gly Thr Lys Leu
385                 390                 395                 400

Glu Ile Thr Gly Ser Thr Ser Gly Ser Gly Lys Pro Gly Ser Gly Glu
                405                 410                 415

Gly Ser Thr Lys Gly Glu Val Lys Leu Gln Glu Ser Gly Pro Gly Leu
            420                 425                 430

Val Ala Pro Ser Gln Ser Leu Ser Val Thr Cys Thr Val Ser Gly Val
            435                 440                 445

Ser Leu Pro Asp Tyr Gly Val Ser Trp Ile Arg Gln Pro Pro Arg Lys
        450                 455                 460

Gly Leu Glu Trp Leu Gly Val Ile Trp Gly Ser Glu Thr Thr Tyr Tyr
465                 470                 475                 480

Asn Ser Ala Leu Lys Ser Arg Leu Thr Ile Ile Lys Asp Asn Ser Lys
                485                 490                 495
```

```
Ser Gln Val Phe Leu Lys Met Asn Ser Leu Gln Thr Asp Thr Ala
            500                 505                 510
Ile Tyr Tyr Cys Ala Lys His Tyr Tyr Gly Gly Ser Tyr Ala Met
        515                 520                 525
Asp Tyr Trp Gly Gln Gly Thr Ser Val Thr Val Ser Ser Gly Thr
    530                 535                 540
Thr Thr Pro Ala Pro Arg Pro Pro Thr Pro Ala Pro Thr Ile Ala Ser
545                 550                 555                 560
Gln Pro Leu Ser Leu Arg Pro Glu Ala Cys Arg Pro Ala Ala Gly Gly
                565                 570                 575
Ala Val His Thr Arg Gly Leu Asp Phe Ala Cys Asp Ile Tyr Ile Trp
            580                 585                 590
Ala Pro Leu Ala Gly Thr Cys Gly Val Leu Leu Leu Ser Leu Val Ile
        595                 600                 605
Thr Leu Tyr Cys Lys Arg Gly Arg Lys Lys Leu Leu Tyr Ile Phe Lys
    610                 615                 620
Gln Pro Phe Met Arg Pro Val Gln Thr Thr Gln Glu Glu Asp Gly Cys
625                 630                 635                 640
Ser Cys Arg Phe Pro Glu Glu Glu Glu Gly Gly Cys Glu Leu Arg Val
                645                 650                 655
Lys Phe Ser Arg Ser Ala Asp Ala Pro Ala Tyr Gln Gln Gly Gln Asn
            660                 665                 670
Gln Leu Tyr Asn Glu Leu Asn Leu Gly Arg Arg Glu Glu Tyr Asp Val
        675                 680                 685
Leu Asp Lys Arg Arg Gly Arg Asp Pro Glu Met Gly Gly Lys Pro Arg
    690                 695                 700
Arg Lys Asn Pro Gln Glu Gly Leu Tyr Asn Glu Leu Gln Lys Asp Lys
705                 710                 715                 720
Met Ala Glu Ala Tyr Ser Glu Ile Gly Met Lys Gly Glu Arg Arg Arg
                725                 730                 735
Gly Lys Gly His Asp Gly Leu Tyr Gln Gly Leu Ser Thr Ala Thr Lys
            740                 745                 750
Asp Thr Tyr Asp Ala Leu His Met Gln Ala Leu Pro Pro Arg
        755                 760                 765

<210> SEQ ID NO 65
<211> LENGTH: 749
<212> TYPE: PRT
<213> ORGANISM: Artificial Sequence
<220> FEATURE:
<223> OTHER INFORMATION: Synthetic

<400> SEQUENCE: 65

Met Ala Leu Pro Val Thr Ala Leu Leu Leu Pro Leu Ala Leu Leu Leu
1               5                   10                  15
His Ala Ala Arg Pro Gln Val Gln Leu Gln Gln Ser Gly Pro Gly Leu
                20                  25                  30
Val Lys Pro Ser Gln Thr Leu Ser Leu Thr Cys Ala Ile Ser Gly Asp
            35                  40                  45
Ser Val Ser Ser Asn Ser Ala Ala Trp Asn Trp Ile Arg Gln Ser Pro
        50                  55                  60
Ser Arg Gly Leu Glu Trp Leu Gly Arg Thr Tyr Tyr Arg Ser Lys Trp
65                  70                  75                  80
Tyr Asn Asp Tyr Ala Val Ser Val Lys Ser Arg Ile Thr Ile Asn Pro
                85                  90                  95
```

-continued

```
Asp Thr Ser Lys Asn Gln Phe Ser Leu Gln Leu Asn Ser Val Thr Pro
            100                 105                 110
Glu Asp Thr Ala Val Tyr Tyr Cys Ala Arg Glu Val Thr Gly Asp Leu
        115                 120                 125
Glu Asp Ala Phe Asp Ile Trp Gly Gln Gly Thr Met Val Thr Val Ser
    130                 135                 140
Ser Gly Gly Gly Gly Ser Asp Ile Gln Met Thr Gln Ser Pro Ser Ser
145                 150                 155                 160
Leu Ser Ala Ser Val Gly Asp Arg Val Thr Ile Thr Cys Arg Ala Ser
                165                 170                 175
Gln Thr Ile Trp Ser Tyr Leu Asn Trp Tyr Gln Gln Arg Pro Gly Lys
            180                 185                 190
Ala Pro Asn Leu Leu Ile Tyr Ala Ala Ser Ser Leu Gln Ser Gly Val
        195                 200                 205
Pro Ser Arg Phe Ser Gly Arg Gly Ser Gly Thr Asp Phe Thr Leu Thr
    210                 215                 220
Ile Ser Ser Leu Gln Ala Glu Asp Phe Ala Thr Tyr Tyr Cys Gln Gln
225                 230                 235                 240
Ser Tyr Ser Ile Pro Gln Thr Phe Gly Gln Gly Thr Lys Leu Glu Ile
                245                 250                 255
Lys Gly Gly Gly Gly Ser Gly Gly Gly Gly Ser Gly Gly Gly Gly Ser
            260                 265                 270
Gly Gly Gly Gly Ser Asp Ile Gln Met Thr Gln Thr Thr Ser Ser Leu
        275                 280                 285
Ser Ala Ser Leu Gly Asp Arg Val Thr Ile Ser Cys Arg Ala Ser Gln
    290                 295                 300
Asp Ile Ser Lys Tyr Leu Asn Trp Tyr Gln Gln Lys Pro Asp Gly Thr
305                 310                 315                 320
Val Lys Leu Leu Ile Tyr His Thr Ser Arg Leu His Ser Gly Val Pro
                325                 330                 335
Ser Arg Phe Ser Gly Ser Gly Ser Gly Thr Asp Tyr Ser Leu Thr Ile
            340                 345                 350
Ser Asn Leu Glu Gln Glu Asp Ile Ala Thr Tyr Phe Cys Gln Gln Gly
        355                 360                 365
Asn Thr Leu Pro Tyr Thr Phe Gly Gly Gly Thr Lys Leu Glu Ile Thr
    370                 375                 380
Gly Ser Thr Ser Gly Ser Gly Lys Pro Gly Ser Gly Glu Gly Ser Thr
385                 390                 395                 400
Lys Gly Glu Val Lys Leu Gln Glu Ser Gly Pro Gly Leu Val Ala Pro
                405                 410                 415
Ser Gln Ser Leu Ser Val Thr Cys Thr Val Ser Gly Val Ser Leu Pro
            420                 425                 430
Asp Tyr Gly Val Ser Trp Ile Arg Gln Pro Pro Arg Lys Gly Leu Glu
        435                 440                 445
Trp Leu Gly Val Ile Trp Gly Ser Glu Thr Thr Tyr Tyr Asn Ser Ala
    450                 455                 460
Leu Lys Ser Arg Leu Thr Ile Ile Lys Asp Asn Ser Lys Ser Gln Val
465                 470                 475                 480
Phe Leu Lys Met Asn Ser Leu Gln Thr Asp Asp Thr Ala Ile Tyr Tyr
                485                 490                 495
Cys Ala Lys His Tyr Tyr Tyr Gly Gly Ser Tyr Ala Met Asp Tyr Trp
            500                 505                 510
Gly Gln Gly Thr Ser Val Thr Val Ser Ser Thr Ser Ser Gly Thr Thr
```

```
              515                 520                 525
Thr Pro Ala Pro Arg Pro Pro Thr Pro Ala Pro Thr Ile Ala Ser Gln
        530                 535                 540

Pro Leu Ser Leu Arg Pro Glu Ala Cys Arg Pro Ala Ala Gly Gly Ala
545                 550                 555                 560

Val His Thr Arg Gly Leu Asp Phe Ala Cys Asp Ile Tyr Ile Trp Ala
                565                 570                 575

Pro Leu Ala Gly Thr Cys Gly Val Leu Leu Ser Leu Val Ile Thr
            580                 585                 590

Leu Tyr Cys Lys Arg Gly Arg Lys Leu Leu Tyr Ile Phe Lys Gln
            595                 600                 605

Pro Phe Met Arg Pro Val Gln Thr Thr Gln Glu Glu Asp Gly Cys Ser
        610                 615                 620

Cys Arg Phe Pro Glu Glu Glu Glu Gly Gly Cys Glu Leu Arg Val Lys
625                 630                 635                 640

Phe Ser Arg Ser Ala Asp Ala Pro Ala Tyr Gln Gln Gly Gln Asn Gln
                645                 650                 655

Leu Tyr Asn Glu Leu Asn Leu Gly Arg Arg Glu Glu Tyr Asp Val Leu
            660                 665                 670

Asp Lys Arg Arg Gly Arg Asp Pro Glu Met Gly Gly Lys Pro Arg Arg
            675                 680                 685

Lys Asn Pro Gln Glu Gly Leu Tyr Asn Glu Leu Gln Lys Asp Lys Met
        690                 695                 700

Ala Glu Ala Tyr Ser Glu Ile Gly Met Lys Gly Glu Arg Arg Arg Gly
705                 710                 715                 720

Lys Gly His Asp Gly Leu Tyr Gln Gly Leu Ser Thr Ala Thr Lys Asp
                725                 730                 735

Thr Tyr Asp Ala Leu His Met Gln Ala Leu Pro Pro Arg
            740                 745

<210> SEQ ID NO 66
<211> LENGTH: 742
<212> TYPE: PRT
<213> ORGANISM: Artificial Sequence
<220> FEATURE:
<223> OTHER INFORMATION: Synthetic

<400> SEQUENCE: 66

Ala Thr Met Leu Leu Leu Val Thr Ser Leu Leu Leu Cys Glu Leu Pro
1               5                   10                  15

His Pro Ala Phe Leu Leu Ile Pro Asp Ile Gln Met Thr Gln Thr Thr
            20                  25                  30

Ser Ser Leu Ser Ala Ser Leu Gly Asp Arg Val Thr Ile Ser Cys Arg
        35                  40                  45

Ala Ser Gln Asp Ile Ser Lys Tyr Leu Asn Trp Tyr Gln Gln Lys Pro
    50                  55                  60

Asp Gly Thr Val Lys Leu Leu Ile Tyr His Thr Ser Arg Leu His Ser
65                  70                  75                  80

Gly Val Pro Ser Arg Phe Ser Gly Ser Gly Ser Gly Thr Asp Tyr Ser
                85                  90                  95

Leu Thr Ile Ser Asn Leu Glu Gln Glu Asp Ile Ala Thr Tyr Phe Cys
            100                 105                 110

Gln Gln Gly Asn Thr Leu Pro Tyr Thr Phe Gly Gly Gly Thr Lys Leu
        115                 120                 125

Glu Ile Thr Gly Gly Gly Gly Ser Gly Gly Gly Gly Ser Gly Gly Gly
```

-continued

```
            130                 135                 140
Gly Ser Gln Val Gln Leu Gln Gln Ser Gly Pro Gly Leu Val Lys Pro
145                 150                 155                 160

Ser Gln Thr Leu Ser Leu Thr Cys Ala Ile Ser Gly Asp Ser Val Ser
                165                 170                 175

Ser Asn Ser Ala Ala Trp Asn Trp Ile Arg Gln Ser Pro Ser Arg Gly
            180                 185                 190

Leu Glu Trp Leu Gly Arg Thr Tyr Tyr Arg Ser Lys Trp Tyr Asn Asp
        195                 200                 205

Tyr Ala Val Ser Val Lys Ser Arg Ile Thr Ile Asn Pro Asp Thr Ser
    210                 215                 220

Lys Asn Gln Phe Ser Leu Gln Leu Asn Ser Val Thr Pro Glu Asp Thr
225                 230                 235                 240

Ala Val Tyr Tyr Cys Ala Arg Glu Val Thr Gly Asp Leu Glu Asp Ala
                245                 250                 255

Phe Asp Ile Trp Gly Gln Gly Thr Met Val Thr Val Ser Ser Gly Gly
            260                 265                 270

Gly Gly Ser Asp Ile Gln Met Thr Gln Ser Pro Ser Ser Leu Ser Ala
        275                 280                 285

Ser Val Gly Asp Arg Val Thr Ile Thr Cys Arg Ala Ser Gln Thr Ile
    290                 295                 300

Trp Ser Tyr Leu Asn Trp Tyr Gln Gln Arg Pro Gly Lys Ala Pro Asn
305                 310                 315                 320

Leu Leu Ile Tyr Ala Ala Ser Ser Leu Gln Ser Gly Val Pro Ser Arg
                325                 330                 335

Phe Ser Gly Arg Gly Ser Gly Thr Asp Phe Thr Leu Thr Ile Ser Ser
            340                 345                 350

Leu Gln Ala Glu Asp Phe Ala Thr Tyr Tyr Cys Gln Gln Ser Tyr Ser
        355                 360                 365

Ile Pro Gln Thr Phe Gly Gln Gly Thr Lys Leu Glu Ile Lys Gly Gly
    370                 375                 380

Gly Gly Ser Gly Gly Gly Gly Ser Gly Gly Gly Gly Ser Glu Val Lys
385                 390                 395                 400

Leu Gln Glu Ser Gly Pro Gly Leu Val Ala Pro Ser Gln Ser Leu Ser
                405                 410                 415

Val Thr Cys Thr Val Ser Gly Val Ser Leu Pro Asp Tyr Gly Val Ser
            420                 425                 430

Trp Ile Arg Gln Pro Pro Arg Lys Gly Leu Glu Trp Leu Gly Val Ile
        435                 440                 445

Trp Gly Ser Glu Thr Thr Tyr Tyr Asn Ser Ala Leu Lys Ser Arg Leu
    450                 455                 460

Thr Ile Ile Lys Asp Asn Ser Lys Ser Gln Val Phe Leu Lys Met Asn
465                 470                 475                 480

Ser Leu Gln Thr Asp Asp Thr Ala Ile Tyr Tyr Cys Ala Lys His Tyr
                485                 490                 495

Tyr Tyr Gly Gly Ser Tyr Ala Met Asp Tyr Trp Gly Gln Gly Thr Ser
            500                 505                 510

Val Thr Val Ser Ser Gly Thr Thr Pro Ala Pro Arg Pro Pro Thr Pro
        515                 520                 525

Thr Pro Ala Pro Thr Ile Ala Ser Gln Pro Leu Ser Leu Arg Pro Glu
    530                 535                 540

Ala Cys Arg Pro Ala Ala Gly Gly Ala Val His Thr Arg Gly Leu Asp
545                 550                 555                 560
```

-continued

```
Phe Ala Cys Asp Ile Tyr Ile Trp Ala Pro Leu Ala Gly Thr Cys Gly
                565                 570                 575

Val Leu Leu Leu Ser Leu Val Ile Thr Leu Tyr Cys Lys Arg Gly Arg
            580                 585                 590

Lys Lys Leu Leu Tyr Ile Phe Lys Gln Pro Phe Met Arg Pro Val Gln
        595                 600                 605

Thr Thr Gln Glu Glu Asp Gly Cys Ser Cys Arg Phe Pro Glu Glu Glu
    610                 615                 620

Glu Gly Gly Cys Glu Leu Arg Val Lys Phe Ser Arg Ser Ala Asp Ala
625                 630                 635                 640

Pro Ala Tyr Gln Gln Gly Gln Asn Gln Leu Tyr Asn Glu Leu Asn Leu
                645                 650                 655

Gly Arg Arg Glu Glu Tyr Asp Val Leu Asp Lys Arg Arg Gly Arg Asp
            660                 665                 670

Pro Glu Met Gly Gly Lys Pro Arg Arg Lys Asn Pro Gln Glu Gly Leu
        675                 680                 685

Tyr Asn Glu Leu Gln Lys Asp Lys Met Ala Glu Ala Tyr Ser Glu Ile
    690                 695                 700

Gly Met Lys Gly Glu Arg Arg Arg Gly Lys Gly His Asp Gly Leu Tyr
705                 710                 715                 720

Gln Gly Leu Ser Thr Ala Thr Lys Asp Thr Tyr Asp Ala Leu His Met
                725                 730                 735

Gln Ala Leu Pro Pro Arg
            740

<210> SEQ ID NO 67
<211> LENGTH: 755
<212> TYPE: PRT
<213> ORGANISM: Artificial Sequence
<220> FEATURE:
<223> OTHER INFORMATION: Synthetic

<400> SEQUENCE: 67

Ala Thr Met Leu Leu Leu Val Thr Ser Leu Leu Leu Cys Glu Leu Pro
1               5                   10                  15

His Pro Ala Phe Leu Leu Ile Pro Asp Ile Gln Met Thr Gln Thr Thr
            20                  25                  30

Ser Ser Leu Ser Ala Ser Leu Gly Asp Arg Val Thr Ile Ser Cys Arg
        35                  40                  45

Ala Ser Gln Asp Ile Ser Lys Tyr Leu Asn Trp Tyr Gln Gln Lys Pro
    50                  55                  60

Asp Gly Thr Val Lys Leu Leu Ile Tyr His Thr Ser Arg Leu His Ser
65                  70                  75                  80

Gly Val Pro Ser Arg Phe Ser Gly Ser Gly Ser Gly Thr Asp Tyr Ser
                85                  90                  95

Leu Thr Ile Ser Asn Leu Glu Gln Glu Asp Ile Ala Thr Tyr Phe Cys
            100                 105                 110

Gln Gln Gly Asn Thr Leu Pro Tyr Thr Phe Gly Gly Gly Thr Lys Leu
        115                 120                 125

Glu Ile Thr Gly Gly Cys Gly Ser Gly Gly Gly Ser Gly Gly Gly
    130                 135                 140

Gly Ser Gln Val Gln Leu Gln Gln Ser Gly Pro Gly Leu Val Lys Pro
145                 150                 155                 160

Ser Gln Thr Leu Ser Leu Thr Cys Ala Ile Ser Gly Asp Ser Val Ser
                165                 170                 175
```

```
Ser Asn Ser Ala Ala Trp Asn Trp Ile Arg Gln Ser Pro Ser Arg Gly
            180                 185                 190

Leu Glu Trp Leu Gly Arg Thr Tyr Tyr Arg Ser Lys Trp Tyr Asn Asp
            195                 200                 205

Tyr Ala Val Ser Val Lys Ser Arg Ile Thr Ile Asn Pro Asp Thr Ser
            210                 215                 220

Lys Asn Gln Phe Ser Leu Gln Leu Asn Ser Val Thr Pro Glu Asp Thr
225                 230                 235                 240

Ala Val Tyr Tyr Cys Ala Arg Glu Val Thr Gly Asp Leu Glu Asp Ala
                245                 250                 255

Phe Asp Ile Trp Gly Gln Gly Thr Met Val Thr Val Ser Ser Gly Ser
            260                 265                 270

Thr Ser Gly Ser Gly Lys Pro Gly Ser Gly Glu Gly Ser Thr Lys Gly
            275                 280                 285

Asp Ile Gln Met Thr Gln Ser Pro Ser Ser Leu Ser Ala Ser Val Gly
            290                 295                 300

Asp Arg Val Thr Ile Thr Cys Arg Ala Ser Gln Thr Ile Trp Ser Tyr
305                 310                 315                 320

Leu Asn Trp Tyr Gln Gln Arg Pro Gly Lys Ala Pro Asn Leu Leu Ile
                325                 330                 335

Tyr Ala Ala Ser Ser Leu Gln Ser Gly Val Pro Ser Arg Phe Ser Gly
            340                 345                 350

Arg Gly Ser Gly Thr Asp Phe Thr Leu Thr Ile Ser Ser Leu Gln Ala
            355                 360                 365

Glu Asp Phe Ala Thr Tyr Tyr Cys Gln Gln Ser Tyr Ser Ile Pro Gln
            370                 375                 380

Thr Phe Gly Gln Gly Thr Lys Leu Glu Ile Lys Gly Gly Gly Gly Ser
385                 390                 395                 400

Gly Gly Gly Gly Ser Gly Gly Cys Gly Ser Glu Val Lys Leu Gln Glu
                405                 410                 415

Ser Gly Pro Gly Leu Val Ala Pro Ser Gln Ser Leu Ser Val Thr Cys
            420                 425                 430

Thr Val Ser Gly Val Ser Leu Pro Asp Tyr Gly Val Ser Trp Ile Arg
            435                 440                 445

Gln Pro Pro Arg Lys Gly Leu Glu Trp Leu Gly Val Ile Trp Gly Ser
450                 455                 460

Glu Thr Thr Tyr Tyr Asn Ser Ala Leu Lys Ser Arg Leu Thr Ile Ile
465                 470                 475                 480

Lys Asp Asn Ser Lys Ser Gln Val Phe Leu Lys Met Asn Ser Leu Gln
                485                 490                 495

Thr Asp Asp Thr Ala Ile Tyr Tyr Cys Ala Lys His Tyr Tyr Tyr Gly
            500                 505                 510

Gly Ser Tyr Ala Met Asp Tyr Trp Gly Gln Gly Thr Ser Val Thr Val
            515                 520                 525

Ser Ser Ser Gly Thr Thr Thr Pro Ala Pro Arg Pro Pro Thr Pro Ala
530                 535                 540

Pro Thr Ile Ala Ser Gln Pro Leu Ser Leu Arg Pro Glu Ala Cys Arg
545                 550                 555                 560

Pro Ala Ala Gly Gly Ala Val His Thr Arg Gly Leu Asp Phe Ala Cys
                565                 570                 575

Asp Ile Tyr Ile Trp Ala Pro Leu Ala Gly Thr Cys Gly Val Leu Leu
            580                 585                 590
```

```
Leu Ser Leu Val Ile Thr Leu Tyr Cys Lys Arg Gly Arg Lys Lys Leu
            595                 600                 605

Leu Tyr Ile Phe Lys Gln Pro Phe Met Arg Pro Val Gln Thr Thr Gln
            610                 615                 620

Glu Glu Asp Gly Cys Ser Cys Arg Phe Pro Glu Glu Glu Glu Gly Gly
625                 630                 635                 640

Cys Glu Leu Arg Val Lys Phe Ser Arg Ser Ala Asp Ala Pro Ala Tyr
            645                 650                 655

Gln Gln Gly Gln Asn Gln Leu Tyr Asn Glu Leu Asn Leu Gly Arg Arg
            660                 665                 670

Glu Glu Tyr Asp Val Leu Asp Lys Arg Arg Gly Arg Asp Pro Glu Met
            675                 680                 685

Gly Gly Lys Pro Arg Arg Lys Asn Pro Gln Glu Gly Leu Tyr Asn Glu
            690                 695                 700

Leu Gln Lys Asp Lys Met Ala Glu Ala Tyr Ser Glu Ile Gly Met Lys
705                 710                 715                 720

Gly Glu Arg Arg Arg Gly Lys Gly His Asp Gly Leu Tyr Gln Gly Leu
            725                 730                 735

Ser Thr Ala Thr Lys Asp Thr Tyr Asp Ala Leu His Met Gln Ala Leu
            740                 745                 750

Pro Pro Arg
        755

<210> SEQ ID NO 68
<211> LENGTH: 744
<212> TYPE: PRT
<213> ORGANISM: Artificial Sequence
<220> FEATURE:
<223> OTHER INFORMATION: Synthetic

<400> SEQUENCE: 68

Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
            20                  25                  30

Ser Ala Ser Leu Gly Asp Arg Val Thr Ile Ser Cys Arg Ala Ser Gln
        35                  40                  45

Asp Ile Ser Lys Tyr Leu Asn Trp Tyr Gln Gln Lys Pro Asp Gly Thr
    50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
            85                  90                  95

Ser Asn Leu Glu Gln Glu Asp Ile Ala Thr Tyr Phe Cys Gln Gln Gly
            100                 105                 110

Asn Thr Leu Pro Tyr Thr Phe Gly Gly Gly Thr Lys Leu Glu Ile Thr
        115                 120                 125

Gly Gly Gly Gly Ser Gly Gly Gly Ser Gln Val Gln Leu Gln Gln
130                 135                 140

Ser Gly Pro Gly Leu Val Lys Pro Ser Gln Thr Leu Ser Leu Thr Cys
145                 150                 155                 160

Ala Ile Ser Gly Asp Ser Val Ser Ser Asn Ser Ala Ala Trp Asn Trp
            165                 170                 175

Ile Arg Gln Ser Pro Ser Arg Gly Leu Glu Trp Leu Gly Arg Thr Tyr
            180                 185                 190
```

-continued

```
Tyr Arg Ser Lys Trp Tyr Asn Asp Tyr Ala Val Ser Val Lys Ser Arg
            195                 200                 205

Ile Thr Ile Asn Pro Asp Thr Ser Lys Asn Gln Phe Ser Leu Gln Leu
    210                 215                 220

Asn Ser Val Thr Pro Glu Asp Thr Ala Val Tyr Tyr Cys Ala Arg Glu
225                 230                 235                 240

Val Thr Gly Asp Leu Glu Asp Ala Phe Asp Ile Trp Gly Gln Gly Thr
                245                 250                 255

Met Val Thr Val Ser Ser Gly Ser Thr Ser Gly Ser Gly Lys Pro Gly
        260                 265                 270

Ser Gly Glu Gly Ser Thr Lys Gly Asp Ile Gln Met Thr Gln Ser Pro
    275                 280                 285

Ser Ser Leu Ser Ala Ser Val Gly Asp Arg Val Thr Ile Thr Cys Arg
    290                 295                 300

Ala Ser Gln Thr Ile Trp Ser Tyr Leu Asn Trp Tyr Gln Gln Arg Pro
305                 310                 315                 320

Gly Lys Ala Pro Asn Leu Leu Ile Tyr Ala Ala Ser Ser Leu Gln Ser
                325                 330                 335

Gly Val Pro Ser Arg Phe Ser Gly Arg Gly Ser Gly Thr Asp Phe Thr
            340                 345                 350

Leu Thr Ile Ser Ser Leu Gln Ala Glu Asp Phe Ala Thr Tyr Tyr Cys
            355                 360                 365

Gln Gln Ser Tyr Ser Ile Pro Gln Thr Phe Gly Gln Gly Thr Lys Leu
        370                 375                 380

Glu Ile Lys Gly Gly Gly Ser Gly Gly Gly Ser Glu Val Lys
385                 390                 395                 400

Leu Gln Glu Ser Gly Pro Gly Leu Val Ala Pro Ser Gln Ser Leu Ser
                405                 410                 415

Val Thr Cys Thr Val Ser Gly Val Ser Leu Pro Asp Tyr Gly Val Ser
            420                 425                 430

Trp Ile Arg Gln Pro Pro Arg Lys Gly Leu Glu Trp Leu Gly Val Ile
        435                 440                 445

Trp Gly Ser Glu Thr Thr Tyr Tyr Asn Ser Ala Leu Lys Ser Arg Leu
    450                 455                 460

Thr Ile Ile Lys Asp Asn Ser Lys Ser Gln Val Phe Leu Lys Met Asn
465                 470                 475                 480

Ser Leu Gln Thr Asp Asp Thr Ala Ile Tyr Tyr Cys Ala Lys His Tyr
                485                 490                 495

Tyr Tyr Gly Gly Ser Tyr Ala Met Asp Tyr Trp Gly Gln Gly Thr Ser
            500                 505                 510

Val Thr Val Ser Ser Thr Ser Ser Gly Thr Thr Thr Pro Ala Pro Arg
        515                 520                 525

Pro Pro Thr Pro Ala Pro Thr Ile Ala Ser Gln Pro Leu Ser Leu Arg
    530                 535                 540

Pro Glu Ala Cys Arg Pro Ala Ala Gly Gly Ala Val His Thr Arg Gly
545                 550                 555                 560

Leu Asp Phe Ala Cys Asp Ile Tyr Ile Trp Ala Pro Leu Ala Gly Thr
                565                 570                 575

Cys Gly Val Leu Leu Leu Ser Leu Val Ile Thr Leu Tyr Cys Lys Arg
            580                 585                 590

Gly Arg Lys Lys Leu Leu Tyr Ile Phe Lys Gln Pro Phe Met Arg Pro
        595                 600                 605

Val Gln Thr Thr Gln Glu Glu Asp Gly Cys Ser Cys Arg Phe Pro Glu
```

```
                610                 615                 620
Glu Glu Glu Gly Gly Cys Glu Leu Arg Val Lys Phe Ser Arg Ser Ala
625                 630                 635                 640

Asp Ala Pro Ala Tyr Lys Gln Gly Gln Asn Gln Leu Tyr Asn Glu Leu
                645                 650                 655

Asn Leu Gly Arg Arg Glu Glu Tyr Asp Val Leu Asp Lys Arg Arg Gly
                660                 665                 670

Arg Asp Pro Glu Met Gly Gly Lys Pro Arg Arg Lys Asn Pro Gln Glu
            675                 680                 685

Gly Leu Tyr Asn Glu Leu Gln Lys Asp Lys Met Ala Glu Ala Tyr Ser
            690                 695                 700

Glu Ile Gly Met Lys Gly Glu Arg Arg Arg Gly Lys Gly His Asp Gly
705                 710                 715                 720

Leu Tyr Gln Gly Leu Ser Thr Ala Thr Lys Asp Thr Tyr Asp Ala Leu
                725                 730                 735

His Met Gln Ala Leu Pro Pro Arg
            740
```

<210> SEQ ID NO 69
<211> LENGTH: 744
<212> TYPE: PRT
<213> ORGANISM: Artificial Sequence
<220> FEATURE:
<223> OTHER INFORMATION: Synthetic

<400> SEQUENCE: 69

```
Met Leu Leu Leu Val Thr Ser Leu Leu Leu Cys Glu Leu Pro His Pro
1               5                   10                  15

Ala Phe Leu Leu Ile Pro Gln Val Gln Leu Gln Gln Ser Gly Pro Gly
                20                  25                  30

Leu Val Lys Pro Ser Gln Thr Leu Ser Leu Thr Cys Ala Ile Ser Gly
            35                  40                  45

Asp Ser Val Ser Ser Asn Ser Ala Ala Trp Asn Trp Ile Arg Gln Ser
    50                  55                  60

Pro Ser Arg Gly Leu Glu Trp Leu Gly Arg Thr Tyr Tyr Arg Ser Lys
65                  70                  75                  80

Trp Tyr Asn Asp Tyr Ala Val Ser Val Lys Ser Arg Ile Thr Ile Asn
                85                  90                  95

Pro Asp Thr Ser Lys Asn Gln Phe Ser Leu Gln Leu Asn Ser Val Thr
            100                 105                 110

Pro Glu Asp Thr Ala Val Tyr Tyr Cys Ala Arg Glu Val Thr Gly Asp
        115                 120                 125

Leu Glu Asp Ala Phe Asp Ile Trp Gly Gln Gly Thr Met Val Thr Val
130                 135                 140

Ser Ser Gly Gly Gly Gly Ser Gly Gly Gly Gly Ser Asp Ile Gln Met
145                 150                 155                 160

Thr Gln Thr Thr Ser Ser Leu Ser Ala Ser Leu Gly Asp Arg Val Thr
                165                 170                 175

Ile Ser Cys Arg Ala Ser Gln Asp Ile Ser Lys Tyr Leu Asn Trp Tyr
            180                 185                 190

Gln Gln Lys Pro Asp Gly Thr Val Lys Leu Leu Ile Tyr His Thr Ser
        195                 200                 205

Arg Leu His Ser Gly Val Pro Ser Arg Phe Ser Gly Ser Gly Ser Gly
    210                 215                 220

Thr Asp Tyr Ser Leu Thr Ile Ser Asn Leu Glu Gln Glu Asp Ile Ala
```

-continued

```
            225                 230                 235                 240
        Thr Tyr Phe Cys Gln Gln Gly Asn Thr Leu Pro Tyr Thr Phe Gly Gly
                        245                 250                 255
        Gly Thr Lys Leu Glu Ile Thr Gly Ser Thr Ser Gly Ser Gly Lys Pro
                        260                 265                 270
        Gly Ser Gly Glu Gly Ser Thr Lys Gly Glu Val Lys Leu Gln Glu Ser
                        275                 280                 285
        Gly Pro Gly Leu Val Ala Pro Ser Gln Ser Leu Ser Val Thr Cys Thr
                        290                 295                 300
        Val Ser Gly Val Ser Leu Pro Asp Tyr Gly Val Ser Trp Ile Arg Gln
        305                 310                 315                 320
        Pro Pro Arg Lys Gly Leu Glu Trp Leu Gly Val Ile Trp Gly Ser Glu
                        325                 330                 335
        Thr Thr Tyr Tyr Asn Ser Ala Leu Lys Ser Arg Leu Thr Ile Ile Lys
                        340                 345                 350
        Asp Asn Ser Lys Ser Gln Val Phe Leu Lys Met Asn Ser Leu Gln Thr
                        355                 360                 365
        Asp Asp Thr Ala Ile Tyr Tyr Cys Ala Lys His Tyr Tyr Tyr Gly Gly
                        370                 375                 380
        Ser Tyr Ala Met Asp Tyr Trp Gly Gln Gly Thr Ser Val Thr Val Ser
        385                 390                 395                 400
        Ser Gly Gly Gly Ser Gly Gly Gly Ser Asp Ile Gln Met Thr
                        405                 410                 415
        Gln Ser Pro Ser Ser Leu Ser Ala Ser Val Gly Asp Arg Val Thr Ile
                        420                 425                 430
        Thr Cys Arg Ala Ser Gln Thr Ile Trp Ser Tyr Leu Asn Trp Tyr Gln
                        435                 440                 445
        Gln Arg Pro Gly Lys Ala Pro Asn Leu Leu Ile Tyr Ala Ala Ser Ser
                        450                 455                 460
        Leu Gln Ser Gly Val Pro Ser Arg Phe Ser Gly Arg Gly Ser Gly Thr
        465                 470                 475                 480
        Asp Phe Thr Leu Thr Ile Ser Ser Leu Gln Ala Glu Asp Phe Ala Thr
                        485                 490                 495
        Tyr Tyr Cys Gln Gln Ser Tyr Ser Ile Pro Gln Thr Phe Gly Gln Gly
                        500                 505                 510
        Thr Lys Leu Glu Ile Lys Thr Ser Ser Gly Thr Thr Thr Pro Ala Pro
                        515                 520                 525
        Arg Pro Pro Thr Pro Ala Pro Thr Ile Ala Ser Gln Pro Leu Ser Leu
        530                 535                 540
        Arg Pro Glu Ala Cys Arg Pro Ala Ala Gly Gly Ala Val His Thr Arg
        545                 550                 555                 560
        Gly Leu Asp Phe Ala Cys Asp Ile Tyr Ile Trp Ala Pro Leu Ala Gly
                        565                 570                 575
        Thr Cys Gly Val Leu Leu Leu Ser Leu Val Ile Thr Leu Tyr Cys Lys
                        580                 585                 590
        Arg Gly Arg Lys Lys Leu Leu Tyr Ile Phe Lys Gln Pro Phe Met Arg
                        595                 600                 605
        Pro Val Gln Thr Thr Gln Glu Glu Asp Gly Ser Cys Arg Phe Pro Glu
                        610                 615                 620
        Glu Glu Glu Gly Gly Cys Glu Leu Arg Val Lys Phe Ser Arg Ser Ala
        625                 630                 635                 640
        Asp Ala Pro Ala Tyr Lys Gln Gly Gln Asn Gln Leu Tyr Asn Glu Leu
                        645                 650                 655
```

```
Asn Leu Gly Arg Arg Glu Glu Tyr Asp Val Leu Asp Lys Arg Arg Gly
            660                 665                 670

Arg Asp Pro Glu Met Gly Gly Lys Pro Arg Arg Lys Asn Pro Gln Glu
            675                 680                 685

Gly Leu Tyr Asn Glu Leu Gln Lys Asp Lys Met Ala Glu Ala Tyr Ser
            690                 695                 700

Glu Ile Gly Met Lys Gly Glu Arg Arg Arg Gly Lys Gly His Asp Gly
705                 710                 715                 720

Leu Tyr Gln Gly Leu Ser Thr Ala Thr Lys Asp Thr Tyr Asp Ala Leu
                725                 730                 735

His Met Gln Ala Leu Pro Pro Arg
            740

<210> SEQ ID NO 70
<211> LENGTH: 747
<212> TYPE: PRT
<213> ORGANISM: Artificial Sequence
<220> FEATURE:
<223> OTHER INFORMATION: Synthetic

<400> SEQUENCE: 70

Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
            35                  40                  45

Gln Asp Ile Ser Lys Tyr Leu Asn Trp Tyr Gln Gln Lys Pro Asp Gly
50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
            115                 120                 125

Thr Gly Gly Gly Gly Ser Gly Gly Gly Gly Ser Cys Gly Gly Gly Ser
            130                 135                 140

Gln Val Gln Leu Gln Gln Ser Gly Pro Gly Leu Val Lys Pro Ser Gln
145                 150                 155                 160

Thr Leu Ser Leu Thr Cys Ala Ile Ser Gly Asp Ser Val Ser Ser Asn
                165                 170                 175

Ser Ala Ala Trp Asn Trp Ile Arg Gln Ser Pro Ser Arg Gly Leu Glu
            180                 185                 190

Trp Leu Gly Arg Thr Tyr Tyr Arg Ser Lys Trp Tyr Asn Asp Tyr Ala
            195                 200                 205

Val Ser Val Lys Ser Arg Ile Thr Ile Asn Pro Asp Thr Ser Lys Asn
            210                 215                 220

Gln Phe Ser Leu Gln Leu Asn Ser Val Thr Pro Glu Asp Thr Ala Val
225                 230                 235                 240

Tyr Tyr Cys Ala Arg Glu Val Thr Gly Asp Leu Glu Asp Ala Phe Asp
                245                 250                 255

Ile Trp Gly Gln Gly Thr Met Val Thr Val Ser Ser Gly Gly Gly Gly
            260                 265                 270
```

```
Ser Gly Gly Gly Gly Ser Asp Ile Gln Met Thr Gln Ser Pro Ser Ser
            275                 280                 285

Leu Ser Ala Ser Val Gly Asp Arg Val Thr Ile Thr Cys Arg Ala Ser
        290                 295                 300

Gln Thr Ile Trp Ser Tyr Leu Asn Trp Tyr Gln Gln Arg Pro Gly Lys
305                 310                 315                 320

Ala Pro Asn Leu Leu Ile Tyr Ala Ala Ser Ser Leu Gln Ser Gly Val
                325                 330                 335

Pro Ser Arg Phe Ser Gly Arg Gly Ser Gly Thr Asp Phe Thr Leu Thr
            340                 345                 350

Ile Ser Ser Leu Gln Ala Glu Asp Phe Ala Thr Tyr Tyr Cys Gln Gln
        355                 360                 365

Ser Tyr Ser Ile Pro Gln Thr Phe Gly Gln Gly Thr Lys Leu Glu Ile
    370                 375                 380

Lys Gly Gly Gly Gly Cys Gly Gly Gly Ser Gly Gly Gly Gly Ser
385                 390                 395                 400

Glu Val Lys Leu Gln Glu Ser Gly Pro Gly Leu Val Ala Pro Ser Gln
                405                 410                 415

Ser Leu Ser Val Thr Cys Thr Val Ser Gly Val Ser Leu Pro Asp Tyr
        420                 425                 430

Gly Val Ser Trp Ile Arg Gln Pro Pro Arg Lys Gly Leu Glu Trp Leu
            435                 440                 445

Gly Val Ile Trp Gly Ser Glu Thr Thr Tyr Tyr Asn Ser Ala Leu Lys
        450                 455                 460

Ser Arg Leu Thr Ile Ile Lys Asp Asn Ser Lys Ser Gln Val Phe Leu
465                 470                 475                 480

Lys Met Asn Ser Leu Gln Thr Asp Asp Thr Ala Ile Tyr Tyr Cys Ala
                485                 490                 495

Lys His Tyr Tyr Tyr Gly Gly Ser Tyr Ala Met Asp Tyr Trp Gly Gln
        500                 505                 510

Gly Thr Ser Val Thr Val Ser Ser Thr Ser Gly Thr Thr Thr Pro
            515                 520                 525

Ala Pro Arg Pro Pro Thr Pro Ala Pro Thr Ile Ala Ser Gln Pro Leu
        530                 535                 540

Ser Leu Arg Pro Glu Ala Cys Arg Pro Ala Ala Gly Gly Ala Val His
545                 550                 555                 560

Thr Arg Gly Leu Asp Phe Ala Cys Asp Ile Tyr Ile Trp Ala Pro Leu
                565                 570                 575

Ala Gly Thr Cys Gly Val Leu Leu Leu Ser Leu Val Ile Thr Leu Tyr
            580                 585                 590

Cys Lys Arg Gly Arg Lys Lys Leu Leu Tyr Ile Phe Lys Gln Pro Phe
        595                 600                 605

Met Arg Pro Val Gln Thr Thr Gln Glu Glu Asp Gly Cys Ser Cys Arg
    610                 615                 620

Phe Pro Glu Glu Glu Glu Gly Gly Cys Glu Leu Arg Val Lys Phe Ser
625                 630                 635                 640

Arg Ser Ala Asp Ala Pro Ala Tyr Lys Gln Gly Gln Asn Gln Leu Tyr
                645                 650                 655

Asn Glu Leu Asn Leu Gly Arg Arg Glu Glu Tyr Asp Val Leu Asp Lys
            660                 665                 670

Arg Arg Gly Arg Asp Pro Glu Met Gly Gly Lys Pro Arg Arg Lys Asn
        675                 680                 685
```

```
Pro Gln Glu Gly Leu Tyr Asn Glu Leu Gln Lys Asp Lys Met Ala Glu
    690                 695                 700
Ala Tyr Ser Glu Ile Gly Met Lys Gly Glu Arg Arg Arg Gly Lys Gly
705                 710                 715                 720
His Asp Gly Leu Tyr Gln Gly Leu Ser Thr Ala Thr Lys Asp Thr Tyr
                725                 730                 735
Asp Ala Leu His Met Gln Ala Leu Pro Pro Arg
                740                 745

<210> SEQ ID NO 71
<211> LENGTH: 2256
<212> TYPE: DNA
<213> ORGANISM: Artificial Sequence
<220> FEATURE:
<223> OTHER INFORMATION: Synthetic

<400> SEQUENCE: 71
```

| | | | | | |
|---|---|---|---|---|---|
| atgctgctgc | tcgtgacatc | tctgctgctg | tgcgagctgc | ccacccccgc | ctttctgctg | 60 |
| attcctgata | ttcagatgac | ccagaccacc | tccagcctgt | ccgccagcct | gggcgatcgc | 120 |
| gtgaccatct | cttgcagagc | cagccaggac | atcagcaagt | atctgaattg | gtatcagcag | 180 |
| aaacccgacg | gcaccgtgaa | gctgctgatc | taccacacca | gcagactgca | ctccggcgtg | 240 |
| ccatccagat | tcagcggctc | tggctccggc | accgattata | gcctgaccat | cagcaacctg | 300 |
| gaacaggaag | atatcgctac | ctactttgt | cagcaaggca | cacccctgcc | ctacaccttc | 360 |
| ggcggaggca | caaaactgga | aattaccggc | agcaccagcg | gcagcggaaa | gcctggaagc | 420 |
| ggcgagggaa | gcaccaaggg | cgaagtgaaa | ctgcaggaaa | gcggacccgg | actggtggcc | 480 |
| ccaagccagt | ctctgagcgt | gacatgtacc | gtgtccggcg | tgtccctgcc | cgactatggc | 540 |
| gtgtcctgga | tcaggcagcc | ccccagaaag | ggactggaat | ggctgggagt | gatctggggc | 600 |
| agcgagacaa | cctactacaa | cagcgccctg | aagtccaggc | tgaccattat | caaggacaac | 660 |
| tccaagagcc | aggtgttcct | gaagatgaac | agcctgcaga | ccgacgacac | agccatctac | 720 |
| tattgcgcca | gcactactac | tacggcggc | agctacgcca | tggactactg | gggacaggga | 780 |
| acctccgtga | ccgtgtcctc | tggcggaggg | ggatctggcg | gcggaggatc | tggggaggc | 840 |
| ggcagtgggg | gcggaggaag | tggcggggga | ggctctcagg | tgcagctgca | gcagtctggc | 900 |
| cctggcctcg | tgaagcctag | ccagaccctg | agcctgacct | gtgccatcag | cggcgatagc | 960 |
| gtgtccagca | atagcgccgc | ctggaactgg | atcagacaga | gccctagcag | aggcctggaa | 1020 |
| tggctgggcc | ggacctacta | ccggtccaag | tggtacaacg | actacgccgt | gtccgtgaag | 1080 |
| tcccggatca | ccatcaaccc | cgacaccagc | aagaaccagt | tctccctgca | gctgaacagc | 1140 |
| gtgaccccg | aggataccgc | cgtgtactac | tgcgccagag | aagtgaccgg | cgacctggaa | 1200 |
| gatgccttcg | acatctgggg | ccagggcaca | atggtcaccg | tgtctagcgg | aggcggcgga | 1260 |
| agcgacatcc | agatgacaca | gagccccagc | tccctgagcg | ccagcgtggg | agacagagtg | 1320 |
| accatcacct | gtcgggccag | ccagaccatc | tggtcctacc | tgaactggta | tcagcagcgg | 1380 |
| cctggcaagg | cccccaacct | gctgatctat | gccgccagct | cactgcagag | cggcgtgccc | 1440 |
| agcagatttt | ccggcagagg | cagcggcacc | gacttcaccc | tgacaatcag | ttccctgcaa | 1500 |
| gccgaggact | tcgccaccta | ctactgccag | cagagctaca | gcatccccca | gaccttcggc | 1560 |
| caggggacca | agctggaaat | caagaccacg | acgccagcgc | cgcgaccacc | aacaccggcg | 1620 |
| cccaccatcg | cgtcgcagcc | cctgtccctg | cgcccagagg | cgtgccggcc | agcggcgggg | 1680 |
| ggcgcagtgc | acacgagggg | gctggacttc | gcctgtgata | tctacatctg | ggcgcccttg | 1740 |

```
gccgggactt gtggggtcct tctcctgtca ctggttatca ccctttactg caaacggggc    1800
agaaagaaac tcctgtatat attcaaacaa ccatttatga gaccagtaca aactactcaa    1860
gaggaagatg gctgtagctg ccgatttcca gaagaagaag aaggaggatg tgaactgaga    1920
gtgaagttca gcaggagcgc agacgccccc gcgtacaagc agggccagaa ccagctctat    1980
aacgagctca atctaggacg aagagaggag tacgatgttt tggacaagag acgtggccgg    2040
gaccctgaga tgggggggaaa gccgagaagg aagaaccctc aggaaggcct gtacaatgaa    2100
ctgcagaaag ataagatggc ggaggcctac agtgagattg ggatgaaagg cgagcgccgg    2160
aggggcaagg ggcacgatgg cctttaccag ggtctcagta cagccaccaa ggacacctac    2220
gacgcccttc acatgcaggc cctgccccct cgctaa                              2256
```

<210> SEQ ID NO 72
<211> LENGTH: 2301
<212> TYPE: DNA
<213> ORGANISM: Artificial Sequence
<220> FEATURE:
<223> OTHER INFORMATION: Synthetic

<400> SEQUENCE: 72

```
atgctgctgc tcgtgacaag cctgctgctg tgcgagctgc cccaccctgc ctttctgctg      60
atccctcagg tgcagctgca gcagtctggc cctggcctcg tgaagcctag ccagaccctg     120
agcctgacct gtgccatcag cggcgatagc gtgtccagca atagcgccgc tggaactggg     180
atccggcaga gcccttctag aggcctggaa tggctgggcc ggacctacta ccggtccaag     240
tggtacaacg actacgccgt gtccgtgaag tcccggatca ccatcaaccc cgacaccagc     300
aagaaccagt tctccctgca gctgaacagc gtgaccccog aggataccgc cgtgtactac     360
tgcgccagag aagtgaccgg cgacctggaa gatgccttcg acatctgggg ccagggcaca     420
atggtcaccg tgtctagcgg cagcacaagc ggctctggca gcctggatc tggcgagggc      480 tctaccaagg gcgacatcca gatgacccag agccccagca gcctgtctgc cagcgtgggc     540
gacagagtga ccatcacctg tagggccagc cagaccatct ggtcctacct gaactggtat     600
cagcagaggc ccggcaaggc ccccaacctg ctgatctatg ccgcctccag tctgcagagc     660
ggcgtgccca gcagattcag cggcagaggc agcggcaccg acttcaccct gaccattagt     720
agtctgcagg ccgaggactt cgccacctac tactgccagc agagctacag catcccccag     780
accttcggcc aggggaccaa gctggaaatc aagggcggag gcggaagtgg cggcggagga     840
tctgggggag gcggatcagg cggagggggc tcagggggg gaggctctga tattcagatg     900
acacagacca cctccagcct gagcgcctct ctgggagatc gcgtgacaat ctcctgccgc     960
gccagccagg acatcagcaa gtatctgaat tggtatcagc agaaacccga cggcaccgtg    1020
aagctgctga tctaccacac cagcagactg cactccggcg tgccatccag atttccggc    1080 agcggctccg gcaccgatta tagcctgacc atcagcaacc tggaacagga agatatcgct    1140
acctactttt gtcagcaagg caacaccctg ccctacacct tcggcggagg cacaaaactg    1200
gaaattaccg gctccaccag cggcagcgga agcctggaa gcggagaggg aagcacaaag    1260
ggcgaagtga aactgcagga aagcggaccc ggactggtgg ccccaagcca gtctctgagc    1320
gtgacatgta ccgtgtccgg cgtgtccctg cccgactatg gcgtgtcctg atcagacag    1380 cccccccagaa agggactgga atggctggga gtgatctggg gcagcgagac aacctactac    1440
aacagcgccc tgaagtccag gctgacaatc atcaaggaca actccaagag ccaggtgttc    1500
```

| | |
|---|---|
| ctgaagatga attccctgca gaccgacgac acagccatct actattgcgc caagcactac | 1560 |
| tactacggcg gcagctacgc catggactac tggggacagg gaacctccgt gaccgtgtcc | 1620 |
| tcttccggaa ccacgacgcc agcgccgcga ccaccaacac cggcgcccac catcgcgtcg | 1680 |
| cagcccctgt ccctgcgccc agaggcgtgc cggccagcgg cggggggcgc agtgcacacg | 1740 |
| aggggggctgg acttcgcctg tgatatctac atctgggcgc ccttggccgg gacttgtggg | 1800 |
| gtccttctcc tgtcactggt tatcacccct tactgcaaac ggggcagaaa gaaactcctg | 1860 |
| tatatattca acaaccatt tatgagacca gtacaaacta ctcaagagga agatggctgt | 1920 |
| agctgccgat ttccagaaga agaagaagga ggatgtgaac tgagagtgaa gttcagcagg | 1980 |
| agcgcagacg cccccgcgta ccaacagggc cagaaccagc tctataacga gctcaatcta | 2040 |
| ggacgaagag aggagtacga tgttttggac aagagacgtg gccggaccc tgagatgggg | 2100 |
| ggaaagccga gaaggaagaa ccctcaggaa ggcctgtaca atgaactgca gaaagataag | 2160 |
| atggcggagg cctacagtga gattgggatg aaaggcgagc gccggagggg caaggggcac | 2220 |
| gatggccttt accagggtct cagtacagcc accaaggaca cctacgacgc ccttcacatg | 2280 |
| caggcccctgc cccctcgcta a | 2301 |

<210> SEQ ID NO 73
<211> LENGTH: 2250
<212> TYPE: DNA
<213> ORGANISM: Artificial Sequence
<220> FEATURE:
<223> OTHER INFORMATION: Synthetic

<400> SEQUENCE: 73

| | |
|---|---|
| atggctctgc ctgtgacagc tctgctgctg cctctggccc tgctgctcca tgctgctaga | 60 |
| cctcaggtgc agctccagca gtctggccca ggactggtca agcctagcca gaccctgagc | 120 |
| ctgacctgcg ccatcagcgg cgacagcgtg tcctctaaca gcgccgcctg gaactggatc | 180 |
| agacagagcc ccagcagagg cctggaatgg ctgggccgga cctactaccg gtccaagtgg | 240 |
| tacaacgact acgccgtgtc cgtgaagtcc cggatcacca tcaaccccga caccagcaag | 300 |
| aaccagttct ccctgcagct gaacagcgtg accctgagg acaccgccgt gtactactgc | 360 |
| gccagagaag tgaccggcga cctggaagat gccttcgaca tctggggcca gggcaccatg | 420 |
| gtcaccgtgt ctagcggagg cggcggaagc gacatccaga tgacccagag ccctagctcc | 480 |
| ctgagcgcca gcgtgggcga cagagtgacc atcacctgtc gggccagcca gaccatctgg | 540 |
| tcctacctga attggtatca gcagcggcca ggcaaggccc ctaacctgct gatctatgcc | 600 |
| gccagcagcc tgcagagcgg cgtgccaagc agattctctg gcagaggctc cggcaccgac | 660 |
| ttcaccctga caatcagttc cctgcaggcc gaggacttcg ccacctacta ctgccagcag | 720 |
| tcctacagca tccctcagac cttcggccag ggaccaagc tggaaatcaa gggtggcgga | 780 |
| ggatctggcg gcgtggtag tggcggcgga ggttcaggtg gtggcggctc cgatattcag | 840 |
| atgacacaga ccacctccag cctgtccgcc tccctgggag atagagtgac aatctcctgc | 900 |
| agggcctccc aggacatcag caagtatctc aactggtacc agcagaaacc gacggcacc | 960 |
| gtgaagctgc tcatctacca caccagcaga ctgcactccg gcgtgccctc tagattttcc | 1020 |
| ggctctggca gcggcacaga ctactccctg accatctcca acctggaaca ggaagatatc | 1080 |
| gctacttact ctgtcagca aggcaacacc ctgccctaca ccttcggcgg aggcacaaaa | 1140 |
| ctggaaatta ccggcagcac cagcggcagc ggaaagcctg gaagcggcga gggctctacc | 1200 |
| aagggcgaag tgaaactgca ggaaagcggc cctggcctgg tggccccttc tcagtctctg | 1260 |

```
tccgtgacct gtaccgtgtc tggcgtgtcc ctgcccgatt acggcgtgtc ctggatcagg    1320
cagcctcccc ggaaaggact cgaatggctc ggcgtgatct ggggcagcga gacaacctac    1380
tacaacagcg ccctgaagtc caggctgacc atcatcaagg acaactccaa gagccaggtg    1440
ttcctgaaga tgaactctct gcagaccgac gataccgcca tctattattg cgccaagcac    1500
tactactacg gcggcagcta cgccatggac tactgggac agggaacctc cgtgaccgtg    1560
tccagtacta gttccggaac cacgacgcca gcgccgcgac caccaacacc ggcgcccacc    1620
atcgcgtcgc agcccctgtc cctgcgccca gaggcgtgcc ggccagcggc ggggggcgca    1680
gtgcacacga gggggctgga cttcgcctgt gatatctaca tctgggcgcc cttggccggg    1740
acttgtgggg tccttctcct gtcactggtt atcaccctt actgcaaacg gggcagaaag    1800
aaactcctgt atatattcaa caaccatttt atgagaccag tacaaactac tcaagaggaa    1860
gatggctgta gctgccgatt ccagaagaa gaagaaggag gatgtgaact gagagtgaag    1920
ttcagcagga gcgcagacgc ccccgcgtac caacagggcc agaaccagct ctataacgag    1980
ctcaatctag gacgaagaga ggagtacgat gttttggaca gagacgtgg ccgggaccct    2040 gagatggggg gaaagccgag aaggaagaac cctcaggaag gcctgtacaa tgaactgcag    2100
aaagataaga tggcggaggc ctacagtgag attgggatga aggcgagcg ccggagggc    2160 aagggcacg atggccttta ccagggtctc agtacagcca ccaaggacac ctacgacgcc    2220
cttcacatgc aggccctgcc ccctcgctaa                                     2250
```

<210> SEQ ID NO 74
<211> LENGTH: 2247
<212> TYPE: DNA
<213> ORGANISM: Artificial Sequence
<220> FEATURE:
<223> OTHER INFORMATION: Synthetic

<400> SEQUENCE: 74

```
atgctgctgc tcgtgacaag cctgctgctg tgcgagctgc ccaccctgc ctttctgctg     60 atccccgaca tccagatgac ccagaccacc agcagcctga cgccagcct gggcgataga    120 gtgaccatca gctgcagagc cagccaggac atcagcaagt acctgaactg gtatcagcag    180
aaacccgacg gcaccgtgaa gctgctgatc taccacacca gcagactgca cagcggcgtg    240
cccagcagat tttctggcag cggctccggc accgactaca gcctgaccat ctccaacctg    300
gaacaggaag atatcgctac ctacttctgt cagcaaggca cacccctgcc ctacaccttc    360
ggcggaggca ccaagctgga aatcacaggc ggcggaggat ccggcggcgg aggatccggc    420
ggcggaggat cccaggtgca gctgcagcag tctggacccg gcctcgtgaa gcctagccag    480
accctgtctc tgacctgcgc catcagcggc gatagcgtgt ccagcaatag cgccgcctgg    540
aactggatcc ggcagagccc ttctagaggc ctggaatggc tgggccggac ctactaccgg    600
tccaagtggt acaacgacta cgccgtgtcc gtgaagtccc ggatcaccat caaccccgac    660
accagcaaga accagttctc cctgcagctg aacagcgtga ccccgagga taccgccgtg    720 tactactgcg ccagagaagt gaccggcgac ctgaagatgc cttcgacat ctggggccag    780 ggcacaatgg tcaccgtgtc tagcggggga ggcggcagcg atattcagat gacacagagc    840
ccctccagcc tgtccgcctc tgtgggagac agagtgacaa tcacctgtcg ggcctcccag    900 accatcggt cctatctgaa ttggtatcag cagcggcctg gcaaggcccc caacctgctg    960
atctatgccg ccagctctct gcagtccggc gtgccatcta gattcagcgg cagaggcagc   1020
```

```
ggcaccgatt tcaccctgac aattagcagt ctgcaggccg aggacttcgc cacctactat    1080
tgccagcaga gctacagcat cccccagacc ttcggccagg gaacaaaact ggaaatcaaa    1140
gggggaggcg gcagcggggg aggcggcagc gggggaggcg gcagcgaagt gaaactgcag    1200
gaatctggcc ctggcctggt ggccccaagc cagtctctga gcgtgacctg taccgtgtct    1260
ggcgtgtccc tgcccgatta cggcgtgtcc tggatcagac agcccccag aaagggactg     1320 gaatggctgg gagtgatctg gggcagcgag acaacctact acaacagcgc cctgaagtcc    1380
aggctgacca tcatcaagga caactccaag agccaggtgt tcctgaagat gaattccctg    1440
cagaccgacg acaccgccat ctattactgt gccaagcact actactacgg cggcagctac    1500
gccatggact actggggaca gggaacctcc gtgaccgtgt cctctactag ttccggaacc    1560
acgacgccag cgccgcgacc accaacaccg gcgcccacca tcgcgtcgca gccctgtcc    1620 ctgcgcccag aggcgtgccg gccagcggcg ggggcgcag tgcacacgag ggggctggac    1680
ttcgcctgtg atatctacat ctgggcgccc ttggccggga cttgtggggt ccttctcctg    1740
tcactggtta tcacccttta ctgcaaacgg ggcagaaaga aactcctgta tatattcaaa    1800
caaccattta tgagaccagt acaaactact caagaggaag atggctgtag ctgccgattt    1860
ccagaagaag aagaaggagg atgtgaactg agagtgaagt tcagcaggag cgcagacgcc    1920
cccgcgtacc agcagggcca gaaccagctc tataacgagc tcaatctagg acgaagagag    1980
gagtacgatg ttttggacaa gagacgtggc cgggaccctg agatgggggg aaagccgaga    2040
aggaagaacc ctcaggaagg cctgtacaat gaactgcaga agataagat ggcggaggcc     2100 tacagtgaga ttgggatgaa aggcgagcgc cggaggggca aggggcacga tggcctttac    2160
cagggtctca gtacagccac caaggacacc tacgacgccc ttcacatgca ggccctgccc    2220
cctcgcggat cctaatgatc agtcgac                                        2247
```

<210> SEQ ID NO 75
<211> LENGTH: 2274
<212> TYPE: DNA
<213> ORGANISM: Artificial Sequence
<220> FEATURE:
<223> OTHER INFORMATION: Synthetic

<400> SEQUENCE: 75

```
atgctgctgc tcgtgacaag cctgctgctg tgcgagctgc cccaccctgc ctttctgctg     60
atccccgaca tccagatgac ccagaccacc agcagcctga gcgccagcct gggcgataga    120
gtgaccatca gctgcagagc cagccaggac atcagcaagt acctgaactg gtatcagcag    180
aaacccgacg gcaccgtgaa gctgctgatc taccacacca gcagactgca cagcggcgtg    240
cccagcagat tttctggcag cggctccggc accgactaca gcctgaccat ctccaacctg    300
gaacaggaag atatcgctac ctacttctgt cagcaaggca cacccctgcc ctacaccttc    360
ggcgaggcca ccaagctgga aatcacaggc ggctgcggat ccggcggcgg aggatccggc    420
ggcggaggat cccaggtgca gctgcagcag tctggacccg gctcgtgaa gcctagccag    480 accctgtctc tgacctgcgc catcagcggc gatagcgtgt ccagcaatag cgccgcctgg    540
aactggatcc ggcagagccc ttctagaggc ctggaatggc tggccggac ctactaccgg     600 tccaagtggt acaacgacta cgccgtgtcc gtgaagtccc ggatcaccat caaccccgac    660
accagcaaga accagttctc cctgcagctg aacagcgtga ccccgagga taccgccgtg    720 tactactgcg ccagagaagt gaccggcgac ctggaagatg ccttcgacat ctggggccag    780
ggcacaatgg tcaccgtgtc tagcggcagc acaagcggct ctggcaagcc tggatctggc    840
```

```
gagggctcta ccaagggcga tattcagatg acacagagcc cctccagcct gtccgcctct    900
gtgggagaca gagtgacaat cacctgtcgg gcctcccaga ccatctggtc ctatctgaat    960
tggtatcagc agcggcctgg caaggccccc aacctgctga tctatgccgc cagctctctg   1020
cagtccggcg tgccatctag attcagcggc agaggcagcg gcaccgattt caccctgaca   1080
attagcagtc tgcaggccga ggacttcgcc acctactatt gccagcagag ctacagcatc   1140
ccccagacct tcggccaggg aacaaaactg gaaatcaaag ggggaggcgg cagcggggga   1200
ggcggcagcg ggggatgcgg cagcgaagtg aaactgcagg aatctggccc tggcctggtg   1260
gccccaagcc agtctctgag cgtgacctgt accgtgtctg gcgtgtccct gcccgattac   1320
ggcgtgtcct ggatcagaca gccccccaga aagggactgg aatggctggg agtgatctgg   1380
ggcagcgaga caacctacta caacagcgcc ctgaagtcca ggctgaccat catcaaggac   1440
aactccaaga gccaggtgtt cctgaagatg aattccctgc agaccgacga caccgccatc   1500
tattactgtg ccaagcacta ctactacggc ggcagctacg ccatggacta ctggggacag   1560
ggaacctccg tgaccgtgtc ctctactagt tccggaacca cgacgccagc gccgcgacca   1620
ccaacaccgg cgcccaccat cgcgtcgcag ccctgtccc tgcgcccaga ggcgtgccgg   1680
ccagcggcgg ggggcgcagt gcacacgagg gggctggact tcgcctgtga tatctacatc   1740
tgggcgccct tggccgggac ttgtggggtc cttctcctgt cactggttat cacccttac   1800 tgcaaacggg gcagaaagaa actcctgtat atattcaaac aaccatttat gagaccagta   1860
caaactactc aagaggaaga tggctgtagc tgccgatttc cagaagaaga agaaggagga   1920
tgtgaactga gagtgaagtt cagcaggagc gcagacgccc ccgcgtacca gcagggccag   1980
aaccagctct ataacgagct caatctagga cgaagagagg agtacgatgt tttggacaag   2040
agacgtggcc gggaccctga gatgggggga aagccgagaa ggaagaaccc tcaggaaggc   2100
ctgtacaatg aactgcagaa agataagatg gcggaggcct acagtgagat tgggatgaaa   2160
ggcgagcgcc ggaggggcaa ggggcacgat ggcctttacc agggtctcag tacagccacc   2220
aaggacacct acgacgccct tcacatgcag gccctgcccc ctcgcggatc ctaa         2274
```

<210> SEQ ID NO 76
<211> LENGTH: 2235
<212> TYPE: DNA
<213> ORGANISM: Artificial Sequence
<220> FEATURE:
<223> OTHER INFORMATION: Synthetic

<400> SEQUENCE: 76

```
atggctctgc ctgtgacagc tctgctgctg cctctggccc tgctgctcca tgccgccaga     60
cccgatatcc agatgaccca gaccaccagc agcctgagcg ccagcctggg cgatagagtg    120
accatcagct gccgggccag ccaggacatc agcaagtacc tgaactggta tcagcagaaa    180
cccgacggca ccgtgaagct gctgatctac cacaccagca gactgcacag cggcgtgccc    240
agcagatttt ctggcagcgg ctccggcacc gactacagcc tgaccatctc caacctggaa    300
caggaagata tcgctaccta cttctgtcag caaggcaaca ccctgcccta caccttcggc    360
ggaggcacca agctggaaat cacaggcggc ggaggatctg gcgaggcgg atctcaggtc    420 cagctccagc agtctggacc cggcctggtc aagcctagcc agaccctgag cctgacctgc    480
gccatcagcg gcgacagcgt gtcctctaac agcgccgcct ggaattggat cagacagagc    540
cccagcagag gcctggaatg gctgggccgg acctactacc ggtccaagtg gtacaacgac    600
```

-continued

| | |
|---|---|
| tacgccgtgt ccgtgaagtc ccggatcacc atcaaccccg acaccagcaa gaaccagttc | 660 |
| tccctgcagc tgaacagcgt gacccctgag gacaccgccg tgtactactg cgccagagaa | 720 |
| gtgaccggcg acctggaaga tgccttcgac atctggggcc agggcaccat ggtcaccgtg | 780 |
| tctagcggca gcacaagcgg ctctggcaag cctggaagcg gcgagggctc taccaagggc | 840 |
| gacattcaga tgactcagag cccctccagc ctgtccgcct ctgtgggaga cagagtgaca | 900 |
| atcacctgta gagcctccca gaccatctgg tcctatctca attggtacca gcagcggcca | 960 |
| ggcaaggccc ctaacctgct catctatgcc gcctctagcc tgcagtccgg cgtgccatct | 1020 |
| agattcagcg gcaggggcag cggcaccgat ttcaccctga caatcagttc cctgcaggcc | 1080 |
| gaggacttcg ccacctacta ttgccagcag tcctacagca tccctcagac cttcggccag | 1140 |
| ggaacaaagc tcgaaatcaa aggtggtggt ggcagtggtg gcggcggaag cgaagtgaaa | 1200 |
| ctgcaggaaa gcggccctgg cctggtggcc ccttctcagt ctctgtccgt gacctgtacc | 1260 |
| gtgtctggcg tgtccctgcc cgattacggc gtgtcctgga tcaggcagcc accccggaaa | 1320 |
| ggactcgaat ggctcggcgt gatctggggc agcgagacaa cctactacaa cagcgccctg | 1380 |
| aagtccaggc tgaccatcat caaggacaac tccaagagcc aggtgttcct gaagatgaac | 1440 |
| agcctgcaga ccgacgatac cgccatctat tactgtgcca gcactacta ctacggcggc | 1500 |
| agctacgcca tggactactg gggacaggga acctccgtga ccgtgtccag tactagttcc | 1560 |
| ggaaccacga cgccagcgcc gcgaccacca acaccggcgc ccaccatcgc gtcgcagccc | 1620 |
| ctgtccctgc gcccagaggc gtgccggcca gcggcggggg gcgcagtgca cacgagggg | 1680 |
| ctggacttcg cctgtgatat ctacatctgg gcgcccttgg ccgggacttg tggggtcctt | 1740 |
| ctcctgtcac tggttatcac cctttactgc aaacgggca gaaagaaact cctgtatata | 1800 |
| ttcaaacaac catttatgag accagtacaa actactcaag aggaagatgg ctgtagctgc | 1860 |
| cgatttccag aagaagaaga aggaggatgt gaactgagag tgaagttcag caggagcgca | 1920 |
| gacgcccccg cgtacaagca gggccagaac cagctctata acgagctcaa tctaggacga | 1980 |
| agagaggagt acgatgtttt ggacaagaga cgtggccggg accctgagat ggggggaaag | 2040 |
| ccgagaagga gaacccctca ggaaggcctg tacaatgaac tgcagaaaga taagatggcg | 2100 |
| gaggcctaca gtgagattgg gatgaaaggc gagcgccgga ggggcaaggg gcacgatggc | 2160 |
| ctttaccagg gtctcagtac agccaccaag gacacctacg acgcccttca catgcaggcc | 2220 |
| ctgccccctc gctaa | 2235 |

<210> SEQ ID NO 77
<211> LENGTH: 2238
<212> TYPE: DNA
<213> ORGANISM: Artificial Sequence
<220> FEATURE:
<223> OTHER INFORMATION: Synthetic

<400> SEQUENCE: 77

| | |
|---|---|
| atgctgctgc tggtcacaag cctgctgctg tgcgagctgc cccacccgc ctttctgctg | 60 |
| attcctcagg tccagctgca gcagtctggc cctggcctgg tcaagcctag ccagaccctg | 120 |
| agcctgacct gcgccatcag cggcgacagc gtgtcctcta cagcgccgc ctggaactgg | 180 |
| atcagacaga gccccagcag aggcctggaa tggctgggcc ggaccctacta ccggtccaag | 240 |
| tggtacaacg actacgccgt gtccgtgaag tcccggatca ccatcaaccc cgacaccagc | 300 |
| aagaaccagt tctccctgca gctgaacagc gtgaccctg aggacaccgc cgtgtactac | 360 |
| tgcgccagag aagtgaccgg cgacctggaa gatgccttcg acatctgggg ccagggcacc | 420 |

```
atggtcaccg tgtctagcgg aggcggagga agtggcggcg gaggcagcga tatccagatg    480
acccagacca ccagcagcct gagcgccagc ctgggcgata gagtgaccat ctcctgccgg    540
gccagccagg acatcagcaa gtacctgaat tggtatcagc agaagcccga cggcaccgtc    600
aagctgctga tctaccacac cagcagactg cacagcggcg tgcccagcag attttctggc    660
agcggctccg gcaccgacta cagcctgacc atcagcaacc tggaacagga agatatcgct    720
acctacttct gtcagcaagg caacaccctg ccctacacct tcggaggcgg caccaagctg    780
gaaatcaccg gcagcacaag cggcagcggc aagcctggat ctggcgaggg ctctaccaag    840
ggcgaagtga agctgcagga aagcggaccc ggactggtgg cccctagcca gtctctgtct    900
gtgacctgta ccgtgtccgg cgtgtccctg cccgattatg gcgtgtcctg gatcaggcag    960
cctccccgga aggactcga atggctcggc gtgatctggg gcagcgagac aacctactac   1020
aacagcgccc tgaagtccag gctgacaatc atcaaggaca actccaagag ccaggtgttc   1080
ctgaagatga cagcctgca gaccgacgat accgccatct actattgtgc caagcactac   1140
tactacggcg gcagctacgc catggactac tggggacagg gaacctccgt gaccgtcagt   1200
agtggtggtg gcggatctgg tggaggcggc tccgacattc agatgactca gagcccttcc   1260
agcctgtccg cctctgtggg agacagagtg acaatcacct gtagagcctc ccagaccatc   1320
tggtcctatc tcaactggta ccagcagcgg ccaggcaagg cccctaacct gctcatctat   1380
gccgcctcta gcctgcagtc cggggtgccc tctagattca gcggcagagg aagcggcacc   1440
gatttcaccc tgacaattag ctcactgcag gccgaggact cgccaccta ttactgccag   1500 cagagctaca gcatccctca gaccttcggc cagggaacaa agctcgaaat caagactagt   1560
tccggaacca cgacgccagc gccgcgacca ccaacaccgg cgcccaccat cgcgtcgcag   1620
cccctgtccc tgcgcccaga ggcgtgccgg ccagcggcgg ggggcgcagt gcacacgagg   1680
gggctggact tcgcctgtga tatctacatc tgggcgccct tggccgggac ttgtggggtc   1740
cttctcctgt cactggttat caccctttac tgcaaacggg gcagaaagaa actcctgtat   1800
atattcaaac aaccatttat gagaccagta caaactactc aagaggaaga tggctgtagc   1860
tgccgatttc cagaagaaga agaaggagga tgtgaactga gagtgaagtt cagcaggagc   1920
gcagacgccc ccgcgtacaa gcagggccag aaccagctct ataacgagct caatctagga   1980
cgaagagagg agtacgatgt tttggacaag agacgtggcc gggaccctga gatgggggga   2040
aagccgagaa ggaagaaccc tcaggaaggc ctgtacaatg aactgcagaa agataagatg   2100
gcggaggcct acagtgagat tgggatgaaa ggcgagcgcc ggaggggcaa ggggcacgat   2160
ggcctttacc agggtctcag tacagccacc aaggacacct acgacgccct tcacatgcag   2220
gccctgcccc ctcgctaa                                                  2238
```

<210> SEQ ID NO 78
<211> LENGTH: 2244
<212> TYPE: DNA
<213> ORGANISM: Artificial Sequence
<220> FEATURE:
<223> OTHER INFORMATION: Synthetic

<400> SEQUENCE: 78

```
atgctgctgc tggtcacaag cctgctgctg tgcgagctgc cccaccccgc ctttctgctg     60
atccccgaca tccagatgac ccagaccacc agcagcctga cgccagcct gggcgataga    120 gtgaccatca gctgccgggc cagccaggac atcagcaagt acctgaactg gtatcagcag    180
```

| | |
|---|---|
| aagcccgacg gcaccgtcaa gctgctgatc taccacacca gcagactgca cagcggcgtg | 240 |
| cccagcagat tttctggcag cggctccggc accgactaca gcctgaccat ctccaacctg | 300 |
| gaacaggaag atatcgctac ctacttctgt cagcaaggca cacccctgcc ctacaccttc | 360 |
| ggcgaggca ccaagctgga aatcacaggc ggcggaggat ctggcggagg cggaagttgt | 420 |
| ggtggcggat ctcaggtcca gctgcagcag agtggccctg gcctggtcaa gcctagccag | 480 |
| accctgagcc tgacctgcgc catcagcggc gacagcgtgt cctctaacag cgccgcctgg | 540 |
| aattggatca gacagagccc cagcagaggc ctggaatggc tgggccggac ctactaccgg | 600 |
| tccaagtggt acaacgacta cgccgtgtcc gtgaagtccc ggatcaccat caaccccgac | 660 |
| accagcaaga accagttctc cctgcagctg aacagcgtga cccctgagga caccgccgtg | 720 |
| tactactgcg ccagagaagt gaccggcgac ctggaagatg ccttcgacat ctggggccag | 780 |
| ggcaccatgg tcaccgtcag tagtggaggc ggtggcagcg gtggcggcgg aagcgatatt | 840 |
| cagatgactc agagccccctc cagcctgtcc gcctctgtgg gagacagagt gacaatcacc | 900 |
| tgtagagcct cccagaccat ctggtcctat ctcaattggt accagcagcg gccaggcaag | 960 |
| gcccctaacc tgctcatcta tgccgcctct agcctgcagt ccggcgtgcc atctagattc | 1020 |
| agcggcagag gcagcggcac cgatttcacc ctgacaatca gttccctgca ggccgaggac | 1080 |
| ttcgccacct actattgcca gcagagctac agcatccctc agaccttcgg ccagggaaca | 1140 |
| aagctcgaaa tcaaggtgg aggcggctgc ggaggtggtg gatctggagg cggaggctcc | 1200 |
| gaagtgaagc tgcaggaaag cggcccagga ctggtggccc ctagccagtc tctgtccgtg | 1260 |
| acctgtaccg tgtctggcgt gtccctgccc gattacggcg tgtcctggat caggcagcca | 1320 |
| ccccggaaag gactcgaatg gctcggcgtg atctggggca gcgagacaac ctactacaac | 1380 |
| agcgccctga gtccagact gaccatcatc aaggacaact ccaagagcca ggtgttcctg | 1440 |
| aagatgaaca gcctgcagac cgacgatacc gccatctatt actgtgccaa gcactactac | 1500 |
| tacgccggca gctacgccat ggactactgg ggacagggaa cctccgtgac cgtgtccagt | 1560 |
| actagttccg gaaccacgac gccagcgccg cgaccaccaa caccggcgcc caccatcgcg | 1620 |
| tcgcagcccc tgtccctgcg cccagaggcg tgccggccag cggcgggggg cgcagtgcac | 1680 |
| acgaggggc tggacttcgc ctgtgatatc tacatctggg cgcccttggc cgggacttgt | 1740 |
| ggggtccttc tcctgtcact ggttatcacc ctttactgca acggggcag aagaaaactc | 1800 |
| ctgtatatat tcaaacaacc atttatgaga ccagtacaaa ctactcaaga ggaagatggc | 1860 |
| tgtagctgcc gatttccaga agaagaagaa ggaggatgtg aactgagagt gaagttcagc | 1920 |
| aggagcgcag acgccccgc gtacaagcag gccagaacc agctctataa cgagctcaat | 1980 |
| ctaggacgaa gagaggagta cgatgttttg gacaagagac gtggccggga ccctgagatg | 2040 |
| ggggaaagc cgagaaggaa gaaccctcag gaaggcctgt acaatgaact gcagaaagat | 2100 |
| aagatggcgg aggcctacag tgagattggg atgaaaggcg agcgccggag gggcaagggg | 2160 |
| cacgatggcc tttaccaggg tctcagtaca gccaccaagg acacctacga cgcccttcac | 2220 |
| atgcaggccc tgccccctcg ctaa | 2244 |

<210> SEQ ID NO 79
<211> LENGTH: 25
<212> TYPE: PRT
<213> ORGANISM: Artificial Sequence
<220> FEATURE:
<223> OTHER INFORMATION: Synthetic

<400> SEQUENCE: 79

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 80
<211> LENGTH: 15
<212> TYPE: PRT
<213> ORGANISM: Artificial Sequence
<220> FEATURE:
<223> OTHER INFORMATION: Synthetic

<400> SEQUENCE: 80

Gly Gly Gly Gly Ser Gly Gly Gly Gly Ser Gly Gly Gly Gly Ser
1               5                   10                  15

<210> SEQ ID NO 81
<211> LENGTH: 15
<212> TYPE: PRT
<213> ORGANISM: Artificial Sequence
<220> FEATURE:
<223> OTHER INFORMATION: Synthetic

<400> SEQUENCE: 81

Gly Gly Cys Gly Ser Gly Gly Gly Gly Ser Gly Gly Gly Gly Ser
1               5                   10                  15

<210> SEQ ID NO 82
<211> LENGTH: 15
<212> TYPE: PRT
<213> ORGANISM: Artificial Sequence
<220> FEATURE:
<223> OTHER INFORMATION: Synthetic

<400> SEQUENCE: 82

Gly Gly Gly Gly Ser Gly Gly Gly Gly Ser Gly Gly Cys Gly Ser
1               5                   10                  15

<210> SEQ ID NO 83
<211> LENGTH: 10
<212> TYPE: PRT
<213> ORGANISM: Artificial Sequence
<220> FEATURE:
<223> OTHER INFORMATION: Synthetic

<400> SEQUENCE: 83

Gly Gly Gly Gly Ser Gly Gly Gly Gly Ser
1               5                   10

<210> SEQ ID NO 84
<211> LENGTH: 15
<212> TYPE: PRT
<213> ORGANISM: Artificial Sequence
<220> FEATURE:
<223> OTHER INFORMATION: Synthetic

<400> SEQUENCE: 84

Gly Gly Gly Gly Ser Gly Gly Gly Gly Ser Cys Gly Gly Gly Ser
1               5                   10                  15

<210> SEQ ID NO 85
<211> LENGTH: 15
<212> TYPE: PRT
<213> ORGANISM: Artificial Sequence
<220> FEATURE:
<223> OTHER INFORMATION: Synthetic

```
<400> SEQUENCE: 85

Gly Gly Gly Gly Cys Gly Gly Gly Gly Ser Gly Gly Gly Gly Ser
1               5                   10                  15

<210> SEQ ID NO 86
<211> LENGTH: 47
<212> TYPE: PRT
<213> ORGANISM: Artificial Sequence
<220> FEATURE:
<223> OTHER INFORMATION: synthetic

<400> SEQUENCE: 86

Ser Gly Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Cys Arg Pro Ala
            20                  25                  30

Ala Gly Gly Ala Val His Thr Arg Gly Leu Asp Phe Ala Cys Asp
        35                  40                  45

<210> SEQ ID NO 87
<211> LENGTH: 20
<212> TYPE: PRT
<213> ORGANISM: Artificial Sequence
<220> FEATURE:
<223> OTHER INFORMATION: synthetic

<400> SEQUENCE: 87

Glu Phe Gly Leu Ser Trp Leu Phe Leu Val Ala Ile Leu Lys Gly Val
1               5                   10                  15

Gln Cys Ser Arg
            20

<210> SEQ ID NO 88
<211> LENGTH: 20
<212> TYPE: PRT
<213> ORGANISM: Artificial Sequence
<220> FEATURE:
<223> OTHER INFORMATION: synthetic

<400> SEQUENCE: 88

Gly Gly Gly Gly Ser Gly Gly Gly Gly Ser Gly Gly Gly Gly Ser Gly
1               5                   10                  15

Gly Gly Gly Ser
            20
```